(12) United States Patent
Hochberg et al.

(10) Patent No.: US 10,004,813 B2
(45) Date of Patent: *Jun. 26, 2018

(54) CONSTRUCTS CONTAINING MULTIPLE EXPRESSION CASSETTES FOR CANCER THERAPY

(71) Applicant: YISSUM RESEARCH DEVELOPMENT COMPANY OF THE HEBREW UNIVERSITY OF JERUSALEM LTD., Jerusalem (IL)

(72) Inventors: Avraham Hochberg, Jerusalem (IL); Doron Amit, Northern Judea (IL)

(73) Assignee: Yissum Research Development Company of the Hebrew University of Jerusalem Ltd., Jerusalem (IL)

(*) Notice: Subject to any disclaimer, the term of this patent is extended or adjusted under 35 U.S.C. 154(b) by 42 days.

This patent is subject to a terminal disclaimer.

(21) Appl. No.: 14/871,187

(22) Filed: Sep. 30, 2015

(65) Prior Publication Data

US 2016/0015834 A1 Jan. 21, 2016

Related U.S. Application Data

(63) Continuation of application No. 12/738,620, filed as application No. PCT/IL2008/001405 on Oct. 23, 2008, now Pat. No. 9,173,964.

(60) Provisional application No. 60/982,442, filed on Oct. 25, 2007.

(51) Int. Cl.
   *C12N 15/85* (2006.01)
   *A61K 48/00* (2006.01)
   *A61K 38/16* (2006.01)

(52) U.S. Cl.
   CPC .......... *A61K 48/005* (2013.01); *A61K 38/164* (2013.01); *A61K 48/0058* (2013.01); *C12N 15/85* (2013.01); *C12N 2830/001* (2013.01); *C12N 2830/008* (2013.01); *C12N 2830/20* (2013.01); *C12N 2840/20* (2013.01)

(58) Field of Classification Search
   CPC ..... A61K 48/005; A61K 38/164; C12N 15/85
   See application file for complete search history.

(56) References Cited

U.S. PATENT DOCUMENTS

| | | |
|---|---|---|
| 5,955,273 A | 9/1999 | Hochberg |
| 6,306,833 B1 | 10/2001 | Hockberg |
| 2004/0082529 A1 | 4/2004 | Hochberg |
| 2007/0190031 A1 | 8/2007 | Sidhu et al. |

FOREIGN PATENT DOCUMENTS

| | | |
|---|---|---|
| WO | 99/18195 A2 | 4/1999 |
| WO | 2004/024957 A2 | 3/2004 |
| WO | 2004/031359 A2 | 4/2004 |
| WO | 2007/007317 A1 | 1/2007 |
| WO | 2007/034487 A1 | 3/2007 |
| WO | 2008/087641 A2 | 7/2008 |
| WO | 2008/087642 A2 | 7/2008 |
| WO | 2008/099396 A1 | 8/2008 |

OTHER PUBLICATIONS

Bouard et al. (Br J Pharmacol, 157(2):153-65, 2009).*
Chen et al. (J Neurosurg, 103(2):311-9, 2005).*
Yahata et al (Journal of Biotechnology, 118: 123-134, 2005.*
Heyes et al (Molecular Therapy, 13(4): 713-720, 2007).*
Ariel et al., "The product of the imprinted H19 gene is an oncofetal RNA," J. Clin Pathol: Mol Pathol. , 50:34-44 (1997).
Ariel et al., "The imprinted H19 gene is a marker of early recurrence in human bladder carcinoma," J. Clin Pathol: Mol Pathol., 53:320-323 (2000).
Ayesh et al., "Inhibition of Tumor Growth by DT-A Expressed Under the Control of IGF2 P3 and P4 Promotor Sequences," Molecular Therapy, 7(4):535-541 (2003).
Bennett et al., "Refined structure of dimeric diphtheria toxin at 2.0 Å Resolution," Protein Science, 3:1444-1463 (1994).
Brandenberger et al., "Transcriptome characterization elucidates signaling networks that control human ES cell growth and differentiation," Nature Biotechnology, 22(6):707-716 (2004).
Brannan et al., "The Product of the H19 Gene May Function as an RNA," Molecular and Cellular Biology, 10(1):28-36 (Jan. 1990).
Brunkow et al., "Ectopic expression of the H19 gene in mice causes prenatal lethality," Genes & Development, 5:1092-1101 (1991).
Davis et al., "Expression of a Single Transfected cDNA Converts Fibroblasts to Myoblasts," Cell, 51:987-1000 (Dec. 24, 1987).
de Groot et al., Genetic Imprinting in Human Embryogenesis H19 and IGF2 Gene Expression, Trophoblast Research, 8:285-302 (1994).
Glassman et al., "Relaxation of Imprinting in Carcinogenesis," Cancer Genet Cytogenet, 89:69-73 (1996).
Hassan et al., "The insulin-like growth factor system as a therapetuic target in colorectal cancer," Annals of Oncology, 13:349-356 (2002).
Holthuizen et al., "Transcriptional Regulation of the Major Promoters of the Human IGF-II Gene," Molecular Reproduction and Development, 35:391-393 (1993).
Hudson et al., "Quantal Entry of Diphtheria Toxin to the Cytosol," The Journal of Biological Chemistry, 260(5):2675-2680 (Mar. 10, 1985).
Hurst et al., "Imprinted genes have few and small introns," Nature Genetics, 12:234-237 (1996).
Mahairas et al., "Sequence-tagged connectors: A sequence approach to mapping and scanning the human genome," Proc. Natl. Acad. Sci. USA, 96:9739-9744 (Aug. 1999).

(Continued)

*Primary Examiner* — Anoop K Singh
*Assistant Examiner* — Magdalene K Sgagias
(74) *Attorney, Agent, or Firm* — Winston & Strawn LLP

(57) ABSTRACT

The present invention relates to the field of cancer treatment, particularly to a novel constructs useful for treating tumors expressing H19 and/or IGF-II. More specifically, the invention provides compositions and methods utilizing a nucleic acid construct enabling expression of a cytotoxic gene product directed by more than one tumor specific promoter.

19 Claims, 34 Drawing Sheets

(56) References Cited

OTHER PUBLICATIONS

Molnar et al., "Factors Influencing the Efficacy, Longevity, and Safety of Electroporation-Assisted Plasmid-Based Gene Transfer into Mouse Muscles," Molecular Therapy, 10(3): 447-455 (Sep. 2004).
Ogawa et al., "Relaxation of insulin-like growth factor II gene imprinting implicated in Wilms' tumour," Nature, 362:749-751 (1993).
Ohana et al., "Use of H19 Regulatory Sequences for Targeted Gene Therapy in Cancer," Int. J. Cancer, 98:645-650 (2002).
Ohana et al., "Regulatory sequences of H19 and IGF2 genes in DNA-based therapy of colorectal rat liver metastases," The Journal of Gene Medicine, 7:366-374 (2005).
Pachnis et al., "Locus unlinkes to a-fetoprotein under the control of the murine raf and Rif genes," Proc. Natl. Acad. Sci. USA, 81:5523-5527 (Sep. 1984).
Poirier et al., "The murine H19 gene is activated during embryonic stem cell differentiation in vitro and at the time of implantation in the developing embryo," Development, 113:1105-1114 (1991).
Raab et al., "Heparin-binding EGF-like growth factor," Biochimica et Biophysica Acta, 1333:F179-F199 (1997).
Rachmilewitz et al., "Transcription of the H19 Gene in Differentiating Cytotrophoblasts from Human Placenta," Molecular Reproduction and Development, 32:196-202 (1992).
Rainier et al., "Relaxation of imprinted genes in human cancer," Nature, 362:747-749 (Apr. 11, 1993).
Seo et al., "Different Protein-Binding Patters in the P3 Promoter Region of the Human Insulin-like Growth Factor II Gene in the Human Liver Cirrhosis and Hepatocellular Carcinoma Tissues," J Korean Med Sci, 13:171-178 (1998).
Singer et al., Genes and Genomes: A Changing Perspective, University Science Books, Mill Valley, CA., Mir. Moscow, 1:123 (1998). English translation of the relevant part of p. 123.
Yin et al., "Investigations of the effect of DNA size in transient transfection assay using dual luciferase system," Analytical Biochemistry, 346:289-294 (2005).
Yu et al., "Lentiviral Vectors with Two Independent Internal Promoters Transfer High-Level Expression of Multiple Transgenes to Human Hemotopoietic Stem-Progenitor Cells," Molecular Therapy, 7(6):827-838 (2003).
Zdanovskaia et al., "Diphtheria toxin NAD affinity and ADP ribosyltransferase activity are reduced at tryptophan 153 substitutions for alanine or phenylalanine," Res. Microbiol., 151:557-562 (2000).
Zhang et al., "Gene Expression Profiles in Normal and Cancer Cells," Science, 273:1268-1272 (May 23, 1997).
Zhou et al., "Construction of a plasmid vector of fused protein genes driven by human insulin-like growth factor II P3 promoter," Zhonghua Yi Xue Za Zhi, 86(2):106-110 (2006).
International application No. PCT/IL2008/001405, Search Report and Written Opinion, dated Mar. 23, 2009.
Russian patent application No. 2010119173, Office Action, dated Jul. 6, 2012. English translation.
U.S. Appl. No. 12/738,620, Restriction Requirement,.
U.S. Appl. No. 12/738,620, Non-Final Office Action, dated Mar. 28, 2012.
U.S. Appl. No. 12/738,620, Final Office Action, dated Dec. 7, 2012.
U.S. Appl. No. 12/738,620, Non-Final Office Action, dated Oct. 9, 2014.
U.S. Appl. No. 12/738,620, Notice of Allowance, dated Jun. 23, 2015.
Reeck et al., "'Homology' in Proteins and Nucleic Acids: A Terminology Muddle and a Way out of it," Cell, 50(5):667 (Aug. 28, 1987).

* cited by examiner

SEQUENCE LISTING

<160> NUMBER OF SEQ ID NOS: 24

<210> SEQ ID NO 1
<211> LENGTH: 830
<212> TYPE: DNA
<213> ORGANISM: Homo sapiens

<400> SEQUENCE: 1

| | | | | | |
|---|---|---|---|---|---|
| ctgcagggcc | ccaacaaccc | tcaccaaagg | ccaaggtggt | gaccgacgga | cccacagcgg | 60 |
| ggtggctggg | ggagtcgaaa | ctcgccagtc | tccactccac | tcccaaccgt | ggtgccccac | 120 |
| gcgggcctgg | gagagtctgt | gaggccgccc | accgcttgtc | agtagagtgc | gcccgcgagc | 180 |
| cgtaagcaca | gcccggcaac | atgcggtctt | cagacaggaa | agtggccgcg | aatgggaccg | 240 |
| gggtgcccag | cggctgtggg | gactctgtcc | tgcggaaacc | gcggtgacga | gcacaagctc | 300 |
| ggtcaactgg | atgggaatcg | gcctgggggg | ctggcaccgc | gcccaccagg | gggtttgcgg | 360 |
| cacttccctc | tgcccctcag | cacccaccc | ctactctcca | ggaacgtgag | gtctgagccg | 420 |
| tgatggtggc | aggaaggggc | cctctgtgcc | atccgagtcc | ccagggaccc | gcagctggcc | 480 |
| cccagccatg | tgcaaagtat | gtgcaggcgc | ctggcaggca | gggagcagca | ggcatggtgt | 540 |
| cccctgaggg | gagacagtgg | tctgggaggg | agaggtcctg | gaccctgagg | gaggtgatgg | 600 |
| ggcaatgctc | agccctgtct | ccggatgcca | aggagggt | gcggggaggc | cgtctttgga | 660 |
| gaattccagg | atgggtgctg | ggtgagagag | acgtgtgctg | gaactgtcca | gggcggaggt | 720 |
| gggcctgcg | ggggccctcg | ggagggccct | gctctgattg | gccggcaggg | cagggcggg | 780 |
| aattctggcg | ggccacccca | gttagaaaaa | gcccgggcta | ggaccgagga | | 830 |

<210> SEQ ID NO 2
<211> LENGTH: 833
<212> TYPE: DNA
<213> ORGANISM: Homo sapiens

<400> SEQUENCE: 2

| | | | | | |
|---|---|---|---|---|---|
| gacaaccctc | accaagggcc | aaggtggtga | ccgacggacc | cacagcgggg | tggctggggg | 60 |
| agtcgaaact | cgccagtctc | cactccactc | ccaaccgtgg | tgccccacgc | gggcctggga | 120 |
| gagtctgtga | ggccgcccac | cgcttgtcag | tagagtgcgc | ccgcgagccg | taagcacagc | 180 |
| ccggcaacat | gcggtcttca | gacaggaaag | tggccgcgaa | tgggaccggg | gtgcccagcg | 240 |
| gctgtgggga | ctctgtcctg | cggaaaccgc | ggtgacgagc | acaagctcgg | tcaactggat | 300 |
| gggaatcggc | ctgggggct | ggcaccgcgc | ccaccagggg | gtttgcggca | cttccctctg | 360 |
| cccctcagca | ccccacccct | actctccagg | aacgtgagtt | ctgagccgtg | atggtggcag | 420 |
| gaagggccc | tctgtgccat | ccgagtcccc | agggacccgc | agctggcccc | cagccatgtg | 480 |
| caaagtatgt | gcaggcgct | ggcaggcagg | agcagcagg | catggtgtcc | cctgagggga | 540 |
| gacagtggtc | tgggagggag | aagtcctggc | cctgaggag | gtgatgggc | aatgctcagc | 600 |
| cctgtctccg | gatgccaaag | gagggtgcg | ggaggccgt | cttggagaa | ttccaggatg | 660 |
| ggtgctgggt | gagagagacg | tgtgctggaa | ctgtccaggg | cggaggtggg | ccctgcgggg | 720 |
| gccctcggga | gggccctgct | ctgattggcc | ggcagggcag | gggcgggaat | tctgggcggg | 780 |
| gccaccccag | ttagaaaaag | cccgggctag | gaccgaggag | cagggtgagg | gag | 833 |

<210> SEQ ID NO 3
<211> LENGTH: 877
<212> TYPE: DNA
<213> ORGANISM: Homo sapiens

<400> SEQUENCE: 3

```
caaggacatg gaatttcgga ccttctgtcc ccaccctctc tgctgagcct aggaacctct      60
gagcagcagg aaggccttgg gtctagagcc tagaaatgga cccccacgtc cacctgccca     120
gcctagaccc ccagcattga agggtggtca gacttcctgt gagaggaagc cactaagcgg     180
gatggacacc atcgcccact ccacccggcc ctgcccagcc ctgcccagtc cagcccagtc     240
cagcccagcc ctgcccttcc cagccctgcc cagcccagct catccctgcc ctacccagcc     300
cagccctgtc ctgccctgcc cagcccagcc cagcccagcc ctgccctgcc ctgccctgcc     360
cttcccagcc ctgaccttcc cagccctgcc cagcccagct catccctgcc ctacccagct     420
cagccctgcc ctgccctgcc ctgccctgcc cagccctacc cagcccagcc ctgccctgcc     480
ctgcccagct cagccctgcc caccccagcc cagcccagcc cagcatgcgt tctctggatg     540
gtgagcacag gcttgacctt agaaagaggc tggcaacgag ggctgaggcc accaggccac     600
tgggtgctca cgggtcagac aagcccagag cctgctcccc tgccacgggt cggggctgtc     660
accgccagca tgctgtggat gtgcatggcc tcagggctgc tggctccagg ctgccccgc      720
cctggctccc gaggccaccc ctcttatgcc atgaaccctg tgccacaccc acctctgagc     780
tgtccccgct cctgccgcct gcaccccctg agcagccccc tgtgtgtttc atgggagtct     840
tagcaaggaa ggggagctcg aattcctgca gcccggg                              877
```

<210> SEQ ID NO 4
<211> LENGTH: 1960
<212> TYPE: DNA
<213> ORGANISM: Homo sapiens
<220> FEATURE:
<221> NAME/KEY: misc_feature
<222> LOCATION: (1016)..(1016)
<223> OTHER INFORMATION: n is a, c, g, or t
<220> FEATURE:
<221> NAME/KEY: misc_feature
<222> LOCATION: (1126)..(1126)
<223> OTHER INFORMATION: n is a, c, g, or t

<400> SEQUENCE: 4

```
ccgggtaccg agctcccagg aagataaatg atttcctcct ctctagagat gggggtggga      60
tctgagcact cagagccaag ggcgcagtgg gtccgggcgg gggccctcct cggccctccc     120
aacatggggg ccaggaggtc agcccctcaa cctggacccc ggctgggtct cagggaatgg     180
tctcccccag tggcccagct tgcttgtgtt ttcagatggg tgtgcatggg tgtgtgtgtg     240
tgtgtgtgtg tgtgtgtgtg tgtgtgtgtg tgtgatgcct gacaagcccc agagagccaa     300
agacctgagt ggagatcttg tgacttctca aaaggggggat tggaaggttc gagaaagagc     360
tgtggtcagc cttgctctcc cttaaggctg tggtaaccac actaggcata gcataggcct     420
gcgccccgtc cctccttccc tcctccgcgc ctctcctttc tctttctccc ccctctaccc     480
cgctccctgg cctgctcctg gtgacaccgt tggccccctt ccaggctga gggaagccag      540
cgggggcccc ttcctgaaag cccacctgca ggccggcttg ctgggaaggg gctgctctcg     600
cagaggctcc cgcccgccct gcagccgttt cctggaagca gtcgctgtgg gtattctgtt     660
ccttgtcagc actgtgcttg caaagaaagc agacactgtg ctccttgtcc ttagggagcc     720
ccgctccatc acccaacacc tggctggaca caggcgggag gccgggtccg cggggagcgg     780
cgcggggctg gggccggacc attaaacaca cacgggcgcc aggcactgca ggctcctcct     840
cctcctcctg cccagcgcct ctgctcacag gcacgtgcca agccctagg ccaggaggcc      900
```

```
agcagtgggt gcagaacaag ctcctgggaa gggggtgcag ggcggacccc cggggagaag      960
ggctggcagg gctgtggggg acgctgaccg tgggcccac gttgcagaaa actggntgcc     1020
tggctggaag atgggggaga tgccaagcct ctgaggcagc acgagcaggg tgcatggagg    1080
ccggggcgcg gggaggctgc actgcagcat gcaccccaaa gcccanaggg agtgagacc    1140 aggccctgga atcgagaagt agaaaggcgg cttggaggcc tcggaaccgg ctgacctcca    1200
acagagtggg tctccagcct ggctctgccc tgccgcaggt cccctcccct cattaccagg    1260
cctagagcct ccagtcccgg tggcccccag cccgagggtg aacggcctca ccctgggtcg    1320
tgggacagag ggcacgttca tcaagagtgg ctcccaaggg acacgtggct gtttgcagtt    1380
cacaggaagc attcgagata aggagcttgt tttcccagtg ggcacggagc cagcagggg    1440 gctgtgggggc agcccagggt gcaaggccag gctgtgggc tgcagctgcc ttgggccca    1500 ctcccaggcc tttgcgggag gtgggaggcg ggaggcggca gctgcacagt ggccccaggc    1560
gaggctctca gccccagtcg ctctccgggt gggcagccca agagggtctg gctgagcctc    1620
ccacatctgg gactccatca cccaacaact taattaaggc tgaatttcac gtgtcctgtg    1680
acttgggtag acaaagcccc tgtccaaagg ggcagccagc ctaaggcagt ggggacggcg    1740
tgggtggcgg gcgacggggg agatggacaa caggaccgag ggtgtgcggg cgatggggga    1800
gatggacaac aggaccgagg gtgtgcgggc gatgggggag atggacaaca ggaccgaggg    1860
tgtgcgggac acgcatgtca ctcatgcacg ccaatggggg gcgtgggagg ctggggagca    1920
gacagactgg gctgggctgg gcgggaagga cgggcagatg                          1960

<210> SEQ ID NO 5
<211> LENGTH: 4085
<212> TYPE: DNA
<213> ORGANISM: Homo sapiens
<220> FEATURE:
<221> NAME/KEY: misc_feature
<222> LOCATION: (1016)..(1016)
<223> OTHER INFORMATION: n is a, c, g, or t
<220> FEATURE:
<221> NAME/KEY: misc_feature
<222> LOCATION: (1126)..(1126)
<223> OTHER INFORMATION: n is a, c, g, or t
<220> FEATURE:
<221> NAME/KEY: misc_feature
<222> LOCATION: (2194)..(2194)
<223> OTHER INFORMATION: n is a, c, g, or t
<220> FEATURE:
<221> NAME/KEY: misc_feature
<222> LOCATION: (3235)..(3235)
<223> OTHER INFORMATION: n is a, c, g, or t

<400> SEQUENCE: 5
ccgggtaccg agctcccagg aagataaatg atttcctcct ctctagagat gggggtggga      60
tctgagcact cagagccaag ggcgcagtgg gtccgggcgg gggccctcct cggccctccc    120
aacatggggg ccaggaggtc agcccctcaa cctggacccc ggctgggtct cagggaatgg    180
tctcccccag tggcccagct tgcttgtgtt ttcagatggg tgtgcatggg tgtgtgtgtg    240
tgtgtgtgtg tgtgtgtgtg tgtgtgtgtg tgtgatgcct gacaagcccc agagagccaa    300
agacctgagt ggagatcttg tgacttctca aaagggggat tggaaggttc gagaaagagc    360
tgtggtcagc cttgctctcc cttaaggctg tggtaaccac actaggcata gcataggcct    420 gcgcccgtc cctccttccc tcctccgcgc ctctcctttc tctttctccc ccctctaccc    480
cgctccctgg cctgctcctg gtgacaccgt tggccccctt ccaggctga gggaagccag    540 cgggggcccc ttcctgaaag cccacctgca ggccggcttg ctgggaaggg gctgctctcg    600
```

```
cagaggctcc cgcccgccct gcagccgttt cctggaagca gtcgctgtgg gtattctgtt    660
ccttgtcagc actgtgcttg caaagaaagc agacactgtg ctccttgtcc ttagggagcc    720
ccgctccatc acccaacacc tggctggaca caggcgggag gccgggtccg cggggagcgg    780
cgcggggctg gggccggacc attaaacaca cacgggcgcc aggcactgca ggctcctcct    840
cctcctcctg cccagcgcct ctgctcacag gcacgtgcca agccctagg ccaggaggcc     900 agcagtgggt gcagaacaag ctcctgggaa ggggtgcag gcggacccc cggggagaag      960 ggctggcagg gctgtggggg acgctgaccg tgggccccac gttgcagaaa actggntgcc   1020
tggctggaag atgggggaga tgccaagcct ctgaggcagc acgagcaggg tgcatggagg   1080
ccggggcgcg gggaggctgc actgcagcat gcaccccaaa gcccanaggg agtggagacc   1140
aggccctgga atcgagaagt agaaaggcgc ttggaggcc tcggaaccgg ctgacctcca    1200
acagagtggg gccggccctg gaggcaaaga ggtgcccggg gtccggccct gcctggggga   1260
gctatgtgtc atgggcaagc acaggatat gtagcccgct ctgagcctat ggacccaggg    1320
cagggctgca aggcagggca ggggagacag cacggggag caaggagcag agaggggcc    1380 tcaggctctc ccaggaggaa cattctcccg acaggaggaa gagacggccc aggggtgact   1440
gtggggagcc atggtggcag ctggggtcgt ggcagatggg agagaggctg gcgaggtgaa   1500
ggtgcagggg tcagggctct ggggcccaca tgcctgtggg agcaggcagg cccagggctc   1560
tccgccactc cccactcccg cttggctcat aggctgggcc caagggtggg gtgggatgag   1620
caggagatgg ggcccagggg gcaagcaggg ccccaaagac atttagaaaa accggtttat   1680
gcaggcagca ttcagagcag gcggcgtgcg tggcggggc cctgggagca cagagaggca    1740
cacgtagggc ccccgagggg ctccccattg gccggcagtg acatcacccc tgtgtcaaca   1800
gtgatgtctg cagctccggc cagccagggt ttatggagcg agacccagcc cggcctgggc   1860
cctcactccc caggcccaca cactagccca ctgttcaggg tccggggtgg cggcatggcc   1920
tgggggtcct ggcaccgctg ctcctctgcc caccctaact tcccggcatc gcggctgccc   1980
cctctgagcg tccccaacca gtaagtgtgg ggcccagcag gcctgccgtc ctcctcctct   2040
tcccctctag agagaaacgt ggaggtcctg gggctggggg cgctcatagc cctgtgacac   2100
aggtgcatgg ggtcagggt cccagaatgg cccctgggaa ggacctcagc tgggccggcg    2160
gctctaggct tcaggggtct gtctgcacag gggntagccc ctcccagacc tctgtgaagc   2220
cagtacgggc ctcccctccc tgccccgtgc tctgtccggt gcttcctgga ctgcactgcg   2280
ggccactggt gagagggtgg acagggaagg ccgccgtgg tgcctgttcc tgcccacctg    2340
gctgtgtggt cccctccaag tagggacaac ccttctgagg gcttggggc acctgggt     2400 tgccaggcc tccagagcc ctgtgagccc ctgggggtc tggcctgatg ccccctcca      2460 cgtccagggc cggctgtggc ccagaaaccc agcttcccag caggccggtg tgcggtggtg   2520
acccaggaga ggcctcgcct ccactgaggg gccaccgacc tctgtcagac cacagagacc   2580
cccaaggagt ctgaaggctg gagacccggg gctgggacca ggtgggactt tcccacggag   2640
ccgtccccag gccagctgg ggacacgtcc cccttctctc cagacacacc ctgcctgcca    2700
ccaggacaca ccggcctgtt gggggtctct tttaagtgct tgccactctg aggtgactgt   2760
ccctttccaa agaggtttct ggggcccagg tgggatgcgt cggcctgagc aggaggatct   2820
gggccgccag gggctgggga ctgtctcctg ggaaggaag cgcctgggag cgtgtgtgct    2880
gacccaggac catccaggga ggcccgtctg tggggcaagc gggaagggag cggctggaga   2940
```

-continued

```
ggcttggccg cccccgccct gcctcccatt ccttagctcc atgcctgtca acctctgtca   3000
cccagtgagt gatgtccagg ggccctggaa aggtcacagc atgtttgagc ggggtgagag   3060
agaggggaaa ggcgggggcg gggaaaagta cgtggaggaa gctttaggcc caaggaagga   3120
gacagggttc tgggagggag ggagccactg ggccgccgg gaaggtccct gcttgctgct    3180
gccacccaga accctcgcct cttagctagc ccccgcagcc ccagcctttc tggcntgtgg   3240
ccctctcccc catccccagg tgtcctgtgc aaccaggcct tggacccaaa ccctcctgcc   3300
ccctcctctc cctcctcacc ctcccaatgc agtggtctcc agcctggctc tgccctgccg   3360
caggtcccct cccctcatta ccaggcctag agcctccagt cccggtggcc cccagcccga   3420
gggtgaacgg cctcaccctg ggtcgtggga cagagggcac gttcatcaag agtggctccc   3480
aagggacacg tggctgtttg cagttcacag gaagcattcg agataaggag cttgttttcc   3540
cagtgggcac ggagccagca ggggggctgt ggggcagccc agggtgcaag gccaggctgt   3600
ggggctgcag ctgccttggg ccccactccc aggcctttgc gggaggtggg aggcgggagg   3660
cggcagctgc acagtggccc caggcgaggc tctcagcccc agtcgctctc cgggtgggca   3720
gcccaagagg gtctggctga gcctccccaca tctgggactc catcacccaa caacttaatt  3780
aaggctgaat ttcacgtgtc ctgtgacttg ggtagacaaa gcccctgtcc aaaggggcag   3840
ccagcctaag gcagtgggga cggcgtgggt ggcgggcgac gggggagatg gacaacagga   3900
ccgagggtgt gcgggcgatg ggggagatgg acaacaggac cgagggtgtg cgggcgatgg   3960
gggagatgga caacaggacc gagggtgtgc gggacacgca tgtcactcat gcacgccaat   4020
ggggggcgtg ggaggctggg gagcagacag actgggctgg gctgggcggg aaggacgggc   4080
agatg                                                                 4085
```

<210> SEQ ID NO 6
<211> LENGTH: 591
<212> TYPE: DNA
<213> ORGANISM: Corynebacterium diphtheriae

<400> SEQUENCE: 6

```
atggatcctg atgatgttgt tgattcttct aaatcttttg tgatggaaaa cttttcttcg     60
taccacggga ctaaacctgg ttatgtagat tccattcaaa aaggtataca aaagccaaaa    120
tctggtacac aaggaaatta tgacgatgat tggaaagggt tttatagtac cgacaataaa    180
tacgacgctg cgggatactc tgtagataat gaaaacccgc tctctggaaa agctggaggc    240
gtggtcaaag tgacgtatcc aggactgacg aaggttctcg cactaaaagt ggataatgcc    300
gaaactatta agaaagagtt aggtttaagt ctcactgaac cgttgatgga gcaagtcgga    360
acggaagagt ttatcaaaag gttcggtgat ggtgcttcgc gtgtagtgct cagccttccc    420
ttcgctgagg ggagttctag cgttgaatat attaataact gggaacaggc gaaagcgtta    480
agcgtagaac ttgagattaa ttttgaaacc cgtggaaaac gtggccaaga tgcgatgtat    540
gagtatatgg ctcaagcctg tgcaggaaat cgtgtcaggc gatctttgtg a             591
```

<210> SEQ ID NO 7
<211> LENGTH: 196
<212> TYPE: PRT
<213> ORGANISM: Corynebacterium diphtheriae

<400> SEQUENCE: 7

```
Met Asp Pro Asp Asp Val Val Asp Ser Ser Lys Ser Phe Val Met Glu
1               5                   10                  15
```

Asn Phe Ser Ser Tyr His Gly Thr Lys Pro Gly Tyr Val Asp Ser Ile
              20                  25                  30

Gln Lys Gly Ile Gln Lys Pro Lys Ser Gly Thr Gln Gly Asn Tyr Asp
          35                  40                  45

Asp Asp Trp Lys Gly Phe Tyr Ser Thr Asp Asn Lys Tyr Asp Ala Ala
      50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
              85                  90                  95

Val Asp Asn Ala Glu Thr Ile Lys Lys Glu Leu Gly Leu Ser Leu Thr
          100                 105                 110

Glu Pro Leu Met Glu Gln Val Gly Thr Glu Glu Phe Ile Lys Arg Phe
      115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
              165                 170                 175

Asp Ala Met Tyr Glu Tyr Met Ala Gln Ala Cys Ala Gly Asn Arg Val
          180                 185                 190

Arg Arg Ser Leu
        195

<210> SEQ ID NO 8
<211> LENGTH: 891
<212> TYPE: DNA
<213> ORGANISM: Homo sapiens

<400> SEQUENCE: 8
gagctcggcc atgcaggtag gatttgagct gtgtttcccg ccctgatcct ctctcctctg     60
gcggccggag cctccgtagg ctccaagcct ggcccagatt cggcggcgca gccggccttc    120
cgcgcgtccg cacctagcgg gggctccggg gctccggcgc ggcaccgggg ggcgctcggg    180
atctggctga ggctccaagg cccgcgtggc cggctcctcc tgctggggca ggtggcggct    240
gcgcgccccg cccgagccca ggggcccccct cagccgcaac aaccagcaag acccccccga    300
ctcagcccca agccacctgc atctgcactc agacggggcg cacccgcagt gcagcctcct    360
ggtggggcgc tgggagcccg cctgcccctg cctgcccgga cccccagct cacgagcaca    420 ggccgcccgg gcaccccaga aacccgggat ggggcccctg aattctctag gacgggcatt    480
cagcatggcc ttggcgctct gcggctccct gccccccacc cagcctcgcc ccgcgcacc    540 ccccagcccc tgcgaccgcc gcccccccc ccggggcccc agggcccccag cccgcacccc    600 ccgcccccgct cttggctcgg gttgcggggg cgggccgggg gcggggcgag ggctccgcgg    660
gcgcccattg gcgcgggcgc gaggccagcg gccccgcgcg ccctgggcc gcggctggcg    720 cgactataag agccgggcgt gggcgcccgc agttcgcctg ctctccggcg gagctgcgtg    780
aggcccggcc ggccccggcc ccccccttcc ggccgcccc gctcctggcc cacgcctgc     840 ccgcgctctg cccaccagcg cctccatcgg gcaaggcggc ccgcgtcga c             891

<210> SEQ ID NO 9
<211> LENGTH: 785
<212> TYPE: DNA
<213> ORGANISM: Homo sapiens

<400> SEQUENCE: 9

```
acttcccggt cggtctgtgg gtgcaggggg tgccgcctca catgtgtgat tcgtgccttg    60
cgggccctgg cctccggggt gctgggtaac gaggaggggc gcggagccgc agaagcccac   120
cctggtatgt tgacgcggtg ccagcgagac cgcgagagga agacggggt gggcggggcc    180
aggatggaga ggggccgagt tggcaggagt catggcagac gccacattcg cgacatctcc   240
cccacacccc ctctggctct gtccgcaaca tttccaaaca ggagtcccgg gagagggga    300
gaggggctgc tggtctgagg ctaagaaggg cagagccttc gacccggaga gaggccgcgg   360
cccctgccca gtgggcagcg tggaagtttc catacaagga ggtgggaagg agaccccccc   420
cccccttcac tgccctgtgc agagatgagc cgggggtgca ggatgggagc ccatggcact   480
tcgctacggg atggtccagg gctcccggtt ggggtgcag gagagaagag actggctggg    540
aggagggaga gggcgggagc aaaggcgcgg gggagtggtc agcagggaga ggggtgggg    600
gtagggtgga gcccgggctg ggaggagtcg gctcacacat aaaagctgag gcactgacca   660
gcctgcaaac tggacattag cttctcctgt gaaagagact tccagcttcc tcctcctcct   720
cttcctcctc ctcctcctgc cccagcgagc cttctgctga gctgtagggg gatcttctag   780
agtcg                                                              785
```

```
<210> SEQ ID NO 10
<211> LENGTH: 8837
<212> TYPE: DNA
<213> ORGANISM: Homo sapiens
<220> FEATURE:
<221> NAME/KEY: misc_feature
<222> LOCATION: (238)..(239)
<223> OTHER INFORMATION: n is a, c, g, or t
<220> FEATURE:
<221> NAME/KEY: misc_feature
<222> LOCATION: (733)..(733)
<223> OTHER INFORMATION: n is a, c, g, or t
<220> FEATURE:
<221> NAME/KEY: misc_feature
<222> LOCATION: (3178)..(3203)
<223> OTHER INFORMATION: n is a, c, g, or t
<220> FEATURE:
<221> NAME/KEY: misc_feature
<222> LOCATION: (7393)..(7393)
<223> OTHER INFORMATION: n is a, c, g, or t
```

<400> SEQUENCE: 10

```
cccaaccccg cgcacagcgg gcactggttt cgggcctctc tgtctcctac gaagtccgta    60
gagcaactcg gatttgggaa atttctctct agcgttgccc aaacacactt gggtcggccg   120
cgcgccctca ggacgtggac agggagggct tccccgtgtc caggaaagcg accgggcatt   180
gcccccagtc tccccaaaat ttgggcattg tcccgggtc ttccaacgga ctgggcgnng    240
ctcccggaca ctgaggactg gccccggggt ctcgctcacc ttcagcagcg tccaccgcct   300
gccacagagc gttcgatcgc tcgctgcctg agctcctggt gcgcccgcgg acgcagcctc   360
cagcttcgcg gtgagctccc cgccgcgccg atccctccg cctctgcgcc cctgaccggc    420
tctcggcccg catctgctgc tgtcccgccg gtgctggcgc tcgtccgctg cgccggggag   480
gccggcgtgg ggcgcgggac acggctgcgg acttgcggct gcgctgcgct cgctcctgct   540
gggcgccccg aaatccgcgc cactttcgtt tgctcattgc aaagatctca tttgtgggga   600
aagcggctgg agggtcccaa agtggggcgg gcagggggct ggggcgaggg acgcggagga   660
gaggcgctcc cgccgggcgg taaagtgcct ctagcccgcg ggcctaggac tccgccggga   720
```

```
gggcgcgcgg agngcgaagt gattgatggc ggaagcgggg gggcaagggg ggcagggggg      780
cgcgggattc cgccggcgac cccttccccct tggctaggct taggcggcgg ggggctggcg     840
gggtgcggga ttttgtgcgt ggttttttgac ttggtaaaaa tcacagtgct ttcttacatc    900
gttcaaactc tccaggagat ggtttcccca gaccccccaaa ttatcgtggt ggccccccgag   960 accgaactcg cgtctatgca agtccaacgc actgaggacg gggtaaccat tatccagata   1020
ttttgggtgg gccgcaaagg cgagctactt agacgcaccc cggtgagctc ggccatgcag   1080
gtaggatttg agctgtgttt cccgccctga tcctctctcc tctggcggcc ggagcctccg   1140
taggctccaa gcctggccca gattcggcgg cgcagccggc cttccgcgcg tccgcaccta   1200 gcggggggctc cggggctccg gcgcggcacc ggggggcgct cgggatctgg ctgaggctcc   1260
aaggcccgcg tggccggctc ctcctgctgg ggcaggtggc ggctgcgcgc cccgcccgag   1320 cccagggggcc ccctcagccg caacaaccag caaggacccc ccgactcagc cccaagccac    1380
ctgcatctgc actcagacgg ggcgcacccg cagtgcagcc tcctggtggg gcgctgggag    1440
cccgcctgcc cctgcctgcc cggagacccc agctcacgag cacaggccgc ccgggcaccc    1500
cagaaacccg ggatggggcc cctgaattct ctaggacggg cattcagcat ggccttggcg    1560
ctctgcggct ccctgccccc cacccagcct cgccccccgcg caccccccag cccctgcgac    1620
cgccgccccc ccccccgggg ccccagggcc ccagcccgca ccccccgccc cgctcttggc    1680
tcgggttgcg ggggcgggcc gggggcgggg cgagggctcc gcgggcgccc attggcgcgg   1740
gcgcgaggcc agcggccccg cgcggccctg ggccgcggct ggcgcgacta taagagccgg   1800
gcgtgggcgc ccgcagttcg cctgctctcc ggcggagctg cgtgaggccc ggccggcccc   1860
ggcccccccc ttccggccgc ccccgcctcc tgcccacgc ctgcccgcgc tctgcccacc    1920
agcgcctcca tcgggcaagg cggccccgcg tcgacgccgc ccgctgcctc gctgctgact   1980
cccgtcccgg gcgccgtccg cggggtcgcg ctccgccggg cctgcggatt cccgccgcc    2040 tcctcttcat ctacctcaac tcccccccatc cccgcttcgc ccgaggaggc ggttcccccc   2100
gcaggcagtc cggctcgcag gccgccggcg ttgtcacccc cccgcgctc cccctccagc   2160 cctcccccccg gcgcgcagcc tcgggccgct ccccctttccg cgctgcgtcc cggagcggcc   2220
ccggtgccgc caccgcctgt cccccctcccg aggcccgggc tcgcgacggc agagggctcc   2280
gtcggcccaa accgagctgg gcgccgcgcgg tccgggtgca gcctccactc cgcccccag    2340 tcaccgcctc ccccggcccc tcgacgtggc gcccttccct ccgcttctct gtgctccccg    2400
cgcccctctt ggcgtctggc cccggccccc gctctttctc ccgcaaccctt cccttcgctc   2460 cctcccgtcc ccccagctc ctagcctccg actccctccc ccctcacgc ccgccctctc     2520 gccttcgccg aaccaaagtg gattaattac acgctttctg tttctctccg tgctgttctc   2580
tcccgctgtg cgcctgcccg cctctcgctg tcctctctcc ccctcgccct ctcttcggcc   2640
cccccctttc acgttcactc tgtctctccc actatctctg ccccccctcta tccttgatac   2700 aacagctgac ctcatttccc gatacctttt ccccccccgaa aagtacaaca tctgcccgc    2760 cccagcccga agacagcccg tcctccctgg acaatcagac gaattctccc cccccccca   2820 aaaaaaagcc atccccccgc tctgcccccgt cgcacattcg gccccgcga ctcggccaga    2880 gcggcgctgg cagaggagtg tccggcagga gggccaacgc ccgctgttcg gtttgcgaca   2940
cgcagcaggg aggtgggcgg cagcgtcgcc ggcttccagg taagcggcgt gtgcgggccg   3000 ggccgggggcc ggggctgggg cggcgcgggc ttgcggcgac gccggccct tcctccgccc    3060 gctcccggcc cggggcctgc ggggctcggc ggggcggctg agccgggggg gaggaggagg   3120
```

-continued

```
aggaggagga ggacggacgg ctgcgggtcc cgttccctgc gcggagcccg cgctaccnnn      3180
nnnnnnnnnn nnnnnnnnnn nnngacgtcc ccgctgaagg gggtcggtct gtgggtgcag      3240
ggggtgccgc ctcacatgtg tgattcgtgc cttgcgggcc ctggcctccg gggtgctggg      3300
taacgaggag gggcgcggag ccgcagaagc ccaccctggt gtcgttgacg ccggtgccag      3360
cgagaccgcg agaggaagac gggggcgggc ggggccagga tggagagggg ccgagttggc      3420
aggagtcatg gcagacgcca cactcgcgac catctccccc acaccctct ggcctctgtc       3480 cgcaacattt ccaaacagga gtcccgggag aggggagag gggctgctgg tctgaggcta       3540
agaagggcag agccttcgac ccggagagag gccgcgccg cctgcccag tggcaacgtt        3600 gaagttttcc atacaacgga ggtcgggaag agacccccc cccccttca ctgccctgtg        3660 aagagatgag ccggggtgc aggatggag cccatggcac ttcgctacgg gatgtccagg        3720
gctccggttg ggggtgcagg agagaagaga ctggctggga ggagggagag ggcgggagca     3780
aaggcgcggg ggtgtggtca gagggagagg ggtgggggtt aggtggagcc cgggctggga     3840
ggagtcggct cacacataaa actgaggcac tgaccagcct gcaaactgga tattagcttc     3900
tcctgtgaaa gagacttcca gcttcctcct cctcctcttc ctcctcctcc tctgccccca    3960
gcgagccttc tgctgagctg taggtaacca gggctgtgga gtgaaggacc cccgctgcca    4020
tcccactcca gcctgaggca gggcagcagg gggcacggcc cacgcctggg cctcgggccc    4080
tgcagccgcc agcccgctgc ctctcggaca gcaccccct cccctctttt cctctgcccc     4140
tgcccccacc tggcgtctct gctccctcac ctgctcctc cctttctgtt ccttcccttc     4200 ggcccctcc ttgcccagct caggacttt cctgggccct cacctgctcc gcaccgctgc      4260
atgcttcctg tcctgctttc tgccggtccc ctgacccgga cctccaagcg cagagtggtg    4320
gggcttgttg cggaagcgcg gcgagggcta gagtggccag ctggcggagt gtgctcttag    4380
aatttggaag ggggtggcag aggggcggt gagaggactg gccagggtcc gccatgtcaa     4440
ggagatgacc aaggaggctt tcagatcctc ggcgcagtcg cccactagtc tttagagagg    4500
gcatgcaaag ttgtgcttct gtcccactgc ctgctcagtc gctcacataa tttattgcat    4560
caaaaactcc cctgggtctg cggagcaagg ctggggctgc ccgcctggag ggtaccacct    4620
tctgcaggag cagggccaac ttgctgtggt ggctcccggc ctcccacccc cgagtgggta    4680 acccggcct gtgacctgca gcctgtgag ggggtgtgcc taagactggc ctccccttcc      4740
agattgtagt ctggggaacc tggtgtcgga cttcccaggt ggcctgagct ggtctcttca    4800
gctccacggg gagagtttgg tagcgcaaat agggagatgt tctgggcccc tggccttact    4860
ggttcgattt gaggcctgga aaggaggctc tgggcgtgtg tgtgtgtgtt tgggggtacc    4920
caaggcagac tggagttgga gaactggtg actgggaaaa caaggtttct agagcatggg     4980
tggcgtggtt gtgttaacca ttggagtcgc ttgacccagg cctggctcag ctgcagactg    5040
gaaaggtgga aaagccaggg ggaggggcgg ggctggccca gcaggactgg cctgctgctt    5100
tgagggcgat ggtcctcctg gacccccct gctcagctgg gggttgtggg gaggaagggg     5160
ctggtcctcc ttggagcaca tgctctgtag gggtggggct gtctgccatc ttggcggcgc    5220
tggaggcctg agaagtggcg atgtaacgct gggctgccc tgccccatg gtgtcatagg      5280 acggaggcag gtcgggtgtc cagcctgggc ccctgcagct gtggatgccg ctgagctcct    5340
gcaataatga ccgtgcagat ggtcacccct cgtgtaaaat tactagtgct tcttgcaaat    5400
ggaaggaact gggcctttc tgtgtgcttc tggacgcttc attctgcaca tggccctgcg     5460
```

```
ccctcacctc ggcattatga cctgtgtgtt acttttgtaa taaaaataat gtttatagga    5520
aagccgtgct ttcaattttc aactgaattt gtaggttggc aaatttggtt tgggaggggc    5580
acctctggcc tggggcttgg cctggctgcc ccgctcacgc cacttctctc ccgccccag     5640 acaccaatgg gaatcccaat ggggaagtcg atgctggtgc ttctcacctt cttggccttc    5700
gcctcgtgct gcattgctgc ttaccgcccc agtgagaccc tgtgcggcgg ggagctggtg    5760
gacaccctcc agttcgtctg tggggaccgc ggcttctact tcagtaagta gcagggaggg    5820
gcttcctcag acctggtcag gcccctagag tgaccggtga ggatctccca tcctcaagcc    5880
aggggagcac actcctaggt cagcagccca gccgcttgct ctgagacttt gaccttcccg    5940
ccgcgtttct gagcacgtgc ggtgtcccag ggcatccaca ccagctgcct ttcccatcac    6000
acgcctcctt cgaagggtgg gccagaggtg cccctagac gtcaggggca tctacagggg     6060
tctccctggg catcagaatt tctgttgggg gccgtgaggc tcctgctcct gaggcaccgc    6120
acgcctagtg cagggcttca ggctctggag aagagcctg ccttcttcc tgcacctttt      6180 ggacattttg acaagggacg tgcgttcggt gaatgatcag aattaaaatc aataaagtga    6240
tttatataat taaaatcaat aagacaagtg cagttggtgg gtggcagggg tgagcggtgc    6300
atgcgcctcc ttgggcccca aggctgccgt gggggtgcc cacctgctga cctcaaggac      6360
gcttcagcct ttcctcatgt ttctctcttg gttctccagc ctgggggctg gcaggtgggt    6420
gcatggccca ttgtccttga accccacc ccagataggg gggctgggtg gatgcagagg       6480
caggcatggt gcctgggcat gcctgatggg gcagggagg ggccgctcct tactggcaga      6540
ggccgcaact tattccacct gacactcacc acgtgacatc tttaccacca ctgcttactc     6600
acgctgtgaa atgggctcac aggatgcaaa tgcacttcaa agcttctctc tgaaaagttc    6660
ctgctgcttg actctggaag cccctgcccg cctggcctc tcctgtgccc tctctcttgc     6720
ctgccccatt tggggtagg aagtggcact gcagggcctg gtgccagcca gtccttgccc     6780
agggagaagc ttccctgcac caggctttcc tgagaggagg ggaggccaa gcccccactt     6840 gggggccccc gtgacggggc ctcctgctcc ctcctccggc tgatggcacc tgcccttggg    6900 cacccccaagg tggagccccc agcgaccttc cccttccagc tgagcattgc tgtggggag    6960 aggggggaaga cggaggaaa gaagggagtg gttccatcac gcctcctcag cctcctctcc   7020
tcccgtcttc tcctctcctg cccttgtctc cctgtctcag cagctccagg ggtggtgtgg    7080 gccctccag cctcccaggt ggtgccaggc cagagtccaa gctcacggac agcagtcctc     7140 ctgtggggc cctgaactgg gctcacatcc cacacatttt ccaaaccact cccattgtga     7200
gcctttggtc ctggtggtgt ccctctggtt gtgggaccaa gagcttgtgc ccattttca     7260 tctgaggaag gaggcagcag aagtcacggg ctggtctggg ccccactcac ctcccctctc    7320
acctctcttc ttcctgggac gcctctgcct gccggctctc acttccctcc cctgacccgc    7380
agggtggctg cgnccttcca gggcctggcc tgagggcagg ggtggtttgc tgggggttcg    7440
gcctccgggg ctggggtc ggtgcggtgc taacacggct ctctctgtgc tgtgggactt       7500
ccaggcaggc ccgcaagccg tgtgagccgt cgcagccgtg gcatcgttga ggagtgctgt    7560
ttccgcagct gtgacctggc cctcctggag acgtactgtg ctaccccgc caagtccgag     7620 agggacgtgt cgaccctcc gaccgtgctt ccggtgaggg tcctgggccc ctttcccact     7680
ctctagagac agagaaatag ggcttcgggc gcccagcgtt tcctgtgcc tctgggacct    7740 cttggccagg gacaaggacc cgtgacttcc ttgcttgctg tgtggcccgg gagcagctca    7800
gacgctggct ccttctgtcc ctctgcccgt ggacattagc tcaagtcact gatcagtcac    7860
```

-continued

```
aggggtggcc tgtcaggtca ggcgggcggc tcaggcggaa gagcgtggag agcaggcacc    7920
tgctgaccag cccctccc tcccaggaca acttccccga gataccctg ggcaagttct    7980 tccaatatga cacctggaag cagtccaccc agcgcctgcg caggggcctg cctgccctcc    8040
tgcgtgcccg ccggggtcac gtgctcgcca aggagctcga ggcgttcagg gaggccaaac    8100
gtcaccgtcc cctgattgct ctacccaccc aagaccccgc ccacggggc gcccccccag    8160 agatggccaa caatcggaag tgagcaaaac tgccgcaagt ctgcagcccg cgccaccat    8220 cctgcagcct cctcctgacc acggacgttt ccatcaggtt ccatcccgaa aatctctcgg    8280
ttccacgtcc cctggggctt ctcctgaccc agtcccgtg cccgcctcc ccgaaacagg    8340 ctactctcct cggcccctc catcgggctg aggaagcaca gcagcatctt caaacatgta    8400
caaaatcgat tggctttaaa cacccttcac atacccctccc cccaaattat ccccaattat    8460
ccccacacat aaaaaatcaa acattaaac taacccct ccccccccc cacaacaacc    8520 ctcttaaaac taattggctt tttagaaaca ccccacaaaa gctcagaaat tggctttaaa    8580
aaaaacaacc accaaaaaaa atcaattggc taaaaaaaaa aagtattaaa aacgaattgg    8640
ctgagaaaca attggcaaaa taaggaatt tggcactccc cacccccct ttctcttct    8700 cccttggact ttgagtcaaa ttggcctgga cttgagtccc tgaaccagca aagagaaaag    8760
aagggcccca gaaatcacag gtgggcacgt cgcgtctacc gccatctccc ttctcacggg    8820
aattttcagg gtaaact                                                   8837
```

<210> SEQ ID NO 11
<211> LENGTH: 6045
<212> TYPE: DNA
<213> ORGANISM: Artificial Sequence
<220> FEATURE:
<223> OTHER INFORMATION: recombinant construct

<400> SEQUENCE: 11

```
ccctcaccaa gggccaaggt ggtgaccgac ggacccacag cggggtggct gggggagtcg      60
aaactcgcca gtctccactc cactcccaac cgtggtgccc cacgcgggcc tgggagagtc     120
tgtgaggccg cccaccgctt gtcagtagag tgcgcccgcg agccgtaagc acagcccggc     180
aacatgcggt cttcagacag gaaagtggcc gcgaatggga ccggggtgcc cagcggctgt     240
ggggactctg tcctgcggaa accgcggtga cgagcacaag ctcggtcaac tggatgggaa     300
tcggcctggg gggctggcac cgcgcccacc agggggtttg cggcacttcc ctctgcccct     360
cagcacccca cccctactct ccaggaacgt gagttctgag ccgtgatggt ggcaggaagg     420
ggccctctgt gccatccgag tccccaggga cccgcagctg cccccagcc atgtgcaaag     480 tatgtgcagg gcgctggcag gcaggagca gcagcatgtg tgtcccctga ggggagacag     540
tggtctggga gggagaagtc ctggaccctg agggaggtga tggggcaatg ctcagccctg     600
tctccggatg ccaaaggagg ggtgcgggga ggccgtctt ggagaattcc aggatgggtg     660
ctgggtgaga gagacgtgtg ctggaactgt ccagggcgga ggtgggccct gcgggggccc     720
tcgggagggc cctgctctga ttggccggca gggcagggc gggaatcctg ggcggggcca     780
ccccagttag aaaaagcccg ggctaggacc gaggagcagg gtgagggaga agcttggcat     840
tccggtactg ttggtaaagc caccatggat cctgatgatg ttgttgattc ttctaaatct     900
tttgtgatgg aaaactttc ttcgtaccac gggactaaac ctggttatgt agattccatt     960
caaaaaggta tacaaaagcc aaaatctggt acacaaggaa attatgacga tgattggaaa    1020
```

```
gggttttata gtaccgacaa taaatacgac gctgcgggat actctgtaga taatgaaaac    1080
ccgctctctg gaaaagctgg aggcgtggtc aaagtgacgt atccaggact gacgaaggtt    1140
ctcgcactaa aagtggataa tgccgaaact attaagaaag agttaggttt aagtctcact    1200
gaaccgttga tggagcaagt cggaacggaa gagtttatca aaaggttcgg tgatggtgct    1260
tcgcgtgtag tgctcagcct tcccttcgct gaggggagtt ctagcgttga atatattaat    1320
aactgggaac aggcgaaagc gttaagcgta gaacttgaga ttaattttga aacccgtgga    1380
aaacgtggcc aagatgcgat gtatgagtat atggctcaag cctgtgcagg aaatcgtgtc    1440
aggcgatctt tgtgaaggaa ccttacttct gtggtgtgac ataattggac aaactaccta    1500
cagagatttg gggatcctct agagtcgggg cggccggccg cttcgagcag acatgataag    1560
atacattgat gagtttggac aaaccacaac tagaatgcag tgaaaaaaat gctttatttg    1620
tgaaatttgt gatgctattg ctttatttgt aaccattata agctgcaata aacaagttaa    1680
caacaacaat tgcattcatt ttatgtttca ggttcagggg gaggtgtggg aggttttta    1740 aagcaagtaa aacctctaca aatgtggtaa aatcgataag gatccgtcga ccgatgccct    1800
tgagagcctt caacccagtc agctccttcc ggtgggcgcg gggcatgact atcgtcgccg    1860
cacttatgac tgtcttcttt atcatgcaac tcgtaggaca ggtgccggca gcgctcttcc    1920
gcttcctcgc tcactgactc gctgcgctcg tcgttcggc tgcggcgagc ggtatcagct    1980
cactcaaagg cggtaatacg gttatccaca gaatcagggg ataacgcagg aaagaacatg    2040
tgagcaaaag gccagcaaaa ggccaggaac cgtaaaaagg ccgcgttgct ggcgtttttc    2100
cataggctcc gccccctga cgagcatcac aaaaatcgac gctcaagtca gaggtggcga    2160
aacccgacag gactataaag ataccaggcg tttccccctg gaagctccct cgtgcgctct    2220
cctgttccga ccctgccgct taccggatac ctgtccgcct ttctcccttc gggaagcgtg    2280
gcgctttctc atagctcacg ctgtaggtat ctcagttcgg tgtaggtcgt tcgctccaag    2340
ctgggctgtg tgcacgaacc cccgttcag cccgaccgct cgccttatc cggtaactat    2400 cgtcttgagt ccaacccggt aagacacgac ttatcgccac tggcagcagc cactggtaac    2460
aggattagca gagcgaggta tgtaggcggt gctacagagt tcttgaagtg gtggcctaac    2520
tacggctaca ctagaagaac agtatttggt atctgcgctc tgctgaagcc agttaccttc    2580
ggaaaaagag ttggtagctc ttgatccggc aaacaaacca ccgctggtag cggtggtttt    2640
tttgtttgca agcagcagat tacgcgcaga aaaaaggat ctcaagaaga tcctttgatc    2700
ttttctacgg ggtctgacgc tcagtggaac gaaaactcac gttaagggat tttggtcatg    2760
agattatcaa aaaggatctt cacctagatc ctttaaatt aaaaatgaag ttttaaatca    2820
atctaaagta tatatgagta aacttggtct gacagttaga aaaactcatc gagcatcaaa    2880
tgaaactgca atttattcat atcaggatta tcaataccat attttgaaa aagccgtttc    2940 tgtaatgaag gagaaaactc accgaggcag ttccatagga tggcaagatc ctggtatcgg    3000
tctgcgattc cgactcgtcc aacatcaata caacctatta atttcccctc gtcaaaaata    3060
aggttatcaa gtgagaaatc accatgagtg acgactgaat ccggtgagaa tggcaaaagt    3120
ttatgcattt ctttccagac ttgttcaaca ggccagccat tacgctcgtc atcaaaatca    3180
ctcgcatcaa ccaaaccgtt attcattcgt gattgcgcct gagcgagacg aaatacgcga    3240
tcgctgttaa aaggacaatt acaaacagga atcgaatgca accggcgcag gaacactgcc    3300
agcgcatcaa caatattttc acctgaatca ggatattctt ctaatacctg gaatgctgtt    3360
ttcccgggga tcgcagtggt gagtaaccat gcatcatcag gagtacggat aaaatgcttg    3420
```

```
atggtcggaa gaggcataaa ttccgtcagc cagtttagtc tgaccatctc atctgtaaca   3480
tcattggcaa cgctaccttt gccatgtttc agaaacaact ctggcgcatc gggcttccca   3540
tacaatcgat agattgtcgc acctgattgc ccgacattat cgcgagccca tttatcccca   3600
tataaatcag catccatgtt ggaatttaat cgcggcctag agcaagacgt ttcccgttga   3660
atatggctca tactcttcct ttttcaatat tattgaagca tttatcaggg ttattgtctc   3720
atgagcggat acatatttga atgtatttag aaaaataaac aaatagggt tccgcgcaca   3780
tttccccgaa aagtgccacc tgacgcgccc tgtagcggcg cattaagcgc ggcgggtgtg   3840
gtggttacgc gcagcgtgac cgctacactt gccagcgccc tagcgcccgc tcctttcgct   3900
ttcttccctt cctttctcgc cacgttcgcc ggctttcccc gtcaagctct aaatcggggg   3960
ctccctttag ggttccgatt tagtgcttta cggcacctcg accccaaaaa acttgattag   4020
ggtgatggtt cacgtagtgg gccatcgccc tgatagacgg ttttcgccc tttgacgttg   4080
gagtccacgt tctttaatag tggactcttg ttccaaactg gaacaacact caaccctatc   4140
tcggtctatt cttttgattt ataagggatt ttgccgattt cggcctattg gttaaaaaat   4200
gagctgattt aacaaaaatt taacgcgaat tttaacaaaa tattaacgct tacaatttgc   4260
cattcgccat tcaggctgcg caactgttgg gaagggcgat cggtgcgggc ctcttcgcta   4320
ttacgccagc ccaagctacc atgataagta agtaatatta aggtacggga ggtacttgga   4380
gcggccgcaa taaaatatct ttattttcat tacatctgtg tgttggtttt ttgtgtgaat   4440
cgatagtact aacatacgct ctccatcaaa acaaaacgaa acaaaacaaa ctagcaaaat   4500
aggctgtccc cagtgcaagt gcaggtgcca gaacatttct ctatcgataa cttcccggtc   4560
ggtctgtggg tgcaggggt gccgcctcac atgtgtgatt cgtgccttgc gggccctggc   4620
ctccggggtg ctgggtaacg aggaggggcg cggagccgca gaagcccacc ctggtatgtt   4680
gacgcggtgc cagcgagacc gcgagaggaa gacggggtg ggcggggcca ggatggagag   4740
gggccgagtt ggcaggagtc atggcagacg ccacattcgc gacatctccc ccacaccccc   4800
tctggctctg tccgcaacat ttccaaacag gagtcccggg agaggggag agggctgct   4860
ggtctgaggc taagaaggc agagccttcg acccggagag aggccgcggc ccctgcccag   4920
tgggcagcgt ggaagtttcc atacaaggag gtgggaagga accccccccc cccttcact   4980
gccctgtgca gagatgagcc ggggtgcag gatgggagcc catggcactt cgctacggga   5040
tggtccaggg ctcccggttg ggggtgcagg agagaagaga ctggctggga ggagggagag   5100
ggcgggagca aaggcgcggg ggagtggtca gcagggagag gggtgggggg tagggtggag   5160
cccgggctgg gaggagtcgg ctcacacata aaagctgagg cactgaccag cctgcaaact   5220
ggacattagc ttctcctgtg aaagagactt ccagcttcct cctcctcctc ttcctcctcc   5280
tcctcctgcc ccagcgagcc ttctgctgag ctgtaggggg atcttctaga gtcggctagc   5340
ggcattccgg tactgttggt aaagccacca tggatcctga tgatgttgtt gattcttcta   5400
aatcttttgt gatggaaaac ttttcttcgt accacgggac taaacctggt tatgtagatt   5460
ccattcaaaa aggtatacaa aagccaaaat ctggtacaca aggaaattat gacgatgatt   5520
ggaaagggtt ttatagtacc gacaataaat acgacgctgc gggatactct gtagataatg   5580
aaaacccgct ctctggaaaa gctggaggcg tggtcaaagt gacgtatcca ggactgacga   5640
aggttctcgc actaaaagtg gataatgccg aaactattaa gaaagagtta ggtttaagtc   5700
tcactgaacc gttgatggag caagtcggaa cggaagagtt tatcaaaagg ttcggtgatg   5760
```

```
gtgcttcgcg tgtagtgctc agccttccct tcgctgaggg gagttctagc gttgaatata      5820
ttaataactg ggaacaggcg aaagcgttaa gcgtagaact tgagattaat tttgaaaccc      5880
gtggaaaacg tggccaagat gcgatgtatg agtatatggc tcaagcctgt gcaggaaatc      5940
gtgtcaggcg atctttgtga aggaacctta cttctgtggt gtgacataat tggacaaact      6000
acctacagag atttggggat ccctcgagac gtagggtacc gacaa                     6045

<210> SEQ ID NO 12
<211> LENGTH: 632
<212> TYPE: DNA
<213> ORGANISM: Homo sapiens

<400> SEQUENCE: 12 gacggggtg ggcgggggcca ggatggagag gggccgagtt ggcaggagtc atggcagacg        60
ccacattcgc gacactctcc ccacaccccc tctggctctg tccgcaacat ttccaaacag       120
gagtcccggg agaggggagg aggggctgct ggtctgaggc taagaagggc agagccttcg       180
acccggagag aggccgcggc ccctgcccag tgggcagcgt ggaagtttcc atacaaggag       240
gtgggaagga acccccccc ccccttcact gccctgtgca gagatgagcc ggggtgcag         300 gatgggagcc catggcactt cgctacggga tggtcagggc tcccggttgg gggtgcagga       360
gagaagagac tggctgggag gagggagagg gcgggagcaa aggcgcgggg gagtggtcag       420
cagggagagg ggtgggggt agggtggagc ccgggctggg aggagtcggc tcacacataa       480
aagctgaggc actgaccagc ctgcaaactg gacattagct tctcctgtga aagagacttc       540
cagcttcctc ctcctcctct tcctcctcct cctcctgccc cagcgagcct tctgctgagc       600
tgtaggtaac cagggccgtg gatgagactc tc                                     632

<210> SEQ ID NO 13
<211> LENGTH: 870
<212> TYPE: DNA
<213> ORGANISM: Homo sapiens

<400> SEQUENCE: 13
ggatccccaa aatgtgttcc ttgctttcat ctgccaattt tacgtaatat ggctctacgg        60
caaaattccc aatttcatat ggagaatttt ctttaactac ccctcctcac aaattggtcc       120
cccaagctag ctggcccta tttgagacct cttttctctat gttcccaatt gcatggagca      180
acttctctca tcccccaaac ctgtaatcta tttttctgga gtctcgagtt tagtcattaa       240
tcacggttcc cacattaacg gagtcccgg ggtcccctcc tccaggacac ccattcgcta        300
agcccgcaag gcagaaagaa ctctgccttg cgttccccaa aatttgggca ttgttccggc       360
tcgccggcca cccactgcag cttccccaac cccgcgcaca gcgggcactg gtttcgggcc       420
tctctgtctc ctacgaagtc cccagagcaa ctcggatttg ggaaatttct ctctagcgtt       480
gcccaaacac acttgggtcg gccgcgcgcc ctcaggacgt ggacagggag ggcttccccg       540
tgtccaggaa agcgaccggg cattgccccc agtctccccc aaatttgggc attgtccccg       600
ggtcttccaa cggactgggc gttgctcccg gacactgagg actggccccg ggtctcgct        660 caccttcagc agcgtccacc gcctgccaca gagcgttcga tcgctcgctg cctgagctcc       720
tggtgcgccc gcggacgcag cctccagctt cgcggtgagc tccccgccgc gccgatcccc       780
tccgcctctg cgccctgac cggctctcgg cccgcatctg ctgctgtccc gccggtgctg        840
gcgctcgtct ccggctgccg ccggggaggc                                        870
```

-continued

<210> SEQ ID NO 14
<211> LENGTH: 720
<212> TYPE: DNA
<213> ORGANISM: Homo sapiens

<400> SEQUENCE: 14

```
tcatgagcac cgagagcatg atcagggatg tggagctggc cgaggaggcc ctgcccaaga    60
aaacaggcgg ccctcagggc agcagaagat gcctgttcct gagcctgttc agcttcctga   120
tcgtggccgg agccaccacc ctgttctgcc tgctgaactt cggcgtgatc ggcccccaga   180
gagaggagtt ccccagagac ctgagcctga tctcccccct ggcccaggct gtgagaagca   240
gcagcagaac ccccagcgac aagcccgtgg cccacgtggt ggccaacccc caggccgagg   300
gccagctgca gtggctgaac agaagagcca acgccctgct ggccaacggc gtggagctga   360
gagacaacca gctggtggtg cccagcgagg gcctgtacct gatctacagc caggtgctgt   420
tcaagggcca gggctgcccc agcacccacg tgctgctgac ccacaccatc agcagaatcg   480
ccgtgtccta ccagaccaag gtgaacctgc tgtccgccat caagagccct tgccagagag   540
agacccccga gggcgccgag gccaagccct ggtacgagcc tatctacctg gcggcgtgt   600
tccagctgga aagggcgac agactgagcg ccgagatcaa cagacccgac tacctggatt   660
tcgccgagag cggccaggtg tacttcggca tcatcgccct gtgataatct agaaccatgg   720
```

<210> SEQ ID NO 15
<211> LENGTH: 233
<212> TYPE: PRT
<213> ORGANISM: Homo sapiens

<400> SEQUENCE: 15

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu Asn Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly 210                 215                 220
Gln Val Tyr Phe Gly Ile Ile Ala Leu
225                 230

<210> SEQ ID NO 16
<211> LENGTH: 4560
<212> TYPE: DNA
<213> ORGANISM: artificial
<220> FEATURE:
<223> OTHER INFORMATION: recombinant construct

<400> SEQUENCE: 16

| | | | | | |
|---|---|---|---|---|---|
| ggtaccgaca | accctcacca | agggccaagg | tggtgaccga | cggacccaca | gcggggtggc | 60 |
| tgggggagtc | gaaactcgcc | agtctccact | ccactcccaa | ccgtggtgcc | ccacgcgggc | 120 |
| ctggagagt | ctgtgaggcc | gcccaccgct | tgtcagtaga | gtgcgcccgc | gagccgtaag | 180 |
| cacagcccgg | caacatgcgg | tcttcagaca | ggaaagtggc | cgcgaatggg | accggggtgc | 240 |
| ccagcggctg | tggggactct | gtcctgcgga | aaccgcggtg | acgagcacaa | gctcggtcaa | 300 |
| ctggatggga | atcggcctgg | ggggctggca | ccgcgcccac | caggggggttt | gcggcacttc | 360 |
| cctctgcccc | tcagcacccc | acccctactc | tccaggaacg | tgagttctga | gccgtgatgg | 420 |
| tggcaggaag | gggccctctg | tgccatccga | gtccccaggg | accgcagct | ggccccccagc | 480 |
| catgtgcaaa | gtatgtgcag | ggcgctggca | ggcagggagc | agcaggcatg | gtgtccctg | 540 |
| aggggagaca | gtggtctggg | agggagaagt | cctggaccct | gagggaggtg | atggggcaat | 600 |
| gctcagccct | gtctccggat | gccaaaggag | gggtgcgggg | aggccgtctt | tggagaattc | 660 |
| caggatgggt | gctgggtgag | agagacgtgt | gctgaactg | tccagggcgg | aggtgggccc | 720 |
| tgcgggggcc | ctcgggaggg | ccctgctctg | attggccggc | agggcagggg | cgggaatcct | 780 |
| gggcggggcc | accccagtta | gaaaaagccc | gggctaggac | cgaggagcag | ggtgagggag | 840 |
| aagcttggca | ttccggtact | gttggtaaag | ccaccatgga | tcctgatgat | gttgttgatt | 900 |
| cttctaaatc | ttttgtgatg | gaaaacttt | cttcgtacca | cgggactaaa | cctggttatg | 960 |
| tagattccat | tcaaaaaggt | atacaaaagc | caaaatctgg | tacacaagga | aattatgacg | 1020 |
| atgattggaa | agggttttat | agtaccgaca | ataaatacga | cgctgcggga | tactctgtag | 1080 |
| ataatgaaaa | cccgctctct | ggaaaagctg | gaggcgtggt | caaagtgacg | tatccaggac | 1140 |
| tgacgaaggt | tctcgcacta | aaagtggata | atgccgaaac | tattaagaaa | gagttaggtt | 1200 |
| taagtctcac | tgaaccgttg | atggagcaag | tcggaacgga | agagtttatc | aaaaggttcg | 1260 |
| gtgatggtgc | ttcgcgtgta | gtgctcagcc | ttccccttcgc | tgaggggagt | tctagcgttg | 1320 |
| aatatattaa | taactgggaa | caggcgaaag | cgttaagcgt | agaacttgag | attaattttg | 1380 |
| aaacccgtgg | aaaacgtggc | caagatgcga | tgtatgagta | tatggctcaa | gcctgtgcag | 1440 |
| gaaatcgtgt | caggcgatct | ttgtgaagga | accttacttc | tgtggtgtga | cataattgga | 1500 |
| caaactacct | acagagattt | ggggatcctc | tagagtcggg | gcggccggcc | gcttcgagca | 1560 |
| gacatgataa | gatacattga | tgagtttgga | caaaccacaa | ctagaatgca | gtgaaaaaaa | 1620 |
| tgctttattt | gtgaaatttg | tgatgctatt | gctttatttg | taaccattat | aagctgcaat | 1680 |
| aaacaagtta | acaacaacaa | ttgcattcat | tttatgtttc | aggttcaggg | ggaggtgtgg | 1740 |
| gaggttttt | aaagcaagta | aaacctctac | aaatgtggta | aaatcgataa | ggatccgtcg | 1800 |
| accgatgccc | ttgagagcct | tcaacccagt | cagctccttc | cggtgggcgc | ggggcatgac | 1860 |
| tatcgtcgcc | gcacttatga | ctgtcttctt | tatcatgcaa | ctcgtaggac | aggtgccggc | 1920 |

```
agcgctcttc cgcttcctcg ctcactgact cgctgcgctc ggtcgttcgg ctgcggcgag    1980
cggtatcagc tcactcaaag gcggtaatac ggttatccac agaatcaggg gataacgcag    2040
gaaagaacat gtgagcaaaa ggccagcaaa aggccaggaa ccgtaaaaag gccgcgttgc    2100
tggcgttttt ccataggctc cgcccccctg acgagcatca caaaaatcga cgctcaagtc    2160
agaggtggcg aaacccgaca ggactataaa gataccaggc gtttccccct ggaagctccc    2220
tcgtgcgctc tcctgttccg accctgccgc ttaccggata cctgtccgcc tttctccctt    2280
cgggaagcgt ggcgctttct catagctcac gctgtaggta tctcagttcg gtgtaggtcg    2340
ttcgctccaa gctgggctgt gtgcacgaac cccccgttca gcccgaccgc tgcgccttat    2400
ccggtaacta tcgtcttgag tccaacccgg taagacacga cttatcgcca ctggcagcag    2460
ccactggtaa caggattagc agagcgaggt atgtaggcgg tgctacagag ttcttgaagt    2520
ggtggcctaa ctacggctac actagaagaa cagtatttgg tatctgcgct ctgctgaagc    2580
cagttacctt cggaaaaaga gttggtagct cttgatccgg caaacaaacc accgctggta    2640
gcggtggttt ttttgtttgc aagcagcaga ttacgcgcag aaaaaaagga tctcaagaag    2700
atcctttgat cttttctacg gggtctgacg ctcagtggaa cgaaaactca cgttaaggga    2760
ttttggtcat gagattatca aaaaggatct tcacctagat ccttttaaat taaaaatgaa    2820
gttttaaatc aatctaaagt atatatgagt aaacttggtc tgacagttag aaaaactcat    2880
cgagcatcaa atgaaactgc aatttattca tatcaggatt atcaatacca tatttttgaa    2940
aaagccgttt ctgtaatgaa ggagaaaact caccgaggca gttccatagg atggcaagat    3000
cctggtatcg gtctgcgatt ccgactcgtc aacatcaat acaacctatt aatttcccct    3060
cgtcaaaaat aaggttatca agtgagaaat caccatgagt gacgactgaa tccggtgaga    3120
atggcaaaag tttatgcatt tctttccaga cttgttcaac aggccagcca ttacgctcgt    3180
catcaaaatc actcgcatca accaaaccgt tattcattcg tgattgcgcc tgagcgagac    3240
gaaatacgcg atcgctgtta aaaggacaat tacaaacagg aatcgaatgc aaccggcgca    3300
ggaacactgc cagcgcatca acaatatttt cacctgaatc aggatattct tctaatacct    3360
ggaatgctgt tttcccgggg atcgcagtgg tgagtaacca tgcatcatca ggagtacgga    3420
taaaatgctt gatggtcgga agaggcataa attccgtcag ccagtttagt ctgaccatct    3480
catctgtaac atcattggca acgctacctt tgccatgttt cagaaacaac tctggcgcat    3540
cgggcttccc atacaatcga tagattgtcg cacctgattg cccgacatta tcgcgagccc    3600
atttataccc atataaatca gcatccatgt tggaatttaa tcgcggccta gagcaagacg    3660
tttcccgttg aatatggctc atactcttcc ttttttcaata ttattgaagc atttatcagg    3720
gttattgtct catgagcgga tacatatttg aatgtattta aaaaataaa caaatagggg    3780 ttccgcgcac atttccccga aaagtgccac ctgacgcgcc ctgtagcggc gcattaagcg    3840
cggcgggtgt ggtggttacg cgcagcgtga ccgctacact tgccagcgcc ctagcgcccg    3900
ctcctttcgc tttcttccct tcctttctcg ccacgttcgc cggctttccc cgtcaagctc    3960
taaatcgggg gctccctta gggttccgat ttagtgcttt acggcacctc gaccccaaaa    4020
aacttgatta gggtgatggt tcacgtagtg gccatcgcc tgatagacg ttttttcgcc    4080 ctttgacgtt ggagtccacg ttctttaata gtggactctt gttccaaact ggaacaacac    4140
tcaaccctat ctcggtctat tcttttgatt tataagggat tttgccgatt tcggcctatt    4200
ggttaaaaaa tgagctgatt taacaaaaat ttaacgcgaa ttttaacaaa atattaacgc    4260
ttacaatttg ccattcgcca ttcaggctgc gcaactgttg ggaagggcga tcggtgcggg    4320
```

```
cctcttcgct attacgccag cccaagctac catgataagt aagtaatatt aaggtacggg    4380
aggtacttgg agcggccgca ataaaatatc tttatttttca ttacatctgt gtgttggttt    4440
tttgtgtgaa tcgatagtac taacatacgc tctccatcaa acaaaacga aacaaaacaa    4500 actagcaaaa taggctgtcc ccagtgcaag tgcaggtgcc agaacatttc tctatcgata    4560
```

<210> SEQ ID NO 17
<211> LENGTH: 885
<212> TYPE: DNA
<213> ORGANISM: Artificial Sequence
<220> FEATURE:
<223> OTHER INFORMATION: recombinant construct

<400> SEQUENCE: 17

```
ggccatgcag gtaggatttg agctgtgttt cccgccctga tcctctctcc tctggcggcc      60
ggagcctccg taggctccaa gcctggccca gattcggcgg cgcagccggc cttccgcgcg     120
tccgcaccta gcggggctc cggggctccg gcgcggcacc gggggggcgct cgggatctgg     180 ctgaggctcc aaggcccgcg tggccggctc ctcctgctgg ggcaggtggc ggctgcgcgc     240
cccgcccgag cccaggggcc ccctcagccg caacaaccag caaggacccc ccgactcagc     300
cccaagccac ctgcatctgc actcagacgg ggcgcacccg cagtgcagcc tcctggtggg     360
gcgctgggag cccgcctgcc cctgcctgcc cggagacccc agctcacgag cacaggccgc     420
ccgggcaccc cagaaacccg ggatgggggcc cctgaattct ctaggacggg cattcagcat     480
ggccttggcg ctctgcggct ccctgccccc cacccagcct cgcccccgcg cacccccag     540 cccctgcgac cgccgccccc ccccccgggg cccagggcc ccagcccgca ccccccgccc     600
cgctcttggc tcgggttgcg ggggcggggcc ggggggcggg cgaggggctccc gcgggcgccc     660 attggcgcgg gcgcgaggcc agcggccccg cgcggccctg ggccgcggct ggcgcgacta     720
taagagccgg gcgtgggcgc ccgcagttcg cctgctctcc ggcggagctg cgtgaggccc     780
ggccggcccc ggcccccccc ttccggccgc ccccgccctcc tggcccacgc ctgcccgcgc     840
tctgcccacc agcgcctcca tcgggcaagg cggccccgcg tcgac                     885
```

<210> SEQ ID NO 18
<211> LENGTH: 6163
<212> TYPE: DNA
<213> ORGANISM: Artificial Sequence
<220> FEATURE:
<223> OTHER INFORMATION: recombinant construct

<400> SEQUENCE: 18

```
ccctcaccaa gggccaaggt ggtgaccgac ggacccacag cggggtggct ggggagtcg       60 aaactcgcca gtctccactc cactcccaac cgtggtgccc cacgcgggcc tgggagagtc     120
tgtgaggccg cccaccgctt gtcagtagag tgcgcccgcg agccgtaagc acagcccggc     180
aacatgcggt cttcagacag gaaagtggcc gcgaatggga ccggggtgcc cagcggctgt     240
ggggactctg tcctgcggaa accgcggtga cgagcacaag ctcggtcaac tggatgggaa     300
tcggcctggg gggctggcac cgcgcccacc agggggtttg cggcacttcc ctctgcccct     360
cagcacccca cccctactct ccaggaacgt gagttctgag ccgtgatggt ggcaggaagg     420
ggccctctgt gccatccgag tcccaggga cccgcagctg ccccagcc atgtgcaaag      480 tatgtgcagg gcgctggcag gcaggagca gcaggcatgg tgtccctga ggggagacag     540 tggtctggga gggagaagtc ctggaccctg agggaggtga tggggcaatg ctcagccctg     600
```

```
tctccggatg ccaaaggagg ggtgcgggga ggccgtcttt ggagaattcc aggatgggtg    660
ctgggtgaga gagacgtgtg ctggaactgt ccagggcgga ggtgggccct gcggggggccc   720
tcgggagggc cctgctctga ttggccggca gggcagggc gggaatcctg gcggggcca     780
ccccagttag aaaagcccg gctaggacc gaggagcagg gtgagggaga agcttggcat      840
tccggtactg ttggtaaagc caccatggat cctgatgatg ttgttgattc ttctaaatct    900
tttgtgatgg aaaacttttc ttcgtaccac gggactaaac ctggttatgt agattccatt    960
caaaaaggta tacaaaagcc aaaatctggt acacaaggaa attatgacga tgattggaaa   1020
gggttttata gtaccgacaa taaatacgac gctgcgggat actctgtaga taatgaaaac   1080
ccgctctctg gaaaagctgg aggcgtggtc aaagtgacgt atccaggact gacgaaggtt   1140
ctcgcactaa aagtggataa tgccgaaact attaagaaag agttaggttt aagtctcact   1200
gaaccgttga tggagcaagt cggaacggaa gagtttatca aaaggttcgg tgatggtgct   1260
tcgcgtgtag tgctcagcct tcccttcgct gagggagtt ctagcgttga atatattaat    1320
aactgggaac aggcgaaagc gttaagcgta gaacttgaga ttaattttga aacccgtgga   1380
aaacgtggcc aagatgcgat gtatgagtat atggctcaag cctgtgcagg aaatcgtgtc   1440
aggcgatctt tgtgaaggaa ccttacttct gtggtgtgac ataattggac aaactaccta   1500
cagagatttg gggatcctct agagtcgggg cggccggccg cttcgagcag acatgataag   1560
atacattgat gagtttggac aaaccacaac tagaatgcag tgaaaaaaat gctttatttg   1620
tgaaatttgt gatgctattg ctttatttgt aaccattata agctgcaata aacaagttaa   1680
caacaacaat tgcattcatt ttatgtttca ggttcagggg gaggtgtggg aggttttta    1740
aagcaagtaa aacctctaca aatgtggtaa aatcgataag gatccgtcga ccgatgccct   1800
tgagagcctt caacccagtc agctccttcc ggtgggcgcg gggcatgact atcgtcgccg   1860
cacttatgac tgtcttcttt atcatgcaac tcgtaggaca ggtgccggca gcgctcttcc   1920
gcttcctcgc tcactgactc gctgcgctcg gtcgttcggc tgcggcgagc ggtatcagct   1980
cactcaaagg cggtaatacg gttatccaca gaatcagggg ataacgcagg aaagaacatg   2040
tgagcaaaag gccagcaaaa ggccaggaac cgtaaaaagg ccgcgttgct ggcgtttttc   2100
cataggctcc gccccctga cgagcatcac aaaaatcgac gctcaagtca gaggtggcga    2160
aacccgacag gactataaag ataccaggcg tttccccctg gaagctccct cgtgcgctct   2220
cctgttccga ccctgccgct taccggatac ctgtccgcct ttctcccttc gggaagcgtg   2280
gcgctttctc atagctcacg ctgtaggtat ctcagttcgg tgtaggtcgt tcgctccaag   2340
ctgggctgtg tgcacgaacc ccccgttcag cccgaccgct gcgccttatc cggtaactat   2400
cgtcttgagt ccaacccggt aagacacgac ttatcgccac tggcagcagc cactggtaac   2460
aggattagca gagcgaggta tgtaggcggt gctacagagt tcttgaagtg gtggcctaac   2520
tacggctaca ctagaagaac agtatttggt atctgcgctc tgctgaagcc agttaccttc   2580
ggaaaaagag ttggtagctc ttgatccggc aaacaaacca ccgctggtag cggtggtttt   2640
tttgtttgca agcagcagat tacgcgcaga aaaaaggat ctcaagaaga tcctttgatc    2700
ttttctacgg ggtctgacgc tcagtggaac gaaaactcac gttaagggat tttggtcatg   2760
agattatcaa aaaggatctt cacctagatc cttttaaatt aaaaatgaag ttttaaatca   2820
atctaaagta tatatgagta aacttggtct gacagttaga aaaactcatc gagcatcaaa   2880
tgaaactgca atttattcat atcaggatta tcaataccat attttgaaa aagccgtttc    2940
tgtaatgaag gagaaaactc accgaggcag ttccatagga tggcaagatc ctggtatcgg   3000
```

```
tctgcgattc cgactcgtcc aacatcaata caacctatta atttccctc gtcaaaaata    3060
aggttatcaa gtgagaaatc accatgagtg acgactgaat ccggtgagaa tggcaaaagt    3120
ttatgcattt ctttccagac ttgttcaaca ggccagccat tacgctcgtc atcaaaatca    3180
ctcgcatcaa ccaaaccgtt attcattcgt gattgcgcct gagcgagacg aaatacgcga    3240
tcgctgttaa aaggacaatt acaaacagga atcgaatgca accggcgcag gaacactgcc    3300
agcgcatcaa caatattttc acctgaatca ggatattctt ctaatacctg gaatgctgtt    3360
ttcccgggga tcgcagtggt gagtaaccat gcatcatcag gagtacggat aaaatgcttg    3420
atggtcggaa gaggcataaa ttccgtcagc cagtttagtc tgaccatctc atctgtaaca    3480
tcattggcaa cgctaccttt gccatgtttc agaaacaact ctggcgcatc gggcttccca    3540
tacaatcgat agattgtcgc acctgattgc ccgacattat cgcgagccca tttatacccca    3600
tataaatcag catccatgtt ggaatttaat cgcggcctag agcaagacgt ttcccgttga    3660
atatggctca tactcttcct ttttcaatat tattgaagca tttatcaggg ttattgtctc    3720
atgagcggat acatatttga atgtatttag aaaaataaac aaatagggt tccgcgcaca    3780
tttccccgaa aagtgccacc tgacgcgccc tgtagcggcg cattaagcgc ggcgggtgtg    3840
gtggttacgc gcagcgtgac cgctacactt gccagcgccc tagcgcccgc tcctttcgct    3900
ttcttccctt cctttctcgc cacgttcgcc ggctttcccc gtcaagctct aaatcggggg    3960
ctcccttag ggttccgatt tagtgcttta cggcacctcg accccaaaaa acttgattag    4020
ggtgatggtt cacgtagtgg gccatcgccc tgatagacgg ttttcgccc tttgacgttg    4080
gagtccacgt tctttaatag tggactcttg ttccaaactg gaacaacact caaccctatc    4140
tcggtctatt cttttgattt ataagggatt tgccgatt cggcctattg gttaaaaaat    4200
gagctgattt aacaaaaatt taacgcgaat tttaacaaaa tattaacgct tacaatttgc    4260
cattcgccat tcaggctgcg caactgttgg gaagggcgat cggtgcgggc ctcttcgcta    4320
ttacgccagc ccaagctacc atgataagta agtaatatta aggtacggga ggtacttgga    4380
gcggccgcaa taaatatct ttattttcat tacatctgtg tgttggtttt ttgtgtgaat    4440
cgatagtact aacatacgct ctccatcaaa acaaaacgaa acaaaacaaa ctagcaaaat    4500
aggctgtccc cagtgcaagt gcaggtgcca gaacatttct ctatcgatac tcgagggcca    4560
tgcaggtagg atttgagctg tgtttcccgc cctgatcctc tctcctctgg cggccggagc    4620
ctccgtaggc tccaagcctg gcccagattc ggcggcgcag ccggccttcc gcgcgtccgc    4680
acctagcggg ggctccgggg ctccggcgcg gcaccggggg gcgctcggga tctggctgag    4740
gctccaaggc ccgcgtggcc ggctcctcct gctggggcag gtggcggctg cgcgccccgc    4800
ccgagcccag gggcccctc agccgcaaca accagcaagg accccccgac tcagcccaa    4860
gccacctgca tctgcactca gacggggcgc accgcagtg cagcctcctg gtggggcgct    4920
gggagcccgc ctgcccctgc ctgcccggag acccagctc acgagcacag gccgcccggg    4980
caccccagaa acccgggatg gggcccctga attctctagg acgggcattc agcatggcct    5040
tggcgctctg cggctccctg ccccccaccc agcctcgccc ccgcgcaccc ccagccccct    5100
gcgaccgccg ccccccccc cggggcccca gggcccagc ccgcaccccc cgccccgctc    5160
ttggctcggg ttgcggggc gggccggggg cggggcgagg gctccgcggg cgcccattgg    5220
cgcgggcgcg aggccagcgg ccccgcgcgg ccctgggccg cggctggcgc gactataaga    5280
gccgggcgtg ggcgcccgca gttcgcctgc tctccggcgg agctgcgtga ggcccggccg    5340
```

| | |
|---|---:|
| gccccggccc ccccccttccg gccgccccccg cctcctggcc cacgcctgcc cgcgctctgc | 5400 |
| ccaccagcgc ctccatcggg caaggcggcc ccgcgtcgac aagcttagct acgctagcgg | 5460 |
| cattccggta ctgttggtaa agccaccatg gatcctgatg atgttgttga ttcttctaaa | 5520 |
| tcttttgtga tggaaaactt ttcttcgtac cacgggacta aacctggtta tgtagattcc | 5580 |
| attcaaaaag gtatacaaaa gccaaaatct ggtacacaag gaaattatga cgatgattgg | 5640 |
| aaagggtttt atagtaccga caataaatac gacgctgcgg gatactctgt agataatgaa | 5700 |
| aacccgctct ctggaaaagc tggaggcgtg gtcaaagtga cgtatccagg actgacgaag | 5760 |
| gttctcgcac taaaagtgga taatgccgaa actattaaga aagagttagg tttaagtctc | 5820 |
| actgaaccgt tgatggagca agtcggaacg gaagagttta tcaaaaggtt cggtgatggt | 5880 |
| gcttcgcgtg tagtgctcag ccttcccttc gctgagggga gttctagcgt tgaatatatt | 5940 |
| aataactggg aacaggcgaa agcgttaagc gtagaacttg agattaattt tgaaacccgt | 6000 |
| ggaaaacgtg gccaagatgc gatgtatgag tatatggctc aagcctgtgc aggaaatcgt | 6060 |
| gtcaggcgat ctttgtgaag gaaccttact tctgtggtgt gacataattg gacaaactac | 6120 |
| ctacagagat ttgggggatcc ctcgagacgt agggtaccga caa | 6163 |

<210> SEQ ID NO 19
<211> LENGTH: 4657
<212> TYPE: DNA
<213> ORGANISM: Artificial Sequence
<220> FEATURE:
<223> OTHER INFORMATION: recombinant construct

<400> SEQUENCE: 19

| | |
|---|---:|
| tctatcgata ggtaccgaca accctcacca agggccaagg tggtgaccgg ccatgcaggt | 60 |
| aggatttgag ctgtgtttcc cgccctgatc ctctctcctc tggcggccgg agcctccgta | 120 |
| ggctccaagc ctggcccaga ttcggcggcg cagccggcct tccgcgcgtc cgcacctagc | 180 |
| gggggctccg gggctccggc gcggcaccgg ggggcgctcg ggatctggct gaggctccaa | 240 |
| ggcccgcgtg gccggctcct cctgctgggg caggtggcgg ctgcgcgccc cgcccgagcc | 300 |
| caggggcccc ctcagccgca acaaccagca aggaccccccc gactcagccc caagccacct | 360 |
| gcatctgcac tcagacgggg cgcacccgca gtgcagcctc ctggtggggc gctgggagcc | 420 |
| cgcctgcccc tgcctgcccg gagacccccag ctcacgagca caggccgccc gggcaccccca | 480 |
| gaaacccggg atggggcccc tgaattctct aggacgggca ttcagcatgg ccttggcgct | 540 |
| ctgcggctcc ctgcccccca cccagcctcg ccccccgcgca cccccagcc cctgcgaccg | 600 |
| ccgcccccc cccggggcc caggggcccc agcccgcacc cccgccccg ctcttggctc | 660 |
| gggttgcggg ggcgggccgg gggcggggcg agggctccgc gggcgcccat ggcgcgggc | 720 |
| gcgaggccag cggccccgcg cggccctggg ccgcggctgg cgcgactata agagccgggc | 780 |
| gtgggcgccc gcagttcgcc tgctctccgg cggagctgcg tgaggccgg ccggccccgg | 840 |
| ccccccccctt ccggccgccc ccgcctcctg gccacgcct gcccgcgctc tgcccaccag | 900 |
| cgcctccatc gggcaaggcg gccccgcaag cttggcattc cggtactgtt ggtaaagcca | 960 |
| ccatggatcc tgatgatgtt gttgattctt ctaaatcttt tgtgatggaa aacttttctt | 1020 |
| cgtaccacgg gactaaacct ggttatgtag attccattca aaaaggtata caaaagccaa | 1080 |
| aatctggtac acaaggaaat tatgacgatg attggaaagg ttttatagt accgacaata | 1140 |
| aatacgacgc tgcgggatac tctgtagata atgaaaaccc gctctctgga aaagctggag | 1200 |
| gcgtggtcaa agtgacgtat ccaggactga cgaaggttct cgcactaaaa gtggataatg | 1260 |

```
ccgaaactat taagaaagag ttaggtttaa gtctcactga accgttgatg gagcaagtcg    1320
gaacggaaga gtttatcaaa aggttcggtg atggtgcttc gcgtgtagtg ctcagccttc    1380
ccttcgctga ggggagttct agcgttgaat atattaataa ctgggaacag gcgaaagcgt    1440
taagcgtaga acttgagatt aattttgaaa cccgtggaaa acgtggccaa gatgcgatgt    1500
atgagtatat ggctcaagcc tgtgcaggaa atcgtgtcag gcgatctttg tgaaggaacc    1560
ttacttctgt ggtgtgacat aattggacaa actacctaca gagatttggg gatcctctag    1620
agtcggggcg gccggccgct tcgagcagac atgataagat acattgatga gtttggacaa    1680
accacaacta gaatgcagtg aaaaaaatgc tttatttgtg aaatttgtga tgctattgct    1740
ttatttgtaa ccattataag ctgcaataaa caagttaaca acaacaattg cattcatttt    1800
atgtttcagg ttcagggggg ggtgtgggag gtttttttaaa gcaagtaaaa cctctacaaa    1860
tgtggtaaaa tcgataagga tccgtcgacc gatgcccttg agagccttca acccagtcag    1920
ctccttccgg tgggcgcggg gcatgactat cgtcgccgca cttatgactg tcttctttat    1980
catgcaactc gtaggacagg tgccggcagc gctcttccgc ttcctcgctc actgactcgc    2040
tgcgctcggt cgttcggctg cggcgagcgg tatcagctca ctcaaaggcg gtaatacggt    2100
tatccacaga atcaggggat aacgcaggaa agaacatgtg agcaaaaggc cagcaaaagg    2160
ccaggaaccg taaaaaggcc gcgttgctgg cgttttccca taggctccgc cccctgacg     2220 agcatcacaa aaatcgacgc tcaagtcaga ggtggcgaaa cccgacagga ctataaagat    2280
accaggcgtt ccccctggaa gctccctcg tgcgctctcc tgttccgacc ctgccgctta    2340
ccggatacct gtccgccttt ctcccttcgg gaagcgtggc gctttctcat agctcacgct    2400
gtaggtatct cagttcggtg taggtcgttc gctccaagct gggctgtgtg cacgaacccc    2460
ccgttcagcc cgaccgctgc gccttatccg gtaactatcg tcttgagtcc aacccggtaa    2520
gacacgactt atcgccactg gcagcagcca ctggtaacag gattagcaga gcgaggtatg    2580
taggcggtgc tacagagttc ttgaagtggt ggcctaacta cggctacact agaagaacag    2640
tatttggtat ctgcgctctg ctgaagccag ttaccttcgg aaaaagagtt ggtagctctt    2700
gatccggcaa acaaaccacc gctggtagcg gtggttttt tgtttgcaag cagcagatta    2760
cgcgcagaaa aaaaggatct caagaagatc ctttgatctt ttctacgggg tctgacgctc    2820
agtggaacga aaactcacgt taagggattt tggtcatgag attatcaaaa aggatcttca    2880
cctagatcct tttaaattaa aaatgaagtt ttaaatcaat ctaaagtata tatgagtaaa    2940
cttggtctga cagttagaaa aactcatcga gcatcaaatg aaactgcaat ttattcatat    3000
caggattatc aataccatat ttttgaaaaa gccgtttctg taatgaagga gaaaactcac    3060
cgaggcagtt ccataggatg gcaagatcct ggtatcggtc tgcgattccg actcgtccaa    3120
catcaataca acctattaat ttcccctcgt caaaaataag gttatcaagt gagaaatcac    3180
catgagtgac gactgaatcc ggtgagaatg gcaaaagttt atgcatttct ttccagactt    3240
gttcaacagg ccagccatta cgctcgtcat caaaatcact cgcatcaacc aaaccgttat    3300
tcattcgtga ttgcgcctga gcgagacgaa atacgcgatc gctgttaaaa ggacaattac    3360
aaacaggaat cgaatgcaac cggcgcagga acactgccag cgcatcaaca atatttttcac   3420 ctgaatcagg atattcttct aatacctgga atgctgtttt cccggggatc gcagtggtga    3480
gtaaccatgc atcatcagga gtacggataa aatgcttgat ggtcggaaga ggcataaatt    3540
ccgtcagcca gtttagtctg accatctcat ctgtaacatc attggcaacg ctacctttgc    3600
```

| | |
|---|---|
| catgtttcag aaacaactct ggcgcatcgg gcttcccata caatcgatag attgtcgcac | 3660 |
| ctgattgccc gacattatcg cgagcccatt tatacccata taaatcagca tccatgttgg | 3720 |
| aatttaatcg cggcctagag caagacgttt cccgttgaat atggctcata ctcttccttt | 3780 |
| ttcaatatta ttgaagcatt tatcaggggt attgtctcat gagcggatac atatttgaat | 3840 |
| gtatttagaa aaataaacaa ataggggttc cgcgcacatt tccccgaaaa gtgccacctg | 3900 |
| acgcgccctg tagcggcgca ttaagcgcgg cgggtgtggt ggttacgcgc agcgtgaccg | 3960 |
| ctacacttgc cagcgcccta gcgcccgctc ctttcgcttt cttcccttcc tttctcgcca | 4020 |
| cgttcgccgg ctttccccgt caagctctaa atcgggggct ccctttaggg ttccgattta | 4080 |
| gtgctttacg gcacctcgac cccaaaaaac ttgattaggg tgatggttca cgtagtgggc | 4140 |
| catcgccctg atagacggtt tttcgccctt gacgttgga gtccacgttc tttaatagtg | 4200 |
| gactcttgtt ccaaactgga acaacactca accctatctc ggtctattct tttgatttat | 4260 |
| aagggatttt gccgatttcg gcctattggt taaaaaatga gctgatttaa caaaaattta | 4320 |
| acgcgaattt taacaaaata ttaacgctta caatttgcca ttcgccattc aggctgcgca | 4380 |
| actgttggga agggcgatcg gtgcgggcct cttcgctatt acgccagccc aagctaccat | 4440 |
| gataagtaag taatattaag gtacgggagg tacttggagc ggccgcaata aaatatcttt | 4500 |
| attttcatta catctgtgtg ttggtttttt gtgtgaatcg atagtactaa catacgctct | 4560 |
| ccatcaaaac aaaacgaaac aaaacaaact agcaaaatag gctgtcccca gtgcaagtgc | 4620 |
| aggtgccaga acatttctct atcgataggt accgaca | 4657 |

<210> SEQ ID NO 20
<211> LENGTH: 8162
<212> TYPE: DNA
<213> ORGANISM: Artificial Sequence
<220> FEATURE:
<223> OTHER INFORMATION: recombinant construct

<400> SEQUENCE: 20

| | |
|---|---|
| gacaaccctc accaagggcc aaggtggtga ccgacggacc cacagcgggg tggctggggg | 60 |
| agtcgaaact cgccagtctc cactccactc ccaaccgtgg tgcccacgc gggcctggga | 120 |
| gagtctgtga ggccgcccac cgcttgtcag tagagtgcgc ccgcgagccg taagcacagc | 180 |
| ccggcaacat gcggtcttca gacaggaaag tggccgcgaa tgggaccggg gtgcccagcg | 240 |
| gctgtgggga ctctgtcctg cggaaaccgc ggtgacgagc acaagctcgg tcaactggat | 300 |
| gggaatcggc ctgggggct ggcaccgcgc ccaccagggg gtttgcggca cttccctctg | 360 |
| cccctcagca ccccaccct actctccagg aacgtgagtt ctgagccgtg atggtggcag | 420 |
| gaagggccc tctgtgccat ccgagtcccc agggacccgc agctggcccc cagccatgtg | 480 |
| caaagtatgt gcagggcgct ggcaggcagg gagcagcagg catggtgtcc cctgagggga | 540 |
| gacagtggtc tggagggag aagtcctggc cctgagggag gtgatggggc aatgctcagc | 600 |
| cctgtctccg gatgccaaag gaggggtgcg gggaggccgt ctttggagaa ttccaggatg | 660 |
| ggtgctgggt gagagagacg tgtgctggaa ctgtccaggg cggaggtggg ccctgcgggg | 720 |
| gccctcggga gggccctgct ctgattgcc ggcagggcag gggcgggaat tctgggcggg | 780 |
| gccacccccag ttagaaaaag cccgggctag gaccgaggag cagggtgagg gaagcttggc | 840 |
| attccggtac tgttggtaaa gccaccatgg aagacgccaa aaacataaag aaaggcccgg | 900 |
| cgccattcta tccgctggaa gatggaaccg ctggagagca actgcataag gctatgaaga | 960 |
| gatacgccct ggttcctgga acaattgctt ttacagatgc acatatcgag gtggacatca | 1020 |

```
cttacgctga gtacttcgaa atgtccgttc ggttggcaga agctatgaaa cgatatgggc    1080
tgaatacaaa tcacagaatc gtcgtatgca gtgaaaactc tcttcaattc tttatgccgg    1140
tgttgggcgc gttatttatc ggagttgcag ttgcgcccgc gaacgacatt tataatgaac    1200
gtgaattgct caacagtatg ggcatttcgc agcctaccgt ggtgttcgtt tccaaaaagg    1260
ggttgcaaaa aattttgaac gtgcaaaaaa agctcccaat catccaaaaa attattatca    1320
tggattctaa aacggattac cagggatttc agtcgatgta cacgttcgtc acatctcatc    1380
tacctcccgg tttaatgaa tacgattttg tgccagagtc cttcgatagg gacaagacaa    1440
ttgcactgat catgaactcc tctggatcta ctggtctgcc taaaggtgtc gctctgcctc    1500
atagaactgc ctgcgtgaga ttctcgcatg ccagagatcc tattttggc aatcaaatca    1560 ttccggatac tgcgatttta agtgttgttc cattccatca cggttttgga atgtttacta    1620
cactcggata tttgatatgt ggatttcgag tcgtcttaat gtatagattt gaagaagagc    1680
tgtttctgag gagccttcag gattacaaga ttcaaagtgc gctgctggtg ccaaccctat    1740
tctccttctt cgccaaaagc actctgattg acaaatacga tttatctaat ttacacgaaa    1800
ttgcttctgg tggcgctccc ctctctaagg aagtcgggga agcggttgcc aagaggttcc    1860
atctgccagg tatcaggcaa ggatatgggc tcactgagac tacatcagct attctgatta    1920
cacccgaggg ggatgataaa ccgggcgcgg tcggtaaagt tgttccattt tttgaagcga    1980
aggttgtgga tctggatacc gggaaaacgc tgggcgttaa tcaaagaggc gaactgtgtg    2040
tgagaggtcc tatgattatg tccggttatg taaacaatcc ggaagcgacc aacgccttga    2100
ttgacaagga tggatggcta cattctggag acatagctta ctgggacgaa gacgaacact    2160
tcttcatcgt tgaccgcctg aagtctctga ttaagtacaa aggctatcag gtggctcccg    2220
ctgaattgga atccatcttg ctccaacacc ccaacatctt cgacgcaggt gtcgcaggtc    2280
ttcccgacga tgacgccggt gaacttcccg ccgccgttgt tgttttggag cacggaaaga    2340
cgatgacgga aaagagatc gtggattacg tcgccagtca agtaacaacc gcgaaaaagt    2400
tgcgcggagg agttgtgttt gtggacgaag taccgaaagg tcttaccgga aaactcgacg    2460
caagaaaaat cagagagatc ctcataaagg ccaagaaggg cggaaagatc gccgtgtaat    2520
tctagagtcg gggcggccgg ccgcttcgag cagacatgat aagatacatt gatgagtttg    2580
gacaaaccac aactagaatg cagtgaaaaa aatgctttat ttgtgaaatt tgtgatgcta    2640
ttgctttatt tgtaaccatt ataagctgca ataaacaagt taacaacaac aattgcattc    2700
attttatgtt tcaggttcag ggggaggtgt gggaggtttt ttaaagcaag taaaacctct    2760
acaaatgtgg taaaatcgat aaggatccgt cgaccgatgc ccttgagagc cttcaaccca    2820
gtcagctcct tccggtgggc gcggggcatg actatcgtcg ccgcacttat gactgtcttc    2880
tttatcatgc aactcgtagg acaggtgccg gcagcgctct ccgcttcct cgctcactga    2940 ctcgctgcgc tcggtcgttc ggctgcggcg agcggtatca gctcactcaa aggcggtaat    3000
acggttatcc acagaatcag gggataacgc aggaaagaac atgtgagcaa aaggccagca    3060
aaaggccagg aaccgtaaaa aggccgcgtt gctggcgttt ttccataggc tccgcccccc    3120
tgacgagcat cacaaaaatc gacgctcaag tcagaggtgg cgaaacccga caggactata    3180
aagataccag gcgtttcccc ctggaagctc cctcgtgcgc tctcctgttc cgaccctgcc    3240
gcttaccgga tacctgtccg cctttctccc ttcgggaagc gtggcgcttt ctcatagctc    3300
acgctgtagg tatctcagtt cggtgtaggt cgttcgctcc aagctgggct gtgtgcacga    3360
```

-continued

| | |
|---|---|
| acccccgtt cagcccgacc gctgcgcctt atccggtaac tatcgtcttg agtccaaccc | 3420 |
| ggtaagacac gacttatcgc cactggcagc agccactggt aacaggatta gcagagcgag | 3480 |
| gtatgtaggc ggtgctacag agttcttgaa gtggtggcct aactacggct acactagaag | 3540 |
| aacagtattt ggtatctgcg ctctgctgaa gccagttacc ttcggaaaaa gagttggtag | 3600 |
| ctcttgatcc ggcaaacaaa ccaccgctgg tagcggtggt ttttttgttt gcaagcagca | 3660 |
| gattacgcgc agaaaaaaag gatctcaaga agatcctttg atcttttcta cggggtctga | 3720 |
| cgctcagtgg aacgaaaact cacgttaagg gattttggtc atgagattat caaaaaggat | 3780 |
| cttcacctag atccttttaa attaaaaatg aagttttaaa tcaatctaaa gtatatatga | 3840 |
| gtaaacttgg tctgacagtt agaaaaactc atcgagcatc aaatgaaact gcaatttatt | 3900 |
| catatcagga ttatcaatac catatttttg aaaagccgt ttctgtaatg aaggagaaaa | 3960 |
| ctcaccgagg cagttccata ggatggcaag atcctggtat cggtctgcga ttccgactcg | 4020 |
| tccaacatca atacaaccta ttaatttccc ctcgtcaaaa ataaggttat caagtgagaa | 4080 |
| atcaccatga gtgacgactg aatccggtga gaatggcaaa agtttatgca tttctttcca | 4140 |
| gacttgttca acaggccagc cattacgctc gtcatcaaaa tcactcgcat caaccaaacc | 4200 |
| gttattcatt cgtgattgcg cctgagcgag acgaaatacg cgatcgctgt taaaaggaca | 4260 |
| attacaaaca ggaatcgaat gcaaccggcg caggaacact gccagcgcat caacaatatt | 4320 |
| ttcacctgaa tcaggatatt cttctaatac ctggaatgct gttttcccgg ggatcgcagt | 4380 |
| ggtgagtaac catgcatcat caggagtacg gataaaatgc ttgatggtcg gaagaggcat | 4440 |
| aaattccgtc agccagttta gtctgaccat ctcatctgta acatcattgg caacgctacc | 4500 |
| tttgccatgt ttcagaaaca actctggcgc atcgggcttc ccatacaatc gatagattgt | 4560 |
| cgcacctgat tgcccgacat tatcgcgagc ccatttatac ccatataaat cagcatccat | 4620 |
| gttggaattt aatcgcggcc tagagcaaga cgtttcccgt tgaatatggc tcatactctt | 4680 |
| cctttttcaa tattattgaa gcatttatca gggttattgt ctcatgagcg gatacatatt | 4740 |
| tgaatgtatt tagaaaaata acaaataggg gttccgcgc acatttcccc gaaaagtgcc | 4800 |
| acctgacgcg ccctgtagcg gcgcattaag cgcggcgggt gtggtggtta cgcgcagcgt | 4860 |
| gaccgctaca cttgccagcg ccctagcgcc cgctcctttc gctttcttcc cttcctttct | 4920 |
| cgccacgttc gccggctttc cccgtcaagc tctaaatcgg gggctccctt tagggttccg | 4980 |
| atttagtgct ttacggcacc tcgaccccaa aaaacttgat tagggtgatg gttcacgtag | 5040 |
| tgggccatcg ccctgataga cggtttttcg ccctttgacg ttggagtcca cgttctttaa | 5100 |
| tagtggactc ttgttccaaa ctggaacaac actcaaccct atctcggtct attcttttga | 5160 |
| tttataaggg attttgccga tttcggccta ttggttaaaa aatgagctga tttaacaaaa | 5220 |
| atttaacgcg aattttaaca aaatattaac gcttacaatt tgccattcgc cattcaggct | 5280 |
| gcgcaactgt tgggaagggc gatcggtgcg ggcctcttcg ctattacgcc agcccaagct | 5340 |
| accatgataa gtaagtaata ttaaggtacg ggaggtactt ggagcggccg caataaaata | 5400 |
| tctttatttt cattacatct gtgtgttggt ttttgtgtg aatcgatagt actaacatac | 5460 |
| gctctccatc aaaacaaaac gaaacaaaac aaactagcaa aataggctgt ccccagtgca | 5520 |
| agtgcaggtg ccagaacatt tctctatcga tactcgaggg ccatgcaggt aggatttgag | 5580 |
| ctgtgtttcc cgccctgatc ctctctcctc tggcggccgg agcctccgta ggctccaagc | 5640 |
| ctggcccaga ttcggcggcg cagccggcct tccgcgcgtc cgcacctagc gggggctccg | 5700 |
| gggctccggc gcggcaccgg ggggcgctcg ggatctggct gaggctccaa ggcccgcgtg | 5760 |

```
gccggctcct cctgctgggg caggtggcgg ctgcgcgccc cgcccgagcc caggggcccc      5820
ctcagccgca acaaccagca aggaccccca gactcagccc caagccacct gcatctgcac      5880
tcagacgggg cgcacccgca gtgcagcctc ctggtggggc gctgggagcc cgcctgcccc      5940
tgcctgcccg gagaccccag ctcacgagca caggccgccc gggcacccca gaaacccggg      6000
atggggcccc tgaattctct aggacgggca ttcagcatgg ccttggcgct ctgcggctcc      6060 ctgccccca cccagcctcg cccccgcgca cccccagcc cctgcgaccg ccgcccccc        6120 ccccggggcc ccagggcccc agcccgcacc ccccgccccg ctcttggctc gggttgcggg      6180
ggcgggccgg gggcggggcg agggctccgc gggcgcccat ggcgcgggc gcgaggccag       6240 cggccccgcg cggccctggg ccgcggctgg cgcgactata agagccgggc gtgggcgccc      6300
gcagttcgcc tgctctccgg cggagctgcg tgaggcccgg ccggcccggg cccccccctt      6360
ccggccgccc ccgcctcctg gcccacgcct gcccgcgctc tgcccaccag cgcctccatc      6420
gggcaaggcg gccccgcgtc gacaagctta gctacgctag cggcattccg gtactgttgg      6480
taaagccacc atggaagacg ccaaaaacat aagaaaggc ccggcgccat tctatccgct       6540
ggaagatgga accgctggag agcaactgca taaggctatg aagagatacg ccctggttcc      6600
tggaacaatt gcttttacag atgcacatat cgaggtggac atcacttacg ctgagtactt      6660
cgaaatgtcc gttcggttgg cagaagctat gaaacgatat gggctgaata caaatcacag      6720
aatcgtcgta tgcagtgaaa actctcttca attctttatg ccggtgttgg gcgcgttatt      6780
tatcggagtt gcagttgcgc ccgcgaacga catttataat gaacgtgaat tgctcaacag      6840
tatgggcatt tcgcagccta ccgtggtgtt cgtttccaaa aaggggttgc aaaaaatttt      6900
gaacgtgcaa aaaagctcc caatcatcca aaaaattatt atcatggatt ctaaaacgga      6960
ttaccaggga tttcagtcga tgtacacgtt cgtcacatct catctacctc ccggttttaa      7020
tgaatacgat tttgtgccag agtccttcga tagggacaag acaattgcac tgatcatgaa      7080
ctcctctgga tctactggtc tgcctaaagg tgtcgctctg cctcatagaa ctgcctgcgt      7140
gagattctcg catgccagag atcctatttt tggcaatcaa atcattccgg atactgcgat      7200
tttaagtgtt gttccattcc atcacggttt tggaatgttt actacactcg gatatttgat      7260
atgtggattt cgagtcgtct taatgtatag atttgaagaa gagctgtttc tgaggagcct      7320
tcaggattac aagattcaaa gtgcgctgct ggtgccaacc ctattctcct tcttcgccaa      7380
aagcactctg attgacaaat acgatttatc taatttacac gaaattgctt ctggtggcgc      7440 tccctctct aaggaagtcg gggaagcggt tgccaagagg ttccatctgc caggtatcag      7500
gcaaggatat gggctcactg agactacatc agctattctg attacacccg agggggatga      7560
taaaccgggc gcggtcggta agttgttcc attttttgaa gcgaaggttg tggatctgga      7620
taccgggaaa acgctgggcg ttaatcaaag aggcgaactg tgtgtgagag gtcctatgat      7680
tatgtccggt tatgtaaaca atccggaagc gaccaacgcc ttgattgaca aggatggatg      7740
gctacattct ggagacatag cttactggga cgaagacgaa cacttcttca tcgttgaccg      7800
cctgaagtct ctgattaagt acaaaggcta tcaggtggct cccgctgaat tggaatccat      7860
cttgctccaa caccccaaca tcttcgacgc aggtgtcgca ggtcttcccg acgatgacgc      7920
cggtgaactt cccgccgccg ttgttgtttt ggagcacgga aagacgatga cggaaaaaga      7980
gatcgtggat tacgtcgcca gtcaagtaac aaccgcgaaa aagttgcgcg gaggagttgt      8040
gtttgtggac gaagtaccga aaggtcttac cggaaaactc gacgcaagaa aaatcagaga      8100
```

```
gatcctcata aaggccaaga agggcggaaa gatcgccgtg taatctcgag acgtagggta    8160
cc                                                                  8162

<210> SEQ ID NO 21
<211> LENGTH: 3579
<212> TYPE: DNA
<213> ORGANISM: Artificial Sequence
<220> FEATURE:
<223> OTHER INFORMATION: recombinant construct

<400> SEQUENCE: 21
ctaaattgta agcgttaata ttttgttaaa attcgcgtta aattttgtt aaatcagctc      60 attttttaac caataggccg aaatcggcaa atcccttat aaatcaaaag aatagaccga     120 gataggttg agtgttgttc cagtttggaa caagagtcca ctattaaaga acgtggactc     180
caacgtcaaa gggcgaaaaa ccgtctatca gggctatggc ccactacgtg aaccatcacc    240
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta gggcgaat tgggtaccct     660 acgtctcgag ggatccccaa atctctgtag gtagtttgtc caattatgtc acaccacaga    720
agtaaggttc cttcacaaag atcgcctgac acgatttcct gcacaggctt gagccatata    780
ctcatacatc gcatcttggc cacgttttcc acgggtttca aaattaatct caagttctac    840
gcttaacgct ttcgcctgtt cccagttatt aatatattca acgctagaac tcccctcagc    900
gaagggaagg ctgagcacta cacgcgaagc accatcaccg aaccttttga taaactcttc    960
cgttccgact tgctccatca acggttcagt gagacttaaa cctaactctt tcttaatagt   1020
ttcggcatta tccactttta gtgcgagaac cttcgtcagt cctggatacg tcactttgac   1080
cacgcctcca gcttttccag agagcgggtt ttcattatct acagagtatc ccgcagcgtc   1140
gtatttattg tcggtactat aaaaccctt ccaatcatcg tcataatttc cttgtgtacc    1200
agattttggc ttttgtatac cttttttgaat ggaatctaca taaccaggtt tagtcccgtg   1260
gtacgaagaa aagttttcca tcacaaaaga tttagaagaa tcaacaacat catcaggatc    1320
catggtggct ttaccaacag taccggaatg ccgctagcgt agctgcggcc gcgagctcca    1380
gcttttgttc cctttagtga gggttaattg cgcgcttggc gtaatcatgg tcatagctgt    1440
ttcctgtgtg aaattgttat ccgctcacaa ttccacacaa catacgagcc ggaagcataa    1500
agtgtaaagc ctggggtgcc taatgagtga gctaactcac attaattgcg ttgcgctcac    1560
tgcccgcttt ccagtcggga aacctgtcgt gccagctgca ttaatgaatc ggccaacgcg    1620
cggggagagg cggtttgcgt attgggcgct cttccgcttc ctcgctcact gactcgctgc    1680
gctcggtcgt tcggctgcgg cgagcggtat cagctcactc aaaggcggta atacggttat    1740
ccacagaatc aggggataac gcaggaaaga acatgtgagc aaaaggccag caaaaggcca    1800
ggaaccgtaa aaaggccgcg ttgctggcgt ttttccatag gctccgcccc cctgacgagc    1860
atcacaaaaa tcgacgctca agtcagaggt ggcgaaaccc gacaggacta taaagatacc    1920
aggcgtttcc ccctggaagc tccctcgtgc gctctcctgt tccgaccctg ccgcttaccg    1980
```

```
gatacctgtc cgcctttctc ccttcgggaa gcgtggcgct ttctcatagc tcacgctgta    2040
ggtatctcag ttcggtgtag gtcgttcgct ccaagctggg ctgtgtgcac gaacccccg     2100 ttcagcccga ccgctgcgcc ttatccggta actatcgtct tgagtccaac ccggtaagac    2160
acgacttatc gccactggca gcagccactg gtaacaggat tagcagagcg aggtatgtag    2220
gcggtgctac agagttcttg aagtggtggc ctaactacgg ctacactaga agaacagtat    2280
ttggtatctg cgctctgctg aagccagtta ccttcggaaa agagttggt agctcttgat     2340 ccggcaaaca aaccaccgct ggtagcggtg ttttttttgt ttgcaagcag cagattacgc    2400
gcagaaaaaa aggatctcaa gaagatcctt tgatctttc tacggggtct gacgctcagt     2460
ggaacgaaaa ctcacgttaa gggattttgg tcatgagatt atcaaaaagg atcttcacct    2520
agatcctttt aaattaaaaa tgaagtttta aatcaatcta agtatatat gagtaaactt     2580 ggtctgacag ttaccaatgc ttaatcagtg aggcacctat ctcagcgatc tgtctatttc    2640
gttcatccat agttgcctga ctccccgtcg tgtagataac tacgatacgg gagggcttac    2700
catctggccc cagtgctgca atgataccgc gagaaccacg ctcaccggct ccagatttat    2760
cagcaataaa ccagccagcc ggaagggccg agcgcagaag tggtcctgca actttatccg    2820
cctccatcca gtctattaat tgttgccggg aagctagagt aagtagttcg ccagttaata    2880
gtttgcgcaa cgttgttgcc attgctacag gcatcgtggt gtcacgctcg tcgtttggta    2940
tggcttcatt cagctccggt tcccaacgat caaggcgagt tacatgatcc cccatgttgt    3000
gcaaaaaagc ggttagctcc ttcggtcctc cgatcgttgt cagaagtaag ttggccgcag    3060
tgttatcact catggttatg gcagcactgc ataattctct tactgtcatg ccatccgtaa    3120
gatgcttttc tgtgactggt gagtactcaa ccaagtcatt ctgagaatag tgtatgcggc    3180
gaccgagttg ctcttgcccg gcgtcaatac gggataatac cgcgccacat agcagaactt    3240
taaaagtgct catcattgga aaacgttctt cggggcgaaa actctcaagg atcttaccgc    3300
tgttgagatc cagttcgatg taacccactc gtgcacccaa ctgatcttca gcatctttta    3360
ctttcaccag cgtttctggg tgagcaaaaa caggaaggca aaatgccgca aaaaagggaa    3420
taagggcgac acgaaaatgt tgaatactca tactcttcct ttttcaatat tattgaagca    3480
tttatcaggg ttattgtctc atgagcggat acatatttga atgtatttag aaaaataaac    3540 aaatagggt tccgcgcaca tttccccgaa aagtgccac                             3579

<210> SEQ ID NO 22
<211> LENGTH: 8086
<212> TYPE: DNA
<213> ORGANISM: Artificial Sequence
<220> FEATURE:
<223> OTHER INFORMATION: recombinant construct

<400> SEQUENCE: 22
ggtgcgggcc tcttcgctat tacgccagcc caagctacca tgataagtaa gtaatattaa      60
ggtacgggag gtacttggag cggccgcaat aaaatatctt tattttcatt acatctgtgt     120
gttggttttt tgtgtgaatc gatagtacta acatacgctc tccatcaaaa caaaacgaaa     180
caaaacaaac tagcaaaata ggctgtcccc agtgcaagtg caggtgccag aacatttctc     240
tatcgataac ttcccggtcg gtctgtgggt gcaggggtg ccgcctcaca tgtgtgattc      300
gtgccttgcg ggccctggcc tccggggtgc tgggtaacga ggaggggcgc ggagccgcag     360
aagcccaccc tggtatgttg acgcggtgcc agcgagaccg cgagaggaag acggggtgg      420
```

```
gcggggccag gatggagagg ggccgagttg gcaggagtca tggcagacgc cacattcgcg    480
acatctcccc cacaccccct ctggctctgt ccgcaacatt tccaaacagg agtcccggga    540
gagggggaga ggggctgctg gtctgaggct aagaagggca gagccttcga cccggagaga    600
ggccgcggcc cctgcccagt gggcagcgtg gaagtttcca tacaaggagg tgggaaggag    660 acccccccc cccttcactg ccctgtgcag agatgagccg ggggtgcagg atgggagccc    720
atggcacttc gctacgggat ggtccagggc tcccggttgg gggtgcagga gagaagagac    780
tggctgggag gagggagagg gcgggagcaa aggcgcgggg gagtggtcag cagggagagg    840 ggtgggggt agggtggagc ccgggctggg aggagtcggc tcacacataa agctgaggc    900 actgaccagc ctgcaaactg gacattagct tctcctgtga aagagacttc cagcttcctc    960
ctcctcctct tcctcctcct cctcctgccc cagcgagcct tctgctgagc tgtaggggga   1020
tcttctagag tcggctagcg gcattccggt actgttggta aagccaccat ggaagacgcc   1080
aaaaacataa agaaaggccc ggcgccattc tatccgctgg aagatggaac cgctggagag   1140
caactgcata aggctatgaa gagatacgcc ctggttcctg gaacaattgc ttttacagat   1200
gcacatatcg aggtggacat cacttacgct gagtacttcg aaatgtccgt tcggttggca   1260
gaagctatga acgatatgg gctgaataca aatcacagaa tcgtcgtatg cagtgaaaac   1320
tctcttcaat tctttatgcc ggtgttgggc gcgttattta tcggagttgc agttgcgccc   1380
gcgaacgaca tttataatga acgtgaattg ctcaacagta tgggcatttc gcagcctacc   1440
gtggtgttcg tttccaaaaa ggggttgcaa aaaatttga acgtgcaaaa aaagctccca   1500
atcatccaaa aaattattat catggattct aaaacggatt accagggatt tcagtcgatg   1560
tacacgttcg tcacatctca tctacctccc ggttttaatg aatacgattt tgtgccagag   1620
tccttcgata gggacaagac aattgcactg atcatgaact cctctggatc tactggtctg   1680
cctaaaggtg tcgctctgcc tcatagaact gcctgcgtga gattctcgca tgccagagat   1740 cctattttg gcaatcaaat cattccggat actgcgattt taagtgttgt tccattccat   1800
cacggttttg gaatgtttac tacactcgga tatttgatat gtggatttcg agtcgtctta   1860
atgtatagat ttgaagaaga gctgtttctg aggagccttc aggattacaa gattcaaagt   1920
gcgctgctgg tgccaaccct attctccttc ttcgccaaaa gcactctgat tgacaaatac   1980
gatttatcta atttacacga aattgcttct ggtggcgctc ccctctctaa ggaagtcggg   2040
gaagcggttg ccaagaggtt ccatctgcca ggtatcaggc aaggatatgg gctcactgag   2100
actacatcag ctattctgat tacacccgag ggggatgata aaccgggcgc ggtcggtaaa   2160
gttgttccat tttttgaagc gaaggttgtg gatctggata ccgggaaaac gctgggcgtt   2220
aatcaaagag gcgaactgtg tgtgagaggt cctatgatta tgtccggtta tgtaaacaat   2280
ccggaagcga ccaacgcctt gattgacaag gatggatggc tacattctgg agacatagct   2340
tactgggacg aagacgaaca cttcttcatc gttgaccgcc tgaagtctct gattaagtac   2400
aaaggctatc aggtggctcc cgctgaattg gaatccatct tgctccaaca ccccaacatc   2460
ttcgacgcag gtgtcgcagg tcttcccgac gatgacgccg gtgaacttcc cgccgccgtt   2520
gttgttttgg agcacggaaa gacgatgacg gaaaaagaga tcgtggatta cgtcgccagt   2580
caagtaacaa ccgcgaaaaa gttgcgcgga ggagttgtgt ttgtggacga agtaccgaaa   2640
ggtcttaccg gaaaactcga cgcaagaaaa atcagagaga tcctcataaa ggccaagaag   2700
ggcggaaaga tcgccgtgta atctgagggc ccatgcaggt aggatttgag ctgtgtttcc   2760
cgccctgatc ctctctcctc tggcggccgg agcctccgta ggctccaagc ctggcccaga   2820
```

```
ttcggcggcg cagccggcct tccgcgcgtc cgcacctagc gggggctccg gggctccggc    2880
gcggcaccgg ggggcgctcg ggatctggct gaggctccaa ggcccgcgtg gccggctcct    2940
cctgctgggg caggtggcgg ctgcgcgccc cgcccgagcc caggggcccc ctcagccgca    3000
acaaccagca aggaccccc gactcagccc caagccacct gcatctgcac tcagacgggg     3060
cgcacccgca gtgcagcctc ctggtggggc gctgggagcc cgcctgcccc tgcctgcccg    3120 gagacccag ctcacgagca caggccgccc ggcacccca gaaacccggg atggggcccc      3180
tgaattctct aggacgggca ttcagcatgg ccttggcgct ctgcggctcc ctgccccca    3240 cccagcctcg cccccgcgca cccccagcc cctgcgaccg ccgccccccc ccccggggcc     3300
ccagggcccc agcccgcacc cccgccccg ctcttggctc gggttgcggg ggcgggccgg     3360
gggcggggcg agggctccgc gggcgcccat tggcgcgggc gcgaggccag cggccccgcg    3420
cggccctggg ccgcggctgg cgcgactata agagccgggc gtgggcgccc gcagttcgcc    3480
tgctctccgg cggagctgcg tgaggccgg ccggcccgg ccccccctt ccggccgccc       3540 ccgcctcctg gcccacgcct gcccgcgctc tgcccaccag cgcctccatc gggcaaggcg    3600
gccccgcgtc gacaagcttg gcattccggt actgttggta aagccaccat ggaagacgcc    3660
aaaaacataa agaaaggccc ggcgccattc tatccgctgg aagatggaac cgctggagag    3720
caactgcata aggctatgaa gagatacgcc ctggttcctg aacaattgc ttttacagat     3780 gcacatatcg aggtggacat cacttacgct gagtacttcg aaatgtccgt tcggttggca    3840
gaagctatga acgatatgg gctgaataca aatcacagaa tcgtcgtatg cagtgaaaac    3900
tctcttcaat tctttatgcc ggtgttgggc gcgttattta tcggagttgc agttgcgccc    3960
gcgaacgaca tttataatga acgtgaattg ctcaacagta tgggcatttc gcagcctacc    4020
gtggtgttcg tttccaaaaa ggggttgcaa aaattttga acgtgcaaaa aaagctccca    4080
atcatccaaa aaattattat catggattct aaaacggatt accagggatt tcagtcgatg    4140
tacacgttcg tcacatctca tctacctccc ggttttaatg aatacgattt tgtgccagag    4200
tccttcgata gggacaagac aattgcactg atcatgaact cctctggatc tactggtctg    4260
cctaaaggtg tcgctctgcc tcatagaact gcctgcgtga gattctcgca tgccagagat    4320 cctattttg gcaatcaaat cattccggat actgcgattt taagtgttgt tccattccat    4380
cacggttttg gaatgtttac tacactcgga tatttgatat gtggatttcg agtcgtctta    4440
atgtatagat ttgaagaaga gctgtttctg aggagccttc aggattacaa gattcaaagt    4500
gcgctgctgg tgccaacct attctccttc ttcgccaaaa gcactctgat tgacaaatac    4560
gatttatcta atttacacga aattgcttct ggtggcgctc ccctctctaa ggaagtcggg    4620
gaagcggttg ccaagaggtt ccatctgcca ggtatcaggc aaggatatgg gctcactgag    4680
actacatcag ctattctgat tacacccgag ggggatgata aaccgggcgc ggtcggtaaa    4740
gttgttccat ttttgaagc gaaggttgtg gatctggata ccgggaaaac gctgggcgtt    4800
aatcaaagag gcgaactgtg tgtgagaggt cctatgatta tgtccggtta tgtaaacaat    4860
ccggaagcga ccaacgcctt gattgacaag gatggatggc tacattctgg agacatagct    4920
tactgggacg aagacgaaca cttcttcatc gttgaccgcc tgaagtctct gattaagtac    4980
aaaggctatc aggtggctcc cgctgaattg gaatccatct tgctccaaca ccccaacatc    5040
ttcgacgcag gtgtcgcagg tcttcccgac gatgacgccg gtgaacttcc cgccgccgtt    5100
gttgttttgg agcacggaaa gacgatgacg gaaaaagaga tcgtggatta cgtcgccagt    5160
```

```
caagtaacaa ccgcgaaaaa gttgcgcgga ggagttgtgt ttgtggacga agtaccgaaa    5220
ggtcttaccg gaaaactcga cgcaagaaaa atcagagaga tcctcataaa ggccaagaag    5280
ggcggaaaga tcgccgtgta attctagagt cggggcggcc ggccgcttcg agcagacatg    5340
ataagataca ttgatgagtt tggacaaacc acaactagaa tgcagtgaaa aaaatgcttt    5400
atttgtgaaa tttgtgatgc tattgcttta tttgtaacca ttataagctg caataaacaa    5460
gttaacaaca acaattgcat tcattttatg tttcaggttc aggggaggt gtgggaggtt    5520 ttttaaagca agtaaaacct ctacaaatgt ggtaaaatcg ataaggatcc gtcgaccgat    5580
gcccttgaga gccttcaacc cagtcagctc cttccggtgg gcgcggggca tgactatcgt    5640
cgccgcactt atgactgtct tctttatcat gcaactcgta ggacaggtgc cggcagcgct    5700
cttccgcttc ctcgctcact gactcgctgc gctcggtcgt tcggctgcgg cgagcggtat    5760
cagctcactc aaaggcggta atacggttat ccacagaatc aggggataac gcaggaaaga    5820
acatgtgagc aaaaggccag caaaaggcca ggaaccgtaa aaaggccgcg ttgctggcgt    5880
ttttccatag gctccgcccc cctgacgagc atcacaaaaa tcgacgctca agtcagaggt    5940
ggcgaaaccc gacaggacta taaagatacc aggcgtttcc ccctggaagc tccctcgtgc    6000
gctctcctgt tccgaccctg ccgcttaccg gatacctgtc cgcctttctc ccttcgggaa    6060
gcgtggcgct ttctcatagc tcacgctgta ggtatctcag ttcggtgtag gtcgttcgct    6120
ccaagctggg ctgtgtgcac gaaccccccg ttcagcccga ccgctgcgcc ttatccggta    6180
actatcgtct tgagtccaac ccggtaagac acgacttatc gccactggca gcagccactg    6240
gtaacaggat tagcagagcg aggtatgtag gcggtgctac agagttcttg aagtggtggc    6300
ctaactacgg ctacactaga agaacagtat ttggtatctg cgctctgctg aagccagtta    6360
ccttcggaaa aagagttggt agctcttgat ccggcaaaca aaccaccgct ggtagcggtg    6420
gtttttttgt ttgcaagcag cagattacgc gcagaaaaaa aggatctcaa gaagatcctt    6480
tgatcttttc tacggggtct gacgctcagt ggaacgaaaa ctcacgttaa gggattttgg    6540
tcatgagatt atcaaaaagg atcttcacct agatcctttt aaattaaaaa tgaagtttta    6600
aatcaatcta agtatatat gagtaaactt ggtctgacag ttagaaaaac tcatcgagca    6660
tcaaatgaaa ctgcaatttt ttcatatcag gattatcaat accatatttt tgaaaaagcc    6720
gtttctgtaa tgaaggagaa aactcaccga ggcagttcca taggatgca agatcctggt    6780 atcggtctgc gattccgact cgtccaacat caatacaacc tattaatttc ccctcgtcaa    6840
aaataaggtt atcaagtgag aaatcaccat gagtgacgac tgaatccggt gagaatggca    6900
aaagtttatg catttctttc cagacttgtt caacaggcca gccattacgc tcgtcatcaa    6960
aatcactcgc atcaaccaaa ccgttattca ttcgtgattg cgcctgagcg agacgaaata    7020
cgcgatcgct gttaaaagga caattacaaa caggaatcga atgcaaccgg cgcaggaaca    7080
ctgccagcgc atcaacaata ttttcacctg aatcaggata ttcttctaat acctggaatg    7140
ctgtttttcc ggggatcgca gtggtgagta accatgcatc atcaggagta cggataaaat    7200
gcttgatggt cggaagaggc ataaattccg tcagccagtt tagtctgacc atctcatctg    7260
taacatcatt ggcaacgcta cctttgccat gtttcagaaa caactctggc gcatcgggct    7320
tcccatacaa tcgatagatt gtcgcacctg attgcccgac attatcgcga gcccatttat    7380
acccatataa atcagcatcc atgttggaat ttaatcgcgg cctagagcaa gacgtttccc    7440
gttgaatatg gctcatactc ttcctttttc aatattattg aagcatttat cagggttatt    7500
gtctcatgag cggatacata tttgaatgta tttagaaaaa taaacaaata ggggttccgc    7560
```

-continued

```
gcacatttcc ccgaaaagtg ccacctgacg cgccctgtag cggcgcatta agcgcggcgg    7620
gtgtggtggt tacgcgcagc gtgaccgcta cacttgccag cgccctagcg cccgctcctt    7680
tcgctttctt cccttccttt ctcgccacgt tcgccggctt tccccgtcaa gctctaaatc    7740
gggggctccc tttagggttc cgatttagtg ctttacggca cctcgacccc aaaaaacttg    7800
attagggtga tggttcacgt agtgggccat cgccctgata gacggttttt cgcccttga    7860 cgttggagtc cacgttcttt aatagtggac tcttgttcca aactggaaca acactcaacc    7920
ctatctcggt ctattctttt gatttataag ggattttgcc gatttcggcc tattggttaa    7980
aaaatgagct gatttaacaa aaatttaacg cgaattttaa caaatatta acgcttacaa      8040 tttgccattc gccattcagg ctgcgcaact gttgggaagg gcgatc                    8086
```

<210> SEQ ID NO 23
<211> LENGTH: 3843
<212> TYPE: DNA
<213> ORGANISM: Artificial Sequence
<220> FEATURE:
<223> OTHER INFORMATION: recombinant construct

<400> SEQUENCE: 23

```
ctaaattgta agcgttaata ttttgttaaa attcgcgtta aattttgtt aaatcagctc      60 attttttaac caataggccg aaatcggcaa atcccttat aaatcaaaag aatagaccga     120
gatagggttg agtgttgttc cagtttggaa caagagtcca ctattaaaga acgtggactc    180
caacgtcaaa gggcgaaaaa ccgtctatca gggctatggc ccactacgtg aaccatcacc    240
ctaatcaagt tttttggggt cgaggtgccg taaagcacta atcggaacc ctaaagggag     300 cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tgggtaccct    660
acgtctcgag gtagctgcta gccgactcta gaagatcccc ctacagctca gcagaaggct    720
cgctggggca ggaggaggag gaggaagagg aggaggagga agctggaagt ctcttcaca   780 ggagaagcta atgtccagtt tgcaggctgg tcagtgcctc agcttttatg tgtgagccga    840
ctcctcccag cccgggctcc accctacccc ccacccctct ccctgctgac cactcccccg    900
cgcctttgct cccgccctct ccctcctccc agccagtctc ttctctcctg cacccccaac    960
cgggagccct ggaccatccc gtagcgaagt gccatgggct cccatcctgc accccggct    1020 catctctgca cagggcagtg aaggggggg ggggtctcct tcccacctcc ttgtatggaa    1080
acttccacgc tgcccactgg caggggccg cggcctctct ccgggtcgaa ggctctgccc     1140
ttcttagcct cagaccagca gcccctctcc ccctctcccg ggactcctgt ttggaaatgt    1200
tgcggacaga gccagagggg gtgtggggga gatgtcgcga atgtggcgtc tgccatgact    1260
cctgccaact cggcccctct ccatcctggc cccgcccacc ccgtcttcc tctcgcggtc     1320 tcgctggcac cgcgtcaaca taccagggtg ggcttctgcg gctccgcgcc cctcctcgtt    1380
acccagcacc ccggaggcca gggccgcaa ggcacgaatc acacatgtga ggcggcaccc     1440
cctgcaccca cagaccgacc gggaagttat cgatagagaa atgttctggc acctgcactt    1500
```

```
gcactgggga cagcctattt tgctagtttg ttttgtttcg ttttgttttg atggagagcg    1560
tatgttagta ctatcgattc acacaaaaaa ccaacacaca gatgtaatga aaataaagat    1620
attttattgc ggccgcgagc tccagctttt gttcccttta gtgagggtta attgcgcgct    1680
tggcgtaatc atggtcatag ctgtttcctg tgtgaaattg ttatccgctc acaattccac    1740
acaacatacg agccggaagc ataaagtgta aagcctgggg tgcctaatga gtgagctaac    1800
tcacattaat tgcgttgcgc tcactgcccg ctttccagtc gggaaacctg tcgtgccagc    1860
tgcattaatg aatcggccaa cgcgcgggga gaggcggttt gcgtattggg cgctcttccg    1920
cttcctcgct cactgactcg ctgcgctcgg tcgttcggct gcggcgagcg gtatcagctc    1980
actcaaaggc ggtaatacgg ttatccacag aatcagggga taacgcagga agaacatgt    2040
gagcaaaagg ccagcaaaag gccaggaacc gtaaaaaggc cgcgttgctg gcgttttcc    2100
ataggctccg cccccctgac gagcatcaca aaaatcgacg ctcaagtcag aggtggcgaa    2160
acccgacagg actataaaga taccaggcgt ttccccctgg aagctccctc gtgcgctctc    2220
ctgttccgac cctgccgctt accggatacc tgtccgcctt tctcccttcg ggaagcgtgg    2280
cgctttctca tagctcacgc tgtaggtatc tcagttcggt gtaggtcgtt cgctccaagc    2340
tgggctgtgt gcacgaaccc cccgttcagc ccgaccgctg cgccttatcc ggtaactatc    2400
gtcttgagtc caacccggta agacacgact tatcgccact ggcagcagcc actggtaaca    2460
ggattagcag agcgaggtat gtaggcggtg ctacagagtt cttgaagtgg tggcctaact    2520
acggctacac tagaagaaca gtatttggta tctgcgctct gctgaagcca gttaccttcg    2580
gaaaaagagt tggtagctct tgatccggca acaaaccac cgctggtagc ggtggttttt    2640
ttgtttgcaa gcagcagatt acgcgcagaa aaaaggatc tcaagaagat cctttgatct    2700
tttctacggg gtctgacgct cagtggaacg aaaactcacg ttaagggatt ttggtcatga    2760
gattatcaaa aaggatcttc acctagatcc ttttaaatta aaaatgaagt tttaaatcaa    2820
tctaaagtat atatgagtaa acttggtctg acagttacca atgcttaatc agtgaggcac    2880
ctatctcagc gatctgtcta tttcgttcat ccatagttgc ctgactcccc gtcgtgtaga    2940
taactacgat acgggagggc ttaccatctg gccccagtgc tgcaatgata ccgcgagaac    3000
cacgctcacc ggctccagat ttatcagcaa taaaccagcc agccggaagg gccgagcgca    3060
gaagtggtcc tgcaacttta tccgcctcca tccagtctat taattgttgc cgggaagcta    3120
gagtaagtag ttcgccagtt aatagtttgc gcaacgttgt tgccattgct acaggcatcg    3180
tggtgtcacg ctcgtcgttt ggtatggctt cattcagctc cggttcccaa cgatcaaggc    3240
gagttacatg atccccccatg ttgtgcaaaa aagcggttag ctccttcggt cctccgatcg    3300
ttgtcagaag taagttggcc gcagtgttat cactcatggt tatggcagca ctgcataatt    3360
ctcttactgt catgccatcc gtaagatgct tttctgtgac tggtgagtac tcaaccaagt    3420
cattctgaga atagtgtatg cggcgaccga gttgctcttg cccggcgtca tacgggata    3480
ataccgcgcc acatagcaga actttaaaag tgctcatcat tggaaaacgt tcttcggggc    3540
gaaaactctc aaggatctta ccgctgttga tccagttc gatgtaaccc actcgtgcac    3600
ccaactgatc ttcagcatct tttactttca ccagcgtttc tgggtgagca aaaacaggaa    3660
ggcaaaatgc cgcaaaaaag ggaataaggg cgacacggaa atgttgaata ctcatactct    3720
tcctttttca atattattga agcatttatc agggttattg tctcatgagc ggatacatat    3780
ttgaatgtat ttagaaaaat aaacaaatag gggttccgcg cacatttccc cgaaaagtgc    3840
cac                                                                 3843
```

<210> SEQ ID NO 24
<211> LENGTH: 6084
<212> TYPE: DNA
<213> ORGANISM: Artificial Sequence
<220> FEATURE:
<223> OTHER INFORMATION: recombinant construct

<400> SEQUENCE: 24

| | | | | | |
|---|---|---|---|---|---|
| gcggccgcaa | taaaatatct | ttattttcat | tacatctgtg | tgttggtttt | ttgtgtgaat | 60 |
| cgatagtact | aacatacgct | ctccatcaaa | acaaaacgaa | acaaaacaaa | ctagcaaaat | 120 |
| aggctgtccc | cagtgcaagt | gcaggtgcca | gaacatttct | ctatcgataa | cttcccggtc | 180 |
| ggtctgtggg | tgcagggggt | gccgcctcac | atgtgtgatt | cgtgccttgc | gggccctggc | 240 |
| ctccggggtg | ctgggtaacg | aggaggggcg | cggagccgca | gaagcccacc | ctggtatgtt | 300 |
| gacgcggtgc | cagcgagacc | gcgagaggaa | gacggggtg | ggcggggcca | ggatggagag | 360 |
| gggccgagtt | ggcaggagtc | atggcagacg | ccacattcgc | gacatctccc | ccacacccccc | 420 |
| tctggctctg | tccgcaacat | ttccaaacag | gagtcccggg | agaggggag | aggggctgct | 480 |
| ggtctgaggc | taagaagggc | agagccttcg | acccggagag | aggccgcggc | ccctgcccag | 540 |
| tgggcagcgt | ggaagtttcc | atacaaggag | gtgggaagga | gaccccccccc | ccccttcact | 600 |
| gccctgtgca | gagatgagcc | gggggtgcag | gatgggagcc | catggcactt | cgctacggga | 660 |
| tggtccaggg | ctcccggttg | ggggtgcagg | agagaagaga | ctggctggga | ggagggagag | 720 |
| ggcgggagca | aaggcgcggg | ggagtggtca | gcagggagag | gggtgggggg | tagggtggag | 780 |
| cccgggctgg | gaggagtcgg | ctcacacata | aaagctgagg | cactgaccag | cctgcaaact | 840 |
| ggacattagc | ttctcctgtg | aaagagactt | ccagcttcct | cctcctcctc | ttcctcctcc | 900 |
| tcctcctgcc | ccagcgagcc | ttctgctgag | ctgtaggggg | atcttctaga | gtcggctagc | 960 |
| ggcattccgg | tactgttggt | aaagccacca | tggatcctga | tgatgttgtt | gattcttcta | 1020 |
| aatcttttgt | gatggaaaac | ttttcttcgt | accacgggac | taaacctggt | tatgtagatt | 1080 |
| ccattcaaaa | aggtatacaa | aagccaaaat | ctggtacaca | aggaaattat | gacgatgatt | 1140 |
| ggaaagggtt | ttatagtacc | gacaataaat | acgacgctgc | gggatactct | gtagataatg | 1200 |
| aaaacccgct | ctctggaaaa | gctggaggcg | tggtcaaagt | gacgtatcca | ggactgacga | 1260 |
| aggttctcgc | actaaaagtg | gataatgccg | aaactattaa | gaaagagtta | ggtttaagtc | 1320 |
| tcactgaacc | gttgatggag | caagtcggaa | cggaagagtt | tatcaaaagg | ttcggtgatg | 1380 |
| gtgcttcgcg | tgtagtgctc | agccttccct | tcgctgaggg | gagttctagc | gttgaatata | 1440 |
| ttaataactg | ggaacaggcg | aaagcgttaa | gcgtagaact | tgagattaat | tttgaaaccc | 1500 |
| gtggaaaacg | tggccaagat | gcgatgtatg | agtatatggc | tcaagcctgt | gcaggaaatc | 1560 |
| gtgtcaggcg | atctttgtga | aggaaccta | cttctgtggt | gtgacataat | tggacaaact | 1620 |
| acctacagag | atttgggat | ccctcgaggg | ccatgcaggt | aggatttgag | ctgtgtttcc | 1680 |
| cgccctgatc | ctctctcctc | tggcggccgg | agcctccgta | ggctccaagc | ctggcccaga | 1740 |
| ttcggcggcg | cagccggcct | tccgcgcgtc | cgcacctagc | gggggctccg | ggctccggc | 1800 |
| gcggcaccgg | ggggcgctcg | ggatctggct | gaggctccaa | ggcccgcgtg | gccggctcct | 1860 |
| cctgctgggg | caggtggcgg | ctgcgcgccc | cgcccgagcc | caggggcccc | ctcagccgca | 1920 |
| acaaccagca | aggaccccccc | gactcagccc | caagccacct | gcatctgcac | tcagacgggg | 1980 |
| cgcacccgca | gtgcagcctc | ctggtggggc | gctgggagcc | cgcctgcccc | tgcctgcccg | 2040 |

```
gagacoccag ctcacgagca caggccgccc gggcacccca gaaacccggg atggggcccc      2100
tgaattctct aggacgggca ttcagcatgg ccttggcgct ctgcggctcc ctgcccccca      2160
cccagcctcg ccccgcgca cccccagcc cctgcgaccg ccgccccccc ccccggggcc        2220
ccagggcccc agcccgcacc ccccgcccg ctcttggctc gggttgcggg ggcgggccgg       2280
gggcggggcg agggctccgc gggcgccat ggcgcgggc gcgaggccag cggccccgcg        2340
cggccctggg ccgcggctgg cgcgactata agagccgggc gtgggcgccc gcagttcgcc      2400
tgctctccgg cggagctgcg tgaggcccgg ccggccccgg ccccccctt ccggccgccc       2460 ccgcctcctg gcccacgcct gcccgcgctc tgcccaccag cgcctccatc gggcaaggcg      2520
gccccgcgtc gacaagcttg gcattccggt actgttggta aagccaccat ggatcctgat      2580
gatgttgttg attcttctaa atcttttgtg atggaaaact tttcttcgta ccacgggact      2640
aaacctggtt atgtagattc cattcaaaaa ggtatacaaa agccaaaatc tggtacacaa      2700
ggaaattatg acgatgattg gaagggtttt tatagtaccg acaataaata cgacgctgcg      2760
ggatactctg tagataatga aaacccgctc tctggaaaag ctggaggcgt ggtcaaagtg      2820
acgtatccag gactgacgaa ggttctcgca ctaaaagtgg ataatgccga aactattaag      2880
aaagagttag gtttaagtct cactgaaccg ttgatggagc aagtcggaac ggaagagttt      2940
atcaaaaggt tcggtgatgg tgcttcgcgt gtagtgctca gccttccctt cgctgagggg      3000
agttctagcg ttgaatatat taataactgg gaacaggcga aagcgttaag cgtagaactt      3060
gagattaatt ttgaaacccg tggaaaacgt ggccaagatg cgatgtatga gtatatggct      3120
caagcctgtg caggaaatcg tgtcaggcga tctttgtgaa ggaaccttac ttctgtggtg      3180
tgacataatt ggacaaacta cctacagaga tttggggatc ctctagagtc ggggcggccg      3240
gccgcttcga gcagacatga taagatacat tgatgagttt ggacaaacca aactagaat      3300 gcagtgaaaa aaatgcttta tttgtgaaat ttgtgatgct attgctttat ttgtaaccat      3360
tataagctgc aataaacaag ttaacaacaa caattgcatt catttatgt ttcaggttca      3420 gggggaggtg tgggaggttt tttaaagcaa gtaaacctc tacaaatgtg gtaaaatcga      3480
taaggatccg tcgaccgatg cccttgagag ccttcaaccc agtcagctcc ttccggtggg      3540
cgcggggcat gactatcgtc gccgcactta tgactgtctt ctttatcatg caactcgtag      3600
gacaggtgcc ggcagcgctc ttccgcttcc tcgctcactg actcgctgcg ctcggtcgtt      3660
cggctgcggc gagcggtatc agctcactca aaggcggtaa tacggttatc cacagaatca      3720
ggggataacg caggaaagaa catgtgagca aaaggccagc aaaaggccag gaaccgtaaa      3780
aaggccgcgt tgctggcgtt tttccatagg ctccgccccc ctgacgagca tcacaaaaat      3840
cgacgctcaa gtcagaggtg gcgaaacccg acaggactat aaagatacca ggcgtttccc      3900
cctggaagct ccctcgtgcg ctctcctgtt ccgaccctgc cgcttaccgg atacctgtcc      3960
gcctttctcc cttcgggaag cgtggcgctt tctcatagct cacgctgtag gtatctcagt      4020
tcggtgtagg tcgttcgctc caagctgggc tgtgtgcacg aaccccccgt tcagcccgac      4080
cgctgcgcct tatccggtaa ctatcgtctt gagtccaacc cggtaagaca cgacttatcg      4140
ccactggcag cagccactgg taacaggatt agcagagcga gtatgtagg cggtgctaca       4200 gagttcttga agtggtggcc taactacggc tacactagaa gaacagtatt tggtatctgc      4260
gctctgctga agccagttac cttcggaaaa agagttggta gctcttgatc cggcaaacaa      4320
accaccgctg gtagcggtgg tttttttgtt tgcaagcagc agattacgcg cagaaaaaaa      4380
ggatctcaag aagatccttt gatcttttct acggggtctg acgctcagtg aacgaaaac      4440
```

```
tcacgttaag ggattttggt catgagatta tcaaaaagga tcttcaccta gatccttta    4500 aattaaaaat gaagttttaa atcaatctaa agtatatatg agtaaacttg gtctgacagt    4560
tagaaaaact catcgagcat caaatgaaac tgcaatttat tcatatcagg attatcaata    4620
ccatattttt gaaaaagccg tttctgtaat gaaggagaaa actcaccgag gcagttccat    4680
aggatggcaa gatcctggta tcggtctgcg attccgactc gtccaacatc aatacaacct    4740
attaatttcc cctcgtcaaa aataaggtta tcaagtgaga atcaccatg agtgacgact     4800 gaatccggtg agaatggcaa aagtttatgc atttcttcc agacttgttc aacaggccag     4860
ccattacgct cgtcatcaaa atcactcgca tcaaccaaac cgttattcat tcgtgattgc    4920
gcctgagcga gacgaaatac gcgatcgctg ttaaaaggac aattacaaac aggaatcgaa    4980
tgcaaccggc gcaggaacac tgccagcgca tcaacaatat tttcacctga atcaggatat    5040
tcttctaata cctggaatgc tgttttcccg gggatcgcag tggtgagtaa ccatgcatca    5100
tcaggagtac ggataaaatg cttgatggtc ggaagaggca taaattccgt cagccagttt    5160
agtctgacca tctcatctgt aacatcattg gcaacgctac ctttgccatg tttcagaaac    5220
aactctggcg catcgggctt cccatacaat cgatagattg tcgcacctga ttgcccgaca    5280
ttatcgcgag cccatttata cccatataaa tcagcatcca tgttggaatt taatcgcggc    5340
ctagagcaag acgtttcccg ttgaatatgg ctcatactct tcctttttca atattattga    5400
agcatttatc agggttattg tctcatgagc ggatacatat ttgaatgtat ttagaaaaat    5460
aaacaaatag gggttccgcg cacatttccc cgaaaagtgc cacctgacgc gccctgtagc    5520
ggcgcattaa gcgcggcggg tgtggtggtt acgcgcagcg tgaccgctac acttgccagc    5580
gccctagcgc ccgctccttt cgctttcttc ccttcctttc tcgccacgtt cgccggcttt    5640
ccccgtcaag ctctaaatcg ggggctccct ttagggttcc gatttagtgc tttacggcac    5700
ctcgacccca aaaaacttga ttagggtgat ggttcacgta gtgggccatc gccctgatag    5760
acggtttttc gccctttgac gttggagtcc acgttcttta atagtggact cttgttccaa    5820
actggaacaa cactcaaccc tatctcggtc tattcttttg atttataagg gattttgccg    5880
atttcggcct attggttaaa aaatgagctg atttaacaaa aatttaacgc gaatttaac    5940 aaaatattaa cgcttacaat ttgccattcg ccattcaggc tgcgcaactg ttgggaaggg    6000
cgatcggtgc gggcctcttc gctattacgc cagcccaagc taccatgata agtaagtaat    6060
attaaggtac gggaggtact tgga                                          6084
```

CONSTRUCTS CONTAINING MULTIPLE EXPRESSION CASSETTES FOR CANCER THERAPY

CROSS-REFERENCE TO RELATED APPLICATIONS

This application is a continuation of U.S. patent application Ser. No. 12/738,620 filed on Apr. 22, 2010, which is a 371 filing of International patent application no. PCT/IL2008/001405 filed on Oct. 23, 2008, which claims the benefit of U.S. provisional patent application No. 60/982,442 filed on Oct. 25, 2007, the entire contents of each of which are incorporated herein by reference thereto.

FIELD OF THE INVENTION

The present invention is directed to the field of cancer treatment, specifically to novel nucleic acid constructs that are particularly useful for treating tumors expressing H19 and/or IGF-II.

BACKGROUND OF THE INVENTION

Neoplasia is a process that occurs in cancer, by which the normal controlling mechanisms that regulate cell growth and differentiation are impaired, resulting in progressive growth. This impairment of control mechanisms allows a tumor to enlarge and occupy spaces in vital areas of the body. If the tumor invades surrounding tissue and is transported to distant sites (metastases) it will likely result in death of the individual.

The desired goal of cancer therapy is to eliminate cancer cells preferentially, without having a deleterious effect on normal cells. Several methods have been used in an attempt to reach this goal, including surgery, radiation therapy and chemotherapy.

Local treatments, such as radiation therapy and surgery, offer a means of reducing the tumor mass in regions of the body that is accessible through surgical techniques or high doses of radiation therapy. However, more effective local therapies with fewer side effects are needed. Moreover, these treatments are not applicable to the destruction of widely disseminated or circulating tumor cells eventually found in most cancer patients. To combat the spread of tumor cells, systemic therapies are used.

One such systemic treatment is chemotherapy. Chemotherapy is the main treatment for disseminated, malignant cancers. However, chemotherapeutic agents are limited in their effectiveness for treating many cancer types, including many common solid tumors. This limitation is in part due to the intrinsic or acquired drug resistance of many tumor cells. Another drawback to the use of chemotherapeutic agents is their severe side effects. These include bone marrow suppression, nausea, vomiting, hair loss, and ulcerations in the mouth. Clearly, new approaches are needed to enhance the efficiency with which a chemotherapeutic agent can kill malignant tumor cells, while at the same time avoiding systemic toxicity.

H19 in Diagnosis and Therapy

The H19 gene is one of several genes known to be imprinted in humans (Hurst et al., 1996, Nature Genetics 12:234 237). At the very beginning of embryogenesis, H19 is expressed from both chromosomal alleles (DeGroot et al., 1994, Trophoblast 8:285 302). Shortly afterwards, silencing of the paternal allele occurs, and only the maternally inherited allele is transcribed.

H19 is abundantly expressed during embryogenesis, and was first identified as a gene that was coordinately regulated with alpha-fetoprotein in liver by the trans-acting locus raf (Pachnis et al., 1984, "Locus unlinked to alpha-fetoprotein under the control of the murine raf and Rif genes", Proc Natl Acad Sci. 81:5523 5527). Additionally, H19 has been independently cloned by several groups using screens aimed at isolating genes expressed during tissue differentiation. For example, the mouse homolog of H19 was identified in a screen for genes that are active early during differentiation of C3H10T1/2 cells (Davis et al., 1987, "Expression of a single transfected cDNA converts fibroblasts to myoblasts", Cell 51:987 1000). Similarly, murine H19 was shown to be expressed during stem cell differentiation and at the time of implantation (Poirier et al., 1991, "The murine H19 gene is activated during embryonic stem cell differentiation in vitro and at the time of implantation in the developing embryo", Development 113:1105 1114). Transcription of the human H19 gene was also discovered in differentiating cytotrophoblasts from human placenta (Rachmilewitz et al., 1992, Molec. Reprod. Dev. 32:196 202).

While transcription of H19 RNA occurs in many different embryonic tissues throughout fetal life and placental development, H19 expression is downregulated postnatally, although low levels of H19 transcription have been reported, for example, in murine adult muscle and liver (Brunkow and Tilghman, 1991, "Ectopic expression of the H19 gene in mice causes prenatal lethality", Genes Dev. 5:1092 1101).

H19 transcription can be re-activated postnatally in cancer cells as demonstrated in tumors derived from tissues expressing H19 prenatally (Ariel et al., 1997, "The product of the imprinted H19 gene is an oncofetal RNA", Mol Pathol. 50:34 44). Additionally, H19 RNA is postnatally expressed in some tumors, in particular astrocytoma and ganglioneuroblastoma, which are derived from neural tissues not known to express H19 (Ariel et al. supra). Given that H19 RNA is expressed in many types of tumors and cancers, Ariel et al. speculated that H19 RNA was an oncofetal RNA, and proposed investigating H19 as a tumor marker for human neoplasia.

H19 is significantly expressed in 84% of human bladder carcinomas, expression decreasing with tumor loss differentiation. Independent of tumor grade, the H19 expression level significantly correlated with early tumor recurrence (Ayesh, B., et al, Mol Ther, 2003. 7(4): p. 535-41).

Comparing patterns of gene expression in two homogeneous cell populations that differ only in the presence or absence of H19 RNA have identified a plethora of downstream effectors of H19 RNA. Among these are group of genes that were previously reported to play crucial roles in some aspects of the tumorigenic process. H19 RNA presence may enhance the invasive, migratory and angiogenic capacity of the cell by up-regulating genes that function in those pathways, and thus could contribute at least to the initial steps of the metastatic cascade. Additional studies highlight the potential role of H19 in promoting cancer progression and tumor metastasis by being a gene responsive to Hepatocyte growth factor/scatter factor (HGF/SF).

Specific expression of the H19 gene in cancer cells has prompted its use in clinical applications for diagnosing cancer. For example, U.S. Pat. No. 5,955,273 teaches the use of H19 gene as a tumor specific marker. PCT Pub. No. WO 2004/024957 discloses the use of H19 for the detection, in a patient suspected of having cancer, of the presence of residual cancer cells or micro-metastases originating from solid tumors.

IGF-II

Insulin-like growth factor-II (IGF-II) is expressed in the majority of bladder carcinomas such as transitional cell carcinomas (TCC; Ariel, I., et al., The imprinted H19 gene is a marker of early recurrence in human bladder carcinoma. Mol Pathol, 2000. 53(6): p. 320-3). The biological activities are mediated by the binding to the cell surface-receptors IGF-I receptor (IGF-1R), IGF-II receptor (IGF-2R) and insulin receptor (IR). The IGF receptors are present almost in all tissues of fetal and adult animals. IGF-2R binds IGF-II with the highest affinity, whereas the IGF-1R and IR possess high, but lower affinity to IGF-II than to their respective ligands. IGF-II is a potent embryonic and tumor growth factor that signals via the IGF1R through the Ras/mitogen-activated protein kinase, phosphatidylinositol 3-kinase/Akt/FOXO, and S6K/mammalian target of rapamycin (mTOR) signaling pathways to modify cell proliferation, cell survival, gene expression, and cell growth.

IGF-II is another imprinted gene whose expression depends upon its parental origin. However in contrast to H19, IGF-II is maternally imprinted in both mice and humans, and is therefore expressed from the paternally inherited allele (Rainier et al., 1993, "Relaxation of imprinted genes in human cancer", Nature 362:747 749). The human IGF-II gene exhibits a complex transcriptional pattern. There are four IGF-II promoters that are activated in a tissue-specific and developmentally specific manner. Only three of the IGF-II promoters (i.e., P2, P3 and P4) are imprinted and active during fetal development and in cancer tissues. The P3 promoter of the IGF-II gene has been implicated in the progression of liver cirrhosis and hepatocellular carcinoma (Seo et al., 1998, "Different protein-binding patterns in the P3 promoter region of the human insulin-like growth factor II gene in the human liver cirrhosis and hepatocellular carcinoma tissues", J Korean Med Sci. 13:171 178).

The fourth IGF-II promoter, (i.e., P1) is not imprinted, and is activated in the adult liver and choroid plexus (See Holthuizen et al., 1993, "Transcriptional regulation of the major promoters of the human IGF-II gene", Mol Reprod Dev. 35:391 393).

Loss of imprinting of IGF-II has been implicated in Wilm's tumor (Ogawa et al., 1993, "Relaxation of insulin-like growth factor II gene imprinting implicated in Wilm's tumour", Nature 362:749 751). This observation led many investigators to speculate that the loss of imprinting and biallelic expression of imprinted genes may be involved in growth disorders and the development of cancer (Rainier et al., 1993, Nature 362:747 749; Glassman et al., 1996, "Relaxation of imprinting in carcinogenesis", Cancer Genet Cytogenet. 89:69 73).

Epigenetic modification and mutations of the IGF-II signaling system occur in cancers such as human colorectal tumors (Hassan A B, Macaulay V M. The insulin-like growth factor system as a therapeutic target in colorectal cancer. Ann Oncol 2002; 13:349-56). Supply of IGF-II is frequently up-regulated, and serial analysis of gene expression has shown IGF-II as a commonly overexpressed gene in a number of cancer cell lines and tumors, e.g. human bladder carcinoma and colorectal cancer (Zhang L, Zhou W, Velculescu V E, et al. Gene expression profiles in normal and cancer cells. Science 1997; 276:1268-72).

WO 99/18195 and U.S. Pat. No. 7,041,654 teach the specific expression of heterologous sequences, particularly genes encoding cytotoxic products (e.g. Diphtheria toxin), in tumor cells under the control of a cancer specific promoter (e.g., an H19 promoter and enhancer, IGF-II P3 promoter, IGF-II P4 promoter, or IGF-1 promoter).

WO 04/031359 teaches a method for regulating the expression of angiogenesis-controlling genes in cells that are involved in neo-vascularization, comprising administering to the cells an effective amount of an H19 modulator.

WO 2007/034487 discloses a nucleic acid construct comprising: (i) a first nucleic acid sequence encoding TNF alpha; (ii) a second nucleic acid sequence encoding a Diphtheria toxin; and (iii) at least one additional nucleic acid sequence comprising a cancer specific promoter (e.g. H19, IGF-1, IGF-II P3, or IGF-II P4 promoters); the TNF alpha and Diphtheria toxin encoding sequences being under an expression control of the cancer specific promoter. Also provided are construct systems and methods and uses of same.

WO 2007/007317 discloses isolated oligonucleotides capable of down-regulating a level of H19 mRNA in cancer cells, articles of manufacture comprising agents capable of downregulating H19 mRNA in combination with an additional anti-cancer treatment as well as methods of treating cancer by administering same. WO 2007/007317 discloses that anti-cancer drugs can be co-administered with the claimed oligonucleotides.

WO 2008/087641 discloses compositions and methods for treating rheumatoid arthritis, utilizing H19-silencing nucleic acid agents such as inhibitory RNA.

WO 2008/087642 discloses compositions and methods for the treatment of cancer and other conditions that are associated with elevated expression of the H19 gene, utilizing H19-silencing nucleic acid agents such as inhibitory RNA.

WO 2008/099396 discloses compositions and methods for treating restenosis, utilizing H19-silencing nucleic acid agents such as inhibitory RNA.

None of the above references discloses or suggests a single construct containing multiple Diphtheria toxin-expressing open reading frames, wherein the Diphtheria toxin is expressed from a plurality of promoters.

Use of a single promoter (e.g. an H19 promoter or an IGF-II P3 or P4 promoter) alone for expression of a cytotoxic or cytostatic gene from an anti-cancer therapeutic construct presents several unresolved problems. For one, not every tumor of a given type of cancer (e.g. bladder carcinoma, superficial bladder cancer, etc.) is positive for expression via the H19 promoter or the IGF-II P3 or P4 promoter. Thus, such therapy is bound to fail in a sizable proportion of patients, even without accounting for tumor mutagenesis. Determination of responsiveness to such constructs would involve the costly and difficult step of genotyping individual tumors.

Tumors are known to exhibit significant genomic instability and heterogeneity. Thus, even individuals with an H19-expressing tumor, for example, are likely to contain a sizable number of cancer cells that have downregulated or abrogated H19 expression via mutation. Therefore, expressing the cytotoxic or cytostatic gene from a single promoter in such patients may result in temporary and partial tumor regression that will rapidly be reversed when the cells containing these mutations survive and rapidly multiply.

There remains an unmet medical need for developing additional safe and effective therapeutic modalities useful in cancer therapy.

The inclusion or description of literary references in this section or any other part of this application does not constitute an admission that the references are regarded as prior art to this invention.

SUMMARY OF THE INVENTION

The present invention relates to the field of cancer treatment, in particular to novel nucleic acid constructs and expression vectors that are particularly useful for treating tumors expressing H19 and/or Insulin-Like Growth Factor-II (IGF-II). The invention further provides compositions, methods and kits utilizing the nucleic acid constructs of the invention.

Specifically, the novel vectors of the invention comprise a nucleic acid construct containing multiple expression cassettes that enable expression of a cytotoxic agent, e.g. a Diphtheria toxin, from a plurality of cancer-specific promoters, selected from H19-, IGF-II P3-, and IGF-II P4-derived sequences.

According to a first aspect of the present invention, there is provided a nucleic acid construct, comprising:
- (a) a first open reading frame encoding a cytotoxic or cytostatic gene product, the first open reading frame being operably linked to a first transcription-regulating sequence; and
- (b) a second open reading frame encoding the cytotoxic or cytostatic gene product, the second open reading frame being operably linked to a second transcription-regulating sequence;
- wherein the first transcription-regulating sequence and the second transcription-regulating sequence are different, and are selected from the group consisting of: i) H19-specific transcription-regulating sequences and ii) IGF-II transcription-regulating sequences selected from IGF-II P3 and IGF-II P4.

For example, the transcription regulating sequences may be:
- i) a first transcription-regulating sequence being an H19-specific transcription-regulating sequence, and a second transcription-regulating sequence being an IGF-II P4 transcription-regulating sequence;
- ii) a first transcription-regulating sequence being an H19-specific transcription-regulating sequence, and a second transcription-regulating sequence being an IGF-II P3 transcription-regulating sequence; or
- iii) a first transcription-regulating sequence being an IGF-II P4 transcription-regulating sequence, and a second transcription-regulating sequence being an IGF-II P3 transcription-regulating sequence.

Optionally, said construct may further comprise a third open reading frame encoding the cytotoxic or cytostatic gene product, the third open reading frame being operably linked to a third transcription-regulating sequence selected from H19-specific transcription-regulating sequences, IGF-II P3 transcription-regulating sequences and IGF-II P4 transcription-regulating sequences.

In another aspect, the invention provides a nucleic acid construct, comprising: a) a first open reading frame encoding a diphtheria toxin, the first open reading frame being operably linked to an H19-specific transcription-regulating sequence, and b) a second open reading frame encoding a diphtheria toxin, the second open reading frame being operably linked to a first IGF-II transcription-regulating sequence selected from IGF-II P4 and IGF-II P3 sequences.

In one embodiment, said nucleic acid construct further comprises a third open reading frame encoding a diphtheria toxin, said third open reading frame being operably linked to a second IGF-II transcription-regulating sequence selected from IGF-II P4 and IGF-II P3 sequences, wherein the first IGF-II transcription-regulating sequence and the second IGF-II transcription-regulating sequence are different. For example, the second open reading frame may be operably linked to an IGF-II P4 transcription regulating sequence and the third open reading frame may be operably linked to an IGF-II P3 transcription regulating sequence, or alternatively the second open reading frame may be operably linked to an IGF-II P3 transcription regulating sequence and the third open reading frame may be operably linked to an IGF-II P4 transcription regulating sequence.

In another aspect, the invention provides a nucleic acid construct, comprising: a) a first open reading frame encoding a diphtheria toxin, said first open reading frame being operably linked to an IGF-II P3 transcription-regulating sequence; and b) a second open reading frame encoding a diphtheria toxin, said second open reading frame being operably linked to an IGF-II P4 transcription-regulating sequence.

In another embodiment, said nucleic acid construct further comprises a third open reading frame encoding a diphtheria toxin, said third open reading frame being operably linked to an H19-specific transcription-regulating sequence.

In the constructs of the invention, the diphtheria toxin may be, for example, a diphtheria toxin A chain (diphtheria toxin A, DTA), e.g. a toxin having an amino acid sequence comprising a sequence as set forth in SEQ ID NO: 7, as detailed hereinbelow.

According to various embodiments, the transcription regulating sequence may be a regulatory sequence (e.g. a promoter or enhancer) that induces or enhances expression selectively (or, in other embodiments, preferentially) in cancer cells, as detailed herein.

The term "IGF-II transcription-regulating sequence" refers, in another embodiment, to a sequence that regulates transcription in a specific (or differential) manner and is found in association with an IGF-II gene on a chromosome, e.g. a human chromosome. According to specific embodiments, "IGF-II P3 transcription-regulating sequence" and "IGF-II P4 transcription-regulating sequence" refer to a P3 or P4 (respectively) promoter. In another embodiment, the terms refer to a transcription-regulating sequence derived from a P3 or P4 (respectively) promoter. In another embodiment, the terms refer to one of the P3- or P4 (respectively)-specific transcription-regulating sequences disclosed herein. Each possibility represents a separate embodiment of the present invention.

For example, without limitation, the IGF-II P4 transcription-regulating sequence may be a promoter comprising a nucleic acid sequence set forth in SEQ ID NO: 9, as detailed hereinbelow. Non-limitative examples of IGF-II P3 promoters include promoters comprising a nucleic acid sequence as set forth in a sequence selected from SEQ ID NO: 8, SEQ ID NO: 12, and SEQ ID NO: 17, as detailed hereinbelow.

"H19-specific transcription-regulating sequence" refers, in another embodiment, to a sequence that regulates transcription in a specific (or differential) manner and is found in association with an H19 gene on a chromosome, e.g. a human chromosome. In another embodiment, the term refers to an H19-specific promoter. In another embodiment, the terms refer to a transcription-regulating sequence derived from an H19 promoter. In another embodiment, the term refers to one of the H19-specific transcription-regulating sequences disclosed herein. Each possibility represents a separate embodiment of the present invention. For example, without limitation, the H19-specific transcription-regulating sequence may be a promoter comprising a nucleic acid sequence set forth in any one of SEQ ID NOS: 1-2, as detailed hereinbelow.

The present invention discloses for the first time that such constructs provide a particularly effective and safe treatment targeted specifically to malignancies expressing H19 and/or expressing IGF-II from the P3 and/or P4 promoter. Advantageously, it is now disclosed that the constructs of the invention elicit responses in a higher number of cells and/or higher proportion of patients, thus providing improved cancer treatment compared to hitherto known therapy.

In another embodiment, said nucleic acid construct is a plasmid. In another embodiment, the present invention provides a eukaryotic expression vector comprising a nucleic acid construct of the present invention.

In another embodiment, the present invention provides a method for treating a tumor in a human subject in need thereof, comprising administering to the human subject a nucleic acid construct (e.g. a therapeutically effective amount of the nucleic acid construct) of the present invention, thereby treating a tumor in a human subject in need thereof.

In another embodiment, the present invention provides a method for inhibiting tumor progression in a human subject in need thereof, comprising administering to the human subject a nucleic acid construct (e.g. a therapeutically effective amount of the nucleic acid construct) of the present invention, thereby inhibiting tumor progression in a human subject in need thereof.

In another embodiment, the present invention provides a method for inhibiting tumor metastasis in a human subject in need thereof, comprising administering to the human subject a nucleic acid construct (e.g. a therapeutically effective amount of the nucleic acid construct) of the present invention, thereby inhibiting tumor progression in a human subject in need thereof.

In another embodiment, the present invention provides a method for reducing or alleviating a symptom associated with a neoplastic disorder in a human subject in need thereof, comprising administering to the human subject a nucleic acid construct (e.g. a therapeutically effective amount of the nucleic acid construct) of the present invention, thereby reducing or alleviating a symptom associated with a neoplastic disorder in a human subject in need thereof.

In the methods of the invention, said subject is afflicted, in one embodiment, with a tumor characterized by expression of H19 RNA in at least a portion of the cells of the tumor, e.g. wherein a cell of said tumor is capable of expressing a transcript directed by the H19 promoter, a transcript directed by the IGF-II P4 promoter and/or a transcript directed by the IGF-II P3 promoter.

The constructs of the invention may also be in form of a kit or a pharmaceutical pack containing one or more courses of treatment for a neoplasm expressing H19 and/or expressing IGF-II from the P3 and/or P4 promoter in a subject in need thereof. Thus, there is provided in another aspect a kit containing i) a nucleic acid construct of the invention; and ii) instructions for administering said nucleic acid construct to a subject in need thereof (e.g. a subject afflicted with cancer).

The compositions, methods and kits of the present invention are useful in the treatment of a variety of malignancies associated with expression of H19 and/or expression of IGF-II from the P3 and/or P4 promoter. In another embodiment, the tumor is a solid tumor. In another embodiment, the tumor is a carcinoma. In various particular embodiments, the tumor includes, but is not limited to, bladder carcinoma, liver neoplasms (e.g. hepatocellular carcinoma), lung adenocarcinoma (small and non-small cell lung cancer), esophageal, ovarian, rhabdomyosarcoma, cervical carcinoma, head and neck squamous cell carcinoma, colorectal, uterus and testicular germ cell tumors, medulloblastoma, glioblastoma and adenocortical tumors.

According to still further features in the described preferred embodiments, the tumor is selected from the group consisting of bladder carcinoma, hepatocellular carcinoma and colon carcinoma. In another embodiment, the tumor is selected from the group consisting of bladder carcinoma, a hepatocellular carcinoma, an ovarian carcinoma, and a pancreatic carcinoma. In another embodiment, the tumor is selected from the group consisting of a bladder carcinoma, a hepatocellular carcinoma, an ovarian carcinoma, a pancreatic carcinoma, a breast carcinoma, a prostate carcinoma, a cervical carcinoma, a colon carcinoma, and a lung carcinoma. In another particular embodiment, the subject is afflicted with superficial bladder cancer. Each possibility represents a separate embodiment of the present invention.

Exemplary metastasizing tumors include e.g. colorectal cancer metastasizing to the liver and metastasizing breast cancer. In a particular embodiment, the combinations of the invention are used to prevent or inhibit the formation of liver metastases.

Other objects, features and advantages of the present invention will become clear from the following description and drawings.

BRIEF DESCRIPTION OF THE DRAWINGS

FIG. 2A. Luciferase activity at various dosages compared to cells transfected with LucSV40 alone. FIG. 2B. Additional repetition of the experiment described in (A). FIG. 2C. Bar graph of 0.005 μg data. Y axis (for A-C): luciferase activity (% of control). X axis (for A-B): μg plasmid/well. Error bars in this Figure and throughout the Figures reflect 1 standard error of the mean.

FIG. 3A. Luciferase activity at various dosages compared to cells transfected with LucSV40 alone. FIG. 3B. Additional repetition of the experiment described in (A). FIG. 3C. Bar graph of 0.005 μg data.

FIG. 4A. Luciferase activity at various dosages compared to cells transfected with LucSV40 alone. FIG. 4B. Bar graph of 0.005 μg data.

FIG. 5A. Luciferase activity at various dosages compared to cells transfected with LucSV40 alone. FIG. 5B. Bar graph of 0.005 μg data.

FIG. 6A. Luciferase activity at various dosages compared to cells transfected with LucSV40 alone. FIG. 6B. Bar graph of 0.005 μg data.

FIG. 7A. Luciferase activity at various dosages compared to cells transfected with LucSV40 alone. FIG. 7B. Bar graph of 0.005 μg data.

FIG. 8A. Luciferase activity at various dosages compared to cells transfected with LucSV40 alone. FIG. 8B. Bar graph of 0.005 μg data. Y axis (for A-B): luciferase activity (% of control). X axis (for A): μg plasmid/well. Axes are same as FIG. 2.

FIG. 9A. Luciferase activity at various dosages compared to cells transfected with LucSV40 alone. FIG. 9B. Bar graph of 0.005 μg data.

FIG. 10A. Luciferase activity at various dosages compared to cells transfected with LucSV40 alone. FIG. 10B. Bar graph of 0.005 μg data.

FIG. 11A. Luciferase activity at various dosages compared to cells transfected with LucSV40 alone. FIG. 11B. Bar graph of 0.005 μg data.

FIG. 12A. Luciferase activity at various dosages compared to cells transfected with LucSV40 alone. FIG. 12B. Bar graph of 0.005 μg data.

FIG. 13A. Luciferase activity at various dosages compared to cells transfected with LucSV40 alone. FIG. 13B. Bar graph of 0.005 μg data.

FIG. 14A. Luciferase activity at various dosages compared to cells transfected with LucSV40 alone. FIG. 14B. Bar graph of 0.005 μg data. Y axis (for A-B): luciferase activity (% of control). X axis (for A): μg plasmid/well. Axes are same as FIG. 2.

FIG. 15A. Luciferase activity at various dosages compared to cells transfected with LucSV40 alone. FIG. 15B. Bar graph of 0.005 μg data. Y axis (for A-B): luciferase activity (% of control). X axis (for A): μg plasmid/well.

FIG. 16A. Luciferase activity at various dosages compared to cells transfected with LucSV40 alone. FIG. 16B. Bar graph of 0.005 μg data.

FIG. 17A. Luciferase activity at various dosages compared to cells transfected with LucSV40 alone. FIG. 17B. Bar graph of 0.005 μg data.

FIG. 18A. Luciferase activity at various dosages compared to cells transfected with LucSV40 alone. FIG. 18B. Bar graph of 0.005 μg data.

FIG. 19A. Luciferase activity at various dosages compared to cells transfected with LucSV40 alone. FIG. 19B. Bar graph of 0.005 μg data.

FIG. 20A. Luciferase activity at various dosages compared to cells transfected with LucSV40 alone. FIG. 20B. Bar graph of 0.005 μg data. Axes are same as for FIG. 15.

FIG. 21A. Luciferase activity at various dosages compared to cells transfected with LucSV40 alone. FIG. 21B. Bar graph of 0.005 μg data. Axes are same as for FIG. 15

FIG. 23A. Luciferase activity at various dosages compared to cells transfected with LucSV40 alone. FIG. 23B. Additional repetition of the experiment described in (A). C. Bar graph of 0.005 μg data.

FIG. 24A. Luciferase activity at various dosages compared to cells transfected with LucSV40 alone. FIG. 24B. Bar graph of 0.005 μg data. Experiment was performed as described for FIG. 21. Axes are same as for FIG. 15.

FIG. 40A. Luciferase activity at various dosages compared to cells transfected with LucSV40 alone. FIG. 40B. Bar graph of 0.005 μg data.

DETAILED DESCRIPTION OF THE INVENTION

Figure 1:
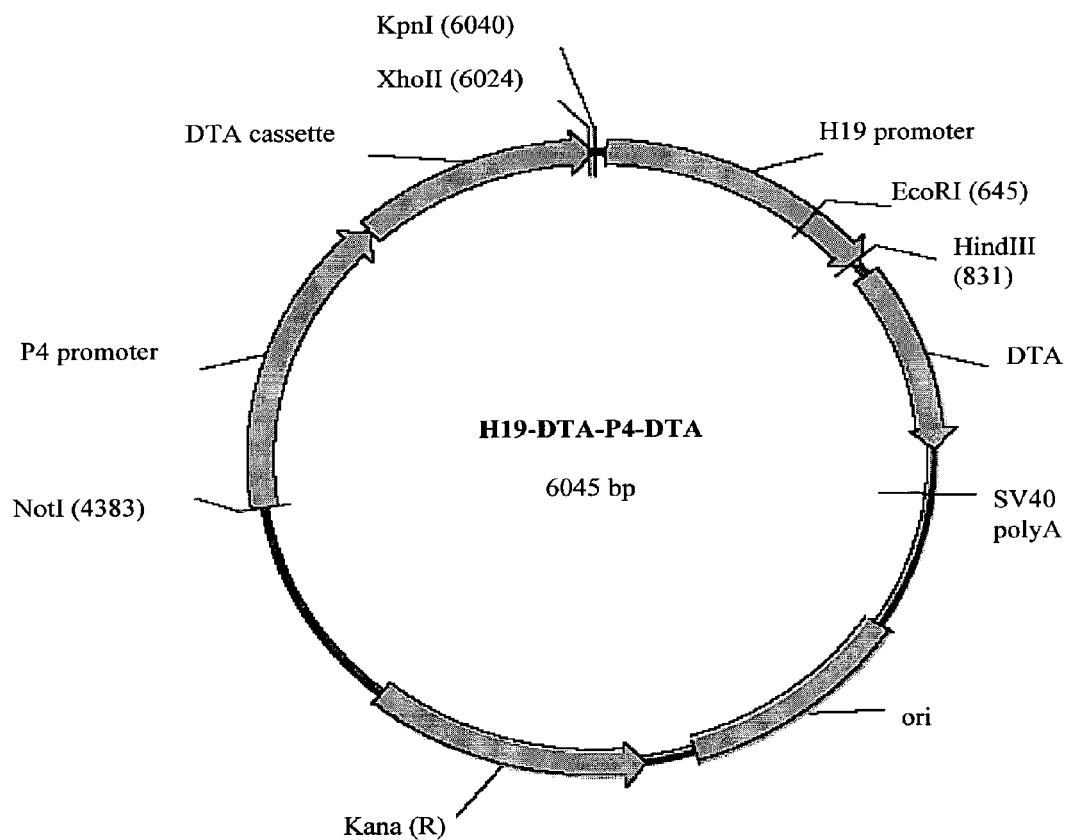
FIG. 1. A schematic illustration depicting the construction of the double promoter H19-DTA-P4-DTA expression vector. The coding sequence of each DTA is under the transcriptional control of both IGF-II-P4 and H19 promoter sequences, respectively, Kana (R)-kanamycin resistance gene.

The present invention relates to the field of cancer treatment, particularly to a novel therapy useful for treating H19-expressing and/or Insulin-Like Growth Factor-II (IGF-II)-expressing tumors.

Specifically, the novel vectors of the invention comprise a nucleic acid construct comprising multiple expression cassettes that enable expression of a cytotoxic agent from a plurality of promoters, selected from H19, IGF-II P3, and IGF-II P4.

Thus, the invention provides in some embodiments a nucleic acid construct comprising:
(a) a first open reading frame encoding a cytotoxic or cytostatic gene product, the first open reading frame being operably linked to a first cancer-specific transcription-regulating sequence; and
(b) a second open reading frame encoding the cytotoxic or cytostatic gene product (i.e. the same gene product or a variant thereof), the second open reading frame being operably linked to a second cancer-specific transcription-regulating sequence;
wherein the first transcription-regulating sequence and the second transcription-regulating sequence are different and selected from the group consisting of i) an H19-specific transcription-regulating sequence (e.g. an H19 promoter) and ii) an IGF-II transcription-regulating sequences (e.g. an IGF-II P3 or IGF-II P4 promoter).

In other words, the construct contains at least two different transcription-regulating sequences, each being derived from a different regulatory sequence (H19, P4 or P3), and each being operably linked to a separate sequence encoding the cytotoxic or cytostatic gene product. For example, the two transcription-regulating sequences may be:
i) a first transcription-regulating sequence being an H19-specific transcription-regulating sequence, and a second transcription-regulating sequence being an IGF-II P4 transcription-regulating sequence;
ii) a first transcription-regulating sequence being an H19-specific transcription-regulating sequence, and a second transcription-regulating sequence being an IGF-II P3 transcription-regulating sequence; or
iii) a first transcription-regulating sequence being an IGF-II P4 transcription-regulating sequence, and a second transcription-regulating sequence being an IGF-II P3 transcription-regulating sequence.

It should be understood, that the multiple expression cassettes are operably linked to distinct transcription-regulating sequences, enabling independent regulation of transcription from each open reading frame encoding the cytotoxic agent. Thus, the arrangement of the open reading frames within the construct may vary in different embodiments of the present invention, for example, the construct may be designed such that the first expression cassette is either upstream or downstream to the second expression cassette.

In one embodiment, the present invention provides a single nucleic acid molecule, comprising a first open reading frame encoding a cytotoxic or cytostatic gene product, the first open reading frame being operably linked to an H19-specific transcription-regulating sequence; and a second open reading frame encoding the cytotoxic or cytostatic gene product, the second open reading frame being operably linked to an IGF-II P3 transcription-regulating sequence. In another embodiment, the nucleic acid molecule further comprises a third open reading frame encoding the cytotoxic or cytostatic gene product, said third open reading frame being operably linked to an IGF-II P4 transcription-regulating sequence. Each possibility represents a separate embodiment of the present invention.

In another embodiment, the present invention provides a single nucleic acid molecule, comprising a first open reading frame encoding a cytotoxic or cytostatic gene product, the first open reading frame being operably linked to an H19-specific transcription-regulating sequence; and a second open reading frame encoding the cytotoxic or cytostatic gene product, the second open reading frame being operably linked to an IGF-II P4 transcription-regulating sequence. In another embodiment, the nucleic acid molecule further comprises a third open reading frame encoding the cytotoxic or cytostatic gene product, said third open reading frame being operably linked to an IGF-II P3 transcription-regulating sequence. Each possibility represents a separate embodiment of the present invention.

In another embodiment, the present invention provides a single nucleic acid molecule, comprising a first open reading frame encoding a cytotoxic or cytostatic gene product, the o first pen reading frame being operably linked to an IGF-II P4 transcription-regulating sequence; and a second open reading frame encoding the cytotoxic or cytostatic gene product, the second open reading frame being operably linked to an IGF-II P3 transcription-regulating sequence. In another embodiment, the nucleic acid molecule further comprises a third open reading frame encoding the cytotoxic or cytostatic gene product, said third open reading frame being operably linked to an H19-specific transcription-regulating sequence. Each possibility represents a separate embodiment of the present invention.

An exemplary construct of the invention, expressing a cytotoxic agent (DTA) under separate expression control of H19 and P4 promoters, H19-DTA-P4-DTA, is depicted in FIG. 1 and is further described herein (Example 1). Exemplary constructs of the invention expressing DTA under separate expression control of P4 and P3 promoters (P4-DTA-P3-DTA), and of H19 and P3 promoters (H19-DTA-P3-DTA) are described as well in the Experimental Details section in Example 5 and Example 6, respectively. These constructs are represented by the nucleic acid sequences as set forth in SEQ ID NOs: 11, 24 and 18, respectively, as detailed hereinbelow.

As demonstrated herein, administration of a single expression vector comprising two different sequences, each expressing DTA under the transcriptional control of a different tumor-specific promoter, namely, the H19 and IGF-II P4 promoters, resulted in enhanced killing of a wide variety of carcinoma cells, compared to each construct (expressing DTA under control of the H19 or P4 promoter) administered separately (Examples 1-4). Moreover, results were shown to be greater-than additive compared to administering the single-promoter constructs in combination (Example 7). The enhanced ability of the single expression vector comprising the two different genes was borne out by in vivo testing as well (Example 10).

In addition, administration of a single expression vector comprising two different sequences, each expressing DTA under the transcriptional control of a different tumor-specific promoter, namely, the IGF-II P3 and IGF-II P4 promoters, resulted in enhanced killing of a wide variety of carcinoma cells, compared to each construct (expressing DTA under control of the P3 or P4 promoter) administered separately (Example 5). Moreover, results were shown to be greater-than additive compared to administering the single-promoter constructs in combination (Example 8). The enhanced ability of the single expression vector comprising the two different genes was borne out by in vivo testing as well (Example 11).

In addition, administration of a single expression vector comprising two different sequences, each expressing DTA under the transcriptional control of a different tumor-specific promoter, namely, the H19 and IGF-II P3 promoters, resulted in enhanced killing of bladder carcinoma cells, compared to each construct (expressing DTA under control of the P3 or H19 promoter) administered separately (Example 6). The enhanced ability of the single expression vector comprising the two different genes was borne out by in vivo testing as well (Example 12).

The cytotoxic gene product of methods and compositions of the present invention is, according to a currently preferred embodiment of the present invention, a diphtheria toxin. In another embodiment, both sequences encode the same diphtheria toxin. In another embodiment, each sequence encodes a different variant of a diphtheria toxin. In another embodiment, the diphtheria toxin is DTA. Each possibility represents a separate embodiment of the present invention.

In another embodiment, the construct further comprises an additional open reading frame encoding a TNF alpha, the additional open reading frame being operably linked to an additional transcription regulating sequence selected from an H19-specific transcription-regulating sequence, an IGF-II P3 transcription-regulating sequences or an IGF-II P4 transcription-regulating sequence.

In another embodiment, the cytotoxic gene product is thymidine kinase. In another embodiment, the cytotoxic gene product is *Pseudomonas* toxin. In another embodiment, the cytotoxic gene product is ricin. In another embodiment, the cytotoxic gene product is cholera toxin. In another embodiment, the cytotoxic gene product is retinoblastoma gene product. In another embodiment, the cytotoxic gene product is p53. In another embodiment, the cytotoxic gene product is a retinoblastoma gene product.

In another embodiment, the cytotoxic agent is tumoricidal, i.e. of greater toxicity to tumor cells relative to non-tumor cells. Each possibility represents a separate embodiment of the present invention.

The cytostatic gene product of methods and compositions of the present invention is, in another embodiment, p21. In another embodiment, the cytostatic gene product is p27. In another embodiment, the cytostatic gene product is p53. In another embodiment, the cytostatic gene product is p53175P. In another embodiment, the cytostatic gene product is p57. In another embodiment, the cytostatic gene product is p15. In another embodiment, the cytostatic gene product is p16. In another embodiment, the cytostatic gene product is p18. In another embodiment, the cytostatic gene product is p19. In another embodiment, the cytostatic gene product is p73. In another embodiment, the cytostatic gene product is GADD45. In another embodiment, the cytostatic gene product is APC1. In another embodiment, the cytostatic gene product is p73RB1. In another embodiment, the cytostatic gene product is WT1. In another embodiment, the cytostatic gene product is NF1. In another embodiment, the cytostatic gene product is VH. In another embodiment, the cytostatic gene product is p53. In another embodiment, the cytotoxic agent is tumoristatic, i.e. of greater toxicity to tumor cells relative to non-tumor cells. Each possibility represents a separate embodiment of the present invention. A nucleic acid sequence encoding a cytotoxic or cytostatic agent may be obtained by methods well known in the art, e.g. as exemplified hereinbelow.

In another embodiment, the present invention provides a pharmaceutical composition comprising a nucleic acid construct of the present invention and a pharmaceutically acceptable carrier, excipient or diluent. Each possibility represents a separate embodiment of the present invention.

In another embodiment, the present invention provides eukaryotic expression constructs and vectors comprising a nucleic acid construct of the present invention.

In another embodiment, the present invention provides a method for treating a tumor in a human subject in need thereof, comprising administering to the human subject a nucleic acid construct of the present invention, thereby treating a tumor in a human subject in need thereof. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, the cytotoxic gene product is a diphtheria toxin. In another embodiment, a therapeutically effective amount of the nucleic acid construct is administered. In another embodiment, the tumor is characterized by expression of H19 RNA and/or IGF-II from the P3 and/or P4 promoter. Each possibility represents a separate embodiment of the present invention.

In another embodiment, the present invention provides a method for inhibiting tumor progression in a human subject in need thereof, comprising administering to the human subject a nucleic acid construct of the present invention, thereby inhibiting tumor progression in a human subject in need thereof. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, the cytotoxic gene product is a diphtheria toxin. In another embodiment, a therapeutically effective amount of the nucleic acid construct is administered. In another embodiment, the tumor is characterized by expression of H19 RNA and/or IGF-II from the P3 and/or P4 promoter. Each possibility represents a separate embodiment of the present invention.

In another embodiment, the present invention provides a method for inhibiting tumor metastasis in a human subject in need thereof, comprising administering to the human subject a nucleic acid construct of the present invention, thereby inhibiting tumor metastasis in a human subject in need thereof. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, the cytotoxic gene product is a diphtheria toxin. In another embodiment, a therapeutically effective amount of the nucleic acid construct is administered. In another embodiment, the tumor is characterized by expression of H19 RNA and/or IGF-II from the P3 and/or P4 promoter. Each possibility represents a separate embodiment of the present invention.

In another embodiment, the present invention provides a method for reducing or alleviating a symptom associated with a neoplastic disorder in a human subject in need thereof, comprising administering to the human subject a nucleic acid construct of the present invention, thereby reducing or alleviating a symptom associated with a neoplastic disorder in a human subject in need thereof. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, the cytotoxic gene product is a diphtheria toxin. In another embodiment, a therapeutically effective amount of the nucleic acid construct is administered. In another embodiment, the neoplastic disorder is characterized by expression of H19 RNA and/or IGF-II from the P3 and/or P4 promoter. Each possibility represents a separate embodiment of the present invention.

In another embodiment, the present invention provides use of a nucleic acid construct of the present invention for the manufacture of a medicament for treating a tumor in a human subject. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, the cytotoxic gene product is a diphtheria toxin. In another embodiment, a therapeutically effective amount of the nucleic acid construct is administered. In another embodiment, the tumor is characterized by expression of H19 RNA and/or IGF-II from the P3 and/or P4 promoter. Each possibility represents a separate embodiment of the present invention.

In another embodiment, the present invention provides use of a nucleic acid construct of the present invention for the manufacture of a medicament for inhibiting tumor progression in a human subject. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, the cytotoxic gene product is a diphtheria toxin. In another embodiment, a therapeutically effective amount of the nucleic acid construct is administered. In another embodiment, the tumor is characterized by expression of H19 RNA and/or IGF-II from the P3 and/or P4 promoter. Each possibility represents a separate embodiment of the present invention.

In another embodiment, the present invention provides use of a nucleic acid construct of the present invention for the manufacture of a medicament for inhibiting tumor metastasis in a human subject. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, the cytotoxic gene product is a diphtheria toxin. In another embodiment, a therapeutically effective amount of the nucleic acid construct is administered. In another embodiment, the tumor is characterized by expression of H19 RNA and/or IGF-II from the P3 and/or P4 promoter. Each possibility represents a separate embodiment of the present invention.

In another embodiment, the present invention provides use of a nucleic acid construct of the present invention for the manufacture of a medicament for reducing or alleviating a symptom associated with a neoplastic disorder in a human subject. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, a therapeutically effective amount of the nucleic acid construct is administered. In another embodiment, the neoplastic disorder is characterized by expression of H19 RNA and/or IGF-II from the P3 and/or P4 promoter. Each possibility represents a separate embodiment of the present invention.

In another embodiment, the present invention provides a composition for treating a tumor in a human subject, comprising a nucleic acid construct of the present invention. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, a therapeutically effective amount of the nucleic acid construct is administered. In another embodiment, the tumor is characterized by expression of H19 RNA and/or IGF-II from the P3 and/or P4 promoter. Each possibility represents a separate embodiment of the present invention.

In another embodiment, the present invention provides a composition for inhibiting tumor progression in a human subject, comprising a nucleic acid construct of the present invention. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, the cytotoxic gene product is a diphtheria toxin. In another embodiment, a therapeutically effective amount of the nucleic acid construct is administered. In another embodiment, the tumor is characterized by expression of H19 RNA and/or IGF-II from the P3 and/or P4 promoter. Each possibility represents a separate embodiment of the present invention.

In another embodiment, the present invention provides a composition for inhibiting tumor metastasis in a human subject, comprising a nucleic acid construct of the present invention. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, the cytotoxic gene product is a diphtheria toxin. In another embodiment, a therapeutically effective amount of the nucleic acid construct is administered. In another embodiment, the tumor is characterized by expression of H19 RNA and/or IGF-II from the P3 and/or P4 promoter. Each possibility represents a separate embodiment of the present invention.

In another embodiment, the present invention provides a composition for reducing or alleviating a symptom associated with a neoplastic disorder in a human subject, comprising a nucleic acid construct of the present invention. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, a therapeutically effective amount of the nucleic acid construct is administered. In another embodiment, the neoplastic disorder is characterized by expression of H19 RNA and/or IGF-II from the P3 and/or P4 promoter. Each possibility represents a separate embodiment of the present invention.

In some embodiments of the present invention, the neoplastic disorder of methods and compositions of the present invention is a carcinoma, e.g. a bladder carcinoma, a hepatocellular carcinoma, an ovarian carcinoma, and a pancreatic carcinoma. In another embodiment, the neoplastic disorder of methods and compositions of the present invention is a bladder carcinoma. In another embodiment, the neoplastic disorder is a hepatocellular carcinoma. In another embodiment, the neoplastic disorder is an ovarian carcinoma. In another embodiment, the neoplastic disorder is a pancreatic carcinoma. In another embodiment, the neoplastic disorder is a colon carcinoma. In another embodiment, the neoplastic disorder is another type of solid tumor. Each possibility represents a separate embodiment of the present invention.

In another embodiment, the H19-specific transcription-regulating sequence of methods of the present invention is an H19 promoter. In another embodiment, the H19 promoter comprises a nucleic acid sequence as set forth in a sequence disclosed herein. In another embodiment, the H19 promoter comprises a fragment of a nucleic acid sequence as set forth in a sequence disclosed herein. In another embodiment, the H19 promoter consists of a nucleic acid sequence as set forth in a sequence disclosed herein. Each possibility represents a separate embodiment of the present invention.

In another embodiment, the H19-specific transcription-regulating sequence of methods of the present invention comprises an H19 enhancer. In another embodiment, the H19 enhancer comprises a nucleic acid sequence as set forth in a sequence disclosed herein. In another embodiment, the H19 enhancer comprises a fragment of a nucleic acid sequence as set forth in a sequence disclosed herein. In another embodiment, the H19 enhancer consists of a nucleic acid sequence as set forth in a sequence disclosed herein. Each possibility represents a separate embodiment of the present invention.

In another embodiment, the IGF-II P3 transcription-regulating sequence of methods of the present invention is an IGF-II P3 promoter. In another embodiment, the IGF-II P3 promoter comprises a nucleic acid sequence as set forth in a sequence disclosed herein. In another embodiment, the IGF-II P3 promoter comprises a fragment of a nucleic acid sequence as set forth in a sequence disclosed herein. In another embodiment, the IGF-II P3 promoter consists of a nucleic acid sequence as set forth in a sequence disclosed herein. Each possibility represents a separate embodiment of the present invention.

In another embodiment, the IGF-II P3 transcription-regulating sequence of methods of the present invention comprises an H19 enhancer. In another embodiment, the H19 enhancer comprises a nucleic acid sequence as set forth in a sequence disclosed herein. In another embodiment, the H19 enhancer comprises a fragment of a nucleic acid sequence as set forth in a sequence disclosed herein. In another embodiment, the H19 enhancer consists of a nucleic acid sequence as set forth in a sequence disclosed herein. Each possibility represents a separate embodiment of the present invention.

In another embodiment, the IGF-II P4 transcription-regulating sequence of methods of the present invention is an IGF-II P4 promoter. In another embodiment, the IGF-II P4 promoter comprises a nucleic acid sequence as set forth in a sequence disclosed herein. In another embodiment, the IGF-II P4 promoter comprises a fragment of a nucleic acid sequence as set forth in a sequence disclosed herein. In another embodiment, the IGF-II P4 promoter consists of a nucleic acid sequence as set forth in a sequence disclosed herein. Each possibility represents a separate embodiment of the present invention.

In another embodiment, the IGF-II P4 transcription-regulating sequence of methods of the present invention comprises an H19 enhancer. In another embodiment, the H19 enhancer comprises a nucleic acid sequence as set forth in a sequence disclosed herein. In another embodiment, the H19 enhancer comprises a fragment of a nucleic acid sequence as set forth in a sequence disclosed herein. In another embodiment, the H19 enhancer consists of a nucleic acid sequence as set forth in a sequence disclosed herein. Each possibility represents a separate embodiment of the present invention.

Nucleic Acid Constructs

The term "nucleic acid construct" or "construct" as used herein includes a nucleic acid sequence encoding a cytotoxic or cytostatic gene product (e.g. Diphtheria toxin, DT) according to the present invention, the nucleic acid sequence being operably linked to a promoter and optionally other transcription regulation sequences. In the constructs of the invention, the DT-encoding nucleic acid sequence is operably linked to at least one H19-specific transcription-regulating sequence, P3 transcription-regulating sequence and/or P4 transcription-regulating sequence.

The nucleic acid construct of methods and compositions of the present invention is, in another embodiment, a eukaryotic expression vector. In another embodiment, the nucleic acid construct is a plasmid. In another embodiment, the nucleic acid construct is any other type of expression vector capable of mediating expression in a cancer cell. Each possibility represents a separate embodiment of the present invention.

The phrase "operably linked" refers to a nucleic acid sequence linked a to a transcription control sequence in a manner such that the molecule is able to be expressed when transfected (i.e., transformed, transduced, infected, or transfected) into a host cell. Transcription control sequences are sequences, which control the initiation, elongation, and termination of transcription. Particularly important transcription control sequences are those which control transcription initiation, such as promoter, enhancer, operator and repressor sequences.

In another embodiment, the nucleic acid molecule of methods and compositions of the present invention is a DNA molecule. In another embodiment, the molecule is an RNA molecule. In another embodiment, the molecule is any other type of nucleic acid molecule known in the art. Each possibility represents a separate embodiment of the present invention.

As used herein, the term "vector" refers to a construct, comprising a regulatory sequence operatively linked to a heterologous polynucleotide, that is administered to target cells. The vector can be a viral expression vector, a plasmid or a construct of naked DNA, and, optionally, can include additional sequences required for construction, selection, stability, penetration, etc.

As used herein, the term "variant" refers to a pharmaceutically acceptable salt, homologue, analogue, or fragment of a nucleotide sequence useful for the invention (e.g., vector sequences, transcriptional regulatory sequences, cloned polynucleotides of interest, etc.). Encompassed within the term "variant" are chemically modified natural and synthetic nucleotide molecules. Also encompassed within the term "variant" are conservative substitutions within the nucleotide sequence of the molecule. In addition, non-conservative substitutions within the nucleotide sequence of the molecule are encompassed within the term "variant" as used herein, as long as the sequence substantially retains its required function.

In other embodiments, a "variant", e.g. a "variant" of a cytotoxic or cytostatic gene product, as used herein, refers to a gene recognized in the art to be a product of another version of the same e.g. cytotoxic or cytostatic gene. Gene sequences and their products are routinely classified as being sequences of a particular gene in public databases such as the U.S. National Center for Biotechnology Information's PubMed database; thus, it is readily within the skill of those of average skill in the art to identify variants of e.g. a cytotoxic or cytostatic gene product of the present invention.

In another embodiment, "variants", e.g. of a cytotoxic or cytostatic gene product of the present invention, are at least 70% homologous, or, in other embodiments, share at least 75%, 80%, 82%, 84%, 86%, 88%, 90%, 92%, 94%, 96%, 98% or 99% sequence homology. Each possibility represents a separate embodiment of the present invention.

As used herein the phrase "Diphtheria toxin" (DT or DTX) refers to a Diphtheria toxin or a fragment thereof containing at least an active portion of the Diphtheria toxin, which promotes cell death, or which may work to promote cell death or to otherwise ameliorate a neoplastic disorder in a subject. DT is comprised of two polypeptide fragments, A and B [Zdanovskaia, M. V.; Zdanovsky, A. G.; Yankovsky, N. K. "Diphtheria toxin NAD affinity and ADP ribosyltransferase activity are reduced at tryptophan 153 substitutions for alanine or phenylalanine" *Research in Microbiology,* 2000, 151, 557-562; Bennet, M. J.; Choe, S.; Eisenberg, D. "Refined structure of dimeric diphtheria toxin at 2.0 angstrom resolution." *Protein Science,* 1994, 3, 1444-1463]. Fragment A (DTA) consists of the catalytic domain (C), whereas fragment B is made up of the receptor domain, (R), and the transmembrane domain, (T). The R domain contains a receptor portion which binds to the HB-EGF receptor on the cell surface [Raab, Gerhard; Klagsbrun, Michael "Heparin-binding EGF-like growth factor" *Biochimica et Biophysica Acta (BBA)/Reviews on Cancer* 1997, 1333, F179-F199]. The bound toxin then enters the cytoplasm by endocytosis. The C-terminus hydrophobic series of α-sheets, known as the T domain, then embeds itself into the membrane, causing the N-termininus C domain to be cleaved and translocated into the cytoplasm. Once cleaved, the C domain becomes an active enzyme, catalyzing the creation of ADP-ribose-EF-2 from the protein synthesis translocation peptide EF-2 and NAD+(Hudson T H et al, Quantal entry of diphtheria toxin to the cytosol. J Biol Chem. 1985 Mar. 10; 260(5):2675-80). A single C domain can use a cell's entire supply of EF-2 within hours, bringing protein synthesis to a halt, resulting in cell death. Since the present invention envisages recombinant preferably intracellular expression of the toxin the minimal C domain may be used. According to presently known preferred embodiments of this aspect of the present invention the toxin is diphtheria A chain toxin (DTA).

In another embodiment, the DTA is encoded by a nucleic acid sequence as set forth in SEQ ID NO: 6:

```
(SEQ ID NO: 6)
atggatcctgatgatgttgttgattcttctaaatcttttgtgatggaaaa cttttcttcgtaccacgggactaaacctggttatgtagattccattcaaa aaggtatacaaaagccaaaatctggtacacaaggaaattatgacgatgat tggaaagggttttatagtaccgacaataaatacgacgctgcgggatactc tgtagataatgaaaacccgctctctggaaaagctggaggcgtggtcaaag tgacgtatccaggactgacgaaggttctcgcactaaaagtggataatgcc gaaactattaagaaagagttaggtttaagtctcactgaaccgttgatgga gcaagtcggaacggaagagtttatcaaaaggttcggtgatggtgcttcgc gtgtagtgctcagccttccttcgctgagggagttctagcgttgaatat attaataactgggaacaggcgaaagcgttaagcgtagaacttgagattaa ttttgaaacccgtggaaaacgtggccaagatgcgatgtatgagtatatgg ctcaagcctgtgcaggaaatcgtgtcaggcgatctttgtga.
```

In another embodiment, the DTA-encoding sequence comprises a nucleic acid sequence as set forth in SEQ ID NO: 6. In another embodiment, the DTA-encoding sequence consists of a nucleic acid sequence as set forth in SEQ ID NO: 6. In another embodiment, the DTA-encoding sequence is a homologue of SEQ ID NO: 6. In another embodiment, the DTA-encoding sequence is a variant of SEQ ID NO: 6. In another embodiment, the DTA-encoding sequence is a fragment of SEQ ID NO: 6. In another embodiment, the DTA-encoding sequence is a homologue of a fragment of SEQ ID NO: 6. In another embodiment, the DTA-encoding sequence is a variant of a fragment of SEQ ID NO: 6. Each possibility represents a separate embodiment of the present invention.

In another embodiment, the amino acid sequence of the DTA is as set forth in SEQ ID NO: 7:

```
(SEQ ID NO: 7)
MDPDDVVDSSKSFVMENFSSYHGTKPGYVDSIQKGIQKPKSGTQGNYDDD

WKGFYSTDNKYDAAGYSVDNENPLSGKAGGVVKVTYPGLTKVLALKVDNA

ETIKKELGLSLTEPLMEQVGTEEFIKRFGDGASRVVLSLPFAEGSSSVEY

INNWEQAKALSVELEINFETRGKRGQDAMYEYMAQACAGNRVRRSL.
```

In another embodiment, the DTA comprises a nucleic acid sequence as set forth in SEQ ID NO: 7. In another embodiment, the DTA consists of a nucleic acid sequence as set forth in SEQ ID NO: 7. In another embodiment, the DTA is a homologue of SEQ ID NO: 7. In another embodiment, the DTA is a variant of SEQ ID NO: 7. In another embodiment, the DTA is a fragment of SEQ ID NO: 7. In another embodiment, the DTA is a homologue of a fragment of SEQ ID NO: 7. In another embodiment, the DTA is a variant of a fragment of SEQ ID NO: 7. Each possibility represents a separate embodiment of the present invention.

In another embodiment, the DTA is at least 60% homologous to SEQ ID NO: 7. In another embodiment, the DTA is at least 65% homologous to SEQ ID NO: 7. In another embodiment, the DTA is at least 70% homologous to SEQ ID NO: 7. In another embodiment, the DTA is at least 72% homologous to SEQ ID NO: 7. In another embodiment, the DTA is at least 74% homologous to SEQ ID NO: 7. In another embodiment, the DTA is at least 76% homologous to SEQ ID NO: 7. In another embodiment, the DTA is at least 78% homologous to SEQ ID NO: 7. In another embodiment, the DTA is at least 80% homologous to SEQ ID NO: 7. In another embodiment, the DTA is at least 82% homologous to SEQ ID NO: 7. In another embodiment, the DTA is at least 84% homologous to SEQ ID NO: 7. In another embodiment, the DTA is at least 86% homologous to SEQ ID NO: 7. In another embodiment, the DTA is at least 88% homologous to SEQ ID NO: 7. In another embodiment, the DTA is at least 90% homologous to SEQ ID NO: 7. In another embodiment, the DTA is at least 92% homologous to SEQ ID NO: 7. In another embodiment, the DTA is at least 94% homologous to SEQ ID NO: 7. In another embodiment, the DTA is at least 95% homologous to SEQ ID NO: 7. In another embodiment, the DTA is at least 96% homologous to SEQ ID NO: 7. In another embodiment, the DTA is at least 97% homologous to SEQ ID NO: 7. In another embodiment, the DTA is at least 98% homologous to SEQ ID NO: 7. In another embodiment, the DTA is at least 99% homologous to SEQ ID NO: 7. In another embodiment, the DTA is over 99% homologous to SEQ ID NO: 7. Each possibility represents a separate embodiment of the present invention.

Constructs of the invention contain, on the same construct, multiple expression cassettes, wherein expression of the cytotoxic or cytostatic gene product is directed by at least two of the following three transcription-regulating sequences: an H19, an IGF-II P3, and an IGF-II P4 regulatory sequence, i.e. the gene product-encoding nucleic acid sequence is under transcriptional control of at least two of these sequences. As used herein, the phrase "being under H19 (or IGF-II P3 or IGF-II P4) expression control" (or "transcriptional control") refers to the transcription of the encoded sequence from an H19-specific (or IGF-II P3 or IGF-II P4) promoter sequence, or a sequence derived therefrom, which is operably-linked thereto to regulate their expression pattern (including spatial and temporal expression pattern).

In another embodiment, the regulatory sequence of methods and compositions of the present invention is derived from an H19, IGF-II P3, or IGF-II P4 transcriptional regulatory sequence. As used herein, a description of a regulatory sequence "derived from an H19, IGF-II P3, or IGF-II P4 transcriptional regulatory sequence" refers to a sequence "derived" (see below) from a region of the gene that regulates and/or controls the expression of the H19 or IGF-II coding sequences. As such, a regulatory sequence includes, without limitation, a sequence derived from a promoter or enhancer of the H19, IGF-II P3, or IGF-II P4 sequences.

The term "derived" refers to the fact that a transcriptional regulatory sequence (for example, a promoter or enhancer) can be the complete native regulatory sequence of the gene, a portion of the native regulatory sequence, a chimeric construction of the native regulatory sequence, a combinatorial construction of one or more native regulatory sequences, or a variant of the native regulatory sequence obtained by, for example, deletion, addition or replacement of at least one nucleotide. A variant regulatory sequence can comprise modified nucleotides. The derived sequence preferably demonstrates properties of control/regulation (e.g., increase) of the expression of coding sequences operably linked thereto.

Described herein are H19 regulatory sequences that can be used in the nucleic acid constructs of the invention to direct the specific expression of a cytotoxic or cytostatic gene product. H19 regulatory sequences useful in the present invention include inter alia the upstream H19 promoter region and the downstream H19 enhancer region. In certain embodiments, H19 promoter and enhancer sequences which can be used in accordance with the present invention include, but are not limited to, those described in U.S. Pat. No. 6,306,833, as detailed herein.

The H19-specific transcription-regulating sequence of compositions of the present invention is, in another embodiment, an H19 promoter. In another embodiment, the H19 promoter comprises a nucleic acid sequence as set forth in any one of SEQ ID NOS: 1-2. In another embodiment, the H19 promoter consists of a nucleic acid sequence as set forth in any one of SEQ ID NOS: 1-2.

The nucleotide sequence of one H19 promoter region is shown in SEQ ID NO: 1:

```
                                            (SEQ ID NO: 1)
ctgcagggccccaacaaccctcaccaaaggccaaggtggtgaccgacgga cccacagcggggtggctgggggagtcgaaactcgccagtctccactccac tcccaaccgtggtgccccacgcgggcctgggagagtctgtgaggccgccc accgcttgtcagtagagtgcgcccgcgagccgtaagcacagcccggcaac atgcggtcttcagacaggaaagtggccgcgaatgggaccggggtgcccag cggctgtggggactctgtcctgcggaaaccgcggtgacgagcacaagctc ggtcaactggatgggaatcggcctggggggctggcaccgcgcccaccagg gggtttgcggcacttccctctgcccctcagcaccccaccctactctcca ggaacgtgaggtctgagccgtgatggtggcaggaaggggccctctgtgcc atccgagtccccagggaccccgcagctggccccccagccatgtgcaaagtat gtgcagggcgctggcaggcagggagcagcaggcatggtgtccctgaggg gagacagtggtctgggagggagaggtcctggaccctgagggaggtgatgg ggcaatgctcagccctgtctccggatgccaaaggagggtgcggggaggc cgtctttggagaattccaggatgggtgctgggtgagagagacgtgtgctg gaactgtccagggcggaggtgggccctgcggggggccctcgggagggccct gctctgattggccggcagggcaggggcgggaattctggcgggccacccca gttagaaaaagcccgggctaggaccgagga.
```

In another embodiment, the H19 sequence is a homologue of SEQ ID NO: 1. In another embodiment, the H19 sequence is a variant of SEQ ID NO: 1. In another embodiment, the H19 sequence is a fragment of SEQ ID NO: 1. In another embodiment, the H19 sequence is a homologue of a fragment of SEQ ID NO: 1. In another embodiment, the H19 sequence is a variant of a fragment of SEQ ID NO: 1. Each possibility represents a separate embodiment of the present invention.

In another embodiment, the H19 sequence is at least 60% homologous to SEQ ID NO: 1. In another embodiment, the H19 sequence is at least 65% homologous to SEQ ID NO: 1. In another embodiment, the H19 sequence is at least 70% homologous to SEQ ID NO: 1. In another embodiment, the H19 sequence is at least 72% homologous to SEQ ID NO: 1. In another embodiment, the H19 sequence is at least 74% homologous to SEQ ID NO: 1. In another embodiment, the H19 sequence is at least 76% homologous to SEQ ID NO: 1. In another embodiment, the H19 sequence is at least 78% homologous to SEQ ID NO: 1. In another embodiment, the H19 sequence is at least 80% homologous to SEQ ID NO: 1. In another embodiment, the H19 sequence is at least 82% homologous to SEQ ID NO: 1. In another embodiment, the H19 sequence is at least 84% homologous to SEQ ID NO: 1. In another embodiment, the H19 sequence is at least 86% homologous to SEQ ID NO: 1. In another embodiment, the H19 sequence is at least 88% homologous to SEQ ID NO: 1. In another embodiment, the H19 sequence is at least 90% homologous to SEQ ID NO: 1. In another embodiment, the H19 sequence is at least 92% homologous to SEQ ID NO: 1. In another embodiment, the H19 sequence is at least 94% homologous to SEQ ID NO: 1. In another embodiment, the H19 sequence is at least 95% homologous to SEQ ID NO: 1. In another embodiment, the H19 sequence is at least 96% homologous to SEQ ID NO: 1. In another embodiment, the H19 sequence is at least 97% homologous to SEQ ID NO: 1. In another embodiment, the H19 sequence is at least 98% homologous to SEQ ID NO: 1. In another embodiment, the H19 sequence is at least 99% homologous to SEQ ID NO: 1. In another embodiment, the H19 sequence is over 99% homologous to SEQ ID NO: 1. Each possibility represents a separate embodiment of the present invention.

This 831 nucleotide sequence extends from −837 to −7 nucleotides from the cap site (as described in Brannan et al. 1990). A consensus TATA sequence occurs at nucleotides −27 to −35. Two consensus AP2 binding sites (8/9 matches) occur at approximately −500 and −40 nucleotides upstream from the initiation of transcription. When placed upstream of the coding region for a heterologous gene, approximately 831 base pairs of the regulatory region is sufficient to direct expression of the operatively linked heterologous gene in cancer cells that also express endogenous H19. In another embodiment, an additional H19 promoter region between nucleotides −819 to +14 (SEQ ID NO: 2) is also sufficient to direct expression of the operatively linked heterologous gene in cancer cells:

gacaaccctcaccaagggcaaggtggtgaccgacggac-ccacagcggggtggctgggggagtcgaaactcgccagtctc cactccactc-ccaaccgtggtgccccacgcgggcctgggagagtctgtgaggccgcccac-cgcttgtcagtagagtgcgcccgcgagcc gtaagcacagcccggcaacatgcggtcttcagacaggaaagtggccgc-gaatgggaccggggtgcccagcggctgtggggactctgtc ctgcggaaac-cgcggtgacgagcacaagctcggtcaactggatgggaatcggc-ctggggggctggcaccgcgcccaccagggggttt geggcacttccctctgcccctcagcaccccaccctactctccaggaacgtgagt-tctgagccgtgatggtggcaggaaggggccctctgt gccatccgagteccca-gggacccgcagctggccccccagccatgtgcaaagtatgtgcagggcgctggca-ggcagggagcagcaggca tggtgtccctgaggggagacagtggtctgggagggagaagtctggccct-gagggaggtgatggggcaatgctcagccctgtctccgg atgc-caaaggaggggtgeggggaggccgtcifiggagaattccaggatgggt-gctgggtgagagagacgtgtgctggaactgtccaggg cggaggtgggccctgcgggggccctcggggagggccctgctctgattggccg-gcagggcagggggegggaattctgggeggggccacc ccagttagaaaaagc-ccgggctaggaccgaggagcagggtgagggag (SEQ ID NO: 2). In another embodiment, the H19 sequence is a homologue of SEQ ID NO: 2. In another embodiment, the H19 sequence is a variant of SEQ ID NO: 2. In another embodiment, the H19 sequence is a fragment of SEQ ID NO: 2. In another embodiment, the H19 sequence is a homologue of a fragment of SEQ ID NO: 2. In another embodiment, the H19 sequence is a variant of a fragment of SEQ ID NO: 2. Each possibility represents a separate embodiment of the present invention.

In another embodiment, the H19 sequence is at least 60% homologous to SEQ ID NO: 2. In another embodiment, the H19 sequence is at least 65% homologous to SEQ ID NO: 2. In another embodiment, the H19 sequence is at least 70% homologous to SEQ ID NO: 2. In another embodiment, the H19 sequence is at least 72% homologous to SEQ ID NO: 2. In another embodiment, the H19 sequence is at least 74% homologous to SEQ ID NO: 2. In another embodiment, the H19 sequence is at least 76% homologous to SEQ ID NO: 2. In another embodiment, the H19 sequence is at least 78% homologous to SEQ ID NO: 2. In another embodiment, the H19 sequence is at least 80% homologous to SEQ ID NO: 2. In another embodiment, the H19 sequence is at least 82% homologous to SEQ ID NO: 2. In another embodiment, the H19 sequence is at least 84% homologous to SEQ ID NO: 2. In another embodiment, the H19 sequence is at least 86% homologous to SEQ ID NO: 2. In another embodiment, the H19 sequence is at least 88% homologous to SEQ ID NO: 2. In another embodiment, the H19 sequence is at least 90% homologous to SEQ ID NO: 2. In another embodiment, the H19 sequence is at least 92% homologous to SEQ ID NO: 2. In another embodiment, the H19 sequence is at least 94% homologous to SEQ ID NO: 2. In another embodiment, the H19 sequence is at least 95% homologous to SEQ ID NO: 2. In another embodiment, the H19 sequence is at least 96% homologous to SEQ ID NO: 2. In another embodiment, the H19 sequence is at least 97% homologous to SEQ ID NO: 2. In another embodiment, the H19 sequence is at least 98% homologous to SEQ ID NO: 2. In another embodiment, the H19 sequence is at least 99% homologous to SEQ ID NO: 2. In another embodiment, the H19 sequence is over 99% homologous to SEQ ID NO: 2. Each possibility represents a separate embodiment of the present invention.

The downstream enhancer region of the human H19 gene can optionally be added to an H19 promoter/DTA construct of the present invention in order to provide enhanced levels of cell-specific expression of the DTA molecule. As expected from an enhancer sequence, the downstream enhancer is able to exert its effect when placed in either reverse or direct orientation (relative to the orientation of the H19 enhancer in the endogenous H19 gene) downstream from the coding region of a heterologous gene under the control of the H19 promoter.

In another embodiment, the H19 enhancer sequence comprises the sequence:

(SEQ ID NO: 3)
caaggacatggaatttcggaccttctgtcccaccctctctgctgagcct aggaacctctgagcagcaggaaggccttgggtctagagcctagaaatgga ccccacgtccacctgcccagcctagaccccagcattgaagggtggtca gacttcctgtgagaggaagccactaagcgggatggacaccatcgccact ccacccggccctgcccagccctgcccagtccagcccagtccagcccagcc ctgcccttccagcccctgcccagcccagctcatccctgccctacccagcc cagccctgtcctgccctgcccagcccagcccagcccagccctgcctgcc ctgccctgcccttccagcccctgaccttcccagccctgcccagcccagct catccctgccctacccagctcagccctgccctgccctgccctgccctgcc cagccctacccagcccagccctgccctgccctgcccagctcagccctgcc cacccccagcccagcccagcccagcatgcgttctctggatggtgagcacag gcttgaccttagaaagaggctggcaacgagggctgaggccaccaggccac tgggtgctcacgggtcagacaagcccagagcctgctccctgccacgggt cggggctgtcaccgccagcatgctgtggatgtgcatggcctcagggctgc tggctccaggctgcccccgccctggctcccgaggccacccctcttatgcc atgaaccctgtgccacacccacctctgagctgtcccgctcctgccgcct gcaccccctgagcagcccctgtgtgtttcatgggagtcttagcaaggaa ggggagctcgaattcctgcagcccggg.

In another embodiment, the H19 sequence is a homologue of SEQ ID NO: 3. In another embodiment, the H19 sequence is a variant of SEQ ID NO: 3. In another embodiment, the H19 sequence is a fragment of SEQ ID NO: 3. In another embodiment, the H19 sequence is a homologue of a fragment of SEQ ID NO: 3. "Homologue" may refer to any degree of homology disclosed herein. In another embodiment, the H19 sequence is a variant of a fragment of SEQ ID NO: 3. Each possibility represents a separate embodiment of the present invention.

In another embodiment, the H19 enhancer sequence comprises the sequence:

(SEQ ID NO: 4)
ccgggtaccgagctcccaggaagataaatgatttcctcctctctagagat gggggtgggatctgagcactcagagccaagggcgcagtgggtccgggcgg gggcctcctcggccctcccaacatgggggccaggaggtcagcccctcaa cctggaccccggctgggtctcagggaatggtctcccccagtggcccagct tgcttgtgttttcagatgggtgtgcatgggtgtgtgtgtgtgtgtgtgtg tgtgtgtgtgtgtgtgtgtgtgtgatgcctgacaagcccagagagccaa agacctgagtggagatcttgtgacttctcaaaaggggattggaaggttc gagaaagagctgtggtcagccttgctctcccttaaggctgtggtaaccac actaggcatagcataggcctgcgcccccgtccctccttccctcctccgcgc ctctcctttctctttctccccctctaccccgctccctggcctgctcctg gtgacaccgttggcccccttccagggctgagggaagccagcgggggcccc ttcctgaaagcccacctgcaggccggcttgctgggaaggggctgctctcg cagaggctcccgcccgccctgcagccgtttcctggaagcagtcgctgtgg gtattctgttccttgtcagcactgtgcttgcaaagaaagcagacactgtg ctccttgtccttagggagccccgctccatcacccaacacctggctggaca caggcgggaggccgggtccgcggggagcggcgcggggctggggccggacc attaaacacacgggcgccaggcactgcaggctcctcctcctcctcctg cccagcgcctctgctcacaggcacgtgccaagcccctaggccaggaggcc agcagtgggtgcagaacaagctcctgggaaggggtgcagggcggacccc cggggagaagggctggcagggctgtggggacgctgaccgtgggcccac gttgcagaaaactggntgcctggctggaagatgggggagatgccaagcct ctgaggcagcacgagcagggtgcatggaggccggggcgcggggaggctgc

```
actgcagcatgcaccccaaagcccanagggagtggagaccaggccctgga
atcgagaagtagaaaggcggcttggaggcctcggaaccggctgacctcca
acagagtgggtctccagcctggctctgccctgccgcaggtccctcccct
cattaccaggcctagagcctccagtcccggtggccccagcccgagggtg
aacggcctcaccctgggtcgtgggacagagggcacgttcatcaagagtgg
ctcccaaggacacgtggctgtttgcagttcacaggaagcattcgagata
aggagcttgttttcccagtgggcacggagccagcagggggctgtggggc
agcccagggtgcaaggccaggctgtgggctgcagctgccttggccccca
ctcccaggcctttgcgggaggtgggaggcgggaggcggcagctgcacagt
ggccccaggcgaggctctcagcccagtcgctctccgggtgggcagccca
agagggtctggctgagcctcccacatctgggactccatcacccaacaact
taattaaggctgaatttcacgtgtcctgtgacttgggtagacaaagcccc
tgtccaaaggggcagccagcctaaggcagtggggacggcgtgggtggcgg
gcgacggggagatggacaacaggaccgagggtgtgcgggcgatggggga
gatggacaacaggaccgagggtgtgcgggcgatggggagatggacaaca
ggaccgagggtgtgcgggacacgcatgtcactcatgcacgccaatggggg
gcgtggaggctggggagcagacagactgggctgggctgggcgggaagga
cgggcagatg.
```

In another embodiment, the H19 sequence is a homologue of SEQ ID NO: 4. In another embodiment, the H19 sequence is a variant of SEQ ID NO: 4. In another embodiment, the H19 sequence is a fragment of SEQ ID NO: 4. In another embodiment, the H19 sequence is a homologue of a fragment of SEQ ID NO: 4. "Homologue" may refer to any degree of homology disclosed herein. In another embodiment, the H19 sequence is a variant of a fragment of SEQ ID NO: 4. Each possibility represents a separate embodiment of the present invention.

In another embodiment, the H19 enhancer sequence comprises the sequence:

```
                                              (SEQ ID NO: 5)
ccgggtaccgagctcccaggaagataaatgatttcctcctctctagagat
gggggtgggatctgagcactcagagccaagggcgcagtgggtccgggcgg
gggccctcctcggccctcccaacatgggggccaggaggtcagcccctcaa
cctggacccggctgggtctcagggaatggtctcccccagtggcccagct
tgcttgtgttttcagatgggtgtgcatgggtgtgtgtgtgtgtgtgtg
tgtgtgtgtgtgtgtgtgtgtgatgcctgacaagccccagagagccaa
agacctgagtggagatcttgtgacttctcaaaaggggattggaaggttc
gagaaagagctgtggtcagccttgctctcccttaaggctgtggtaaccac
actaggcatagcataggcctgcgcccgtcctccttccctcctccgcgc
ctctcctttctctttctccccctctaccccgctccctggcctgctcctg
gtgacaccgttggccccttccagggctgagggaagccagcggggcccc
ttcctgaaagcccacctgcaggccggcggcttgctgggaaggggctgctctcg
cagaggctcccgcccgcctgcagccgtttcctgaagcagtcgctgtgg
gtattctgttccttgtcagcactgtgcttgcaaagaaagcagacactgtg
ctccttgtccttagggagccccgctccatcacccaacacctggctggaca
caggcgggaggccgggtccgcggggagcggcgcggggctggggccggacc
attaaacacacacgggcgccaggcactgcaggctcctcctcctcctcctg
cccagcgcctctgctcacaggcacgtgccaagccctaggccaggaggcc
agcagtgggtgcagaacaagctcctgggaaggggtgcagggcggacccc
cggggagaagggctggcagggctgtggggacgctgaccgtgggcccac
gttgcagaaaactggntgcctggctggaagatgggggagatgccaagcct
ctgaggcagcacgagcagggtgcatggaggccggggcgcggggaggctgc
actgcagcatgcaccccaaagcccanagggagtggagaccaggccctgga
atcgagaagtagaaaggcggcttggaggcctcggaaccggctgacctcca
acagagtggggccggccctggaggcaaagaggtgcccggggtccggccct
gcctggggggagctatgtgtcatgggcaagccacaggatatgtagcccgct
ctgagcctatggacccagggcagggctgcaaggcagggcaggggagacag
cacgggggagcaaggagcagagagggggcctcaggctctcccaggaggaa
cattctcccgacaggaggaagagacgcccaggggtgactgtggggagcc
atggtggcagctggggtcgtggcagatgggagagaggctggcgaggtgaa
ggtgcagggtcagggctctggggcccacatgcctgtgggagcaggcagg
cccagggctctccgccactccccactcccgcttggctcataggctgggcc
caagggtggggtgggatgagcaggagatggggcccaggggggcaagcaggg
ccccaaagacatttagaaaaaccggtttatgcaggcagcattcagagcag
gcggcgtgcgtggcgggggccctgggagcacagagaggcacacgtagggc
ccccgaggggctccccattggccggcagtgacatcacccctgtgtcaaca
gtgatgtctgcagctccggccagccagggtttatggagcgagacccagcc
cggcctgggccctcactccccaggcccacacactagccactgttcaggg
tccggggtggcggcatggcctgggggtcctggcaccgctgctcctctgcc
caccctaacttcccggcatcgcggctgcccctctgagcgtccccaacca
gtaagtgtggggcccagcaggcctgccgtcctcctcctcttcccctctag
agagaaacgtggaggtcctggggctgggggcgctcatagccctgtgacac
aggtgcatgggtcaggggtcccagaatggcccctgggaaggacctcagc
tgggccggcggctctaggcttcaggggtctgtctgcacaggggntagccc
ctcccagacctctgtgaagccagtacgggcctcccctccctgccccgtgc
tctgtccggtgcttcctggactgcactgcgggccactggtgagagggtgg
acagggaagggccgccgtggtgcctgttcctgcccacctggctgtgtggt
ccctccaagtagggacaacccttctgagggcttgggggcaccctgggt
tgccagggcctcccagagccctgtgagccctggggggtctggcctgatg
cccccctccacgtccagggccggctgtggcccagaacccagcttcccag
caggccggtgtgcggtggtgacccaggagaggcctcgcctccactgaggg
gccaccgacctctgtcagaccacagagaccccccaaggagtctgaaggctg
gagaccggggctgggaccaggtgggactttcccacggagccgtccccag
gcccagctggggacacgtcccccttctctccagacacaccctgcctgcca
```

-continued
```
ccaggacacaccggcctgttgggggtctcttttaagtgcttgccactctg
aggtgactgtccctttccaaagaggtttctggggcccaggtgggatgcgt
cggcctgagcaggaggatctgggccgccaggggctggggactgtctcctg
gggaaggaagcgcctgggagcgtgtgtgctgacccaggaccatccaggga
ggcccgtctgtggggcaagcgggaagggagcggctggagaggcttggccg
cccccgccctgcctcccattccttagctccatgcctgtcaacctctgtca
cccagtgagtgatgtccaggggccctggaaaggtcacagcatgtttgagc
ggggtgagagagaggggaaaggcggggcggggaaaagtacgtggaggaa
gctttaggcccaaggaaggagacagggttctgggagggagggagccactg
gggccgccgggaaggtccctgcttgctgctgccacccagaaccctcgcct
cttagctagcccccgcagcccagcctttctggcntgtggccctctcccc
catcccaggtgtcctgtgcaaccaggccttggacccaaaccctcctgcc
ccctcctctccctcctcaccctcccaatgcagtggtctccagcctggctc
tgccctgccgcaggtcccctcccctcattaccaggcctagagcctccagt
cccggtggccccagcccgagggtgaacggcctcaccctgggtcgtggga
cagagggcacgttcatcaagagtggctcccaagggacacgtggctgtttg
cagttcacaggaagcattcgagataaggagcttgttttcccagtgggcac
ggagccagcaggggggctgtggggcagcccagggtgcaaggccaggctgt
ggggctgcagctgccttgggcccactcccaggcctttgcgggaggtggg
aggcgggaggcggcagctgcacagtggcccaggcgaggctctcagcccc
agtcgctctccgggtgggcagcccaagagggtctggctgagcctccaca
tctgggactccatcacccaacaacttaattaaggctgaatttcacgtgtc
```
-continued
```
ctgtgacttgggtagacaaagcccctgtccaaaggggcagccagcctaag
gcagtggggacggcgtgggtggcgggcgacggggagatggacaacagga
ccgagggtgtgcgggcgatgggggagatggacaacaggaccgagggtgtg
cgggcgatgggggagatggacaacaggaccgagggtgtgcgggacacgca
tgtcactcatgcacgccaatgggggcgtgggaggctggggagcagacag
actgggctgggctgggcgggaaggacgggcagatg.
```

In another embodiment, the H19 sequence is a homologue of SEQ ID NO: 5. In another embodiment, the H19 sequence is a variant of SEQ ID NO: 5. In another embodiment, the H19 sequence is a fragment of SEQ ID NO: 5. In another embodiment, the H19 sequence is a homologue of a fragment of SEQ ID NO: 5. "Homologue" may refer to any degree of homology disclosed herein. In another embodiment, the H19 sequence is a variant of a fragment of SEQ ID NO: 5. Each possibility represents a separate embodiment of the present invention.

In another embodiment, fragments of this enhancer, e.g. fragments of the sequences set forth in any one of SEQ ID NOS: 3-5 may also be used to facilitate gene expression. In one embodiment, the enhancer consists of a sequence as set forth in any one of SEQ ID NOs: 3-5.

Further described herein are IGF-II P3 regulatory sequences that can be used in the nucleic acid constructs of the invention to direct the specific expression of a cytotoxic or cytostatic gene product. In another embodiment, the IGF-II P3 transcription-regulating sequence of compositions of the present invention is an IGF-II P3 promoter. In another embodiment, the P3 promoter corresponds to nucleotide sequence −1229 to +140 of the IGF-II gene (one example of an IGF-II gene sequence is found in Chromosome 11, NC 000011.8, base pairs 2106926 . . . 2116578).

In another embodiment, an IGF-II gene sequence of methods and compositions of the present invention is:

(SEQ ID NO: 10)
```
cccaaccccgcgcacagcgggcactggtttcgggcctctctgtctcctacgaagtccgtagagcaactcggatttgggaaatttc
tctctagcgttgcccaaacacacttgggtcggccgcgcgccctcaggacgtggacagggagggcttccccgtgtccaggaaagcgaccg
ggcattgccccagtctcccccaaatttgggcattgtcccgggtcttccaacggactgggcgnngctcccggacactgaggactggccc
cggggtctcgctcaccttcagcagcgtccaccgcctgccacagagcgttcgatcgctcgctgcctgagctcctggtgcgcccgcggacgc
agcctccagcttcgcggtgagctccccgccgcgccgatcccctccgcctctgcgccctgaccggctctcggcccgcatctgctgctgtcc
cgccggtgctggcgctcgtccgctgcgccggggaggccggcgtggggcgcgggacacggctgcggacttgcggctgcgctgcgctcg
ctcctgctgggcgccccgaaatccgcgccactttcgtttgctcattgcaaagatctcatttgtggggaaagcggctggagggtcccaaagtg
gggcgggcagggggctggggcgagggacgcggaggagaggcgctcccgccgggcggtaaagtgcctctagcccgcgggcctagga
ctccgccgggagggcgcgcggagngcgaagtgattgatggcggaagcggggggggcaagggggcagggggggcgcgggattccgc
cggcgacccctccccttggctaggcttaggcggcggggggctggcggggtgcgggatttttgtgcgtggtttttgacttggtaaaaatcaca
gtgctttcttacatcgttcaaactctccaggagatggtttccccagaccccaaattatcgtggtggcccccgagaccgaactcgcgtctatgc
aagtccaacgcactgaggacggggtaaccattatccagatattttgggtgggccgcaaaggcgagctacttagacgcacccggtgagct
cggccatgcaggtaggatttgagctgtgtttcccgccctgatcctctctcctctggcggccggagcctccgtaggctccaagcctggcccag
attcggcggcgcagccggccttccgcgcgtccgcacctagcgggggctccggggctccggcgcggcaccggggggcgctcgggatct
ggctgaggctccaaggcccgcgtggccggctcctcctgctggggcaggtggcggctgcgcgcccccgcccgagcccaggggcccctc
agccgcaacaaccagcaaggaccccccgactcagcccaagccacctgcatctgcactcagacggggcgcacccgcagtgcagcctc
```

-continued

```
ctggtggggcgctgggagcccgcctgccctgcctgcccggagacccagctcacgagcacaggccgcccgggcaccccagaaacc cgggatggggcccctgaattctctaggacgggcattcagcatggccttggcgctctgcggctccctgcccccacccagcctcgcccccg cgcaccccagccctgcgaccgccgccccccccccggggccccagggcccagcccgcaccccccgccccgctcttggctcgg gttgcggggcgggccgggggcggggcgagggctccgcgggcgccattggcgcgggcgcgaggccagcggcccgcgcggccc tgggccgcggctggcgcgactataagagccgggcgtgggcgcccgcagttcgcctgctctccggcggagctgcgtgaggcccggccg gccccggccccccccttccggccgcccccgcctcctggcccacgcctgcccgcgctctgcccaccagcgcctccatcgggcaaggcgg ccccgcgtcgacgccgcccgctgcctcgctgctgactcccgtcccgggcgccgtccgcggggtcgcgctccgccgggcctgcggattc cccgccgcctcctcttcatctacctcaactcccccatcccgcttcgcccgaggaggcggttcccccgcaggcagtccggctcgcagg ccgccggcgttgtcaccccccccgcgctccccctccagccctccccggcgcgcagcctcgggccgctccccttccgcgctgcgtccc ggagcggccccggtgccgccaccgcctgtccccctcccgaggcccgggctcgcgacggcagagggctccgtcggcccaaaccgagct gggcgcccgcggtccgggtgcagcctccactccgccccccagtcaccgcctcccccggcccctcgacgtggcgcccttccctccgcttct ctgtgctccccgcgcccctcttggcgtctggccccggccccgctctttctcccgcaaccttcccttcgctccctcccgtcccccccagctcct agcctccgactccctccccccctcacgcccgccctctcgccttcgccgaaccaaagtggattaattacacgctttctgtttctctccgtgctgtt ctctcccgctgtgcgcctgcccgcctctcgctgtcctctctcccccctcgccctctcttcggccccccccttttcacgttcactctgtctctcccact atctctgcccccctctatccttgatacaacagctgacctcatttcccgatacctttttcccccccgaaaagtacaacatctggcccgccccagcc cgaagacagcccgtcctccctggacaatcagacgaattctccccccccccccaaaaaaaagccatccccccgctctgccccgtcgcacatt cggccccgcgactcggccagagcggcgctggcagaggagtgtccggcaggagggccaacgcccgctgttcggtttgcgacacgcag caggaggtgggcggcagcgtcgccggcttccaggtaagcggcgtgtgcgggccgggccggggccggggctggggcggcgcggg cttgcggcgacgcccggcccttcctccgcccgctcccggcccggggcctgcggggctcggcggggcggctgagccggggggagga ggaggaggaggaggacggacggctgcgggtcccgttccctgcgcggagcccgcgctaccnnnnnnnnnnnnnnnnnnnn nnnnngacgtccccgctgaaggggtcggtctgtgggtgcaggggtgccgcctcacatgtgtgattcgtgccttgcgggccctggcctc cggggtgctgggtaacgaggaggggcgcggagccgcagaagcccaccctggtgtcgttgacgccggtgccagcgagaccgcgagag gaagacggggcgggcggggccaggatggagaggggccgagttggcaggagtcatggcagacgccacactcgcgaccatctccccc acacccctctggcctctgtccgcaacatttccaaacaggagtcccgggagaggggagagggctgctggtctgaggctaagaagggca gagccttcgacccggagagaggccgcggccgcctgccccagtggcaacgttgaagttttccatacaacggaggtcgggaaggagaccc cccccccccttcactgccctgtgaagagatgagccggggtgcaggatgggagcccatggcacttcgctacgggatgtccagggctccg gttggggtgcaggagagaagagactggctgggaggagggagagggcgggagcaaaggcgcgggggtgtggtcagagggagagg ggtgggggttaggtggagcccgggctgggaggagtcggctcacacataaaactgaggcactgaccagcctgcaaactggatattagcttc tcctgtgaaagagacttccagcttcctcctcctcctcttcctcctcctcctcctgccccagcgagccttctgctgagctgtaggtaaccagggct gtggagtgaaggaccccgctgccatcccactccagcctgaggcagggcagcaggggcacggcccacgcctgggcctcgggccctg cagccgccagcccgctgcctctcggacagcaccccctccctcttttcctctgccctgccccacctggcgtctctgctccctcacctgct ccttccattctgttccttcccttcggcccctccttgcccagctcaggacttttcctgggccctcacctgctccgcaccgctgcatgcttcctgtc ctgctttctgccggtccctgacccgacctccaagcgcagagtggtggggcttgttgcggaagcgcggcgagggctagagtggccagc tggcggagtgtgctcttagaatttggaaggggtggcagagggggcggtgagaggactggccagggtccgccatgtcaaggagatgac caaggaggctttcagatcctcggcgcagtcgcccactagtctttagagagggcatgcaaagttgtgcttctgtcccactgcctgctcagtcgc tcacataatttattgcatcaaaaactcccctgggtctgcggagcaaggctggggctgcccgcctggagggtaccaccttctgcaggagcag ggccaacttgctgtggtggctcccggcctccaccccgagtgggtaacccggccctgtgacctgcagcctgtggaggggtgtgcctaa gactggcctccccttccagattgtagtctggggaacctggtgtcggacttcccaggtggcctgagctggtctcttcagctccacggggagag tttggtagcgcaaatagggagatgttctgggcccctggccttactggttcgatttgaggcctggaaaggaggctctgggcgtgtgtgtgtg tttgggggtaccaaggcagactggagttggagaactgggtgactgggaaaacaaggtttctagagcatgggtggcgtggttgtgttaacc attggagtcgcttgacccaggcctggctcagctgcagactggaaaggtggaaaagccaggggagggggcggggctggcccagcagga
```

-continued

```
ctggcctgctgctttgagggcgatggtcctcctggaccccccctgctcagctgggggttgtggggaggaaggggctggtcctccttggagc
acatgctctgtaggggtggggctgtctgccatcttggcggcgctggaggcctgagaagtggcgatgtaacgctgggctggccctgccccc
atggtgtcataggacggaggcaggtcgggtgtccagcctgggcccctgcagctgtggatgccgctgagctcctgcaataatgaccgtgca
gatggtcaccccctcgtgtaaaattactagtgcttcttgcaaatggaaggaactgggccttttctgtgtgcttctggacgcttcattctgcacatgg
ccctgcgccctcacctcggcattatgacctgtgtgttactttttgtaataaaaataatgtttataggaaagccgtgctttcaattttcaactgaatttgt
aggttggcaaatttggtttgggaggggcacctctggcctggggcttggcctggctgccccgctcacgccacttctctcccgccccagaca
ccaatgggaatcccaatggggaagtcgatgctggtgcttctcaccttcttggccttcgcctcgtgctgcattgctgcttaccgcccagtgaga
ccctgtgcggcggggagctggtggacaccctccagttcgtctgtggggaccgcggcttctacttcagtaagtagcagggagggcttcctc
agacctggtcaggcccctagagtgaccggtgaggatctcccatcctcaagccaggggagcacactcctaggtcagcagcccagccgctt
gctctgagactttgaccttcccgccgcgtttctgagcacgtgcggtgtcccaggcatccacaccagctgcctttcccatcacacgcctcctt
cgaagggtgggccagaggtgcccctagacgtcaggggcatctacaggggtctccctgggcatcagaatttctgttgggggccgtgagg
ctcctgctcctgaggcaccgcacgcctagtgcagggcttcaggctctggaggaagagcctgcctttcttcctgcaccttttggacattttgaca
agggacgtgcgttcggtgaatgatcagaattaaaatcaataaagtgatttatataattaaaatcaataagacaagtgcagttggtgggtggcag
gggtgagcggtgcatgcgcctccttgggccccaaggctgccgtgggggtgcccacctgctgacctcaaggacgcttcagcctttcctcat
gtttctctcttggttctccagcctgggggctggcaggtgggtgcatggcccattgtccttgagaccccaccccagataggggggctgggtg
gatgcagaggcaggcatggtgcctgggcatgcctgatggggcagggagggccgctccttactggcagaggccgcaacttattccacc
tgacactcaccacgtgacatctttaccaccactgcttactcacgctgtgaaatgggctcacaggatgcaaatgcacttcaaagcttctctctga
aaagttcctgctgcttgactctggaagcccctgcccgccctggcctctcctgtgccctctctcttgcctgcccatttggggggtaggaagtggc
actgcagggcctggtgccagccagtccttgcccagggagaagcttccctgcaccaggctttcctgagaggagggagggccaagcccc
cacttgggggcccccgtgacggggcctcctgctccctcctccggctgatggcacctgcccttggcaccccaaggtggagccccagcga
ccttcccctttccagctgagcattgctgtgggggagagggggaagacgggaggaaagaagggagtggttccatcacgcctcctcagcctc
ctctcctcccgtcttctcctctcctgcccttgtctccctgtctcagcagctccaggggtggtgtgggcccctccagcctcccaggtggtgccag
gccagagtccaagctcacggacagcagtcctcctgtgggggcccctgaactgggctcacatcccacacattttccaaaccactcccattgtga
gcctttggtcctggtggtgtccctctggttgtgggaccaagagcttgtgcccatttttcatctgaggaaggaggcagcagaagtcacgggctg
gtctgggccccactcacctcccctctcacctctcttcttcctgggacgcctctgcctgccggctctcacttccctcccctgaccgcagggtgg
ctgcgnccttccagggcctggcctgagggcagggtggtttgctgggggttcggcctccggggctgggggtcggtgcggtgctaacac
ggctctctctgtgctgtgggacttccaggcaggcccgcaagccgtgtgagccgtcgcagccgtggcatcgttgaggagtgctgtttccgca
gctgtgacctggccctcctggagacgtactgtgctaccccgccaagtccgagagggacgtgtcgacccctccgaccgtgcttccggtga
gggtcctgggcccctttcccactctctagagacagagaaataggctccgggcgcccagcgtttcctgtggcctctgggacctcttggccag
ggacaaggacccgtgacttccttgcttgctgtgtggcccgggagcagctcagacgctggctccttctgtccctctgcccgtggacattagctc
aagtcactgatcagtcacaggggtggcctgtcaggtcaggcgggcggctcaggcggaagagcgtggagagcaggcacctgctgacca
gccccttcccctcccaggacaacttccccgagataccctgggcaagttcttccaatatgacacctggaagcagtccacccagcgcctgcg
caggggcctgcctgccctcctgcgtgcccgccggggtcacgtgctcgccaaggagctcgaggcgttcagggaggccaaacgtcaccgt
cccctgattgctctacccacccaagacccgcccacggggggcgcccccccagagatggccagcaatcggaagtgagcaaaactgccgc
aagtctgcagcccggcgccaccatcctgcagcctcctcctgaccacggacgtttccatcaggttccatcccgaaaatctctcggttccacgtc
ccctggggcttctcctgacccagtccccgtgcccgcctccccgaaacaggctactctcctcggcccctccatcgggctgaggaagcac
agcagcatcttcaaacatgtacaaaatcgattggattaaacaccatcacataccctcccccaaattatccccaattatccccacacataaaa
```

```
aatcaaaacattaaactaaccccttcccccccccacaacaaccctcttaaaactaattggcttttagaaacacccacaaaagctcaga aattggctttaaaaaaaacaaccaccaaaaaaatcaattggctaaaaaaaaaagtattaaaaacgaattggctgagaaacaattggcaaa ataaaggaatttggcactcccaccccctctttctcttctccttggactttgagtcaaattggcctggacttgagtccctgaaccagcaaaga gaaaagaagggcccagaaatcacaggtgggcacgtcgcgtctaccgccatctcccttctcacgggaattttcagggtaaact.
```

In another embodiment, the IGF-II sequence comprises a nucleic acid sequence as set forth in SEQ ID NO: 10. In another embodiment, the nucleic acid sequence of the IGF-II sequence consists of SEQ ID NO: 10. In another embodiment, the IGF-II sequence is homologous to SEQ ID NO: 10. In another embodiment, the IGF-II sequence is a variant of SEQ ID NO: 10. In another embodiment, the IGF-II sequence is a fragment of SEQ ID NO: 10. In another embodiment, the IGF-II sequence is a homologue of a fragment of SEQ ID NO: 10. In another embodiment, the IGF-II sequence is a variant of a fragment of SEQ ID NO: 10. Each possibility represents a separate embodiment of the present invention.

The IGF-II P3 transcription-regulating sequence of methods of the present invention is, in another embodiment, an IGF-II P3 promoter (also referred to herein as "P3"). In another embodiment, the sequence of the P3 promoter is:

```
gagctcggccatgcaggtaggatttgagctgtgtttcccgccctgatcctctctcctctggcggccggagcctccgtaggctcca agcctggcccagattcggcggcgcagccggccttccgcgcgtccgcacctagcgggggctccggggctccggcgcggcaccggggg gcgctcgggatctggctgaggctccaaggcccgcgtggccggctcctcctgctggggcaggtggcggctgcgcgccccgcccgagcc caggggcccctcagccgcaacaaccagcaaggaccccccgactcagccccaagccacctgcatctgcactcagacggggcgcaccc gcagtgcagcctcctggtggggcgctgggagcccgcctgcccctgcctgcccggagacccagctcacgagcacaggccgcccggg caccccagaaacccgggatggggcccctgaattctctaggacgggcattcagcatggccttggcgctctgcggctccctgcccccaccc agcctcgccccgcgcaccccccagccctgcgaccgccgcccccccccgggccccagggcccagcccgcaccccccgccc cgctcttggctcggttgcgggggcgggccggggcggggcgagggctccgcgggcgcccattggcgcgggcgcgaggccagcgg ccccgcgcggccctgggccgcggctggcgcgactataagagccgggcgtgggcgcccgcagttcgcctgctctccggcggagctgcg tgaggcccggccggccccggcccccccctccggccgccccccgcctcctggcccacgcctgcccgcgctctgcccaccagcgcctcca tcgggcaaggcggccccgcgtcgac (SEQ ID NO: 8; the first 6 base pairs [bp] are an added
restriction site that can optionally be used in subcloning).
```

In another embodiment, the IGF-II P3 promoter comprises a nucleic acid sequence as set forth in SEQ ID NO: 8. In another embodiment, the nucleic acid sequence of the IGF-II P3 promoter consists of SEQ ID NO: 8. In another embodiment, the IGF-II P3 promoter is homologous to SEQ ID NO: 8. In another embodiment, the IGF-II P3 promoter is a variant of SEQ ID NO: 8. In another embodiment, the IGF-II P3 promoter is a fragment of SEQ ID NO: 8. In another embodiment, the IGF-II P3 promoter is a homologue of a fragment of SEQ ID NO: 8. In another embodiment, the IGF-II P3 promoter is a variant of a fragment of SEQ ID NO: 8. Each possibility represents a separate embodiment of the present invention.

In another embodiment, the sequence of the P3 promoter is:

```
                                                                        (SEQ ID NO: 12)
gacgggggtgggcggggccaggatggagaggggccgagttggcaggagtcatggcagacgccacattcgcgacactctcc ccacacccctctggctctgtccgcaacatttccaaacaggagtcccggagaggggagagggggctgctggtctgaggctaagaagg gcagagccttcgacccggagagaggccgcggcccctgcccagtgggcagcgtggaagtttccatacaaggaggtgggaaggagaccc ccccccccttcactgccctgtgcagagatgagccgggggtgcaggatgggagcccatggcacttcgctacgggatggtcagggctccc ggttgggggtgcaggagagaagagactggctgggaggagggagagggcgggagcaaaggcgcggggggagtggtcagcagggaga ggggtgggggtagggtggagcccgggctgggaggagtcggctcacacataaaagctgaggcactgaccagcctgcaaactggacat
```

-continued

```
tagcttctcctgtgaaagagacttccagatcctcctcctcctcttcctcctcctcctgccccagcgagccttctgctgagctgtaggt aaccagggccgtggatgagactctc.
```

In another embodiment, the IGF-II P3 promoter comprises a nucleic acid sequence as set forth in SEQ ID NO: 12. In another embodiment, the nucleic acid sequence of the IGF-II P3 promoter consists of SEQ ID NO: 12. In another embodiment, the IGF-II P3 promoter is homologous to SEQ ID NO: 12. In another embodiment, the IGF-II P3 promoter is a variant of SEQ ID NO: 12. In another embodiment, the IGF-II P3 promoter is a fragment of SEQ ID NO: 12. In another embodiment, the IGF-II P3 promoter is a homologue of a fragment of SEQ ID NO: 12. In another embodiment, the IGF-II P3 promoter is a variant of a fragment of SEQ ID NO: 12. Each possibility represents a separate embodiment of the present invention.

In another embodiment, the IGF-II P3 promoter comprises an Sp1-binding site thereof. In another embodiment, the Sp1-binding site is residues 10-18 of SEQ ID NO: 12. In another embodiment, the Sp1-binding site is residues 388-399 of SEQ ID NO: 12. In another embodiment, the Sp1-binding site is another Sp1-binding site found in SEQ ID NO: 8 or SEQ ID NO: 12. In another embodiment, the IGF-II P3 promoter comprises a TATA box. In another embodiment, the TATA box is residues 476-482 of SEQ ID NO: 12. In another embodiment, the TATA box is another TATA box found in SEQ ID NO: 8 or SEQ ID NO: 12. Each possibility represents a separate embodiment of the present invention.

In another embodiment, the IGF-II P3 sequence is at least 60% homologous to a sequence selected from SEQ ID NO: 8, SEQ ID NO: 12, and SEQ ID NO: 17. In another embodiment, the IGF-II P3 sequence is at least 65% homologous to SEQ ID NO: 8 or SEQ ID NO: 12. In another embodiment, the IGF-II P3 sequence is at least 70% homologous to SEQ ID NO: 8 or SEQ ID NO: 12. In another embodiment, the IGF-II P3 sequence is at least 72% homologous to SEQ ID NO: 8 or SEQ ID NO: 12. In another embodiment, the IGF-II P3 sequence is at least 74% homologous to SEQ ID NO: 8 or SEQ ID NO: 12. In another embodiment, the IGF-II P3 sequence is at least 76% homologous to SEQ ID NO: 8 or SEQ ID NO: 12. In another embodiment, the IGF-II P3 sequence is at least 78% homologous to SEQ ID NO: 8 or SEQ ID NO: 12. In another embodiment, the IGF-II P3 sequence is at least 80% homologous to SEQ ID NO: 8 or SEQ ID NO: 12. In another embodiment, the IGF-II P3 sequence is at least 82% homologous to SEQ ID NO: 8 or SEQ ID NO: 12. In another embodiment, the IGF-II P3 sequence is at least 84% homologous to SEQ ID NO: 8 or SEQ ID NO: 12. In another embodiment, the IGF-II P3 sequence is at least 86% homologous to SEQ ID NO: 8 or SEQ ID NO: 12. In another embodiment, the IGF-II P3 sequence is at least 88% homologous to SEQ ID NO: 8 or SEQ ID NO: 12. In another embodiment, the IGF-II P3 sequence is at least 90% homologous to SEQ ID NO: 8 or SEQ ID NO: 12. In another embodiment, the IGF-II P3 sequence is at least 92% homologous to SEQ ID NO: 8 or SEQ ID NO: 12. In another embodiment, the IGF-II P3 sequence is at least 94% homologous to SEQ ID NO: 8 or SEQ ID NO: 12. In another embodiment, the IGF-II P3 sequence is at least 95% homologous to SEQ ID NO: 8 or SEQ ID NO: 12. In another embodiment, the IGF-II P3 sequence is at least 96% homologous to SEQ ID NO: 8 or SEQ ID NO: 12. In another embodiment, the IGF-II P3 sequence is at least 97% homologous to SEQ ID NO: 8 or SEQ ID NO: 12. In another embodiment, the IGF-II P3 sequence is at least 98% homologous to SEQ ID NO: 8 or SEQ ID NO: 12. In another embodiment, the IGF-II P3 sequence is at least 99% homologous to SEQ ID NO: 8 or SEQ ID NO: 12. In another embodiment, the IGF-II P3 sequence is over 99% homologous to SEQ ID NO: 8 or SEQ ID NO: 12. Each possibility represents a separate embodiment of the present invention.

In another embodiment, the IGF-II P3 promoter contains the promoter elements found in $^-291$-$^+130$, relative to the P3 start site. In another embodiment, the IGF-II P3 promoter contains the promoter elements found in $^+1232$-$^-812$, relative to the P3 start site. In another embodiment, the IGF-II P3 promoter contains the promoter elements found in $^-238$-$^+140$, relative to the P3 start site. In another embodiment, the IGF-II P3 promoter contains the promoter elements found 5' to residue $^-515$, relative to the P3 start site. In another embodiment, the IGF-II P3 promoter contains the promoter elements found 5' to residue $^-238$, relative to the P3 start site. Each possibility represents a separate embodiment of the present invention.

Further described herein are IGF-II P4 regulatory sequences that can be used in the nucleic acid constructs of the invention to direct the specific expression of a cytotoxic or cytostatic gene product. In another embodiment, the IGF-II P4 transcription-regulating sequence of compositions of the present invention is an IGF-II P4 promoter (also referred to herein as "P4"). In another embodiment, the sequence of the P4 promoter is set forth in SEQ ID NO: 9, as set forth hereinbelow.

In another embodiment, the IGF-II P4 promoter comprises a nucleic acid sequence as set forth in SEQ ID NO: 9. In another embodiment, the nucleic acid sequence of the IGF-II P4 promoter consists of SEQ ID NO: 9. In another embodiment, the IGF-II P4 promoter is homologous to SEQ ID NO: 9. In another embodiment, the IGF-II P4 promoter is a variant of SEQ ID NO: 9. In another embodiment, the IGF-II P4 promoter is a fragment of SEQ ID NO: 9. In another embodiment, the IGF-II P4 promoter is a homologue of a fragment of SEQ ID NO: 9. In another embodiment, the IGF-II P4 promoter is a variant of a fragment of SEQ ID NO: 9. Each possibility represents a separate embodiment of the present invention.

In another embodiment, the sequence of the P4 promoter is set forth in SEQ ID NO: 13:

```
                                                                    (SEQ ID NO: 13)
ggatccccaaaatgtgttccttgctttcatctgccaattttacgtaatatggctctacggcaaaattcccaatttcatatggagaatttctttt aactacccctcctcacaaattggtcccccaagctagctggcccctatttgagacctctttctctatgttcccaattgcatggagcaacttctc tcatccccaaacctgtaatctatttttctggagtctcgagtttagtcattaatcacggttcccacattaacggagtccccggggtcccctcct
```

-continued

```
ccaggacacccattcgctaagcccgcaaggcagaaagaactctgccttgcgttccccaaaatttgggcattgttccggctcgccggccaccca ctgcagcttccccaaccccgcgcacagcgggcactggtttcgggcctctctgtctcctacgaagtccccagagcaactcggatttgggaaa tttctctctagcgttgcccaaacacacttgggtcggccgcgcgccctcaggacgtggacagggagggcttccccgtgtccaggaaagcga ccgggcattgccccagtctcccccaaatttgggcattgtcccgggtcttccaacggactgggcgttgctcccggacactgaggactggc cccggggtctcgctcaccttcagcagcgtccaccgcctgccacagagcgttcgatcgctcgctgcctgagctcctggtgcgcccgcggac gcagcctccagcttcgcggtgagctccccgccgcgccgatccctccgcctctgcgccctgaccggctctcggcccgcatctgctgctg tcccgccggtgctggcgctcgtctccggctgccgccggggaggc.
```

In another embodiment, the IGF-II P4 promoter comprises a nucleic acid sequence as set forth in SEQ ID NO: 13. In another embodiment, the nucleic acid sequence of the IGF-II P4 promoter consists of SEQ ID NO: 13. In another embodiment, the IGF-II P4 promoter is homologous to SEQ ID NO: 13. In another embodiment, the IGF-II P4 promoter is a variant of SEQ ID NO: 13. In another embodiment, the IGF-II P4 promoter is a fragment of SEQ ID NO: 13. In another embodiment, the IGF-II P4 promoter is a homologue of a fragment of SEQ ID NO: 13. In another embodiment, the IGF-II P4 promoter is a variant of a fragment of SEQ ID NO: 13. Each possibility represents a separate embodiment of the present invention.

In another embodiment, the IGF-II P4 sequence is at least 60% homologous to a sequence selected from SEQ ID NO: 9 and SEQ ID NO: 13. In another embodiment, the IGF-II P4 sequence is at least 65% homologous to SEQ ID NO: 9 or SEQ ID NO: 13. In another embodiment, the IGF-II P4 sequence is at least 70% homologous to SEQ ID NO: 9 or SEQ ID NO: 13. In another embodiment, the IGF-II P4 sequence is at least 72% homologous to SEQ ID NO: 9 or SEQ ID NO: 13. In another embodiment, the IGF-II P4 sequence is at least 74% homologous to SEQ ID NO: 9 or SEQ ID NO: 13. In another embodiment, the IGF-II P4 sequence is at least 76% homologous to SEQ ID NO: 9 or SEQ ID NO: 13. In another embodiment, the IGF-II P4 sequence is at least 78% homologous to SEQ ID NO: 9 or SEQ ID NO: 13. In another embodiment, the IGF-II P4 sequence is at least 80% homologous to SEQ ID NO: 9 or SEQ ID NO: 13. In another embodiment, the IGF-II P4 sequence is at least 82% homologous to SEQ ID NO: 9 or SEQ ID NO: 13. In another embodiment, the IGF-II P4 sequence is at least 84% homologous to SEQ ID NO: 9 or SEQ ID NO: 13. In another embodiment, the IGF-II P4 sequence is at least 86% homologous to SEQ ID NO: 9 or SEQ ID NO: 13. In another embodiment, the IGF-II P4 sequence is at least 88% homologous to SEQ ID NO: 9 or SEQ ID NO: 13. In another embodiment, the IGF-II P4 sequence is at least 90% homologous to SEQ ID NO: 9 or SEQ ID NO: 13. In another embodiment, the IGF-II P4 sequence is at least 92% homologous to SEQ ID NO: 9 or SEQ ID NO: 13. In another embodiment, the IGF-II P4 sequence is at least 94% homologous to SEQ ID NO: 9 or SEQ ID NO: 13. In another embodiment, the IGF-II P4 sequence is at least 95% homologous to SEQ ID NO: 9 or SEQ ID NO: 13. In another embodiment, the IGF-II P4 sequence is at least 96% homologous to SEQ ID NO: 9 or SEQ ID NO: 13. In another embodiment, the IGF-II P4 sequence is at least 97% homologous to SEQ ID NO: 9 or SEQ ID NO: 13. In another embodiment, the IGF-II P4 sequence is at least 98% homologous to SEQ ID NO: 9 or SEQ ID NO: 13. In another embodiment, the IGF-II P4 sequence is at least 99% homologous to SEQ ID NO: 9 or SEQ ID NO: 13. In another embodiment, the IGF-II P4 sequence is over 99% homologous to SEQ ID NO: 9 or SEQ ID NO: 13. Each possibility represents a separate embodiment of the present invention.

In another embodiment, the P4 promoter corresponds to nucleotide sequence −546 to +102 of the IGF-II gene, relative to the IGF-P4 start site.

In another embodiment, these regulatory sequences from genomically imprinted and non-imprinted genes that are expressed in cancer cells can be further delineated to define the minimal regulatory sequences required to obtain the desired tumor specific expression. For example, the promoter region may be altered by additions, substitutions or deletions and assayed for retention of tumor specific expression function. Various portions of the H19 downstream enhancer may be tested individually for the ability to enhance transcription from the H19 promoter.

The TNF-alpha protein of methods and compositions of the present invention is, in another embodiment, encoded by a nucleotide molecule having the sequence:

(SEQ ID NO: 14)
```
tcatgagcaccgagagcatgatcagggatgtggagctggccgaggaggccctgcccaagaaaacaggcggccctcagggcagca gaagatgcctgttcctgagcctgttcagcttcctgatcgtggccggagccaccaccctgttctgcctgctgaacttcggcgtgatcggc ccccagagagaggagttccccagagacctgagcctgatctcccccctggcccaggctgtgagaagcagcagcagaaccccccagcgaca agcccgtggcccacgtggtggccaaccccaggccgagggccagctgcagtggctgaacagaagagccaacgccctgctggccaacg gcgtggagctgagagacaaccagctggtggtgcccagcgagggcctgtacctgatctacagccaggtgctgttcaagggccagggctgc cccagcacccacgtgctgctgacccacaccatcagcagaatcgccgtgtcctaccagaccaaggtgaacctgctgtccgccatcaagagc ccttgccagagagagaccccgagggcgccgaggccaagccctggtacgagcctatctacctgggcggcgtgttccagctggagaagg gcgacagactgagcgccgagatcaacagacccgactacctggatttcgccgagagcggccaggtgtacttcggcatcatcgccctgtgat aatctagaaccatgg.
```

In another embodiment, the nucleic acid sequence encoding the TNF-alpha consists of SEQ ID NO: 14. In another embodiment, the sequence encoding the TNF-alpha is homologous to SEQ ID NO: 14. In another embodiment, the sequence encoding the TNF-alpha is a variant of SEQ ID NO: 14. In another embodiment, the sequence encoding the TNF-alpha is a fragment of SEQ ID NO: 14. In another embodiment, the sequence encoding the TNF-alpha is a homologue of a fragment of SEQ ID NO: 14. In another embodiment, the sequence encoding the TNF-alpha is a variant of a fragment of SEQ ID NO: 14. Each possibility represents a separate embodiment of the present invention.

In another embodiment, the amino acid sequence of the TNF-alpha is (SEQ ID NO: 15)
MSTESMIRDVELAEEALPKKTGGPQGSRRCLFLSLFSFLIVAGATTLFCL

LNFGVIGPQREEFPRDLSLISPLAQAVRSSSRTPSDKPVAHVVANPQAEG

QLQWLNRRANALLANGVELRDNQLVVPSEGLYLIYSQVLFKGQGCPSTHV

LLTHTISRIAVSYQTKVNLLSAIKSPCQRETPEGAEAKPWYEPIYLGGVF

QLEKGDRLSAEINRPDYLDFAESGQVYFGIIAL.

In another embodiment, the sequence of the TNF-alpha consists of SEQ ID NO: 15. In another embodiment, the sequence of the TNF-alpha is homologous to SEQ ID NO: 15. In another embodiment, the sequence of the TNF-alpha is a variant of SEQ ID NO: 15. In another embodiment, the sequence of the TNF-alpha is a fragment of SEQ ID NO: 15. In another embodiment, the sequence of the TNF-alpha is a homologue of a fragment of SEQ ID NO: 15. In another embodiment, the sequence of the TNF-alpha is a variant of a fragment of SEQ ID NO: 15. Each possibility represents a separate embodiment of the present invention.

Alterations in a regulatory sequences of the present invention or (e.g. a sequence encoding a cytotoxic or cytostatic gene product) can be generated using a variety of chemical and enzymatic methods which are well known to those skilled in the art. For example, regions of the sequences defined by restriction sites can be deleted. Oligonucleotide-directed mutagenesis can be employed to alter the sequence in a defined way and/or to introduce restriction sites in specific regions within the sequence. Additionally, deletion mutants can be generated using DNA nucleases such as Bal31 or ExoIII and S1 nuclease. Progressively larger deletions in the regulatory sequences are generated by incubating the DNA with nucleases for increased periods of time.

The altered sequences are evaluated for their ability to fulfill the required function, e.g. to direct tumor specific expression of heterologous coding sequences in appropriate host cells. It is within the scope of the present invention that any altered regulatory sequences which retain their ability to direct tumor specific expression be incorporated into the nucleic acid constructs of the present invention for further use.

The constructs of the present invention may be produced using standard recombinant and synthetic methods well known in the art. An isolated nucleic acid sequence can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis (see e.g. Sambrook et al., 2001, Molecular Cloning: A Laboratory Manual, Cold Springs Harbor Laboratory, New York; Ausubel, et al., 1989, Chapters 2 and 4). Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional oligonucleotide of the invention.

A nucleic acid molecule analog can be produced using a number of methods known to those skilled in the art (see, for example, Sambrook et al., 2001, ibid). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. For example, nucleic acid molecule analogs can be selected from a mixture of modified nucleic acids by screening for the function of the oligonucleic acid encoded by the nucleic acid with respect to tumor progression, for example by the methods described herein.

Optionally, the construct may further comprise one or more sequences encoding additional gene products under a cancer-specific (e.g. an H19-specific) transcriptional control. The construct may also comprise other regulatory sequences or selectable markers, as known in the art. The nucleic acid construct (also referred to herein as an "expression vector") or construct system of the present invention may include additional sequences that render this vector suitable for replication and integration in prokaryotes, eukaryotes, or preferably both (e.g., shuttle vectors). In addition, a typical cloning vector may also contain transcription and translation initiation sequences, transcription and translation terminators, and a polyadenylation signal.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancers that are suitable for the present invention include those derived from polyoma virus, human or murine cytomegalovirus (CMV), the long term repeat from various retroviruses such as murine leukemia virus, murine or Rous sarcoma virus and HIV.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase RNA stability. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Exemplary termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, and pNMT81, which are available from Invitrogen, pCI which is available from Promega, pMbac, pPbac, pBK-RSV and pBK-CMV, which are available from Strategene, pTRES which is available from Clontech, and their derivatives. These may serve as vector backbone for the constructs of the present invention.

Expression vectors containing regulatory elements from eukaryotic viruses such as retroviruses can be also used. SV40 vectors include pSVT7 and pMT2, for instance. Vectors derived from bovine papilloma virus include pBV-1MTHA, and vectors derived from Epstein-Barr virus include pHEBO and p2O5. Other exemplary vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells. These may serve as vector backbone for the constructs of the present invention.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinarily skilled artisan and as such, no general description of selection considerations is provided herein. For example, bone marrow cells can be targeted using the human T-cell leukemia virus type I (HTLV-I) and kidney cells may be targeted using the heterologous promoter present in the baculovirus *Autographa californica* multiple nucleopolyhedrovirus (AcMNPV), as described by Liang, C. Y. et al. (2004). High efficiency gene transfer into mammalian kidney cells using baculovirus vectors. Arch Virol 149, 51-60.

Recombinant viral vectors are useful for in vivo expression of the genes of the present invention since they offer advantages such as lateral infection and targeting specificity. Lateral infection is inherent in the life cycle of retrovirus, for example, and is the process by which a single infected cell produces many progeny virions that bud off and infect neighboring cells. The result is the rapid infection of a large area of cells, most of which were not initially infected by the original viral particles. This is in contrast to vertical-type infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of the present invention into cells. Such methods are generally described in Sambrook et al, ibid; Ausubel et al., Current Protocols in Molecular Biology, John Wiley and Sons, Baltimore, Md. (1989); Chang et al., Somatic Gene Therapy, CRC Press, Ann Arbor, Mich. (1995); Vega et al., Gene Targeting, CRC Press, Ann Arbor Mich. (1995), Vectors: A Survey of Molecular Cloning Vectors and Their Uses, Butterworths, Boston Mass. (1988); and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Gene Therapy

Gene therapy approaches can be used in accordance with the present invention to prevent or treat cancer. Gene therapy refers to therapy performed by the administration to a subject of an expressed or expressible nucleic acid.

Any of the methods for gene therapy available in the art can be used in accordance with the present invention. Long-term effective use of a gene therapy vector to ameliorate disease in large mammals has been demonstrated. For example, administration of an adeno-associated virus ("AAV") containing a wild-type gene to dogs suffering from Leber congenital amaurosis, a condition that results in blindness due to a mutation of a gene (RPE65) in the retinal pigment epithelium, has successfully corrected the genetic defect (Ackland et al., 2001, Nature Genetics 28:92). Expression of the wild-type RPE65 gene was confirmed by RT PCR. Furthermore, restoration of function was demonstrated by electrophysiological studies of the retina, as well as by unbiased observations of the treated animals. The treatment was shown to be effective for at least four months.

Gene therapy has also proven useful in treatment of a complication of diabetes. Gene therapy with functional therapeutic angiogenesis VEGF (Vascular Endothelial Growth Factor) and other proteins are already in clinical trials for treating polygenic and complex diseases such as myocardial ischemia, hypertension, atherosclerosis and restenosis (Pachori A S et al, Gene therapy: role in myocardial protection. Handb Exp Pharmacol. 2006; (176 Pt 2):335-50). Further, VEGF-expressing plasmids were shown to have efficacy in a phase III study comparing intramuscular delivery of ANG1 with placebo in diabetic patients with critical limb ischemia was carried out on thirteen patients (Kusumanto et al., Molecular Therapy 3:S73).

Gene therapy has also been successfully used to treat an inherited disorder of the X-chromosome, namely severe combined immunodeficiency (SCID), and chronic granulomatous disease (CGD), as reviewed in Blaese R M, Immunol Res. 2007; 38(1-3):274-84.

Further, recent studies have shown that, p53 can successfully and therapeutically be expressed in normal and malignant tissues (Fischer U, Janssen K, Schulze-Osthoff K, BioDrugs. 2007; 21 (5):273-97).

Accordingly, gene therapy approaches using the vectors of the invention, which comprise a heterologous polynucleotide operatively linked to more than one transcriptional regulatory sequences, can be used to prevent or treat cancer and hyperproliferative diseases.

A vector of the invention can be delivered in vivo (i.e., directly into a subject). Accordingly, in one embodiment, a vector of the invention is injected directly into the target tissue or cell derivation site. In another embodiment, a vector of the invention can be introduced into the target tissue as an implant such as, for example, in a polymer formulation (See, e.g., U.S. Pat. No. 5,702,717). In another embodiment, a vector of the invention is targeted to the desired cells or tissues.

In certain embodiments, in vivo nucleic acid transfer techniques (i.e., in vivo gene therapy) include transfection with viral or non-viral constructs, such as adenovirus, lentivirus, Herpes simplex I virus, or adeno-associated virus (AAV) and lipid-based systems.

The vector of the invention can be injected directly into a target tissue as naked DNA. In another embodiment, a vector of the invention can be introduced intracellularly using microparticle bombardment, for example, by using a Biolistic gene gun (DuPont). Plasmid DNA can be delivered with the help of, for example, cationic polymers, cationic liposomes (e.g. lipofectin, cholesterol derivatives such as D.D.A.B. and cationic phospholipids) or derivatized (e.g., antibody conjugated), polylysine conjugates, gramicidin S, artificial viral envelopes or other such intracellular carriers, as well as direct injection of the naked gene construct, electroporation or $CaPO_4$ precipitation carried out in vivo as well as polyethylenimine-based non-viral gene delivery systems. Reviews on nucleic acid transfer and expression systems for cancer gene therapy include Lungwitz (2005) Eur. J. Phar. Biopharm. 60 (2):247-66; Aigner (2006) J. Biotechnol. 254:12-25; Christopher and Wong (2006) Curr. Pharm. Des. 1995-2006; and Wolff (2005) Acta Myol. 24:202-8.

Measuring Expression of Genes in Tumor Cells

Expression driven by H19, IGF-II P3, and IGF-II P4 in tumors and cell lines can be determined, for example, using the techniques of RNA analysis, in situ hybridization, or reporter gene constructs. In addition, tumor cells with activated IGF-1 gene expression can be similarly determined and targeted in gene therapy using the IGF-1 promoter to direct expression of a heterologous polynucleotide.

For most RNA analysis applications, a labeled probe that specifically hybridizes to the gene transcript of interest is prepared using any number of techniques well known in the art. The labeled probe can contain at least 15-30 bases complementary to the H19 nucleotide sequence, and more preferably contains at least 50 to 150 bases complementary to the H19 transcript. A particularly preferred hybridization probe for H19 expression is a polynucleotide complementary to the 3' end of the H19 message from approximately 800 base pairs upstream of the poly A site to the poly A site.

In a specific embodiment of the invention, a labeled antisense RNA probe is generated in vitro using a T7 or T3 expression plasmid. H19 probes can also be labeled by random priming in the presence of labeled nucleotide, for example, using the Prime-It kit (Stratagene™, La Jolla, Calif.; Catalog No. 300392). Alternatively, labeled probes can be generated in a PCR reaction using a cDNA clone of the H19 coding region and primers designed to amplify a region of the coding region, or by a standard nick translation reaction.

Labels appropriate for polynucleotide probes include nucleotides incorporating radioactive isotopes (such as $^{35}S$ and $^{32}P$), fluorescent, luminescent and color tags, and enzymatic moieties.

The labeled probe is hybridized in situ to a cell or tissue sample using standard techniques such as described in U.S. Pat. No. 5,955,273, incorporated herein by reference. Alternatively, if a sufficient quantity of the appropriate cells can be obtained, standard RNA analysis (e.g., Northern analysis, RNase protection, or primer extension) can be performed to determine the level of mRNA expression of the gene of interest.

Additionally, such gene expression assays can be performed "in situ," i.e., directly upon tissue sections (fixed and/or frozen) of patient tissue obtained from biopsies or resections, such that no nucleic acid purification is necessary. Nucleic acid reagents such as those described above can be used as probes and/or primers for such in situ procedures (See, e.g., Nuovo, 1992, "PCR In Situ Hybridization: Protocols And Applications," Raven Press, NY).

An alternative method to determine if a cell type or tumor will be capable of specifically activating expression constructs containing the particular transcriptional regulatory sequences operatively linked to a heterologous polynucleotide is to actually transfect such expression constructs into the cell. For these purposes, the heterologous polynucleotide is preferably a marker gene product. A positive result in an assay for the marker gene product reveals that the cell or cell line is capable of activating expression from the transcriptional regulatory sequences.

In addition, various amplification methods, which are sensitive enough to detect to minute amounts of RNA, can also be used to determine whether the tumor expresses H19 and/or IGF-II. Such methods include, PCR, RT-PCR and in situ PCR (all the above referring also to "nested" PCR, and nested RT-PCR), LCR (ligase chain reaction) and 3SR (self sustained sequence replication). In accordance with a preferred embodiment RT-PCR and nested RT-PCR are used. The amplification products are identified by methods used in the art such as by separation on a gel.

Pharmaceutical Compositions and Kits

In another aspect, the invention provides a pharmaceutical composition comprising a nucleic acid construct of the invention, and optionally one or more pharmaceutically acceptable carriers, excipients or diluents.

According to one aspect, the invention provides a pharmaceutical composition comprising i) a nucleic acid construct containing at least two nucleic acid sequences encoding a cytotoxic gene protein, wherein one nucleic acid sequence is operably linked to an H19-specific transcription-regulating sequence and another nucleic acid sequence is operably linked to an IGF-II P4 transcription-regulating sequence; and ii) a pharmaceutically acceptable carrier, excipient or diluent.

In another aspect, the invention provides a pharmaceutical composition comprising i) a nucleic acid construct containing at least two nucleic acid sequences encoding a cytotoxic gene protein, wherein one nucleic acid sequence is operably linked to an IGF-II P3 transcription-regulating sequence and another nucleic acid sequence is operably linked to an IGF-II P4 transcription-regulating sequence; and ii) a pharmaceutically acceptable carrier, excipient or diluent.

In another aspect, the invention provides a pharmaceutical composition comprising i) a nucleic acid construct containing at least two nucleic acid sequences encoding a cytotoxic gene protein, wherein one nucleic acid sequence is operably linked to an H19-specific transcription-regulating sequence and another nucleic acid sequence is operably linked to an IGF-II P3 transcription-regulating sequence; and ii) a pharmaceutically acceptable carrier, excipient or diluent.

According to one embodiment, the invention provides a pharmaceutical composition comprising i) a nucleic acid construct containing a first open reading frame encoding a diphtheria toxin, the first open reading frame being operably linked to an H19-specific transcription-regulating sequence, and a second open reading frame encoding a diphtheria toxin, the second open reading frame being operably linked to an IGF-II P4 transcription-regulating sequence; and ii) a pharmaceutically acceptable carrier, excipient or diluent. In one embodiment, said nucleic acid construct further comprises a third open reading frame encoding a diphtheria toxin, said third open reading frame being operably linked to an IGF-II P3 transcription-regulating sequence.

In another embodiment, the invention provides a pharmaceutical composition comprising i) a nucleic acid construct containing a first open reading frame encoding a diphtheria toxin, the first open reading frame being operably linked to an H19-specific transcription-regulating sequence, and a second open reading frame encoding a diphtheria toxin, the second open reading frame being operably linked to an IGF-II P3 transcription-regulating sequence; and ii) a pharmaceutically acceptable carrier, excipient or diluent. In another embodiment, said nucleic acid construct further comprises a third open reading frame encoding a diphtheria toxin, said third open reading frame being operably linked to an IGF-II P4 transcription-regulating sequence.

In another embodiment, the invention provides a pharmaceutical composition comprising i) a nucleic acid construct containing a first open reading frame encoding a diphtheria toxin, the first open reading frame being operably linked to an IGF-II P3 transcription-regulating sequence, and a second open reading frame encoding a diphtheria toxin, the second open reading frame being operably linked to an IGF-II P4 transcription-regulating sequence; and ii) a pharmaceutically acceptable carrier, excipient or diluent. In another embodiment, said nucleic acid construct further comprises a third open reading frame encoding a diphtheria toxin, said third open reading frame being operably linked to an H19-specific transcription-regulating sequence.

In another embodiment, the diphtheria toxin is diphtheria toxin A (DTA). In another embodiment, said diphtheria toxin comprises a sequence as set forth in SEQ ID NO: 7.

In another embodiment, the H19-specific transcription-regulating sequence is a promoter comprising a nucleic acid sequence set forth in any one of SEQ ID NOS: 1-2.

In another embodiment, the IGF-II P4 transcription-regulating sequence is a promoter comprising a nucleic acid sequence set forth in SEQ ID NO: 9.

In another embodiment, the IGF-II P3 transcription-regulating sequence is a promoter comprising a nucleic acid sequence as set forth in a sequence selected from SEQ ID NO: 8, SEQ ID NO: 12, and SEQ ID NO: 17.

In another embodiment, said nucleic acid construct is a plasmid or a eukaryotic expression vector.

In another embodiment, there is provided a pharmaceutical pack containing a course of anti-neoplastic treatment for one individual mammal comprising a container having a unit of a nucleic acid construct of the invention in unit dosage form.

In some embodiments, the constructs of the invention are provided in packs in a form ready for administration. In other embodiments, the constructs of the invention are provided in concentrated form in packs, optionally with the diluent required to make final solution(s) for administration.

In still other embodiments, the product contains a compound useful in the invention in solid form and, optionally, a separate container with a suitable solvent or carrier for the compound useful in the invention.

In still other embodiments, the above packs/kits include other components, e.g., instructions for dilution, mixing and/or administration of the product, other containers, syringes, needles, etc. Other such pack/kit components will be readily apparent to one of skill in the art.

In a particular embodiment, the kits further comprise instructions for administering said nucleic acid construct to a subject afflicted with cancer, particularly with a tumor characterized by expression of H19 RNA and/or expression of IGF-II from the P3 and/or P4 promoter in at least a portion of the cells of the tumor, as detailed herein.

As used herein, a "pharmaceutical composition" refers to a preparation of one or more of the active ingredients described herein, e.g. a construct encoding a DTA molecule, with other components such as physiologically suitable carriers and excipients. The purpose of a pharmaceutical composition is to facilitate administration of a compound to a subject.

Hereinafter, the phrases "therapeutically acceptable carrier" and "pharmaceutically acceptable carrier," which may be used interchangeably, refer to a carrier or a diluent that does not cause significant irritation to an organism and does not abrogate the biological activity and properties of the administered compound. As used herein, a "pharmaceutically acceptable carrier, excipient or diluent" may refer to a single auxiliary material or to various mixtures and combinations of such therapeutically inert ingredients.

Herein, the term "excipient" refers to an inert substance added to a pharmaceutical composition to further facilitate administration of an active ingredient. Examples, without limitation, of excipients particularly suitable for administering nucleic acid agents include calcium carbonate, calcium phosphate, various sugars and types of starch, cellulose derivatives, gelatin, vegetable oils, and polyethylene glycols.

In another embodiment of the present invention, a therapeutic composition further comprises a pharmaceutically acceptable carrier. As used herein, a "carrier" refers to any substance suitable as a vehicle for delivering a therapeutic agent, e.g. a nucleic acid molecule of the present invention to a suitable in vivo or in vitro site. As such, carriers can act as a pharmaceutically acceptable excipient of a therapeutic composition containing a nucleic acid molecule of the present invention. Preferred carriers particularly suitable for administering nucleic acid agents are capable of maintaining a nucleic acid molecule of the present invention in a form that, upon arrival of the nucleic acid molecule to a cell, the nucleic acid molecule is capable of entering the cell and being expressed by the cell. Carriers of the present invention include: (1) excipients or formularies that transport, but do not specifically target a nucleic acid molecule to a cell (referred to herein as non-targeting carriers); and (2) excipients or formularies that deliver a nucleic acid molecule to a specific site in a subject or a specific cell (i.e., targeting carriers). Examples of non-targeting carriers include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- and o-cresol, formalin and benzol alcohol. Preferred auxiliary substances for aerosol delivery include surfactant substances non-toxic to a subject, for example, esters or partial esters of fatty acids containing from about six to about twenty-two carbon atoms. Examples of esters include caproic, octanoic, lauric, palmitic, stearic, linoleic, linolenic, olesteric, and oleic acids. Other carriers can include metal particles (e.g., gold particles) for use with, for example, a biolistic gun through the skin. Therapeutic compositions of the present invention can be sterilized by conventional methods.

Targeting carriers are herein referred to as “delivery vehicles”. Delivery vehicles of the present invention are capable of delivering a therapeutic composition of the present invention to a target site in a subject. A “target site” refers to a site in a subject to which one desires to deliver a therapeutic composition. Examples of delivery vehicles particularly suitable for administering nucleic acid agents include, but are not limited to, artificial and natural lipid-containing delivery vehicles. Natural lipid-containing delivery vehicles include cells and cellular membranes. Artificial lipid-containing delivery vehicles include liposomes and micelles. A delivery vehicle of the present invention can be modified to target to a particular site in a subject, thereby targeting and making use of a nucleic acid molecule of the present invention at that site. Suitable modifications include manipulating the chemical formula of the lipid portion of the delivery vehicle and/or introducing into the vehicle a compound capable of specifically targeting a delivery vehicle to a preferred site, for example, a preferred cell type. Specifically targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. For example, an antibody specific for an antigen found on the surface of a target cell can be introduced to the outer surface of a liposome delivery vehicle so as to target the delivery vehicle to the target cell. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

In certain particular embodiments, a delivery vehicle particularly suitable for administering nucleic acid agents is a liposome. A liposome is capable of remaining stable in a subject for a sufficient amount of time to deliver a nucleic acid molecule of the present invention to a preferred site in the subject. A liposome of the present invention is preferably stable in the subject into which it has been administered for at least about 30 minutes, more preferably for at least about 1 hour and even more preferably for at least about 24 hours.

A liposome of the present invention comprises a lipid composition that is capable of targeting a nucleic acid molecule of the present invention to a particular, or selected, site in a subject.

Suitable liposomes for use with the present invention include any liposome. Preferred liposomes of the present invention include those liposomes standardly used in, for example, gene delivery methods known to those of skill in the art. In certain embodiments, more preferred liposomes comprise liposomes having a polycationic lipid composition and/or liposomes having a cholesterol backbone conjugated to polyethylene glycol.

Preferably the pharmaceutical composition can also include a transfection agent such as DOTMA, DOPE, and DC-Chol (Tonkinson et al., 1996). A preferred example of a transfection agent is poly(ethylamine) (PEI).

Other agents particularly suitable for administering nucleic acid agents can be used are e.g. cationic lipids, polylysine, and dendrimers. Alternatively, naked DNA can be administered.

Therapeutic Use

In another aspect, the invention provides a method for treating cancer in a subject in need thereof, comprising administering to the subject a therapeutically effective amount of a nucleic acid molecule of the present invention, wherein said subject is afflicted with a tumor characterized by expression of H19 RNA and/or IGF-II from the P3 and/or P4 promoter, in at least a portion of the cells of the tumor.

In another aspect, there is provided a method for inhibiting tumor progression in a subject in need thereof, comprising administering to the subject a therapeutically effective amount of a nucleic acid molecule of the present invention, wherein said subject is afflicted with a tumor characterized by expression of H19 RNA and/or IGF-II from the P3 and/or P4 promoter, in at least a portion of the cells of the tumor.

In another aspect, there is provided a method for inhibiting or preventing tumor metastasis in a subject in need thereof, comprising administering to the subject a therapeutically effective amount of a nucleic acid molecule of the present invention, wherein the tumor is characterized by expression of H19 RNA and/or IGF-II from the P3 and/or P4 promoter, in at least a portion of the cells of the tumor.

In another aspect, there is provided a method for reducing or alleviating symptoms associated with a neoplastic disorder in a subject in need thereof, wherein the subject is afflicted with a tumor characterized by expression of H19 RNA and/or IGF-II from the P3 and/or P4 promoter, in at least a portion of the cells of the tumor, the method comprising administering to the subject a therapeutically effective amount of a nucleic acid molecule of the present invention.

In another embodiment, the nucleic acid construct contains a first open reading frame encoding a diphtheria toxin, the first open reading frame being operably linked to an H19-specific transcription-regulating sequence, and a second open reading frame encoding a diphtheria toxin, the second open reading frame being operably linked to an IGF-II P4 transcription-regulating sequence. In another embodiment, a cell of said tumor is capable of expressing a transcript directed by the H19 promoter and/or a transcript directed by the IGF-II P4 promoter. In one embodiment, said nucleic acid construct further comprises a third open reading frame encoding a diphtheria toxin, said third open reading frame being operably linked to an IGF-II P3 transcription-regulating sequence.

In another embodiment, the nucleic acid construct contains a first open reading frame encoding a diphtheria toxin, the first open reading frame being operably linked to an H19-specific transcription-regulating sequence, and a second open reading frame encoding a diphtheria toxin, the second open reading frame being operably linked to an IGF-II P3 transcription-regulating sequence. In another embodiment, a cell of said tumor is capable of expressing a transcript directed by the H19 promoter and/or a transcript directed by the IGF-II P3 promoter. In another embodiment, said nucleic acid construct further comprises a third open reading frame encoding a diphtheria toxin, said third open reading frame being operably linked to an IGF-II P4 transcription-regulating sequence.

In another embodiment, the nucleic acid construct contains a first open reading frame encoding a diphtheria toxin, the first open reading frame being operably linked to an IGF-II P3 transcription-regulating sequence, and a second open reading frame encoding a diphtheria toxin, the second open reading frame being operably linked to an IGF-II P4 transcription-regulating sequence. In another embodiment, a cell of said tumor is capable of expressing a transcript directed by the IGF-II P3 promoter and/or a transcript directed by the IGF-II P4 promoter. In another embodiment, said nucleic acid construct further comprises a third open reading frame encoding a diphtheria toxin, said third open reading frame being operably linked to an H19-specific transcription-regulating sequence.

In another embodiment, the diphtheria toxin is diphtheria toxin A (DTA). In another embodiment, said diphtheria toxin comprises a sequence as set forth in SEQ ID NO: 7.

In another embodiment, the H19-specific transcription-regulating sequence is a promoter comprising a nucleic acid sequence set forth in any one of SEQ ID NOS: 1-2.

In another embodiment, the IGF-II P4 transcription-regulating sequence is a promoter comprising a nucleic acid sequence set forth in SEQ ID NO: 9.

In another embodiment, the IGF-II P3 transcription-regulating sequence is a promoter comprising a nucleic acid sequence as set forth in a sequence selected from SEQ ID NO: 8, SEQ ID NO: 12, and SEQ ID NO: 17.

The present invention also relates to a method for increasing a subject's sensitivity to a therapeutic agent, comprising administering to a subject in need thereof an effective amount of a nucleic acid molecule of the present invention.

As used herein, "treating" cancer (or treating a subject with cancer) refers to taking steps to obtain beneficial or desired results, including but not limited to, alleviation or amelioration of one or more symptoms of cancer, diminishment of extent of disease, delay or slowing of disease progression, amelioration, palliation or stabilization of the disease state, partial or complete remission, prolonged survival and other beneficial results known in the art.

In another embodiment, the subject is human.

In another embodiment, tumors that may be treated according to the method of the present invention are those express H19 RNA and/or express IGF-II from the P3 and/or P4 promoter during tumor onset or progression. In another embodiment, a cell of a target tumor of a method of the present invention expresses endogenously a transcript directed by the H19 promoter (e.g. an H19 transcript) and a transcript directed by the IGF-II P3 promoter (e.g. an IGF-II transcript). In another embodiment, a cell of the target tumor expresses endogenously a transcript directed by the H19 promoter and a transcript directed by the IGF-II P4 promoter (e.g. an IGF-II transcript). In another embodiment, a cell of the target tumor expresses endogenously a transcript directed by the IGF-II P3 promoter and a transcript directed by the IGF-II P4 promoter. In another embodiment, the target tumor is a tumor that endogenously expresses the P3-driven IGF-II transcript, P4-driven IGF-II transcript, and H19 transcript. In another embodiment, the target tumor endogenously expresses at least two of the IGF-II-P3, IGF-II-P4 and H19 driven transcripts. Each possibility represents a separate embodiment of the present invention.

In another embodiment, the target tumor has been genotyped for expression of H19 and/or expression of IGF-II under control of the P3 or P4 promoter, or both. In another embodiment, the target tumor has not been genotyped. Each possibility represents a separate embodiment of the present invention.

For example, in some embodiments, the tumor is selected from Wilm's tumor, hepatoblastoma, embryonal rhabdomyosarcoma, germ cell tumors and trophoblastic tumors, testicular germ cell tumors, testicular seminoma, teratoma, immature teratoma of ovary, sacrococcygeal tumor, choriocarcinoma, placental site trophoblastic tumors, bladder carcinoma, hepatocellular carcinoma, ovarian carcinoma, cervical carcinoma, lung carcinoma, breast carcinoma, squamous cell carcinoma in head and neck, esophageal carcinoma, thyroid carcinoma, neurogenic tumors, astrocytoma, ganglioblastoma, neuroblastoma, osteosarcoma, melanoma, pancreatic canrcinoma, prostate cancer, uterus cancer, renal cell carcinoma, colorectal carcinoma, colon cancer, medulloblastoma, glioblastoma, adrenocortical tumors, small cell lung cancer, non-small cell lung cancer, acute lymphoblastic leukemia (ALL), head and neck cancers, oral cancers, gestational trophoblastic tumors, meningioma and hepatoma. In some particular embodiments, the tumor is selected from head and neck cancers, oral cancers and gestational trophoblastic tumors.

In another embodiment, the subject is afflicted with Beckwith-Wiedermann syndrome (BWS), thus having a predisposition for developing an H19 and/or IGF-II-associated tumor such as Wilm's tumor or hepatoblastoma.

In another embodiment, the target tumor is a solid tumor. In another embodiment, the target tumor is a carcinoma. In certain particular embodiments, the tumor may be a bladder cancer (e.g. bladder carcinoma), liver cancer (e.g. hepatocellular carcinoma) ovarian cancer (e.g. clear cell carcinoma), pancreatic cancer (e.g. pancreatic ductal carcinoma, epithelioid carcinoma).

In certain other preferable embodiments, the tumor is selected from the group consisting of a bladder carcinoma, a hepatocellular carcinoma, an ovarian carcinoma, and a pancreatic carcinoma. In another embodiment, the target tumor is a bladder carcinoma. In another embodiment, the target tumor is a hepatocellular carcinoma. In another embodiment, the target tumor is a colon carcinoma. In another embodiment, the target tumor is a superficial bladder cancer. In another embodiment, the target tumor is a cervical carcinoma. In another embodiment, the target tumor is lung carcinoma. In another embodiment, the target tumor is lung adenocarcinoma. In another embodiment, the target tumor is small cell lung carcinoma. In another embodiment, the target tumor is a breast carcinoma. In another embodiment, the target tumor is a squamous cell carcinoma in head and neck. In another embodiment, the target tumor is a renal cell carcinoma. In another embodiment, the target tumor is an esophageal carcinoma. In another embodiment, the target tumor is a pancreatic cancer. In another embodiment, the target tumor is a hepatoblastoma. In another embodiment, the target tumor is a rhabdomyosarcoma. In another embodiment, the target tumor is a thyroid carcinoma. In another embodiment, the target tumor is a ganglioblastoma. In another embodiment, the target tumor is an ovarian carcinoma. In another embodiment, the target tumor is a squamous cell bronchogenic carcinoma. In another embodiment, the target tumor is a liver neoplasm. In another embodiment, the target tumor is a colorectal carcinoma. In another embodiment, the target tumor is an endometrial carcinoma. In another embodiment, the target tumor is a testicular tumor. In another embodiment, the target tumor is a testicular germ cell tumor. In another embodiment, the target tumor is a squamous cell bronchogenic carcinoma. In another embodiment, the target tumor is prostate cancer. In another embodiment, the target tumor is Wilm's tumor. In another embodiment, the target tumor is an astrocytoma. In another embodiment, the target tumor is a neuroblastoma. Each possibility represents a separate embodiment of the present invention.

In another embodiment, the target disease of a method of the present invention is a cell-proliferative disorder wherein at least some of the cells are capable of expressing a transcript under the control of the H19 promoter and/or the IGF-II P4 promoter. In another embodiment, the target disease is a cell-proliferative disorder wherein at least some of the cells are capable of expressing a transcript under the control of the H19 promoter and/or the IGF-II P3 promoter. In another embodiment, the target disease is a cell-proliferative disorder wherein at least some of the cells are capable of expressing a transcript under the control of the IGF-II P4 promoter and/or the IGF-II P3 promoter. Each possibility represents a separate embodiment of the present invention.

In another embodiment, the methods of the invention further comprise a step of detecting the presence of H19 RNA and/or IGF-II RNA in tumor cells obtained from the subject, wherein the presence of the RNA in at least a portion of the tumor cells is indicative that said tumor is treatable by the methods of the present invention. For example, the presence of H19 RNA and/or IGF-II RNA may be detected by methods known in the art such as PCR, RT-PCR, in situ PCR, in situ RT-PCR, LCR and, 3SR, and hybridization with a probe comprising a detectable moiety. In other embodiments, the presence of an RNA may be determined in a cell or tissue sample derived from the tumor, or, in alternate embodiments, in cell-containing specimens of body fluids, rinse fluids that were in contact with the primary tumor site, or tissues or organs other than the tissue primary tumor site (e.g. for detecting tumor metastases).

Exemplary metastasizing tumors include, e.g. colorectal cancer metastasizing to the liver and metastasizing breast cancer. In a particular embodiment, the constructs of the invention are used to prevent or inhibit the formation of liver metastases.

In order to treat a subject with a disease, pharmaceutical compositions of the present invention are administered to the subject in an effective manner such that the compositions are capable of treating that subject from disease. According to the present invention, treatment of a disease refers to alleviating a disease and/or associated symptoms and/or preventing the development of a secondary disease resulting from the occurrence of a primary disease.

Thus, the term "therapeutically effective amount" referred to herein means that the nucleic acid constructs of the invention are administered to the subject in an amount that is effective, when administered to said subject, to treat that subject.

An effective administration protocol (i.e., administering a pharmaceutical composition in an effective manner) comprises suitable dose parameters and modes of administration that result in treatment of a disease. Effective dose parameters and modes of administration can be determined using methods standard in the art for a particular disease. Such methods include, for example, determination of survival rates, side effects (i.e., toxicity) and progression or regression of disease.

In accordance with the present invention, a suitable single dose size is a dose that is capable of treating a subject with disease when administered one or more times over a suitable time period. For example, a suitable single dose size may induce a reduction in tumor cell mass in a subject in need thereof. Doses of a pharmaceutical composition of the present invention suitable for use with direct injection techniques can be used by one of skill in the art to determine appropriate single dose sizes for systemic administration based on the size of a subject.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, intraarterial, intravesicle (into the bladder) or intraocular injections.

Alternatively, one may administer a preparation in a local rather than systemic manner, for example, via injection of the preparation directly into a specific region of a patient's body or by direct administration into a body cavity such as the bladder, uterus etc. in another particular embodiment, intralesional administration, e.g. intratumoral injection, is contemplated.

Solutions or suspensions used for parenteral, intradermal, or subcutaneous application can include the following components: a sterile diluent such as water for injection, saline solution, fixed oils, polyethylene glycols, glycerine, propylene glycol (or other synthetic solvents), antibacterial agents (e.g., benzyl alcohol, methyl parabens), antioxidants (e.g., ascorbic acid, sodium bisulfite), chelating agents (e.g., ethylenediaminetetraacetic acid), buffers (e.g., acetates, citrates, phosphates), and agents that adjust tonicity (e.g., sodium chloride, dextrose). The pH can be adjusted with acids or bases, such as hydrochloric acid or sodium hydroxide, for example. The parenteral preparation can be enclosed in ampules, disposable syringes or multiple dose vials made of glass or plastic.

Pharmaceutical compositions adapted for parenteral administration include, but are not limited to, aqueous and non-aqueous sterile injectable solutions or suspensions, which can contain antioxidants, buffers, bacteriostats and solutes that render the compositions substantially isotonic with the blood of an intended recipient. Such compositions can also comprise water, alcohols, polyols, glycerine and vegetable oils, for example. Extemporaneous injection solutions and suspensions can be prepared from sterile powders, granules and tablets. Such compositions should comprise a therapeutically effective amount of a vector of the invention and/or other therapeutic agent, together with a suitable amount of carrier so as to provide the form for proper administration to the subject. The formulation should suit the mode of administration.

In certain embodiments, the compositions of the present invention can be used to treat cancer alone or with other established or experimental therapeutic regimens against cancer. Therapeutic methods for treatment of cancer suitable for combination with the present invention include, but are not limited to, chemotherapy, radiotherapy, phototherapy and photodynamic therapy, surgery, nutritional therapy, ablative therapy, combined radiotherapy and chemotherapy, brachiotherapy, proton beam therapy, immunotherapy, cellular therapy, and photon beam radiosurgical therapy.

Anti-cancer drugs that can be co-administered with the constructs of the invention include, but are not limited to the following: acivicin; aclarubicin; acodazole hydrochloride; acronine; adriamycin; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; taxol; tecogalan sodium; tegafur; teloxantrone hydrochloride; temoporfin; teniposide; teroxirone; testolactone; thiamiprine; thioguanine; thiotepa; tiazofuirin; tirapazamine; topotecan hydrochloride; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride. Additional antineoplastic agents include those disclosed in Chapter 52, "Antineoplastic Agents" (Calabresi, P. and Chabner, B. A.), and the introduction thereto, pp. 1202-1263, of Goodman and Gilman, The Pharmacological Basis of Therapeutics, Eighth Edition, 1990, McGraw-Hill, Inc. (Health Professions Division). Each possibility represents a separate embodiment of the present invention.

The following examples are presented in order to more fully illustrate some embodiments of the invention. They should, in no way be construed, however, as limiting the broad scope of the invention.

EXPERIMENTAL DETAILS SECTION

Overview of Multiple-Promoter Vectors

Double promoter expression vectors were created, carrying on a single construct two separate genes expressing the DTA toxin, from two different regulatory sequences, as follows:

H19+IGF-II-P4 promoters (hereinafter "H19-DTA-P4-DTA"; depicted in FIG. 1);
IGF-II-P3+IGF-II-P4 promoters (hereinafter "P4-DTA-P3-DTA"; described subsequently); and
H19+IGF-II-P3 promoters; (hereinafter "H19-DTA-P3-DTA"; described subsequently).

Transfections

Transfections were performed using the in vitro jetPEI™ transfection reagent (Polyplus Transfection) as recommended by the manufacturer. After 48 hours, cells were harvested and luciferase activity was determined using the Luciferase Assay System kit (Promega). Light output was measured using a Lumac Biocounter apparatus. Total protein content of the lysates was determined by the Bio-Rad protein assay reagent, and results were normalized to the total protein and expressed as Light units/µg protein. A plasmid that expresses luciferase under SV40 transcription control, LucSV40 (Promega) was used as a positive control for the efficiency of transfection, as it contains the SV40 promoter and enhancer, while a plasmid containing Luc1 but lacking regulatory sequences (Promega) was used as a negative control to determine the basal nonspecific luciferase expression (this was negligible in all cell lines). All experiments were performed in triplicate.

Creation of H19-DTA-P4-DTA

The synthetic DTA cassette and synthetic P4 cassette were each assembled from PCR products and subcloned into pGA4 (ampR, available from GeneArt, Regensburg, Germany) using SacI and KpnI restriction sites. Plasmid DNA was purified (Pure Yield™ Plasmid Midiprep, Promega) from transformed K12 XL10 gold bacteria and concentration determined by UV spectroscopy. The final constructs were verified by sequencing and were named 0704870 (SEQ ID NO: 21) and 0704867 (SEQ ID NO: 23), respectively. Sequence congruence was 100%.

The P4 promoter that was utilized had the following sequence:

(SEQ ID NO: 9)
```
acttcccggtcggtctgtgggtgcagggggtgccgcctcacatgtgtgattcgtgccttgcgggccctggcctccggggtgctg ggtaacgaggaggggcgcggagccgcagaagcccaccctggtatgttgacgcggtgccagcgagaccgcgagaggaagacggggt gggcggggccaggatggagaggggccgagttggcaggagtcatggcagacgccacattcgcgacatctcccccacacccctctggct ctgtccgcaacatttccaaacaggagtcccgggagaggggagaggggctgctggtctgaggctaagaagggcagagccttcgacccg
```

-continued

```
gagagaggccgcggcccctgcccagtgggcagcgtggaagtttccatacaaggaggtgggaaggagaccccccccccccttcactgcc ctgtgcagagatgagccgggggtgcaggatgggagcccatggcacttcgctacgggatggtccagggctcccggttgggggtgcagga gagaagagactggctgggaggagggagagggcgggagcaaaggcgcgggggagtggtcagcagggagaggggtgggggtagg gtggagcccgggctgggaggagtcggctcacacataaaagctgaggcactgaccagcctgcaaactggacattagcttctcctgtgaaag agacttccagcttcctcctcctcctcttcctcctcctcctcctgcccagcgagccttctgctgagctgtaggggatcttctagagtcg.
```

Next, a vector that expressed DTA from the IGF-II P4 promoter alone was created. To create this vector, the DTA sequence was amplified from 0704870 and subcloned into 0704867 using NheI and KpnI restriction sites. The plasmid DNA was purified from transformed K12 KH10B bacteria and concentration determined by UV spectroscopy. The final construct (0704877) was verified by sequencing. The sequence congruence was 100%.

To create the H19-DTA-P4-DTA vector, the P4-DTA cassette was amplified from 0704877, and subcloned into 052966, a vector that expresses DTA from the H19 promoter, using NotI and KpnI restriction sites. 052966 is referred to hereinafter as "H19-DTA" and has the following sequence:

(SEQ ID NO: 16)

```
ggtaccgacaaccctcaccaagggccaaggtggtgaccgacggacccacagcggggtggctgggggagtcgaaactcgccagtc tccactccactcccaaccgtggtgcccacgcggggcctgggagagtctgtgaggccgcccaccgcttgtcagtagagtgcgcccgc gagccgtaagcacagcccggcaacatgcggtcttcagacaggaaagtggccgcgaatgggaccggggtgcccagcggctgtggggac tctgtcctgcggaaaccgcggtgacgagcacaagctcggtcaactggatgggaatcggcctgggggctggcaccgcgcccaccaggg ggtttgcggcacttccctctgcccctcagcaccccaccctactctccaggaacgtgagttctgagccgtgatggtggcaggaagggccc tctgtgccatccgagtccccagggacccgcagctggccccagccatgtgcaaagtatgtgcagggcgctggcaggcagggagcagca ggcatggtgtccctgaggggagacagtggtctgggagggagaagtcctggaccctgagggaggtgatggggcaatgctcagccctgtc tccggatgccaaaggaggggtgcggggaggccgtctttggagaattccaggatgggtgctgggtgagagagacgtgtgctggaactgtc cagggcggaggtgggccctgcgggggccctcgggagggccctgctctgattggccggcagggcagggcgggaatcctgggcggg gccacccagttagaaaaagcccgggctaggaccgaggagcagggtgagggagaagcttggcattccggtactgttggtaaagccaccatgg atcctgatgatgttgttgattcttctaaatcttttgtgatggaaaacttttcttcgtaccacgggactaaacctggttatgtagattccattcaa aaaggtatacaaaagccaaaatctggtacacaaggaaattatgacgatgattggaaagggttttatagtaccgacaataaatacgacgctgc gggatactctgtagataatgaaaacccgctctctggaaaagctggaggcgtggtcaaagtgacgtatccaggactgacgaaggttctcgca ctaaaagtggataatgccgaaactattaagaaagagttaggtttaagtctcactgaaccgttgatggagcaagtcggaacggaagagtttatc aaaaggttcggtgatggtgcttcgcgtgtagtgctcagccttcccttcgctgaggggagttctagcgttgaatatattaataactgggaacagg cgaaagcgttaagcgtagaacttgagattaattttgaaacccgtggaaaacgtggccaagatgcgatgtatgagtatatggctcaagcctgtg caggaaatcgtgtcaggcgatctttgtgaaggaaccttacttctgtggtgtgacataattggacaaactacctacagagatttgggatcctct agagtcggggcggccggccgcttcgagcagacatgataagatacattgatgagtttggacaaaccacaactagaatgcagtgaaaaaaatgcttt atttgtgaaatttgtgatgctattgctttatttgtaaccattataagctgcaataaacaagttaacaacaacaattgcattcattttatgtttcag gttcaggggaggtgtgggaggttttttaaagcaagtaaaacctctacaaatgtggtaaaatcgataaggatccgtcgaccgatgcccttga gagccttcaacccagtcagctccttccggtgggcgcggggcatgactatcgtcgccgcacttatgactgtcttctttatcatgcaactcgtagg acaggtgccggcagcgctcttccgcttcctcgctcactgactcgctgcgctcggtcgttcggctgcggcgagcggtatcagctcactcaaa ggcggtaatacggttatccacagaatcaggggataacgcaggaaagaacatgtgagcaaaaggccagcaaaaggccaggaaccgtaaa aaggccgcgttgctggcgtttttccataggctccgcccccctgacgagcatcacaaaaatcgacgctcaagtcagaggtggcgaaacccg acaggactataaagataccaggcgtttccccctggaagctccctcgtgcgctctcctgttccgaccctgccgcttaccggatacctgtccgcc tttctcccttcgggaagcgtggcgctttctcatagctcacgctgtaggtatctcagttcggtgtaggtcgttcgctccaagctgggctgtgtgca cgaacccccgttcagcccgaccgctgcgccttatccggtaactatcgtcttgagtccaacccggtaagacacgacttatcgccactggcag cagccactggtaacaggattagcagagcgaggtatgtaggcggtgctacagagttcttgaagtggtgcctaactacggctacactagaag
```

-continued

```
aacagtatttggtatctgcgctctgctgaagccagttaccttcggaaaaagagttggtagctcttgatccggcaaacaaaccaccgctggtag cggtggttttttgtttgcaagcagcagattacgcgcagaaaaaaaggatctcaagaagatcctttgatcttttctacggggtctgacgctcagt ggaacgaaaactcacgttaagggattttggtcatgagattatcaaaaaggatcttcacctagatcctttaaattaaaaatgaagttttaaatcaat ctaaagtatatatgagtaaacttggtctgacagttagaaaaactcatcgagcatcaaatgaaactgcaatttattcatatcaggattatcaatacc atattttgaaaaagccgtttctgtaatgaaggagaaaactcaccgaggcagttccataggatggcaagatcctggtatcggtctgcgattccg actcgtccaacatcaatacaacctattaatttcccctcgtcaaaaataaggttatcaagtgagaaatcaccatgagtgacgactgaatccggtg agaatggcaaaagtttatgcatttctttccagacttgttcaacaggccagccattacgctcgtcatcaaaatcactcgcatcaaccaaaccgtta ttcattcgtgattgcgcctgagcgagacgaaatacgcgatcgctgttaaaaggacaattacaaacaggaatcgaatgcaaccggcgcagga acactgccagcgcatcaacaatattttcacctgaatcaggatattcttctaatacctggaatgctgttttcccggggatcgcagtggtgagtaac catgcatcatcaggagtacggataaaatgcttgatggtcggaagaggcataaattccgtcagccagtttagtctgaccatctcatctgtaacat cattggcaacgctacctttgccatgtttcagaaacaactctggcgcatcgggcttcccatacaatcgatagattgtcgcacctgattgcccgac attatcgcgagcccatttatacccatataaatcagcatccatgttggaatttaatcgcggcctagagcaagacgtttcccgttgaatatggctcat actcttcctttttcaatattattgaagcatttatcagggttattgtctcatgagcggatacatatttgaatgtatttagaaaaataaacaaatagg ggttccgcgcacatttccccgaaaagtgccacctgacgcgccctgtagcggcgcattaagcgcggcgggtgtggtggttacgcgcagcgtgac cgctacacttgccagcgccctagcgcccgctcctttcgctttcttcccttcctttctcgccacgttcgccggctttccccgtcaagctctaaatcg ggggctccctttagggttccgatttagtgctttacggcacctcgaccccaaaaaacttgattagggtgatggttcacgtagtgggccatcgcc ctgatagacggttttttcgcccttgacgttggagtccacgttctttaatagtggactcttgttccaaactggaacaacactcaaccctatctcggtc tattcttttgatttataagggattttgccgatttcggcctattggttaaaaaatgagctgatttaacaaaaatttaacgcgaattttaacaaaatat taacgcttacaatttgccattcgccattcaggctgcgcaactgttgggaagggcgatcggtgcgggcctcttcgctattacgccagcccaagcta ccatgataagtaagtaatattaaggtacgggaggtacttggagcggccgcaataaaatatctttattttcattacatctgtgtgttggtttttgtgt gaatcgatagtactaacatacgctctccatcaaaacaaaacgaaacaaaacaaactagcaaaataggctgtcccagtgcaagtgcaggtg ccagaacatttctctatcgata.
```

The plasmid DNA was purified from transformed K12 KH10B bacteria and concentration determined by UV spectroscopy. The final construct was verified by sequencing. The sequence congruence was 100%.

The sequence of H19-DTA-P4-DTA was:

(SEQ ID NO: 11)
```
ccctcaccaagggccaaggtggtgaccgacggacccacagcggggtggctggggagtcgaaactcgccagtctccactcc actcccaaccgtggtgccccacgcggggcctgggagagtctgtgaggccgccaccgcttgtcagtagagtgcgcccgcgagccgtaag cacagcccggcaacatgcggtcttcagacaggaaagtggccgcgaatgggaccggggtgcccagcggctgtggggactctgtcctgcg gaaaccgcggtgacgagcacaagctcggtcaactggatgggaatcggcctggggggctggcaccgcgcccaccagggggtttgcggc acttccctctgcccctcagcaccccacccctactctccaggaacgtgagttctgagccgtgatggtggcaggaaggggccctctgtgccatc cgagtccccagggaccgcagctggccccagccatgtgcaaagtatgtgcagggcgctggcaggcagggagcagcaggcatggtgt cccctgaggggagacagtggtctgggagggagaagtcctggaccctgagggaggtgatggggcaatgctcagccctgtctccggatgc caaaggaggggtgcggggaggccgtcttttggagaattccaggatgggtgctgggtgagagagacgtgtgctggaactgtccagggcgg aggtgggccctgcgggggccctcgggagggccctgctctgattggccggcagggcaggggcgggaatcctgggcggggccacccca gttagaaaaagcccgggctaggaccgaggagcagggtgagggagaagcttggcattccggtactgttggtaaagccaccatggatcctg atgatgttgttgattcttctaaatcttttgtgatggaaaacttttcttcgtaccacgggactaaacctggttatgtagattccattcaaaaaggtatac aaaagccaaaatctggtacacaaggaaattatgacgatgattggaaagggttttatagtaccgacaataaatacgacgctgcgggatactct gtagataatgaaaacccgctctctggaaaagctggaggcgtggtcaaagtgacgtatccaggactgacgaaggttctcgcactaaaagtgg ataatgccgaaactattaagaaagagttaggtttaagtctcactgaaccgttgatggagcaagtcggaacggaagagtttatcaaaaggttcg
```

-continued

```
gtgatggtgcttcgcgtgtagtgctcagccttcccttcgctgagggagttctagcgttgaatatattaataactgggaacaggcgaaagcgtt aagcgtagaacttgagattaattttgaaacccgtggaaaacgtggccaagatgcgatgtatgagtatatggctcaagcctgtgcaggaaatc gtgtcaggcgatctttgtgaaggaaccttacttctgtggtgtgacataattggacaaactacctacagagatttggggatcctctagagtcggg gcggccggccgcttcgagcagacatgataagatacattgatgagtttggacaaaccacaactagaatgcagtgaaaaaaatgctttatttgtg aaatttgtgatgctattgctttatttgtaaccattataagctgcaataaacaagttaacaacaacaattgcattcatttt atgtttcaggttcaggggg aggtgtgggaggttttttaaagcaagtaaaacctctacaaatgtggtaaaatcgataaggatccgtcgaccgatgcccttgagagccttcaac ccagtcagctccttccggtgggcgcggggcatgactatcgtcgccgcacttatgactgtcttctttatcatgcaactcgtaggacaggtgccg gcagcgctcttccgcttcctcgctcactgactcgctgcgctcggtcgttcggctgcggcgagcggtatcagctcactcaaaggcggtaatac ggttatccacagaatcaggggataacgcaggaaagaacatgtgagcaaaaggccagcaaaaggccaggaaccgtaaaaaggccgcgtt gctggcgtttttccataggctccgcccccctgacgagcatcacaaaaatcgacgctcaagtcagaggtggcgaaacccgacaggactataa agataccaggcgtttccccctggaagctccctcgtgcgctctcctgttccgaccctgccgcttaccggatacctgtccgcctttctcccttcgg gaagcgtggcgctttctcatagctcacgctgtaggtatctcagttcggtgtaggtcgttcgctccaagctgggctgtgtgcacgaaccccccg ttcagcccgaccgctgcgccttatccggtaactatcgtcttgagtccaacccggtaagacacgacttatcgccactggcagcagccactggt aacaggattagcagagcgaggtatgtaggcggtgctacagagttcttgaagtggtggcctaactacggctacactagaagaacagtatttgg tatctgcgctctgctgaagccagttaccttcggaaaaagagttggtagctcttgatccggcaaacaaaccaccgctggtagcggtggtttttt t gtttgcaagcagcagattacgcgcagaaaaaaaggatctcaagaagatcctttgatcttttctacggggtctgacgctcagtggaacgaaaa ctcacgttaagggattttggtcatgagattatcaaaaaggatcttcacctagatccttttaaattaaaaatgaagttttaaatcaatctaaagtatat atgagtaaacttggtctgacagttagaaaaactcatcgagcatcaaatgaaactgcaatttattcatatcaggattatcaataccatatttttgaaa aagccgtttctgtaatgaaggagaaaactcaccgaggcagttccataggatggcaagatcctggtatcggtctgcgattccgactcgtccaa catcaatacaacctattaatttcccctcgtcaaaaataaggttatcaagtgagaaatcaccatgagtgacgactgaatccggtgagaatggca aaagtttatgcatttctttccagacttgttcaacaggccagccattacgctcgtcatcaaaatcactcgcatcaaccaaaccgttattcattcgtga ttgcgcctgagcgagacgaaatacgcgatcgctgttaaaaggacaattacaaacaggaatcgaatgcaaccggcgcaggaacactgcca gcgcatcaacaatattttcacctgaatcaggatattcttctaatacctggaatgctgttttcccggggatcgcagtggtgagtaaccatgcatcat caggagtacggataaaatgcttgatggtcggaagaggcataaattccgtcagccagtttagtctgaccatctcatctgtaacatcattggcaac gctacctttgccatgtttcagaaacaactctggcgcatcgggcttcccatacaatcgatagattgtcgcacctgattgcccgacattatcgcga gcccatttatacccatataaatcagcatccatgttggaatttaatcgcggcctagagcaagacgtttcccgttgaatatggctcatactcttccttt ttcaatattattgaagcatttatcagggttattgtctcatgagcggatacatatttgaatgtatttagaaaaataaacaaataggggttccgcgcac atttccccgaaaagtgccacctgacgcgccctgtagcggcgcattaagcgcggcgggtgtggtggttacgcgcagcgtgaccgctacact tgccagcgccctagcgcccgctcctttcgctttcttcccttcctttctcgccacgttcgccggctttccccgtcaagctctaaatcgggggctcc ctttagggttccgatttagtgctttacggcacctcgaccccaaaaaacttgattagggtgatggttcacgtagtgggccatcgccctgatagac ggtttttcgccattgacgttggagtccacgttctttaatagtggactcttgttccaaactggaacaacactcaaccctatctcggtctattcttttga tttataagggattttgccgatttcggcctattggttaaaaaatgagctgatttaacaaaaatttaacgcgaattttaacaaaatattaacgcttacaa tttgccattcgccattcaggctgcgcaactgttgggaagggcgatcggtgcgggcctcttcgctattacgccagcccaagctaccatgataa gtaagtaatattaaggtacgggaggtacttggagcggccgcaataaaatatctttattttcattacatctgtgtgttggttttttgtgtgaatcgata gtactaacatacgctctccatcaaaacaaaacgaaacaaaacaaactagcaaaataggctgtccccagtgcaagtgcaggtgccagaacat ttctctatcgataacttcccggtcggtctgtgggtgcaggggtgccgcctcacatgtgtgattcgtgccttgcgggccctggcctccgggt gctgggtaacgaggaggggcgcggagccgcagaagcccaccctggtatgttgacgcggtgccagcgagaccgcgagaggaagacgg gggtgggcggggccaggatggagaggggccgagttggcaggagtcatggcagacgccacattcgcgacatctcccccacaccccctct ggctctgtccgcaacatttccaaacaggagtcccgggagaggggagagggctgctggtctgaggctaagaagggcagagccttcga cccggagagaggccgcggcccctgcccagtgggcagcgtggaagtttccatacaaggaggtgggaaggagaccccccccccccttca
```

-continued

```
ctgccctgtgcagagatgagccgggggtgcaggatgggagcccatggcacttcgctacgggatggtccagggctcccggttgggggtgc aggagagaagagactggctgggaggagggagagggcgggagcaaaggcgcgggggagtggtcagcagggagaggggtgggggg tagggtggagcccgggctggaggagtcggctcacacataaaagctgaggcactgaccagcctgcaaactggacattagcttctcctgtg aaagagacttccagcttcctcctcctcctcttcctcctcctcctcctgccccagcgagccttctgctgagctgtaggggatcttctagagtcgg ctagcggcattccggtactgttggtaaagccaccatggatcctgatgatgttgttgattcttctaaatcttttgtgatggaaaacttttcttcgtacc acgggactaaacctggttatgtagattccattcaaaaaggtatacaaaagccaaatctggtacacaaggaaattatgacgatgattggaaag ggttttatagtaccgacaataaatacgacgctgcgggatactctgtagataatgaaaacccgctctctggaaaagctggaggcgtggtcaaa gtgacgtatccaggactgacgaaggttctcgcactaaaagtggataatgccgaaactattaagaaagagttaggtttaagtctcactgaaccg ttgatggagcaagtcggaacggaagagtttatcaaaaggttcggtgatggtgcttcgcgtgtagtgctcagccttcccttcgctgaggggagt tctagcgttgaatatattaataactgggaacaggcgaaagcgttaagcgtagaacttgagattaattttgaaacccgtggaaaacgtggccaa gatgcgatgtatgagtatatggctcaagcctgtgcaggaaatcgtgtcaggcgatctttgtgaaggaaccttacttctgtggtgtgacataattg gacaaactacctacagagatttggggatccctcgagacgtagggtaccgacaa.
```

Creation P4-DTA-P3-DTA

The P4-DTA-P3-DTA construct was created using a strategy very similar to that used to create the H19-DTA-P4-DTA construct. The final construct was verified by sequencing. Sequence congruence was 100%. The IGF-II P3 promoter had the following sequence:

```
(SEQ ID NO: 17)
ggccatgcaggtaggatttgagctgtgtttcccgccctgatcctctctcctctggcggccggagcctccgtaggctccaagcctg gcccagattcggcggcgcagccggccttccgcgcgtccgcacctagcgggggctccggggctccggcgcggcaccgggggcgctc gggatctggctgaggctccaaggcccgcgtggccggctcctcctgctggggcaggtggcggctgcgcgccccgcccgagcccagggg cccctcagccgcaacaaccagcaaggacccccgactcagccccaagccacctgcatctgcactcagacggggcgcacccgcagtgc agcctcctggtggggcgctgggagcccgcctgcccctgcctgcccggagaccccagctcacgagcacaggccgcccgggcaccccag aaacccgggatggggcccctgaattctctaggacgggcattcagcatggccttggcgctctgcggctccctgcccccacccagcctcgc cccgcgcaccccccagccctgcgaccgccgccccccccgggcccagggccccagcccgcacccccgccccgctcttgg ctcgggttgcgggggcgggccgggggcgggcgagggctccgcgggcgcccattggcgcgggcgcgaggccagcggccccgcgc ggccctgggccgcggctggcgcgactataagagccgggcgtgggcgcccgcagttcgcctgctctccggcggagctgcgtgaggccc ggccggccccggcccccccttccggccgcccccgcctcctggcccacgcctgcccgcgctctgcccaccagcgcctccatcgggcaa ggcggccccgcgtcgac.
```

P4-DTA-P3-DTA had the following sequence:

```
(SEQ ID NO: 24)
gcggccgcaataaaatatctttattttcattacatctgtgtgttggttttttgtgtgaatcgatagtactaacatacgctctccatcaaaa caaaacgaaacaaaacaaactagcaaaataggctgtcccagtgcaagtgcaggtgccagaacatttctctatcgataacttcccggtcggt ctgtgggtgcagggggtgccgcctcacatgtgtgattcgtgccttgcgggccctggcctccggggtgctgggtaacgaggagggcgcg gagccgcagaagccaccctggtatgttgacgcggtgccagcgagaccgcgagaggaagacggggtgggcgggccaggatgga gaggggccgagttggcaggagtcatggcagacgccacattcgcgacatctcccccacacccctctggctctgtccgcaacatttccaaac aggagtcccgggagaggggggagaggggctgctggtctgaggctaagaagggcagagcttcgacccggagagaggccgcggcccct gcccagtgggcagcgtggaagtttccatacaaggaggtgggaaggagaccccccccccccttcactgccctgtgcagagatgagccgg gggtgcaggatgggagcccatggcacttcgctacgggatggtccagggctcccggttgggggtgcaggagagaagagactggctggga ggagggagagggcgggagcaaaggcgcgggggagtggtcagcagggagaggggtgggggtagggtggagcccgggctgggag gagtcggctcacacataaaagctgaggcactgaccagcctgcaaactggacattagcttctcctgtgaaagagacttccagcttcctcctcct cctcttcctcctcctcctcctgccccagcgagccttctgctgagctgtaggggatcttctagagtcggctagcggcattccggtactgttggt
```

-continued

```
aaagccaccatggatcctgatgatgttgttgattcttctaaatcttttgtgatgaaaacttttcttcgtaccacgggactaaacctggttatgtaga
ttccattcaaaaaggtatacaaaagccaaaatctggtacacaaggaaattatgacgatgattggaaagggttttatagtaccgacaataaatac
gacgctgcgggatactctgtagataatgaaaacccgctctctggaaaagctggaggcgtggtcaaagtgacgtatccaggactgacgaag
gttctcgcactaaaagtggataatgccgaaactattaagaaagagttaggtttaagtctcactgaaccgttgatggagcaagtcggaacggaa
gagtttatcaaaaggttcggtgatggtgcttcgcgtgtagtgctcagccttcccttcgctgaggggagttctagcgttgaatatattaataactg
ggaacaggcgaaagcgttaagcgtagaacttgagattaattttgaaaccgtggaaaacgtggccaagatgcgatgtatgagtatatggctc
aagcctgtgcaggaaatcgtgtcaggcgatctttgtgaaggaaccttacttctgtggtgtgacataattggacaaactacctacagagatttgg
ggatccctcgagggccatgcaggtaggatttgagctgtgtttcccgccctgatcctctctcctctggcggccggagcctccgtaggctccaa
gcctggcccagattcggcggcgcagccggccttccgcgcgtccgcacctagcgggggctccggggctccggcgcggcaccgggggg
cgctcgggatctggctgaggctccaaggcccgcgtggccggctcctcctgctggggcaggtggcggctgcgcgccccgcccgagccca
gggcccccctcagccgcaacaaccagcaaggaccccccgactcagccccaagccacctgcatctgcactcagacggggcgcacccgc
agtgcagcctcctggtggggcgctgggagcccgcctgcccctgcctgcccggagaccccagctcacgagcacaggccgcccgggcac
cccagaaacccgggatggggcccctgaattctctaggacgggcattcagcatggccttggcgctctgcggctccctgcccccacccagc
ctcgcccccgcgcaccccccagccctgcgaccgccgccccccccccggggccccagggcccagcccgcaccccccgccccgct
cttggctcgggttgcggggcgggccggggcggggcgagggctccgcgggcgcccattggcgcgggcgcgaggccagcggcccc
gcgcggccctgggccgcggctggcgcgactataagagccgggcgtgggcgcccgcagttcgcctgctctccggcggagctgcgtgag
gcccggccgccccggccccccccttccggccgccccgcctcctggcccacgcctgcccgcgctctgcccaccagcgcctccatcgg
gcaaggcggccccgcgtcgacaagcttggcattccggtactgttggtaaagccaccatggatcctgatgatgttgttgattcttctaaatctttt
gtgatgaaaacttttcttcgtaccacgggactaaacctggttatgtagattccattcaaaaaggtatacaaaagccaaaatctggtacacaag
gaaattatgacgatgattggaaagggttttatagtaccgacaataaatacgacgctgcgggatactctgtagataatgaaaacccgctctctg
gaaaagctggaggcgtggtcaaagtgacgtatccaggactgacgaaggttctcgcactaaaagtggataatgccgaaactattaagaaag
agttaggtttaagtctcactgaaccgttgatggagcaagtcggaacggaagagtttatcaaaaggttcggtgatggtgcttcgcgtgtagtgct
cagccttcccttcgctgaggggagttctagcgttgaatatattaataactgggaacaggcgaaagcgttaagcgtagaacttgagattaatttt
gaaaccgtggaaaacgtggccaagatgcgatgtatgagtatatggctcaagcctgtgcaggaaatcgtgtcaggcgatctttgtgaagga
accttacttctgtggtgtgacataattggacaaactacctacagagatttggggatccctctagagtcggggcggccggccgcttcgagcaga
catgataagatacattgatgagtttggacaaaccacaactagaatgcagtgaaaaaaatgctttatttgtgaaatttgtgatgctattgctttatttg
taaccattataagctgcaataaacaagttaacaacaacaattgcattcattttatgtttcaggttcaggggggaggtgtgggaggttttttaaagca
agtaaaacctctacaaatgtggtaaaatcgataaggatccgtcgaccgatgcccttgagagccttcaacccagtcagctccttccggtgggc
gcggggcatgactatcgtcgccgcacttatgactgtcttctttatcatgcaactcgtaggacaggtgccggcagcgctcttccgcttcctcgct
cactgactcgctgcgctcggtcgttcggctgcggcgagcggtatcagctcactcaaaggcggtaatacggttatccacagaatcaggggat
aacgcaggaaagaacatgtgagcaaaaggccagcaaaaggccaggaaccgtaaaaaggccgcgttgctggcgtttttccataggctccg
cccccctgacgagcatcacaaaaatcgacgctcaagtcagaggtggcgaaacccgacaggactataaagataccaggcgtttccccctgg
aagctccctcgtgcgctctcctgttccgaccctgccgcttaccggatacctgtccgcctttctcccttcgggaagcgtggcgctttctcatagct
cacgctgtaggtatctcagttcggtgtaggtcgttcgctccaagctgggctgtgtgcacgaaccccccgttcagcccgaccgctgcgcctat
ccggtaactatcgtcttgagtccaacccggtaagacacgacttatcgccactggcagcagccactggtaacaggattagcagagcgaggta
tgtaggcggtgctacagagttcttgaagtggtggcctaactacggctacactagaagaacagtatttggtatctgcgctctgctgaagccagtt
accttcggaaaaagagttggtagctcttgatccggcaaacaaaccaccgctggtagcggtggtttttttgtttgcaagcagcagattacgcgc
agaaaaaaaggatctcaagaagatcctttgatcttttctacggggtctgacgctcagtggaacgaaaactcacgttaagggattttggtcatga
gattatcaaaaaggatcttcacctagatccttttaaattaaaaatgaagttttaaatcaatctaaagtatatatgagtaaacttggtctgacagttag
aaaaactcatcgagcatcaaatgaaactgcaatttattcatatcaggattatcaataccatattttgaaaagccgtttctgtaatgaaggagaa
aactcaccgaggcagttccataggatggcaagatcctggtatcggtctgcgattccgactcgtccaacatcaatacaacctattaatttcccct
```

-continued

```
cgtcaaaaataaggttatcaagtgagaaatcaccatgagtgacgactgaatccggtgagaatggcaaaagtttatgcatttctttccagacttg
ttcaacaggccagccattacgctcgtcatcaaaatcactcgcatcaaccaaaccgttattcattcgtgattgcgcctgagcgagacgaaatac
gcgatcgctgttaaaaggacaattacaaacaggaatcgaatgcaaccggcgcaggaacactgccagcgcatcaacaatattttcacctgaa
tcaggatattcttctaatacctggaatgctgttttcccggggatcgcagtggtgagtaaccatgcatcatcaggagtacggataaaatgcttgat
ggtcggaagaggcataaattccgtcagccagtttagtctgaccatctcatctgtaacatcattggcaacgctacctttgccatgtttcagaaaca
actctggcgcatcgggcttcccatacaatcgatagattgtcgcacctgattgcccgacattatcgcgagcccatttatacccatataaatcagc
atccatgttggaatttaatcgcggcctagagcaagacgtttcccgttgaatatggctcatactcttccttttcaatattattgaagcatttatcagg
gttattgtctcatgagcggatacatatttgaatgtatttagaaaaataaacaatagggggttccgcgcacatttccccgaaaagtgccacctgac
gcgccctgtagcggcgcattaagcgcggcgggtgtggtggttacgcgcagcgtgaccgctacacttgccagcgccctagcgcccgctcc
tttcgctttcttcccttcctttctcgccacgttcgccggctttccccgtcaagctctaaatcggggggctccctttagggttccgatttagtgctttac
ggcacctcgaccccaaaaaacttgattagggtgatggttcacgtagtgggccatcgccctgatagacggtttttcgccctttgacgttggagt
ccacgttctttaatagtggactcttgttccaaactggaacaacactcaaccctatctcggtctattcttttgatttataagggattttgccgatttcgg
cctattggttaaaaaatgagctgatttaacaaaaatttaacgcgaattttaacaaaatattaacgcttacaatttgccattcgccattcaggctgcg
caactgttgggaagggcgatcggtgcgggcctcttcgctattacgccagcccaagctaccatgataagtaagtaatattaaggtacgggag
gtacttgga.
```

P3-DTA, expressing DTA under the P3 promoter alone, had the following sequence:

(SEQ ID NO: 19)

```
tctatcgataggtaccgacaaccctcaccaagggccaaggtggtgaccggccatgcaggtaggatttgagctgtgtttcccgcc
ctgatcctctctcctctggcggccggagcctccgtaggctccaagcctggcccagattcggcggcgcagccggccttccgcgcgtccgca
cctagcgggggctccggggctccggcgcggcaccgggggggcgctcgggatctggctgaggctccaaggcccgcgtggccggctcctc
ctgctggggcaggtggcggctgcgcgccccgcccgagcccaggggccccctcagccgcaacaaccagcaaggacccccgactcag
ccccaagccacctgcatctgcactcagacggggcgcaccccgcagtgcagcctcctggtggggcgctgggagcccgcctgcccctgcct
gcccggagaccccagctcacgagcacaggccgcccgggcaccccagaaacccgggatggggcccctgaattctctaggacgggcatt
cagcatggccttggcgctctgcggctccctgccccccacccagcctcgccccgcgcaccccccagccctgcgaccgccgccccccc
ccccggggccccagggcccagcccgcaccccccgccccgctcttggctcgggttgcggggcgggccgggggcgggcgagggc
tccgcgggcgcccattggcgcgggcgcgaggccagcggcccgcgcggccctgggccgcggctggcgcgactataagagccgggc
gtgggcgcccgcagttcgcctgctctccggcggagctgcgtgaggcccggccggccccggcccccccttccggccgcccccgcctcc
tggcccacgcctgcccgcgctctgcccaccagcgcctccatcgggcaaggcggcccgcaagcttggcattccggtactgttggtaaagc
caccatggatcctgatgatgttgttgattcttctaaatcttttgtgatggaaaacttttcttcgtaccacgggactaaacctggttatgtagattccat
tcaaaaaggtatacaaaagccaaatctggtacacaaggaaattatgacgatgattggaaagggttttatagtaccgacaataaatacgacg
ctgcgggatactctgtagataatgaaaacccgctctctggaaaagctggaggcgtggtcaaagtgacgtatccaggactgacgaaggttct
cgcactaaaagtggataatgccgaaactattaagaaagagttaggttttaagtctcactgaaccgttgatggagcaagtcggaacggaagagt
ttatcaaaaggttcggtgatggtgcttcgcgtgtagtgctcagccttcccttcgctgaggggagttctagcgttgaatatattaataactgggaa
caggcgaaagcgttaagcgtagaacttgagattaattttgaaacccgtggaaaacgtggccaagatgcgatgtatgagtatatggctcaagc
ctgtgcaggaaatcgtgtcaggcgatctttgtgaaggaaccttacttctgtggtgtgacataattggacaaactacctacagagatttgggat
cctctagagtcggggcggccggccgcttcgagcagacatgataagatacattgatgagtttggacaaaccacaactagaatgcagtgaaaa
aaatgctttatttgtgaaatttgtgatgctattgctttatttgtaaccattataagctgcaataaacaagttaacaacaacaattgcattcattttatgtt
tcaggttcaggggaggtgtgggaggttttttaaagcaagtaaaacctctacaaatgtggtaaaatcgataaggatccgtcgaccgatgccct
tgagagccttcaacccagtcagctcctccggtgggcgcggggcatgactatcgtcgccgcacttatgactgtcttctttatcatgcaactcgt
```

-continued

```
aggacaggtgccggcagcgctcttccgcttcctcgctcactgactcgctgcgctcggtcgttcggctgcggcgagcggtatcagctcactc aaaggcggtaatacggttatccacagaatcaggggataacgcaggaaagaacatgtgagcaaaaggccagcaaaaggccaggaaccgt aaaaaggccgcgttgctggcgtttttccataggctccgcccccctgacgagcatcacaaaaatcgacgctcaagtcagaggtggcgaaac ccgacaggactataaagataccaggcgtttccccctggaagctccctcgtgcgctctcctgttccgaccctgccgcttaccggatacctgtcc gcctttctcccttcgggaagcgtggcgctttctcatagctcacgctgtaggtatctcagttcggtgtaggtcgttcgctccaagctgggctgtgt gcacgaaccccccgttcagcccgaccgctgcgccttatccggtaactatcgtcttgagtccaacccggtaagacacgacttatcgccactgg cagcagccactggtaacaggattagcagagcgaggtatgtaggcggtgctacagagttcttgaagtggtggcctaactacggctacactag aagaacagtatttggtatctgcgctctgctgaagccagttaccttcggaaaaagagttggtagctcttgatccggcaaacaaaccaccgctgg tagcggtggtttttttgtttgcaagcagcagattacgcgcagaaaaaaaggatctcaagaagatcctttgatcttttctacggggtctgacgctc agtggaacgaaaactcacgttaagggattttggtcatgagattatcaaaaaggatcttcacctagatccttttaaattaaaaatgaagttttaaat caatctaaagtatatatgagtaaacttggtctgacagttagaaaaactcatcgagcatcaaatgaaactgcaatttattcatatcaggattatcaa taccatattttgaaaaagccgtttctgtaatgaaggagaaaactcaccgaggcagttccataggatggcaagatcctggtatcggtctgcgat tccgactcgtccaacatcaatacaacctattaatttccctcgtcaaaaataaggttatcaagtgagaaatcaccatgagtgacgactgaatcc ggtgagaatggcaaaagtttatgcatttctttccagacttgttcaacaggccagccattacgctcgtcatcaaaatcactcgcatcaaccaaac cgttattcattcgtgattgcgcctgagcgagacgaaatacgcgatcgctgttaaaaggacaattacaaacaggaatcgaatgcaaccggcgc aggaacactgccagcgcatcaacaatattttcacctgaatcaggatattcttctaatacctggaatgctgttttcccggggatcgcagtggtga gtaaccatgcatcatcaggagtacggataaaatgcttgatggtcggaagaggcataaattccgtcagccagtttagtctgaccatctcatctgt aacatcattggcaacgctacctttgccatgtttcagaaacaactctggcgcatcgggcttcccatacaatcgatagattgtcgcacctgattgc ccgacattatcgcgagcccatttataccccatataaatcagcatccatgttggaatttaatcgcggcctagagcaagacgtttcccgttgaatatg gctcatactcttccttttcaatattattgaagcatttatcagggttattgtctcatgagcggatacatatttgaatgtatttagaaaaataaacaaata ggggttccgcgcacatttccccgaaaagtgccacctgacgcgccctgtagcggcgcattaagcgcggcgggtgtggtggttacgcgcag cgtgaccgctacacttgccagcgccctagcgcccgctcctttcgctttcttcccttcctttctcgccacgttcgccggctttccccgtcaagctct aaatcggggctcccttagggttccgatttagtgctttacggcacctcgaccccaaaaaacttgattagggtgatggttcacgtagtgggcc atcgccctgatagacggtttttcgccctttgacgttggagtccacgttctttaatagtggactcttgttccaaactggaacaacactcaaccctat ctcggtctattcttttgatttataaggggatttgccgatttcggcctattggttaaaaaatgagctgatttaacaaaaatttaacgcgaattttaacaa aatattaacgcttacaatttgccattcgccattcaggctgcgcaactgttgggaagggcgatcggtgcgggcctcttcgctattacgccagcc caagctaccatgataagtaagtaatattaaggtacgggaggtacttggagcggccgcaataaaatatctttattttcattacatctgtgtgttggtt ttttgtgtgaatcgatagtactaacatacgctctccatcaaaacaaaacgaaacaaaacaaactagcaaaataggctgtccccagtgcaagtg caggtgccagaacatttctctatcgataggtaccgaca.
```

P4-DTA, a plasmid expressing DTA under the P4 promoter, was created by replacing the P3 promoter with the P4 promoter (SEQ ID NO: 9).

In addition, a control construct, P4-Luc-P3-Luc, was created using the same strategy. The sequence of P4-Luc-P3-Luc is as follows:

```
(SEQ ID NO: 22)
ggtgcgggcctcttcgctattacgccagcccaagctaccatgataagtaagtaatattaaggtacgggaggtacttggagcggccgcaataa aatatctttattttcattacatctgtgtgttggttttttgtgtgaatcgatagtactaacatacgctctccatcaaaacaaaacgaaacaaaacaaact agcaaaataggctgtccccagtgcaagtgcaggtgccagaacatttctctatcgataacttcccggtcggtctgtgggtgcagggggtgccg cctcacatgtgtgattcgtgccttgcgggccctggcctccggggtgctgggtaacgaggaggggcgcggagccgcagaagcccaccctg gtatgttgacgcggtgccagcgagaccgcgagaggaagacgggggtgggcgggccaggatggagaggggccgagttggcaggagt catggcagacgccacattcgcgacatctcccccacacccctctggctctgtccgcaacatttccaaacaggagtcccgggagaggggga gagggctgctggtctgaggctaagaagggcagagccttcgacccggagagaggccgcggcccctgcccagtgggcagcgtggaagt
```

-continued

```
ttccatacaaggaggtgggaaggagaccccccccccccttcactgccctgtgcagagatgagccgggggtgcaggatgggagcccatg
gcacttcgctacgggatggtccagggctcccggttgggggtgcaggagagaagagactggctgggaggagggagagggcgggagca
aaggcgcggggagtggtcagcagggagaggggtgggggtagggtggagcccgggctgggaggagtcggctcacacataaaagct
gaggcactgaccagcctgcaaactggacattagcttctcctgtgaaagagacttccagcttcctcctcctcctcttcctcctcctcctgccc
cagcgagccttctgctgagctgtaggggatcttctagagtcggctagcggcattccggtactgttggtaaagccaccatggaagacgcca
aaacataaagaaaggcccggcgccattctatccgctggaagatggaaccgctggagagcaactgcataaggctatgaagagatacgcc
ctggttcctggaacaattgcttttacagatgcacatatcgaggtggacatcacttacgctgagtacttcgaaatgtccgttcggttggcagaag
ctatgaaacgatatgggctgaatacaaatcacagaatcgtcgtatgcagtgaaaactctcttcaattctttatgccggtgtttgggcgcgttattta
tcggagttgcagttgcgcccgcgaacgacatttataatgaacgtgaattgctcaacagtatgggcatttcgcagcctaccgtggtgttcgtttc
caaaaagggggttgcaaaaaattttgaacgtgcaaaaaaagctcccaatcatccaaaaaattattatcatggattctaaaacggattaccaggg
atttcagtcgatgtacacgttcgtcacatctcatctacctcccggttttaatgaatacgattttgtgccagagtccttcgatagggacaagacaatt
gcactgatcatgaactcctctggatctactggtctgcctaaaggtgtcgctctgcctcatagaactgcctgcgtgagattctcgcatgccagag
atcctatttttggcaatcaaatcattccggatactgcgattttaagtgttgttccattccatcacggttttggaatgtttactacactcggatatttgat
atgtggatttcgagtcgtcttaatgtatagatttgaagaagagctgtttctgaggagccttcaggattacaagattcaaagtgcgctgctggtgc
caacccctattctccttcttcgccaaaagcactctgattgacaaatacgatttatctaatttacacgaaattgcttctggtggcgctccctctctaa
ggaagtcggggaagcggttgccaagaggttccatctgccaggtatcaggcaaggatatgggctcactgagactacatcagctattctgatta
cacccgaggggatgataaaccgggcgcggtcggtaaagttgttccattttttgaagcgaaggttgtggatctggataccgggaaaacgct
gggcgttaatcaaagaggcgaactgtgtgtgagaggtcctatgattatgtccggttatgtaaacaatccggaagcgaccaacgccttgattga
caaggatggatggctacattctggagacatagcttactgggacgaagacgaacacttcttcatcgttgaccgcctgaagtctctgattaagta
caaaggctatcaggtggctcccgctgaattggaatccatcttgctccaacaccccaacatcttcgacgcaggtgtcgcaggtcttcccgacg
atgacgccggtgaacttcccgccgccgttgttgtttggagcacggaaagacgatgacgaaaaagagatcgtggattacgtcgccagtca
agtaacaaccgcgaaaaagttgcgcggaggagttgtgtttgtggacgaagtaccgaaaggtcttaccggaaaactcgacgcaagaaaat
cagagagatcctcataaaggccaagaagggcggaaagatcgccgtgtaatctcgagggccatgcaggtaggatttgagctgtgtttcccg
ccctgatcctctctcctctggcggccggagcctccgtaggctccaagcctggcccagattcggcggcgcagccggccttccgcgcgtccg
cacctagcggggctccggggctccgcgcggcaccggggggcgctcgggatctggctgaggctccaaggcccgcgtggccggctc
ctcctgctggggcaggtggcggctgcgcgccccgcccgagcccaggggcccctcagccgcaacaaccagcaaggaccccccgactc
agccccaagccacctgcatctgcactcagacggggcgcaccgcagtgcagcctcctggtggggcgctgggagcccgcctgcccctgc
ctgcccggagacccagctcacgagcacaggccgcccgggcaccccagaaacccgggatggggcccctgaattctctaggacgggca
ttcagcatggccttggcgctctgcggctccctgccccccacccagcctcgccccgcgcaccccccagccctgcgaccgccgcccccc
ccccggggcccagggcccagcccgcacccccgccccgctcttggctcgggttgcggggcgggccggggcggggcgaggg
ctccgcgggcgcccattggcgcgggcgcgaggccagcggccccgcgcggccctgggccgcggctggcgcgactataagagcggg
cgtgggcgcccgcagttcgcctgctctccggcggagctgcgtgaggcccggccgccccggccccccccttccggccgccccgcctc
ctggcccacgcctgccgcgctctgcccaccagcgcctccatcgggcaaggcggccccgcgtcgacaagcttggcattccggtactgttg
gtaaagccaccatggaagacgccaaaaacataaagaaaggcccggcgccattctatccgctggaagatggaaccgctggagagcaact
gcataaggctatgaagagatacgccctggttcctggaacaattgcttttacagatgcacatatcgaggtggacatcacttacgctgagtacttc
gaaatgtccgttcggttggcagaagctatgaaacgatatgggctgaatacaaatcacagaatcgtcgtatgcagtgaaaactctcttcaattct
ttatgccggtgtttgggcgcgttatttatcggagttgcagttgcgcccgcgaacgacatttataatgaacgtgaattgctcaacagtatgggcatt
tcgcagcctaccgtggtgttcgtttccaaaaagggggttgcaaaaaattttgaacgtgcaaaaaaagctcccaatcatccaaaaaattattatcat
ggattctaaaacggattaccagggatttcagtcgatgtacacgttcgtcacatctcatctacctcccggttttaatgaatacgattttgtgccaga
gtccttcgatagggacaagacaattgcactgatcatgaactcctctggatctactggtctgcctaaaggtgtcgctctgcctcatagaactgcc
tgcgtgagattctcgcatgccagagatcctatttttggcaatcaaatcattccggatactgcgattttaagtgttgttccattccatcacggttttgg
```

-continued

```
aatgtttactacactcggatatttgatatgtggatttcgagtcgtcttaatgtatagatttgaagaagagctgtttctgaggagccttcaggattaca
agattcaaagtgcgctgctggtgccaaccctattctccttcttcgccaaaagcactctgattgacaaatacgatttatctaatttacacgaaattg
cttctggtggcgctccctctctaaggaagtcggggaagcggttgccaagaggttccatctgccaggtatcaggcaaggatatgggctcact
gagactacatcagctattctgattacacccgaggggatgataaaccgggcgcggtcggtaaagttgttccattttttgaagcgaaggttgtg
gatctggataccgggaaaacgctgggcgttaatcaaagaggcgaactgtgtgtgagaggtcctatgattatgtccggttatgtaaacaatcc
ggaagcgaccaacgccttgattgacaaggatggatggctacattctggagacatagcttactgggacgaagacgaacacttcttcatcgttg
accgcctgaagtctctgattaagtacaaaggctatcaggtggctcccgctgaattggaatccatcttgctccaacaccccaacatcttcgacg
caggtgtcgcaggtcttcccgacgatgacgccggtgaacttcccgccgcgttgttgttttggagcacggaaagacgatgacggaaaaag
agatcgtggattacgtcgccagtcaagtaacaaccgcgaaaaagttgcgcggaggagttgtgtttgtggacgaagtaccgaaaggtcttac
cggaaaactcgacgcaagaaaaatcagagagatcctcataaaggccaagaagggcggaaagatcgccgtgtaattctagagtcgggc
ggccggccgcttcgagcagacatgataagatacattgatgagtttggacaaaccacaactagaatgcagtgaaaaaaatgctttatttgtgaa
atttgtgatgctattgcttatttgtaaccattataagctgcaataaacaagttaacaacaacaattgcattcattttatgtttcaggttcaggggag
gtgtgggaggttttttaaagcaagtaaaacctctacaaatgtggtaaaatcgataaggatccgtcgaccgatgcccttgagagccttcaaccc
agtcagctccttccggtgggcgcggggcatgactatcgtcgccgcacttatgactgtcttctttatcatgcaactcgtaggacaggtgccggc
agcgctcttccgcttcctcgctcactgactcgctgcgctcggtcgttcggctgcggcgagcggtatcagctcactcaaaggcggtaatacgg
ttatccacagaatcaggggataacgcaggaaagaacatgtgagcaaaaggccagcaaaaggccaggaaccgtaaaaaggccgcgttgc
tggcgtttttccataggctccgcccccctgacgagcatcacaaaaatcgacgctcaagtcagaggtggcgaaacccgacaggactataaag
ataccaggcgtttccccctggaagctccctcgtgcgctctcctgttccgaccctgccgcttaccggatacctgtccgcctttctcccttcggga
agcgtggcgctttctcatagctcacgctgtaggtatctcagttcggtgtaggtcgttcgctccaagctgggctgtgtgcacgaaccccccgttc
agcccgaccgctgcgccttatccggtaactatcgtcttgagtccaacccggtaagacacgacttatcgccactggcagcagccactggtaa
caggattagcagagcgaggtatgtaggcggtgctacagagttcttgaagtggtggcctaactacggctacactagaagaacagtatttggta
tctgcgctctgctgaagccagttaccttcggaaaaagagttggtagctcttgatccggcaaacaaaccaccgctggtagcggtggtttttttgtt
tgcaagcagcagattacgcgcagaaaaaaaggatctcaagaagatcctttgatcttttctacggggtctgacgctcagtggaacgaaaactc
acgttaagggattttggtcatgagattatcaaaaaggatcttcacctagatccttttaaattaaaaatgaagttttaaatcaatctaaagtatatatg
agtaaacttggtctgacagttagaaaaactcatcgagcatcaaatgaaactgcaatttattcatatcaggattatcaataccatattttgaaaaa
gccgtttctgtaatgaaggagaaaactcaccgaggcagttccataggatggcaagatcctggtatcggtctgcgattccgactcgtccaacat
caatacaacctattaatttcccctcgtcaaaaataaggttatcaagtgagaaatcaccatgagtgacgactgaatccggtgagaatggcaaaa
gtttatgcatttctttccagacttgttcaacaggccagccattacgctcgtcatcaaaatcactcgcatcaaccaaaccgttattcattcgtgattg
cgcctgagcgagacgaaatacgcgatcgctgttaaaaggacaattacaaacaggaatcgaatgcaaccggcgcaggaacactgccagc
gcatcaacaatattttcacctgaatcaggatattcttctaatacctggaatgctgttttcccggggatcgcagtggtgagtaaccatgcatcatca
ggagtacggataaaatgcttgatggtcggaagaggcataaattccgtcagccagtttagtctgaccatctcatctgtaacatcattggcaacg
ctacctttgccatgtttcagaaacaactctggcgcatcgggcttcccatacaatcgatagattgtcgcacctgattgcccgacattatcgcgag
cccatttataccccatataaatcagcatccatgttggaatttaatcgcggcctagagcaagacgtttcccgttgaatatggctcatactcttcctttt
caatattattgaagcatttatcagggttattgtctcatgagcggatacatatttgaatgtatttagaaaaataaacaaatagggttccgcgcacat
ttccccgaaaagtgccacctgacgcgcctgtagcggcgcattaagcgcggcgggtgtggtggttacgcgcagcgtgaccgctacacttg
ccagcgccctagcgcccgctcctttcgctttcttcccttcctttctcgccacgttcgccggctttccccgtcaagctctaaatcggggctcccctt
tagggttccgatttagtgctttacggcacctcgaccccaaaaaacttgattagggtgatggttcacgtagtgggccatcgccctgatagacgg
tttttcgccctttgacgttggagtccacgttctttaatagtggactcttgttccaaactggaacaacactcaaccctatctcggtctattcttttgattt
ataagggattttgccgatttcggcctattggttaaaaaatgagctgatttaacaaaaatttaacgcgaattttaacaaaatattaacgcttacaattt
gccattcgccattcaggctgcgcaactgttgggaagggcgatc.
```

Creation of H19-DTA-P3-DTA

The H19-DTA-P3-DTA construct was created using a strategy very similar to that used to create the H19/P4 construct. The final construct was verified by sequencing. Sequence congruence was 100%.

H19-DTA-P3-DTA had the following sequence:

(SEQ ID NO: 18)

```
ccctcaccaagggccaaggtggtgaccgacggacccacagcggggtggctggggagtcgaaactcgccagtctccactcc
actcccaaccgtggtgccccacgcgggcctgggagagtctgtgaggccgcccaccgcttgtcagtagagtgcgcccgcgagccgtaag
cacagcccggcaacatgcggtcttcagacaggaaagtggccgcgaatgggaccggggtgcccagcggctgtggggactctgtcctgcg
gaaaccgcggtgacgagcacaagctcggtcaactggatgggaatcggcctggggggctggcaccgcgcccaccagggggtttgcggc
acttccctctgcccctcagcaccccaccccctactctccaggaacgtgagttctgagccgtgatggtggcaggaagggccctctgtgccatc
cgagtccccagggaccgcagctggccccagccatgtgcaaagtatgtgcagggcgctggcaggcagggagcagcaggcatggtgt
ccctgagggagacagtggtctgggagggagaagtcctggaccctgagggaggtgatggggcaatgctcagccctgtctccggatgc
caaggaggggtgcggggaggccgtctttggagaattccaggatgggtgctgggtgagagagacgtgtgctggaactgtccagggcgg
aggtgggccctgcggggcgcctcgggagggccctgctctgattggccggcagggcaggggcgggaatcctgggcggggccacccca
gttagaaaagcccgggctaggaccgaggagcagggtgagggagaagcttggcattccggtactgttggtaaagccaccatggatcctg
atgatgttgttgattcttctaaatcttttgtgatggaaaacttttcttcgtaccacgggactaaacctggttatgtagattccattcaaaaaggtatac
aaaagccaaaatctggtacacaaggaaattatgacgatgattggaaagggttttatagtaccgacaataaatacgacgctgcgggatactct
gtagataatgaaaacccgctctctggaaaagctggaggcgtggtcaaagtgacgtatccaggactgacgaaggttctcgcactaaaagtgg
ataatgccgaaactattaagaaagagttaggtttaagtctcactgaaccgttgatggagcaagtcggaacggaagagtttatcaaaaggttcg
gtgatggtgcttcgcgtgtagtgctcagccttccttcgctgaggggagttctagcgttaatatattaataactgggaacaggcgaaagcgtt
aagcgtagaacttgagattaattttgaaacccgtggaaaacgtggccaagatgcgatgtatgagtatatggctcaagcctgtgcaggaaatc
gtgtcaggcgatctttgtgaaggaaccttacttctgtggtgtgacataattggacaaactacctacagagatttggggatcctctagagtcggg
gcggccggccgcttcgagcagacatgataagatacattgatgagtttggacaaaccacaactagaatgcagtgaaaaaaatgctttatttgtg
aaatttgtgatgctattgctttatttgtaaccattataagctgcaataaacaagttaacaacaacaattgcattcattttatgtttcaggttcaggggg
aggtgtgggaggttttttaaagcaagtaaaacctctacaaatgtggtaaaatcgataaggatccgtcgaccgatgcccttgagagccttcaac
ccagtcagctccttccggtgggcgcggggcatgactatcgtcgccgcacttatgactgtcttctttatcatgcaactcgtaggacaggtgccg
gcagcgctcttccgcttcctcgctcactgactcgctgcgctcggtcgttcggctgcggcgagcggtatcagctcactcaaaggcggtaatac
ggttatccacagaatcaggggataacgcaggaaagaacatgtgagcaaaaggccagcaaaaggccaggaaccgtaaaaaggccgcgtt
gctggcgtttttccataggctccgcccccctgacgagcatcacaaaaatcgacgctcaagtcagaggtggcgaaacccgacaggactataa
agataccaggcgtttccccctggaagctccctcgtgcgctctcctgttccgaccctgccgcttaccggatacctgtccgcctttctcccttcgg
gaagcgtggcgctttctcatagctcacgctgtaggtatctcagttcggtgtaggtcgttcgctccaagctgggctgtgtgcacgaacccccg
ttcagcccgaccgctgcgccttatccggtaactatcgtatgagtccaacccggtaagacacgacttatcgccactggcagcagccactggt
aacaggattagcagagcgaggtatgtaggcggtgctacagagttcttgaagtggtggcctaactacggctacactagaagaacagtatttgg
tatctgcgctctgctgaagccagttaccttcggaaaaagagttggtagctcttgatccggcaaacaaaccaccgctggtagcggtggtttttt
gtttgcaagcagcagattacgcgcagaaaaaaggatctcaagaagatcctttgatcttttctacggggtctgacgctcagtggaacgaaaa
ctcacgttaagggattttggtcatgagattatcaaaaaggatcttcacctagatccttttaaattaaaaatgaagttttaaatcaatctaaagtatat
atgagtaaacttggtctgacagttagaaaaactcatcgagcatcaaatgaaactgcaatttattcatatcaggattatcaataccatattttgaaa
aagccgtttctgtaatgaaggagaaaactcaccgaggcagttccataggatggcaagatcctggtatcggtctgcgattccgactcgtccaa
catcaatacaacctattaatttcccctcgtcaaaaataaggttatcaagtgagaaatcaccatgagtgacgactgaatccggtgagaatggca
aaagtttatgcatttctttccagacttgttcaacaggccagccattacgctcgtcatcaaaatcactcgcatcaaccaaaccgttattcattcgtga
ttgcgcctgagcgagacgaaatacgcgatcgctgttaaaaggacaattacaaacaggaatcgaatgcaaccggcgcaggaacactgcca
gcgcatcaacaatattttcacctgaatcaggatattcttctaatacctggaatgctgttttcccggggatcgcagtggtgagtaaccatgcatcat
caggagtacggataaaatgcttgatggtcggaagaggcataaattccgtcagccagtttagtctgaccatctcatctgtaacatcattggcaac
```

-continued

```
gctacctttgccatgtttcagaaacaactctggcgcatcgggcttcccatacaatcgatagattgtcgcacctgattgcccgacattatcgcga gcccatttatacccatataaatcagcatccatgttggaatttaatcgcggcctagagcaagacgtttcccgttgaatatggctcatactcttcctttt ttcaatattattgaagcatttatcagggttattgtctcatgagcggatacatatttgaatgtatttagaaaaataaacaaatagggggttccgcgcac atttccccgaaaagtgccacctgacgcgcccgtgagcggcgcattaagcgcggcgggtgtggtggttacgcgcagcgtgaccgctacact tgccagcgccctagcgcccgctcctttcgctttcttccccttcctttctcgccacgttcgccggctttccccgtcaagctctaaatcggggctcc ctttaggggttccgatttagtgctttacggcacctcgaccccaaaaaacttgattagggtgatggttcacgtagtgggccatcgcctgatagac ggttttcgccattgacgttggagtccacgttctttaatagtggactcttgttccaaactggaacaacactcaaccctatctcggtctattctttttga tttataagggattttgccgatttcggcctattggttaaaaaatgagctgatttaacaaaaatttaacgcgaattttaacaaaatattaacgcttacaa tttgccattcgccattcaggctgcgcaactgttgggaagggcgatcggtgcgggcctcttcgctattacgccagcccaagctaccatgataa gtaagtaatattaaggtacggggaggtacttggagcggccgcaataaaatatctttattttcattacatctgtgtgttggttttttgtgtgaatcgata gtactaacatacgctctccatcaaaacaaaacgaaacaaaacaaactagcaaaataggctgtccccagtgcaagtgcaggtgccagaacat ttctctatcgatactcgagggccatgcaggtaggattttgagctgtgtttcccgcccctgatcctctctcctctggcggccggagcctccgtaggc tccaagcctggcccagattcggcggcgcagccggccttccgcgcgtccgcacctagcggggggctccggggctccggcgcggcaccgg ggggcgctcgggatctggctgaggctccaaggcccgcgtggccggctcctcctgctggggcaggtggcggctgcgcgcccccgcccga gcccaggggccccctcagccgcaacaaccagcaaggaccccccgactcagccccaagccacctgcatctgcactcagacggggcgca cccgcagtgcagcctcctggtggggcgctgggagcccgcctgcccctgcctgcccggagaccccagctcacgagcacaggccgcccg ggcaccccagaaacccgggatgggggcccctgaattctctaggacgggcattcagcatggccttggcgctctgcggctccctgcccccac ccagcctcgcccccgcgcacccccagcccctgcgaccgccgccccccccccggggcccagggcccagcccgcaccccccgcc ccgctcttggctcgggttgcggggggcgggccggggcggggcgagggctccgcgggcgcccattggcgcgggcgcgaggccagcg gccccgcgcggcccctgggccgcggctggcgcgactataagagccgggcgtgggcgcccgcagttcgcctgctctccggcggagctgc gtgaggcccggccggcccccggccccccccttccggccgccccccgcctcctggcccacgcctgcccgcgctctgcccaccagcgcctcc atcgggcaaggcggccccgcgtcgacaagcttagctacgctagcggcattccggtactgttggtaaagccaccatggatcctgatgatgtt gttgattcttctaaatcttttgtgatggaaaacttttcttcgtaccacgggactaaacctggttatgtagattccattcaaaaaggtatacaaaagcc aaaatctggtacacaaggaaattatgacgatgattggaaagggttttatagtaccgacaataaatacgacgctgcgggatactctgtagataat gaaaacccgctctctggaaaagctggaggcgtggtcaaagtgacgtatccaggactgacgaaggttctcgcactaaaagtggataatgcc gaaactattaagaaagagttaggtttaagtctcactgaaccgttgatggagcaagtcggaacggaagagtttatcaaaaggttcggtgatggt gcttcgcgtgtagtgctcagccttcccttcgctgaggggagttctagcgttgaatatattaataactgggaacaggcgaaagcgttaagcgta gaacttgagattaattttgaaacccgtggaaaacgtggccaagatgcgatgtatgagtatatggctcaagcctgtgcaggaaatcgtgtcagg cgatctttgtgaaggaaccttacttctgtggtgtgacataattggacaaactacctacagagatttggggatccctcgagacgtagggtaccga caa.
```

In addition, a control construct, H19-Luc-P3-Luc, was created using the same strategy. The sequence of H19-Luc-P3-Luc is as follows:

(SEQ ID NO: 20)

```
gacaaccctcaccaagggccaaggtggtgaccgacggacccacagcggggtggctggggagtcgaaactcgccagtctccactccac tcccaaccgtggtgccccacgcgggcctgggagagtctgtgaggccgcccaccgcttgtcagtagagtgcgcccgcgagccgtaagca cagcccggcaacatgcggtcttcagacaggaaagtggccgcgaatgggaccggggtgcccagcggctgtggggactctgtcctgcgga aaccgcggtgacgagcacaagctcggtcaactggatgggaatcggcctgggggctggcaccgcgcccaccagggggtttgcggcact tccctctgcccctcagcaccccaccctactctccaggaacgtgagttctgagccgtgatggtggcaggaaggggccctctgtgccatccg agtccccagggaccccgcagctggccccccagccatgtgcaaagtatgtgcagggcgctggcaggcagggagcagcaggcatggtgtcc
```

-continued

```
cctgagggagacagtggtctgggagggagaagtcctggccctgagggaggtgatggggcaatgctcagccctgtctccggatgccaa
aggagggtgcggggaggccgtctttggagaattccaggatgggtgctggtgagagagacgtgtgctggaactgtccagggcggagg
tgggccctgcggggcccctcgggagggccctgctctgattggccggcagggcagggcgggaattctgggcggggccaccccagtta
gaaaaagcccgggctaggaccgaggagcagggtgagggaagcttggcattccggtactgttggtaaagccaccatggaagacgccaaa
aacataaagaaaggcccggcgccattctatccgctggaagatggaaccgctggagagcaactgcataaggctatgaagagatacgccct
ggttcctggaacaattgcttttacagatgcacatatcgaggtggacatcacttacgctgagtacttcgaaatgtccgttcggttggcagaagct
atgaaacgatatgggctgaatacaaatcacagaatcgtcgtatgcagtgaaaactctcttcaattctttatgccggtgttgggcgcgttatttatc
ggagttgcagttgcgcccgcgaacgacatttataatgaacgtgaattgctcaacagtatgggcatttcgcagcctaccgtggtgttcgtttcca
aaaggggttgcaaaaaattttgaacgtgcaaaaaaagctcccaatcatccaaaaaattattatcatggattctaaaacggattaccagggatt
tcagtcgatgtacacgttcgtcacatctcatctacctcccggttttaatgaatacgattttgtgccagagtccttcgatagggacaagacaattgc
actgatcatgaactcctctggatctactggtctgcctaaaggtgtcgctctgcctcatagaactgcctgcgtgagattctcgcatgccagagat
cctattttggcaatcaaatcattccggatactgcgattttaagtgttgttccattccatcacggttttggaatgtttactacactcggatatttgatat
gtggatttcgagtcgtcttaatgtatagatttgaagaagagctgtttctgaggagccttcaggattacaagattcaaagtgcgctgctggtgcca
accctattctccttcttcgccaaaagcactctgattgacaaatacgatttatctaatttacacgaaattgcttctggtggcgctcccctctctaagg
aagtcggggaagcggttgccaagaggttccatctgccaggtatcaggcaaggatatgggctcactgagactacatcagctattctgattaca
cccgaggggatgataaaccgggcgcggtcggtaaagttgttccattttttgaagcgaaggttgtggatctggataccgggaaaacgctgg
gcgttaatcaaagaggcgaactgtgtgtgagaggtcctatgattatgtccggttatgtaaacaatccggaagcgaccaacgccttgattgaca
aggatggatggctacattctggagacatagcttactgggacgaagacgaacacttcttcatcgttgaccgcctgaagtctctgattaagtaca
aaggctatcaggtggctcccgctgaattggaatccatcttgctccaacaccccaacatcttcgacgcaggtgtcgcaggtcttcccgacgat
gacgccggtgaacttcccgccgccgttgttgttttggagcacggaaagacgatgacggaaaaagagatcgtggattacgtcgccagtcaa
gtaacaaccgcgaaaaagttgcgcggaggagtgtgtttgtggacgaagtaccgaaaggtcttaccggaaaactcgacgcaagaaaaatc
agagagatcctcataaaggccaagaagggcggaaagatcgccgtgtaattctagagtcggggcggccggccgcttcgagcagacatgat
aagatacattgatgagtttggacaaaccacaactagaatgcagtgaaaaaaatgctttatttgtgaaatttgtgatgctattgctttatttgtaacc
attataagctgcaataaacaagttaacaacaacaattgcattcattttatgtttcaggttcaggggaggtgtgggaggttttttaaagcaagtaa
aacctctacaaatgtggtaaaatcgataaggatccgtcgaccgatgcccttgagagccttcaacccagtcagctccttccggtgggcgcgg
ggcatgactatcgtcgccgcacttatgactgtcttctttatcatgcaactcgtaggacaggtgccggcagcgctcttccgcttcctcgctcactg
actcgctgcgctcggtcgttcggctgcggcgagcggtatcagctcactcaaaggcggtaatacggttatccacagaatcaggggataacgc
aggaaagaacatgtgagcaaaaggccagcaaaaggccaggaaccgtaaaaaggccgcgttgctggcgtttttccataggctccgccccc
ctgacgagcatcacaaaaatcgacgctcaagtcagaggtggcgaaacccgacaggactataaagataccaggcgtttccccctggaagct
ccctcgtgcgctctcctgttccgaccctgccgcttaccggatacctgtccgcctttctcccttcgggaagcgtggcgctttctcatagctcacg
ctgtaggtatctcagttcggtgtaggtcgttcgctccaagctgggctgtgtgcacgaaccccccgttcagcccgaccgctgcgccttatccgg
taactatcgtcttgagtccaacccggtaagacacgacttatcgccactggcagcagccactggtaacaggattagcagagcgaggtatgta
ggcggtgctacagagttcttgaagtggtggcctaactacggctacactagaagaacagtatttggtatctgcgctctgctgaagccagttacc
ttcggaaaaagagttggtagctcttgatccggcaaacaaaccaccgctggtagcggtggtttttttgtttgcaagcagcagattacgcgcaga
aaaaaaggatctcaagaagatcctttgatcttttctacggggtctgacgctcagtggaacgaaaactcacgttaagggattttggtcatgagatt
atcaaaaaggatcttcacctagatccttttaaattaaaaatgaagttttaaatcaatctaaagtatatatgagtaaacttggtctgacagttagaaa
aactcatcgagcatcaaatgaaactgcaatttattcatatcaggattatcaataccatatttttgaaaaagccgtttctgtaatgaaggagaaaac
tcaccgaggcagttccataggatggcaagatcctggtatcggtctgcgattccgactcgtccaacatcaatacaacctattaatttcccctcgt
caaaaataaggttatcaagtgagaaatcaccatgagtgacgactgaatccggtgagaatggcaaaagtttatgcatttctttccagacttgttca
acaggccagccattacgctcgtcatcaaaatcactcgcatcaaccaaaccgttattcattcgtgattgcgcctgagcgagacgaaatacgcg
atcgctgttaaaaggacaattacaaacaggaatcgaatgcaaccggcgcaggaacactgccagcgcatcaacaatattttcacctgaatca
```

-continued ggatattcttctaatacctggaatgctgttttcccggggatcgcagtggtgagtaaccatgcatcatcaggagtacggataaaatgcttgatggt cggaagaggcataaattccgtcagccagtttagtctgaccatctcatctgtaacatcattggcaacgctacctttgccatgtttcagaaacaact ctggcgcatcgggcttcccatacaatcgatagattgtcgcacctgattgcccgacattatcgcgagcccatttatacccatataaatcagcatc catgttggaatttaatcgcggcctagagcaagacgtttcccgttgaatatggctcatactcttccttttcaatattattgaagcatttatcagggtt attgtctcatgagcggatacatatttgaatgtatttagaaaaataaacaatagggggttccgcgcacatttccccgaaaagtgccacctgacgc gccctgtagcggcgcattaagcgcggcgggtgtggtggttacgcgcagcgtgaccgctacacttgccagcgccctagcgcccgctccttt cgctttcttcccttcctttctcgccacgttcgccggctttccccgtcaagctctaaatcgggggctccctttagggttccgatttagtgctttacgg cacctcgaccccaaaaaacttgattagggtgatggttcacgtagtgggccatcgccctgatagacggtttttcgccctttgacgttggagtcca cgttctttaatagtggactcttgttccaaactggaacaacactcaaccctatctcggtctattcttttgatttataagggattttgccgatttcggcct attggttaaaaaatgagctgatttaacaaaaatttaacgcgaattttaacaaaatattaacgcttacaatttgccattcgccattcaggctgcgca actgttgggaagggcgatcggtgcgggcctcttcgctattacgccagcccaagctaccatgataagtaagtaatattaaggtacgggaggta cttggagcggccgcaataaaatatctttattttcattacatctgtgtgttggttttttgtgtgaatcgatagtactaacatacgctctccatcaaaaca aaacgaaacaaaacaaactagcaaaataggctgtccccagtgcaagtgcaggtgccagaacatttctctatcgatactcgagggccatgca ggtaggatttgagctgtgtttcccgccctgatcctctctcctctggcggccggagcctccgtaggctccaagcctggcccagattcggcggc gcagccggccttccgcgcgtccgcacctagcggggcctccggggctccggcgcggcaccgggggcgctcgggatctggctgaggct ccaaggcccgcgtggccggctcctcctgctggggcaggtggcggctgcgcgcccgcccgagcccaggggccccctcagccgcaac aaccagcaaggaccccccgactcagccccaagccacctgcatctgcactcagacggggcgcaccgcagtgcagcctcctggtggggc gctgggagcccgcctgccctgcctgcccggagaccccagctcacgagcacaggccgccgggcaccccagaaacccgggatgggg cccctgaattctctaggacgggcattcagcatggccttggcgctctgcggctccctgcccccacccagcctcgccccgcgcaccccc agccctgcgaccgccgcccccccccggggccccagggcccagcccgcaccccgccccgctcttggctcgggttgcggggc gggccggggcggggcgagggctccgcgggcgcccattggcgcgggcgcgaggccagcggccccgcgcggccctgggccgcgg ctggcgcgactataagagccgggcgtgggcgcccgcagttcgcctgctctccggcggagctgcgtgaggcccggccggccccggcc cccccttccggccgcccccgcctcctggcccacgcctgcccgcgctctgcccaccagcgcctccatcgggcaaggcggccccgcgtcg acaagcttagctacgctagcggcattccggtactgttggtaaagccaccatggaagacgccaaaaacataaagaaaggcccggcgccatt ctatccgctggaagatggaaccgctggagagcaactgcataaggctatgaagagatacgccctggttcctggaacaattgcttttacagatg cacatatcgaggtggacatcacttacgctgagtacttcgaaatgtccgttcggttggcagaagctatgaaacgatatgggctgaatacaaatc acagaatcgtcgtatgcagtgaaaactctcttcaattctttatgccggtgttgggcgcgttatttatcggagttgcagttgcgcccgcgaacgac atttataatgaacgtgaattgctcaacagtatgggcatttcgcagcctaccgtggtgttcgtttccaaaaaggggttgcaaaaaattttgaacgt gcaaaaaagctcccaatcatccaaaaaattattatcatggattctaaaacggattaccagggatttcagtcgatgtacacgttcgtcacatctc atctacctcccggttttaatgaatacgattttgtgccagagtccttcgatagggacaagacaattgcactgatcatgaactcctctggatctactg gtctgcctaaaggtgtcgctctgcctcatagaactgcctgcgtgagattctcgcatgccagagatcctatttttggcaatcaaatcattccggat actgcgattttaagtgttgttccattccatcacggttttggaatgtttactacactcggatatttgatatgtggatttcgagtcgtcttaatgtatagat ttgaagaagagctgtttctgaggagccttcaggattacaagattcaaagtgcgctgctggtgccaacccctattctccttcttcgccaaaagcac tctgattgacaaatacgatttatctaatttacacgaaattgcttctggtggcgctcccctctctaaggaagtcggggaagcggttgccaagagg ttccatctgccaggtatcaggcaaggatatgggctcactgagactacatcagctattctgattacacccgaggggatgataaaccgggcgc ggtcggtaaagttgttccattttttgaagcgaaggttgtggatctggataccgggaaaacgctgggcgttaatcaaagaggcgaactgtgtgt gagaggtcctatgattatgtccggttatgtaaacaatccggaagcgaccaacgccttgattgacaaggatggatggctacattctggagacat agcttactgggacgaagacgaacacttcttcatcgttgaccgcctgaagtctctgattaagtacaaaggctatcaggtggctcccgctgaatt ggaatccatcttgctccaacaccccaacatcttcgacgcaggtgtcgcaggtcttcccgacgatgacgccggtgaacttcccgccgccgttg ttgttttggagcacggaaagacgatgacggaaaaagagatcgtggattacgtcgccagtcaagtaacaaccgcgaaaaagttgcgcggag -continued

```
gagttgtgtttgtggacgaagtaccgaaaggtcttaccggaaaactcgacgcaagaaaaatcagagagatcctcataaaggccaagaagg
gcggaaagatcgccgtgtaatctcgagacgtagggtacc.
```

Figure 2A:
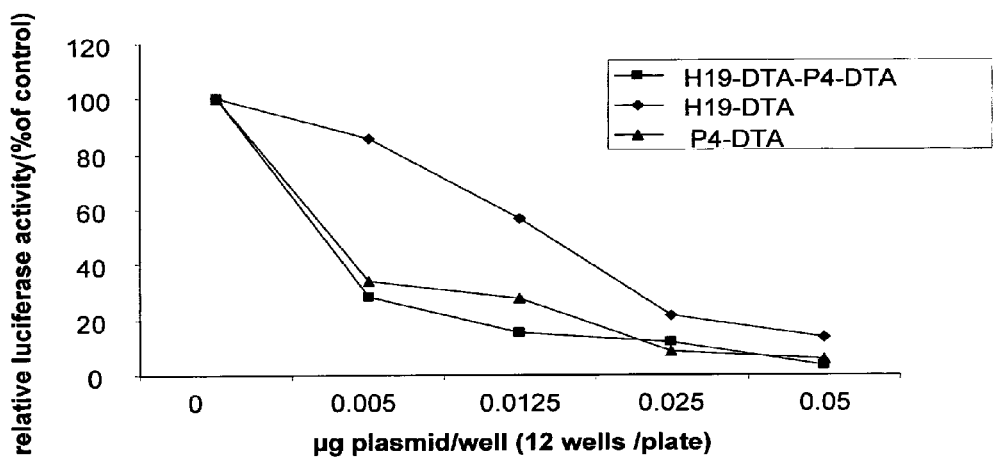
FIGS. 2A-2C. Relative in-vitro activity of DTA-expressing constructs with H19, P4, and H19+P4 regulatory sequences in T24P cells. Human T24P cells were co-transfected with 2 μg of LucSV40 and the indicated concentrations of H19-DTA, P4-DTA, or H19-DTA-P4-DTA.
Figure 2B:
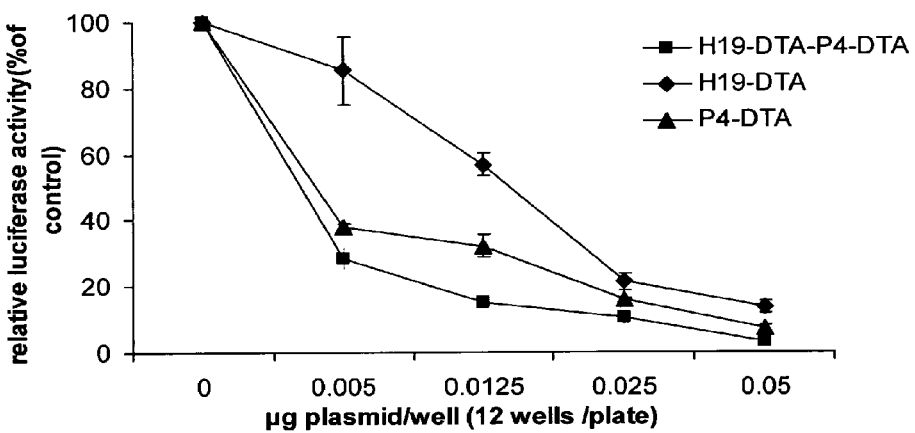
Figure 2C:
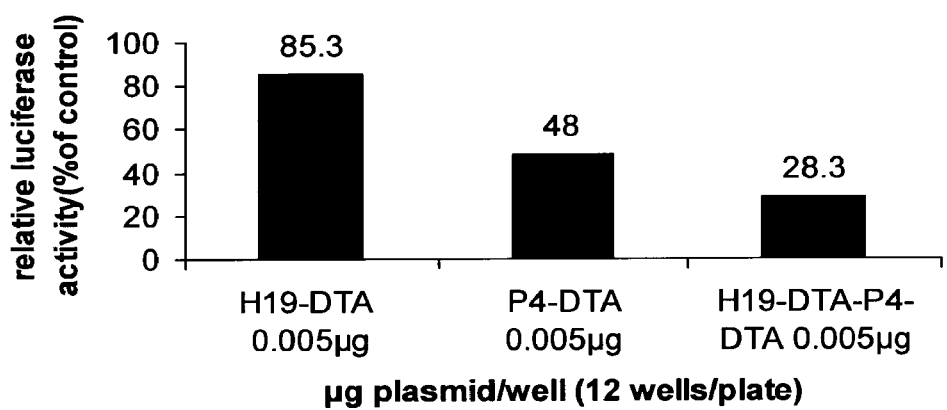
Figure 3A:
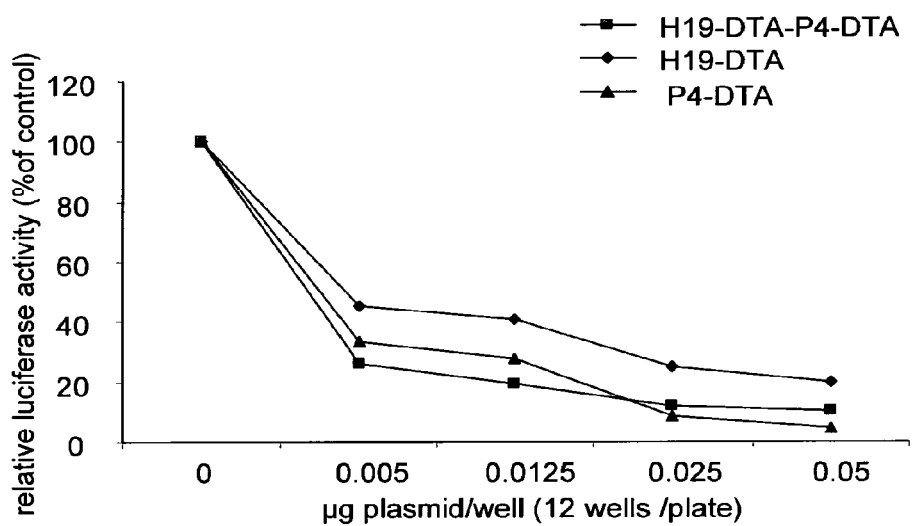
FIGS. 3A-3C. Relative activity of DTA-expressing constructs in UMUC3 cells. Experiment was performed as described for FIG. 2; axes are same as FIG. 2.
Figure 3B:
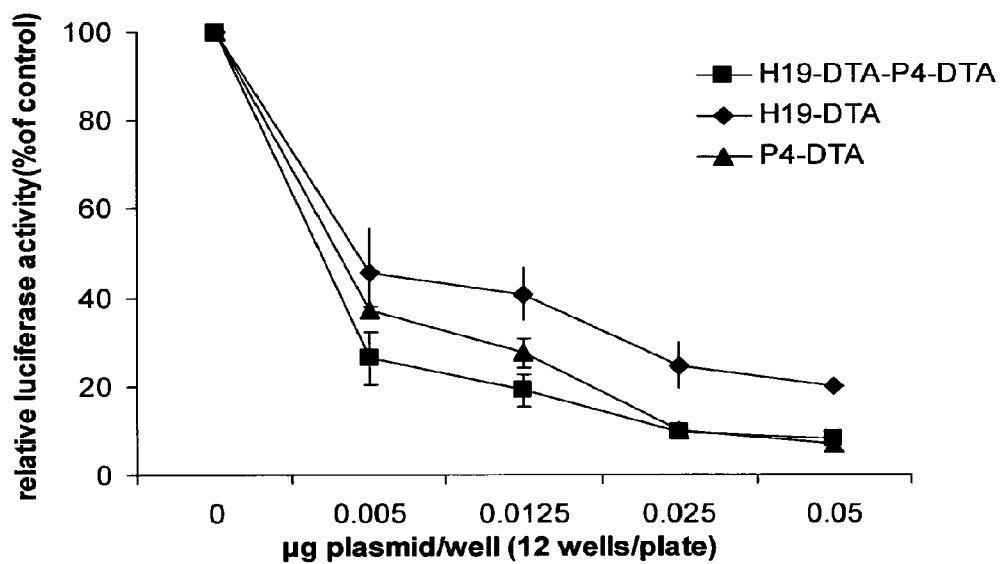
Figure 3C:
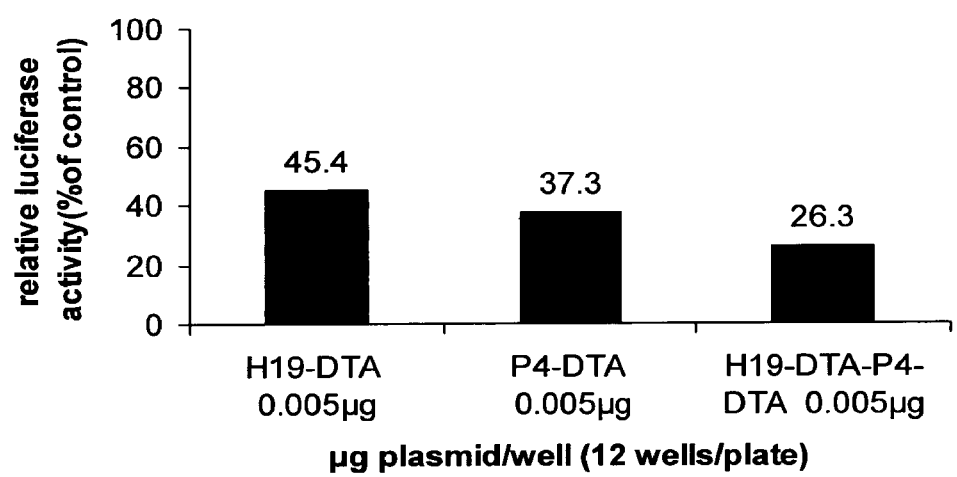
Figure 40A:
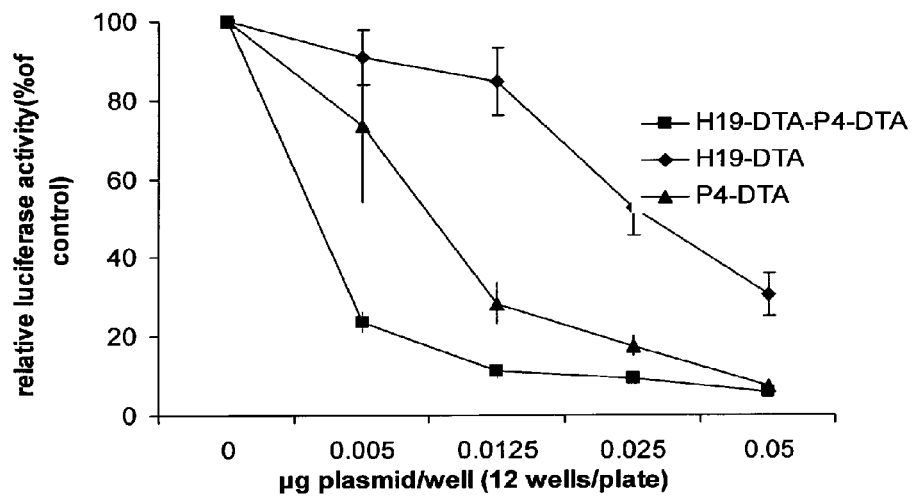
FIGS. 40A-40B. Relative activity of DTA-expressing constructs in HT-1376 cells. Experiment was performed as described for FIG. 2; axes are same as FIG. 2.
Figure 40B:
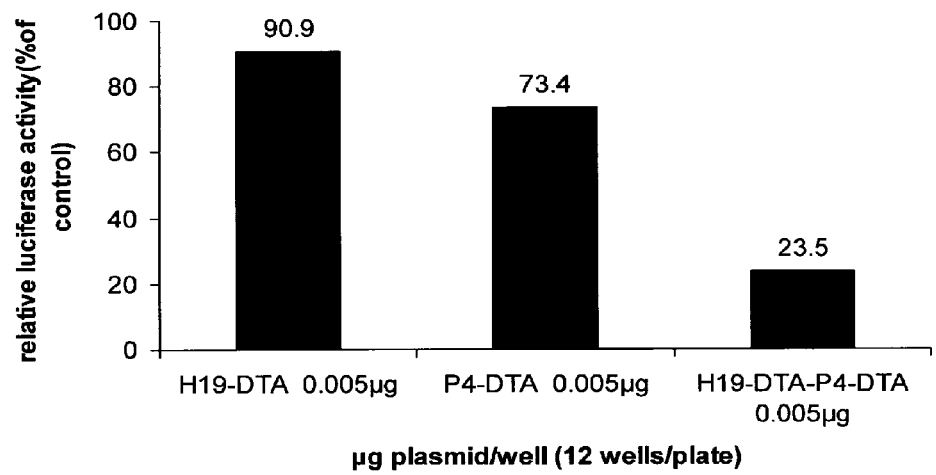

Example 1: Superior Anti-Bladder Carcinoma Activity by a Single Construct Containing DTA Genes Separately Expressed from H19 and P4 Promoters First, the anti-cancer therapeutic effect of the double promoter construct H19-DTA-P4-DTA was tested in vitro by determining its ability to lyse three different human bladder carcinoma lines, relative to the single promoter constructs. Anti-tumor activity was determined by measurement of inhibition of luciferase activity following co-transfection with LucSV40. T24P, Umuc3 and HT-1376 bladder cancer cell lines were co-transfected with H19-DTA, P4-DTA, or H19-DTA-P4-DTA at the indicated concentrations and 2 µg of LucSV40. Luciferase activity as an indicator of survival of the transfected cells was determined and compared to that of cells transfected with LucSV40 alone. H19-DTA and P4-DTA were able to drive the expression of the DTA gene and thus reduce luciferase activity in a dose-response manner. H19-DTA-P4-DTA, however, exhibited far superior efficiency in lysing the cancer cell lines, relative to each of the single promoter constructs, in T24P cells (FIGS. 2A-C). Very similar results were obtained when the experiment was repeated with UMUC3 cells (FIGS. 3A-C) and HT-1376 (FIGS. 40A-B).

Thus, a DTA expression vector, carrying on the same construct two separate genes expressing the DTA toxin from H19 and P4, exhibited significantly superior ability to lyse various human bladder cancer cell lines, relative to expression vectors carrying either gene alone.

Figure 4A:
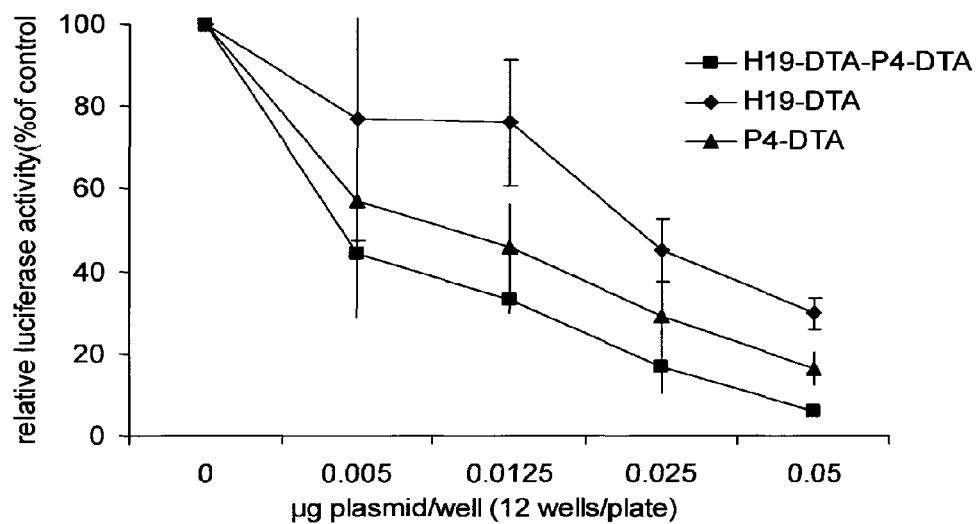
FIGS. 4A-4B. Relative activity of DTA-expressing constructs in Hep3B cells. Experiment was performed as described for FIG. 2; axes are same as FIG. 2.
Figure 4B:
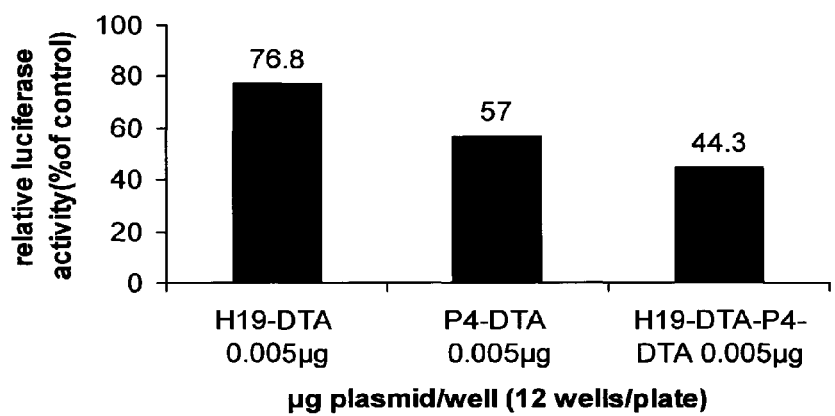

Example 2: Superior Anti-Liver Carcinoma Activity by a Single Construct Containing DTA Genes Separately Expressed from H19 and P4 Promoters The anti-cancer therapeutic effect of the constructs described in Example 1 was tested in vitro on Hep3B human liver cancer (hepatocellular carcinoma) cells. As seen with the bladder carcinoma cell lines, the double promoter construct H19-DTA-P4-DTA exhibited far superior efficiency in lysing the cancer cell lines, relative to each of the single promoter constructs (FIGS. 4A-B).

Thus, H19-DTA-P4-DTA double promoter expression vectors of the present invention exhibit significantly superior ability to lyse liver carcinoma cells, relative to either gene alone.

Figure 5A:
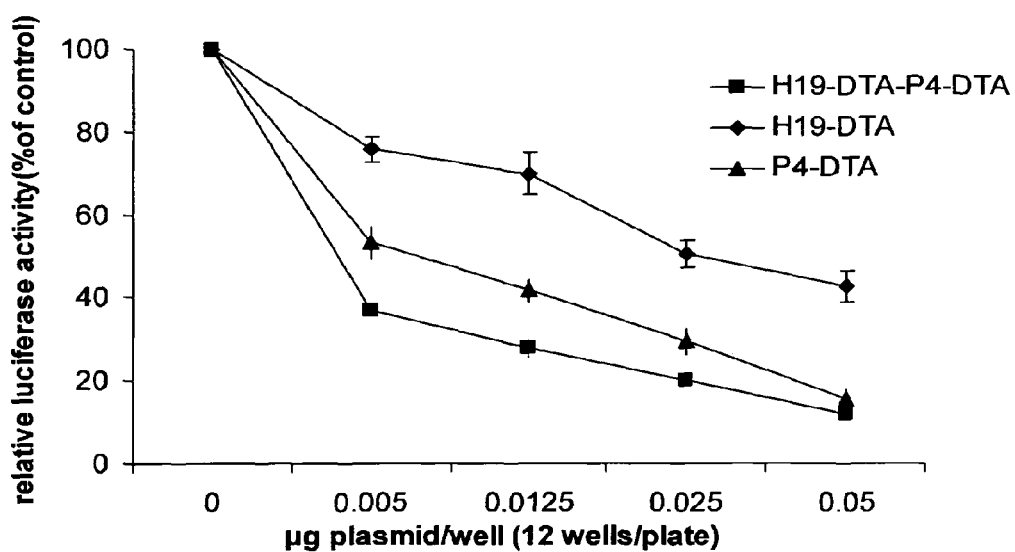
FIGS. 5A-5B. Relative activity of DTA-expressing constructs in ES-2 cells. Experiment was performed as described for FIG. 2; axes are same as FIG. 2.
Figure 5B:
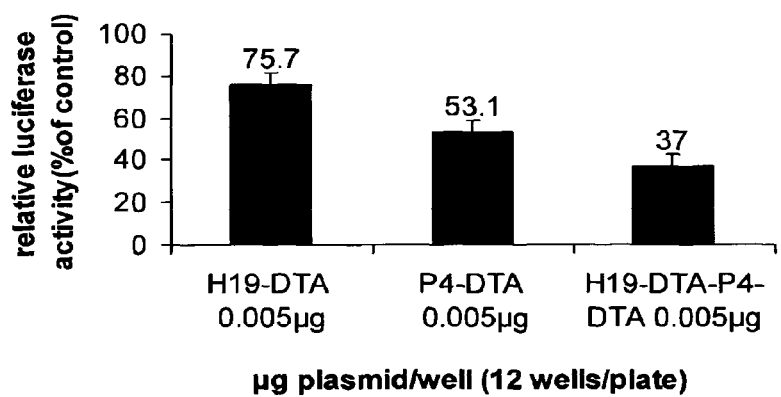

Example 3: Superior Anti-Ovarian Carcinoma Activity by a Single Construct Containing DTA Genes Separately Expressed from H19 and P4 Promoters The anti-cancer therapeutic effect of the constructs described in Example 1 was tested in vitro on ES-2 human ovarian cancer (clear cell carcinoma) cells. As seen with the bladder carcinoma cell lines, the double promoter construct H19-DTA-P4-DTA exhibited far superior efficiency in lysing the cancer cell lines, relative to each of the single promoter constructs (FIGS. 5A-B).

Thus, H19-DTA-P4-DTA double promoter expression vectors of the present invention exhibit significantly superior ability to lyse ovarian carcinoma cells, relative to either gene alone.

Figure 6A:
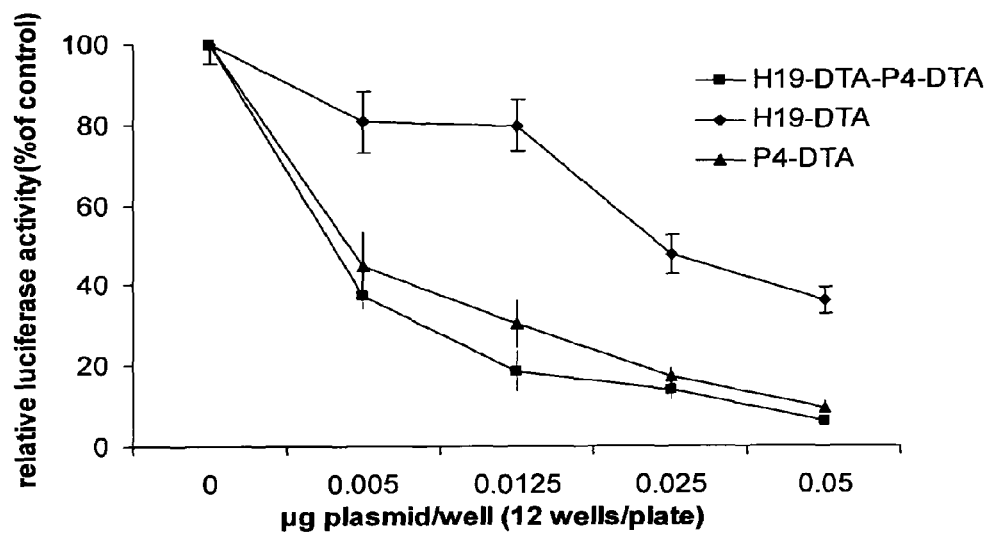
FIGS. 6A-6B. Relative activity of DTA-expressing constructs in PC-1 cells. Experiment was performed as described for FIG. 2; axes are same as FIG. 2.
Figure 6B:
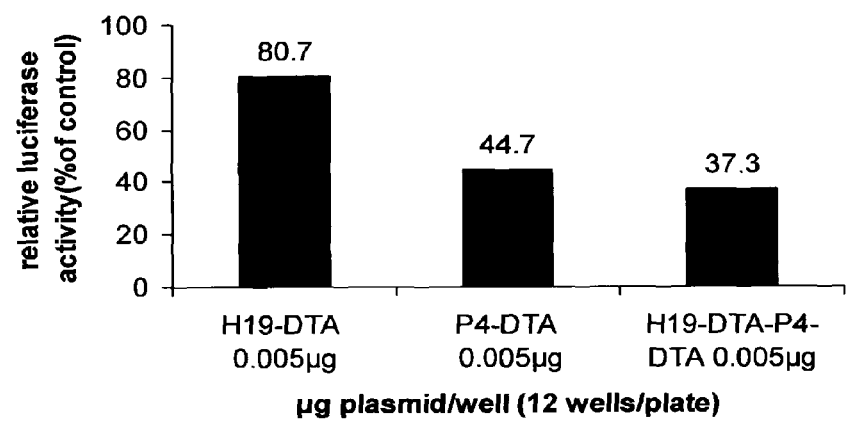
Figure 7A:
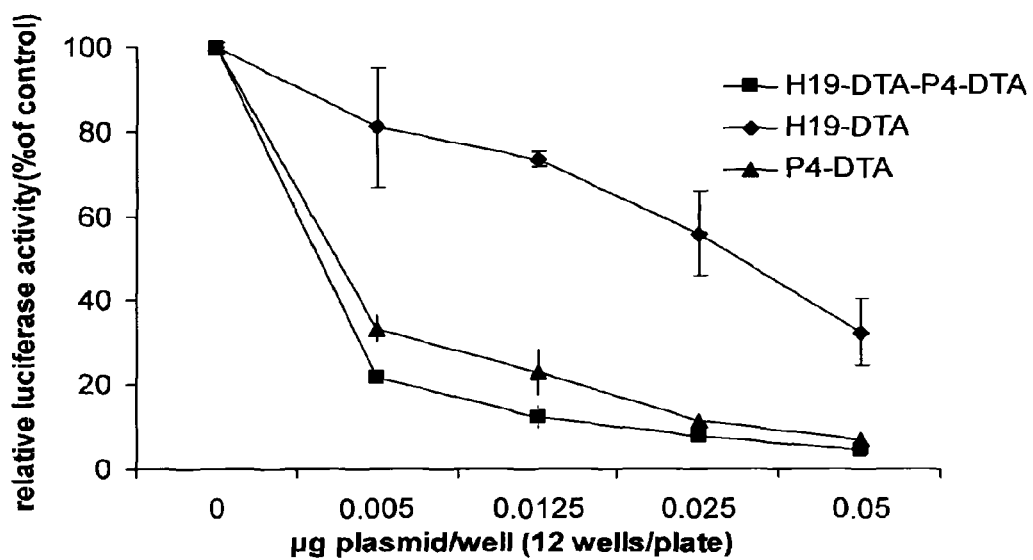
FIGS. 7A-7B. Relative activity of DTA-expressing constructs in CRL-1469 cells. Experiment was performed as described for FIG. 2; axes are same as FIG. 2.
Figure 7B:
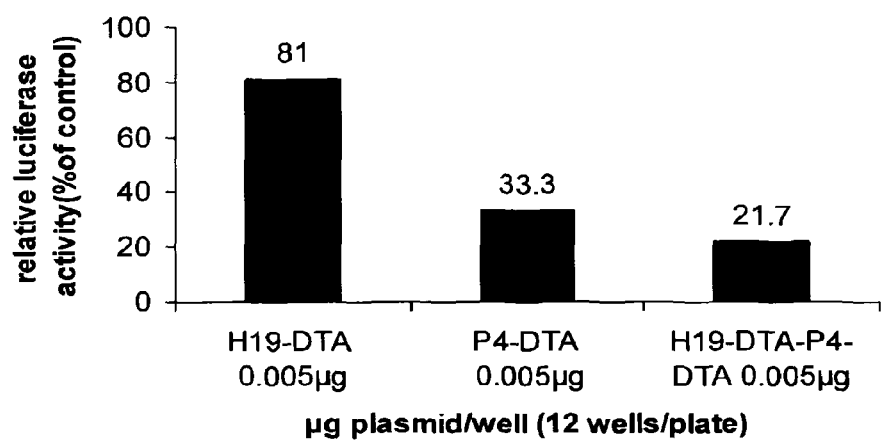

Example 4: Superior Anti-Pancreatic Carcinoma Activity by a Single Construct Containing DTA Genes Separately Expressed from H19 and P4 Promoters The anti-cancer therapeutic effect of the constructs described in Example 1 was tested in vitro on PC-1 hamster pancreatic cancer (pancreatic ductal carcinoma) and CRL-1469 human pancreatic cancer (epithelioid carcinoma) cells. As seen with the bladder carcinoma cell lines, the double promoter construct H19-DTA-P4-DTA exhibited far superior efficiency in lysing the hamster (FIGS. 6A-B) and human (FIGS. 7A-B) pancreatic cancer cell lines, relative to each of the single promoter constructs.

Thus, H19-DTA-P4-DTA double promoter expression vectors of the present invention exhibit significantly superior ability to lyse pancreatic carcinoma cells, relative to either gene alone.

Overall, H19-DTA-P4-DTA expression vectors consistently exhibited significantly superior ability when tested against a broad spectrum of tumor cells, relative to expression vectors carrying either gene alone. The consistency of these results across each of these cancer cell lines demonstrates the superior ability of H19-DTA-P4-DTA constructs of the present invention against cancer in general.

Figure 8A:
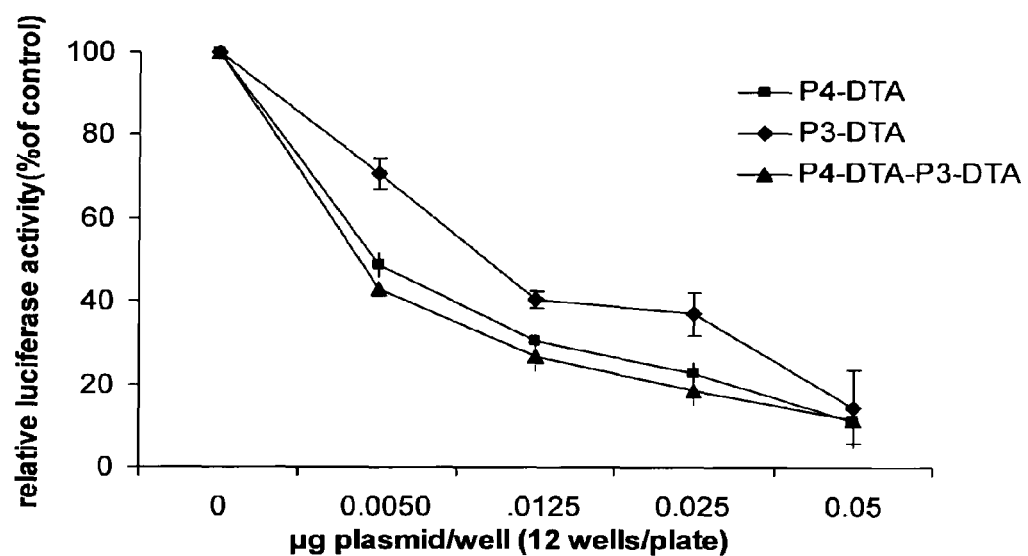
FIGS. 8A-8B. Relative in-vitro activity of DTA-expressing constructs with P3, P4, and P3+P4 regulatory sequences in T24P cells. Human T24P cells were co-transfected with 2 μg of LucSV40 and the indicated concentrations of P3-DTA, P4-DTA, or P4-DTA-P3-DTA.
Figure 8B:
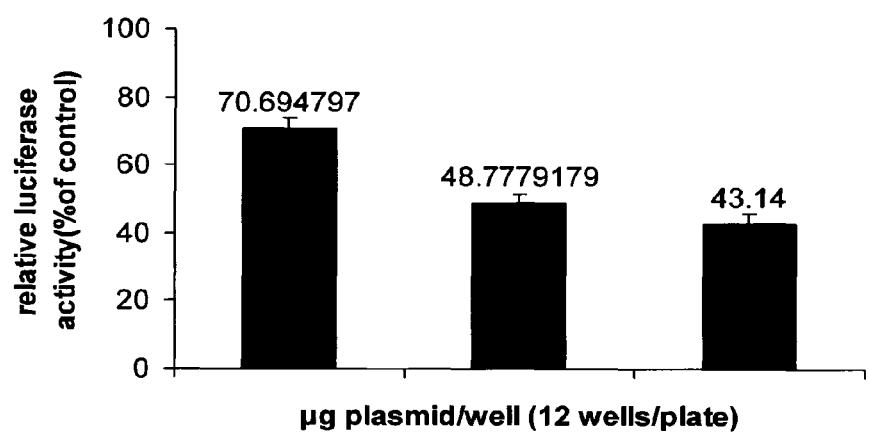
Figure 9A:
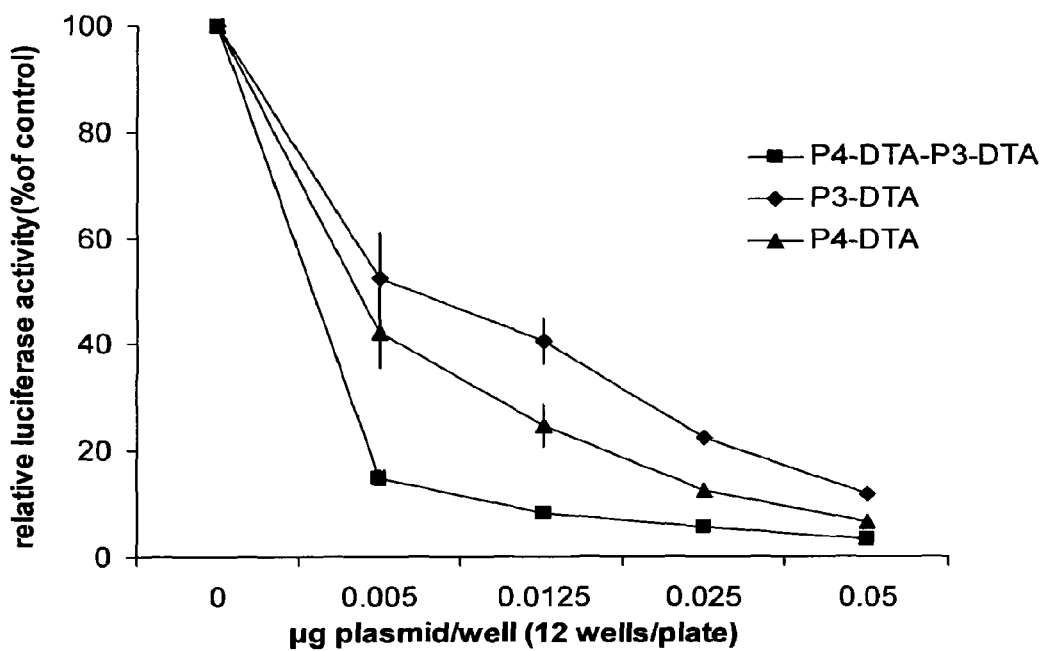
FIGS. 9A-9B. Relative activity of DTA-expressing constructs in HT-1376 cells. Experiment was performed as described for FIG. 8; axes are same as FIG. 8.
Figure 9B:
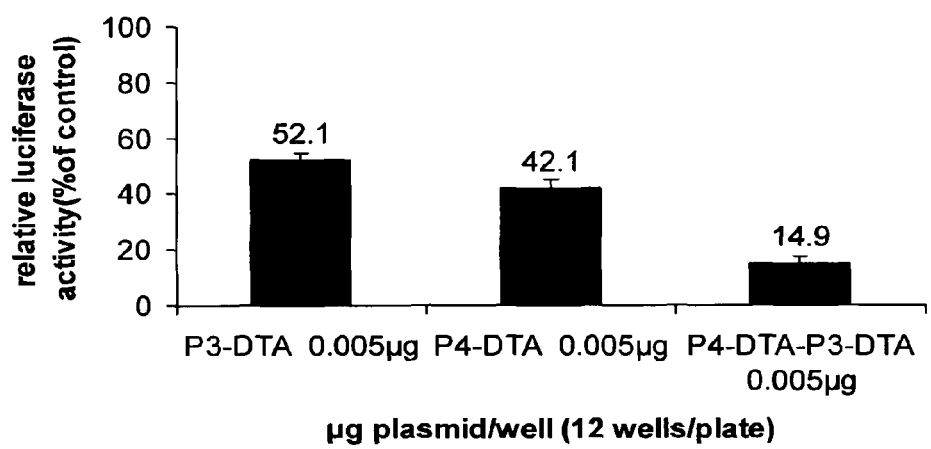
Figure 10A:
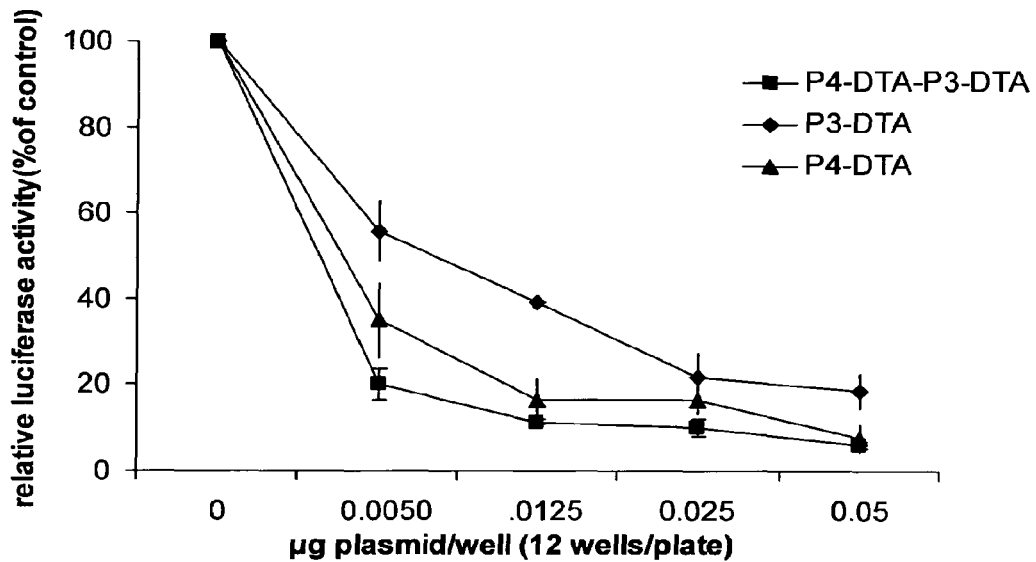
FIGS. 10A-10B. Relative activity of DTA-expressing constructs in Hep3B cells. Experiment was performed as described for FIG. 8; axes are same as FIG. 8.
Figure 10B:
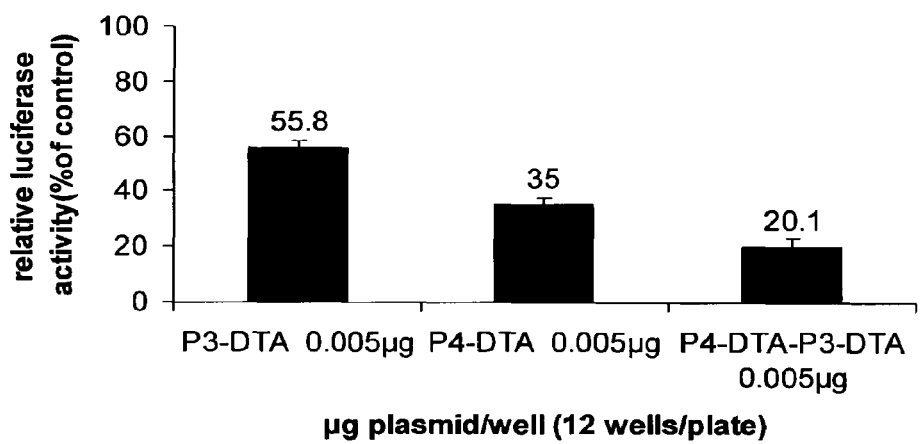
Figure 11A:
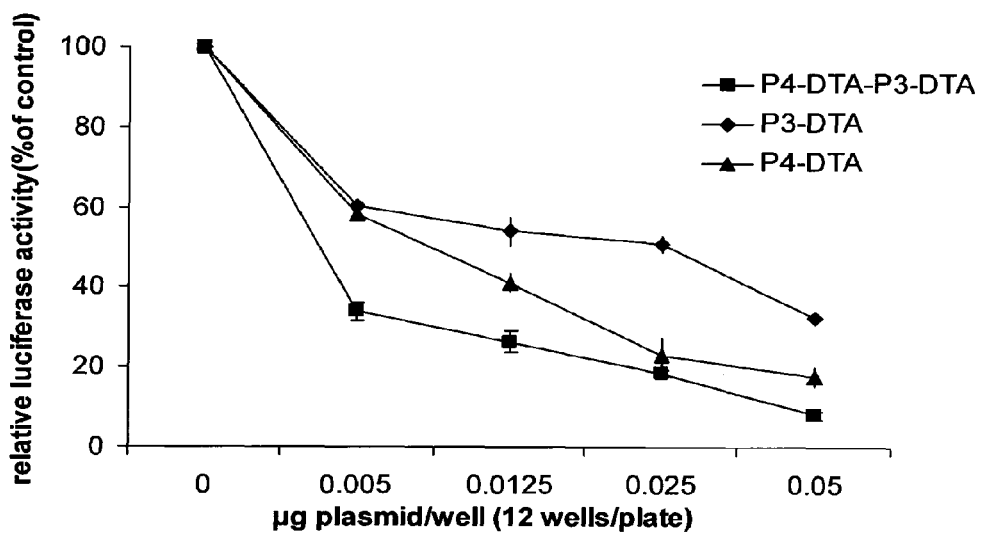
FIGS. 11A-11B. Relative activity of DTA-expressing constructs in ES-2 cells. Experiment was performed as described for FIG. 8; axes are same as FIG. 8.
Figure 11B:
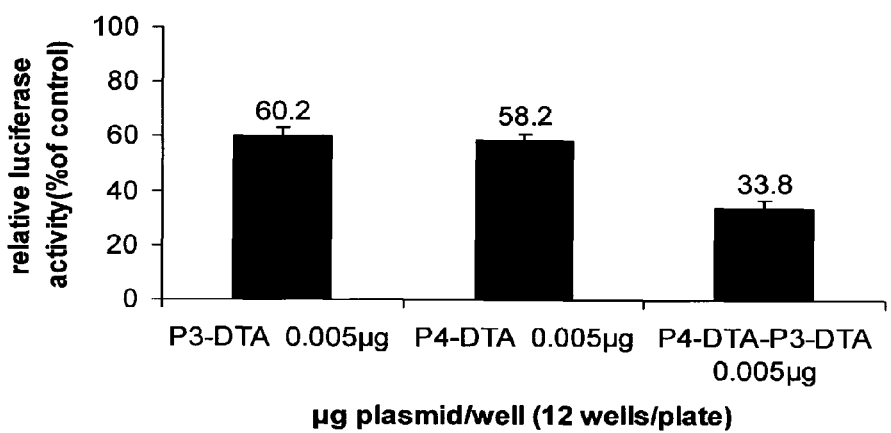
Figure 12A:
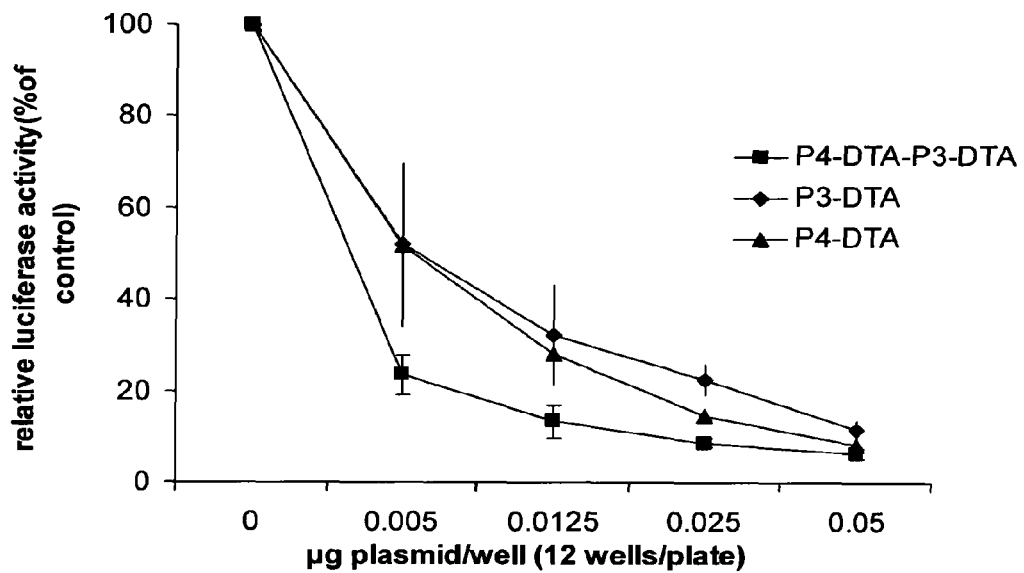
FIGS. 12A-12B. Relative activity of DTA-expressing constructs in PC-1 cells. Experiment was performed as described for FIG. 8; axes are same as FIG. 8.
Figure 12B:
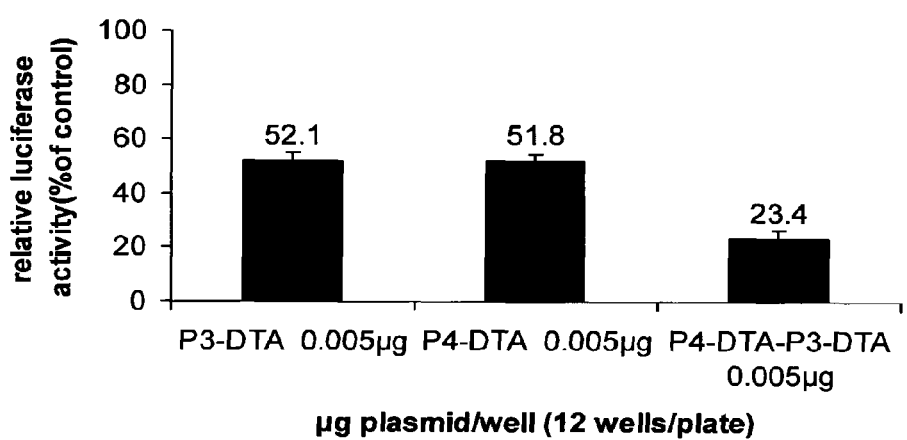
Figure 13A:
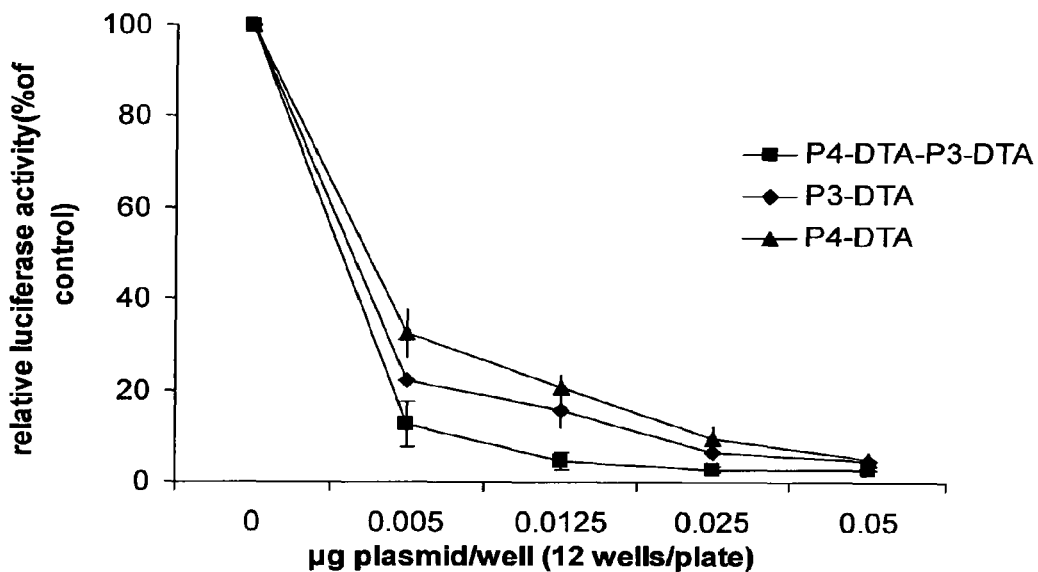
FIGS. 13A-13B. Relative activity of DTA-expressing constructs in CRL-1469 cells. Experiment was performed as described for FIG. 8; axes are same as FIG. 8.
Figure 13B:
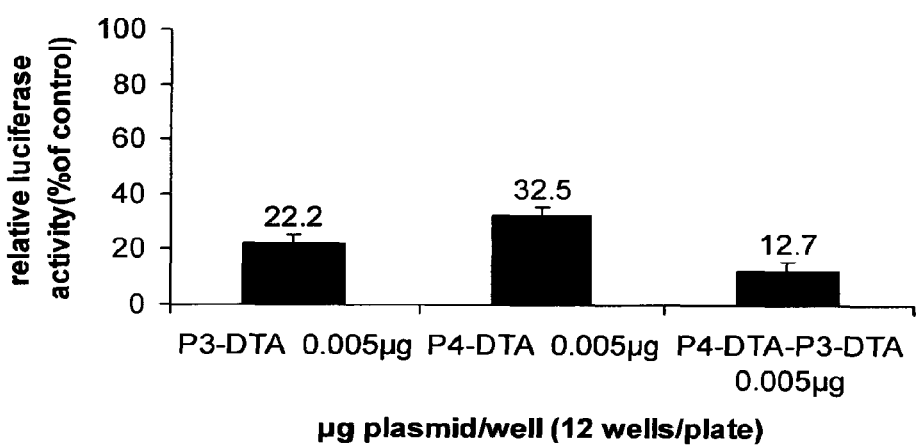

Example 5: Superior Activity by a Single Construct Containing Separate P3- and P4-Driven DTA Genes Against Six Different Carcinoma Types Next, the activity of the double promoter expression construct, expressing DTA from the IGF-II-P3 and IGF-II-P4 promoters, P4-DTA-P3-DTA, was tested against two different human bladder carcinoma cell lines (T24P and HT-1376), compared to the corresponding single-promoter constructs. Cells were co-transfected with 2 µg of LucSV40 and P3-DTA, P4-DTA, or P4-DTA-P3-DTA at the concentrations indicated in the figures. Luciferase activity was determined and compared to that of cells transfected with LucSV40 alone. P3-DTA and P4-DTA were able to drive the expression of the DTA gene and thus reduce luciferase activity in a dose-response manner in both cell lines. The double promoter construct P4-DTA-P3-DTA however, exhibited superior efficiency in lysing the cancer cell lines, relative to each of the single promoter constructs, in T24P cells (FIGS. 8A-B) and HT-1376 cells (FIGS. 9A-B). Very similar results were obtained as well in Hep3B human liver carcinoma cells (FIGS. 10A-B). Very similar results were obtained as well in ES-2 human ovarian carcinoma cells (FIGS. 11A-B). Very similar results were obtained as well in PC-1 hamster pancreatic carcinoma cells (FIGS. 12A-B) and CRL-1469 human pancreatic carcinoma cells (FIGS. 13A-B).

Thus, DTA expression vectors, carrying on the same construct two separate genes expressing the DTA toxin from IGF-II-P3 and IGF-II-P4 promoters, consistently exhibited significantly superior ability when tested against six different cancer cell lines, relative to expression vectors carrying either gene alone. The consistency of these results across a broad spectrum of tumor cells demonstrates the superior ability of P4-DTA-P3-DTA constructs of the present invention against cancers in general.

Example 6: Superior Activity by a Single Construct Containing Separate H19- and P3-Driven DTA Genes Against Bladder Carcinoma Cells Next, the ability of the double promoter expression construct, H19-DTA-P3-DTA was tested against the human bladder carcinoma cell lines T24P, compared to the corresponding single-promoter constructs.

Figure 14A:
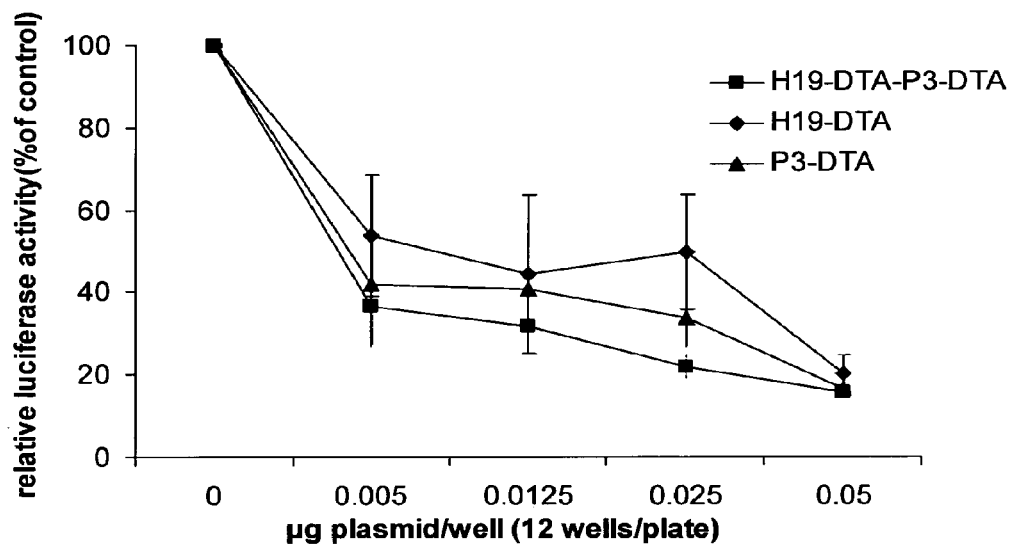
FIGS. 14A-14B. Relative in-vitro activity of DTA expressed from constructs with H19, P3, and H19+P3 regulatory sequences in T24P cells. T24P cells were co-transfected with 2 μg of LucSV40 and the indicated concentrations of H19-DTA, P3-DTA, or H19-DTA-P3-DTA.
Figure 14B:
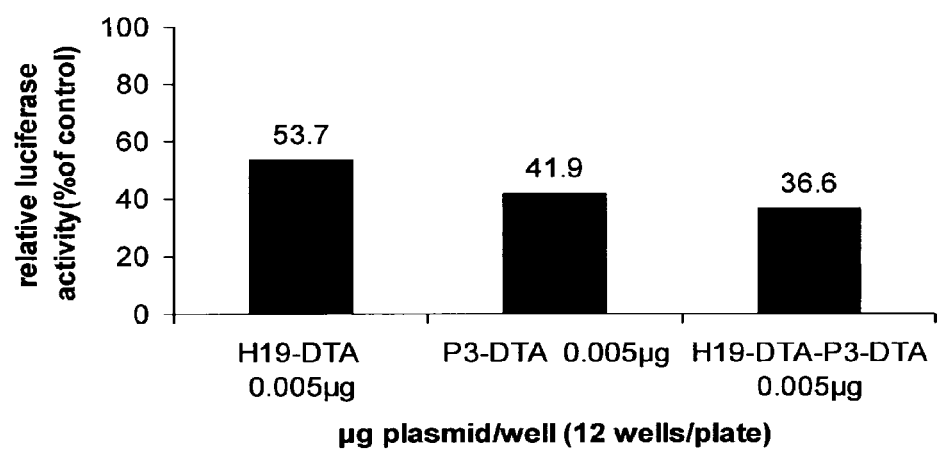

The therapeutic effect of the constructs was tested in vitro by determining their ability to lyse human bladder cancer cell lines, as determined by co-transfection with LucSV40 and measurement of inhibition of luciferase activity. The human bladder cancer cell line T24P was co-transfected with 2 μg of LucSV40 and H19-DTA, P3-DTA, or H19-DTA-P3-DTA at the concentrations indicated in the figures. Luciferase activity was determined and compared to that of cells transfected with LucSV40 alone. H19-DTA and P3-DTA were able to drive the expression of the DTA gene and thus reduce luciferase activity in a dose-response manner in all the three cell lines. The double promoter construct H19-DTA-P3-DTA, however, exhibited superior efficiency in lysing the cancer cell lines, relative to each of the single promoter constructs (FIGS. 14A-B).

Thus, DTA expression vectors, carrying on the same construct two separate genes expressing the DTA toxin from H19 and IGF-II-P3 promoters, exhibited significantly superior ability when tested against bladder carcinoma cells, relative to expression vectors carrying either gene alone.

Figure 15A:
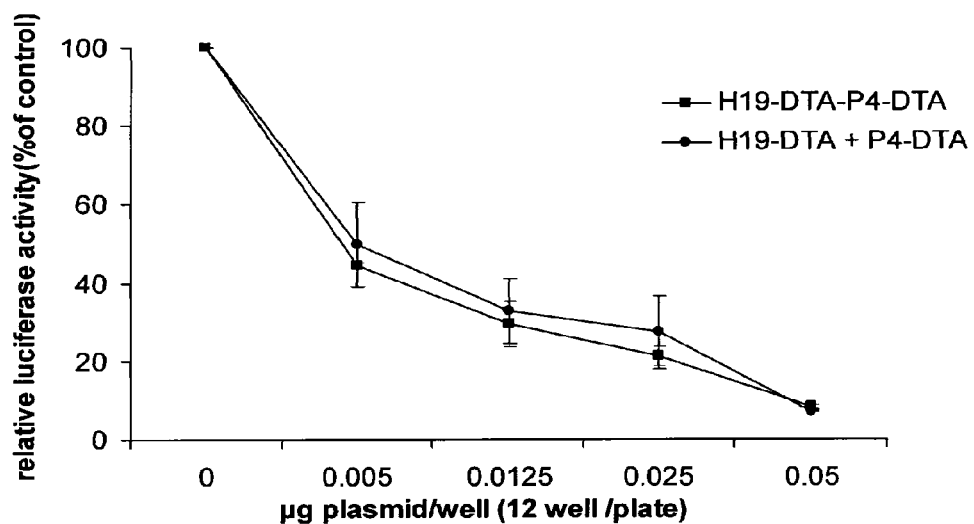
FIGS. 15A-15B. Relative in-vitro activity in T24P cells of H19-DTA-P4-DTA vs. P4-driven and H19-driven constructs in combination. T24P cells were co-transfected with 2 μg of LucSV40 and the indicated concentrations of H19-DTA-P4-DTA or an equal amount of each of P4-DTA+H19-DTA.
Figure 15B:
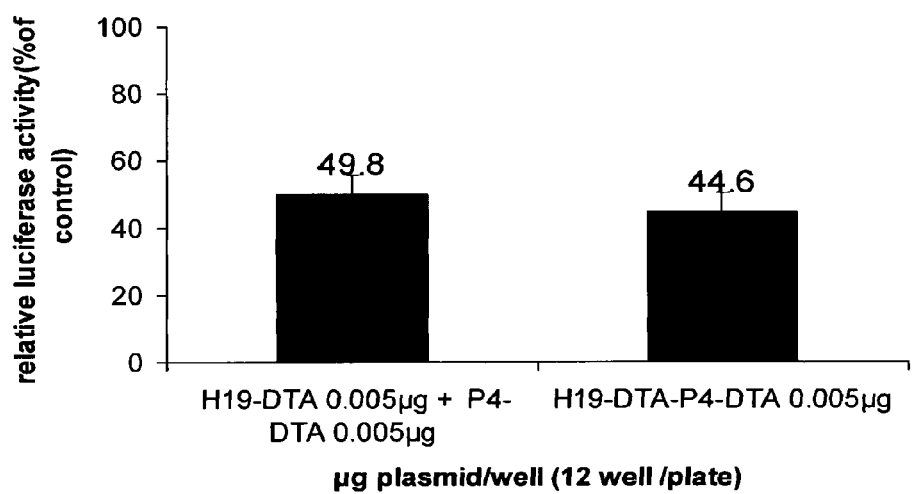
Figure 16A:
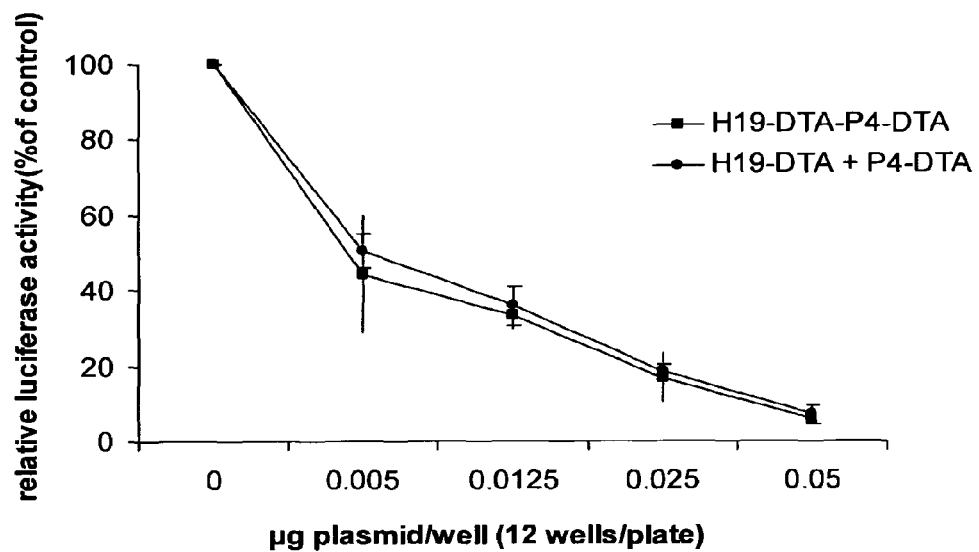
FIGS. 16A-16B. Relative in-vitro activity in Hep3B cells of H19-DTA-P4-DTA vs. P4-driven and H19-driven constructs in combination. Experiment was performed as described for FIG. 15; axes are same as FIG. 15.
Figure 16B:
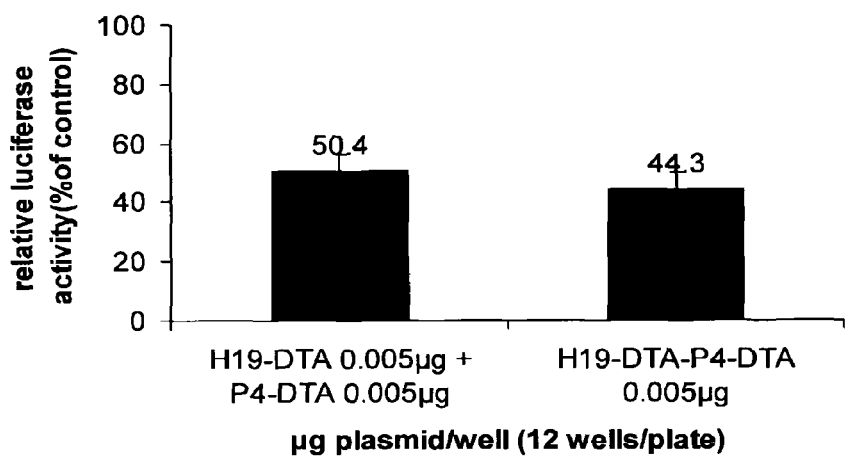
Figure 17A:
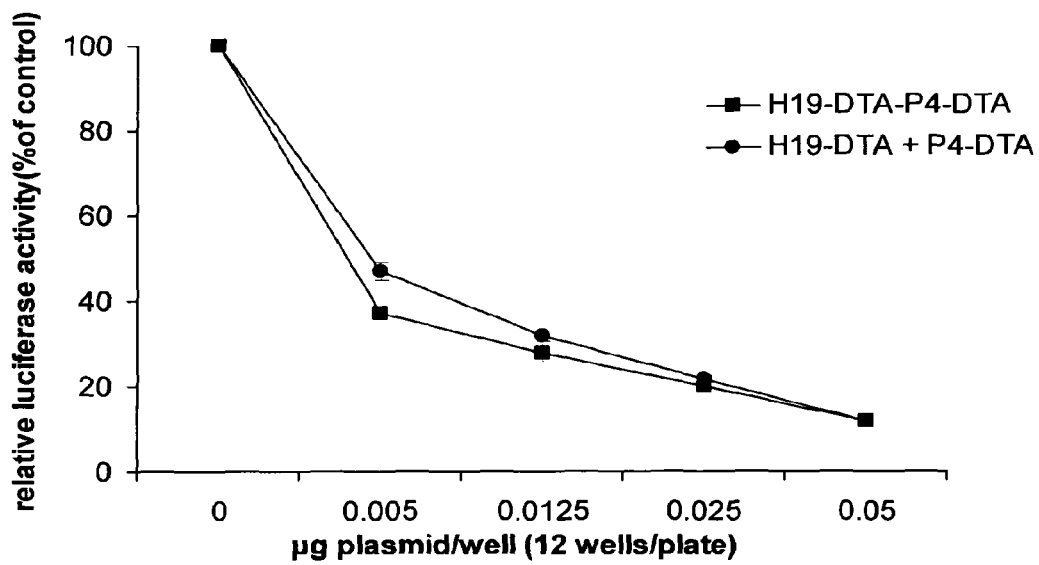
FIGS. 17A-17B. Relative in-vitro activity in ES-2 cells of H19-DTA-P4-DTA vs. P4-driven and H19-driven constructs in combination. Experiment was performed as described for FIG. 15; axes are same as FIG. 15.
Figure 17B:
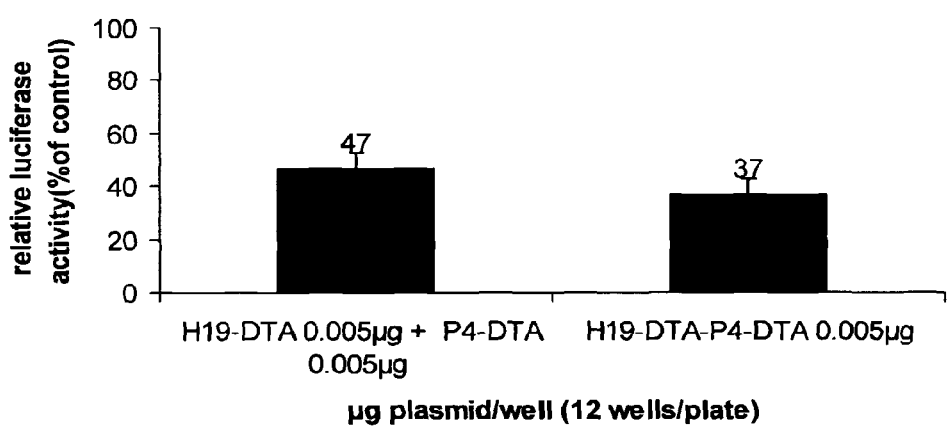
Figure 18A:
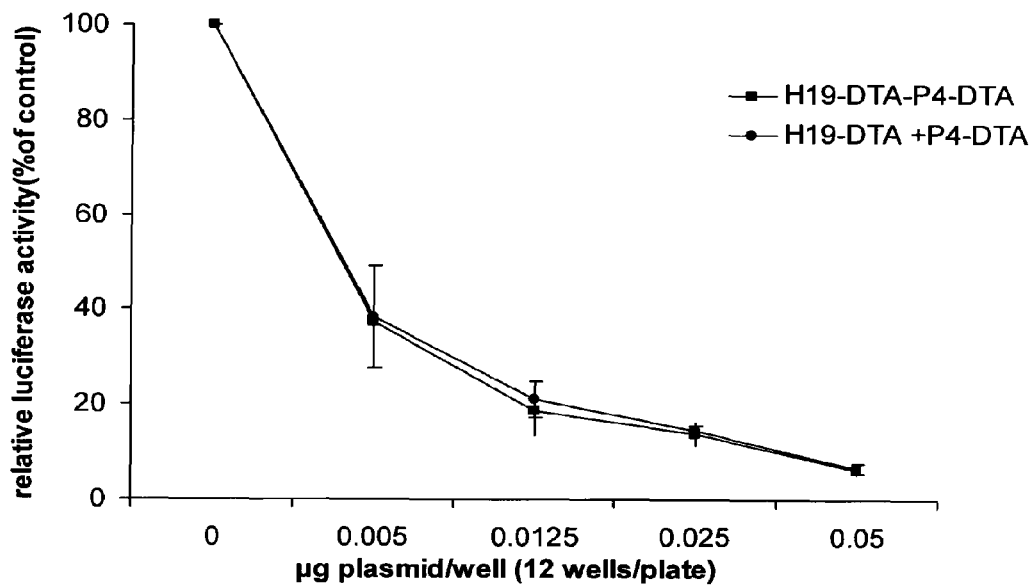
FIGS. 18A-18B. Relative in-vitro activity in PC-1 cells of H19-DTA-P4-DTA vs. P4-driven and H19-driven constructs in combination. Experiment was performed as described for FIG. 15; axes are same as FIG. 15.
Figure 18B:
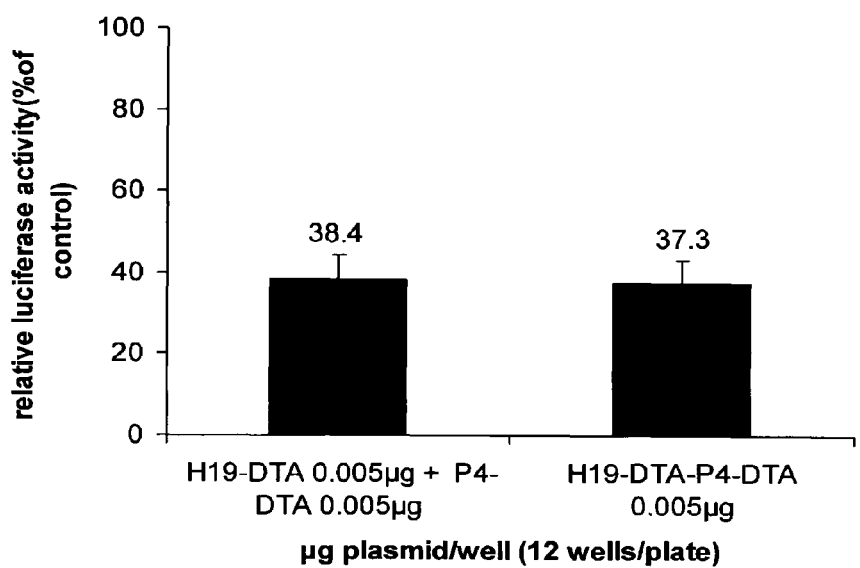
Figure 19A:
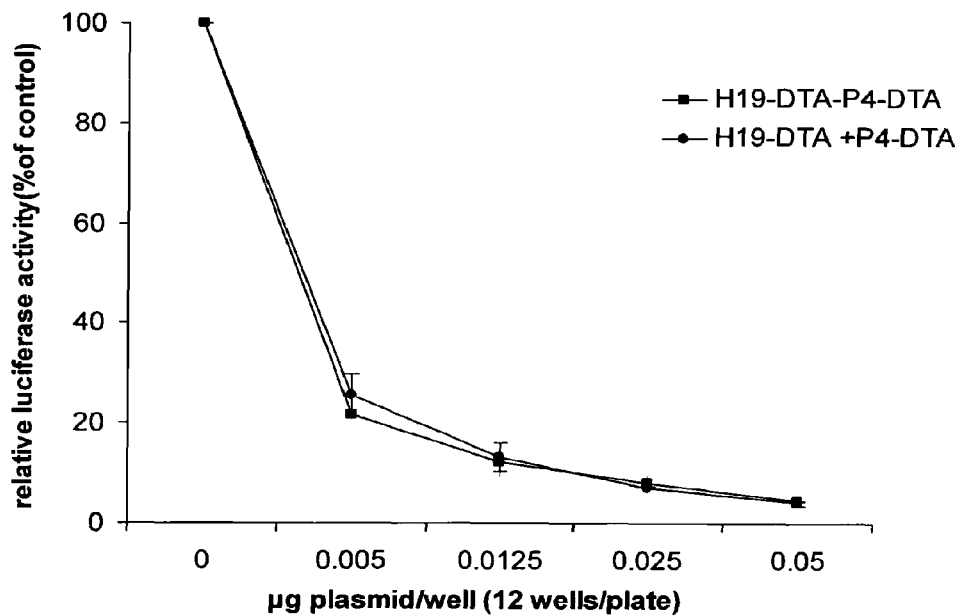
FIGS. 19A-19B. Relative in-vitro activity in CRL-1469 cells of H19-DTA-P4-DTA vs. P4-driven and H19-driven constructs in combination. Experiment was performed as described for FIG. 15; axes are same as FIG. 15.
Figure 19B:
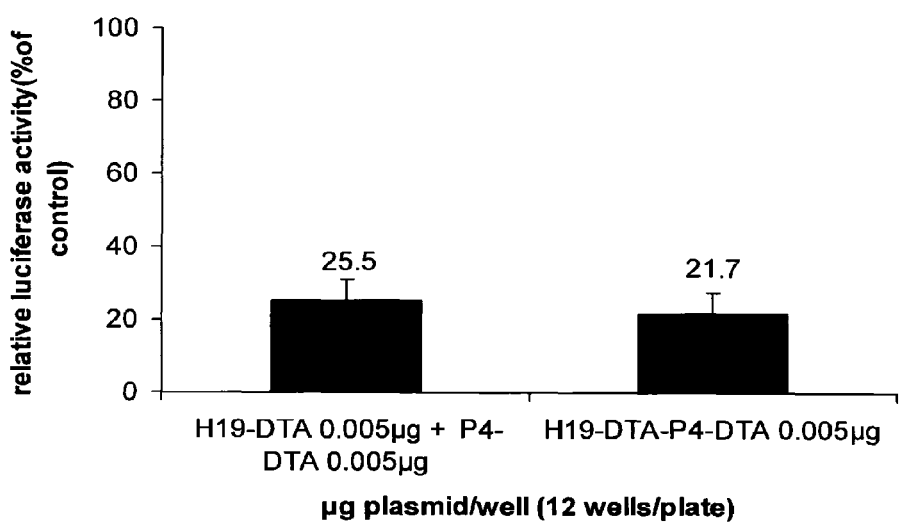
Figure 23A:
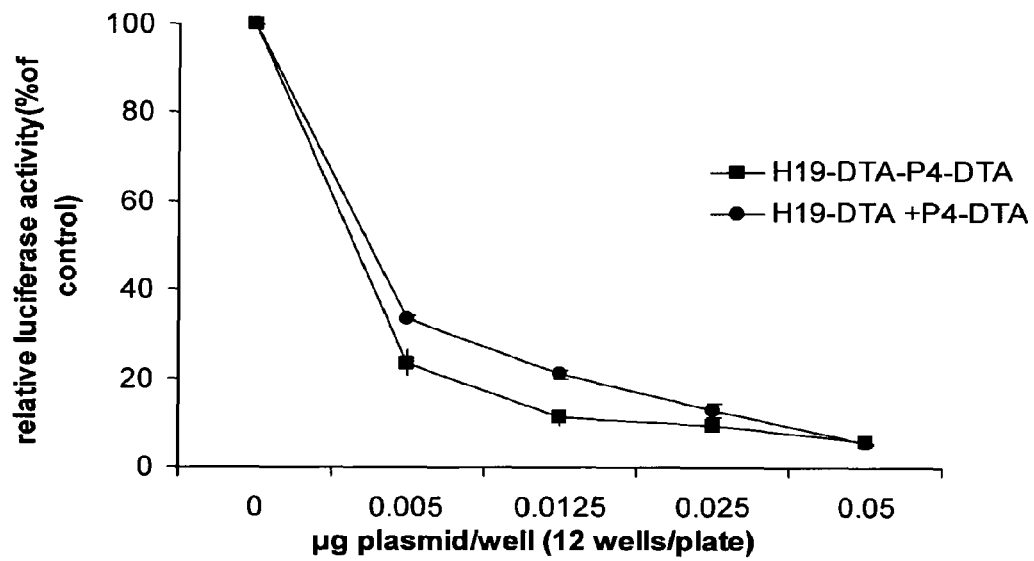
FIGS. 23A-23B. Relative activity of DTA-expressing constructs in HT-1376 cells. Experiment was performed as described for FIG. 15; axes are same as FIG. 15.
Figure 23B:
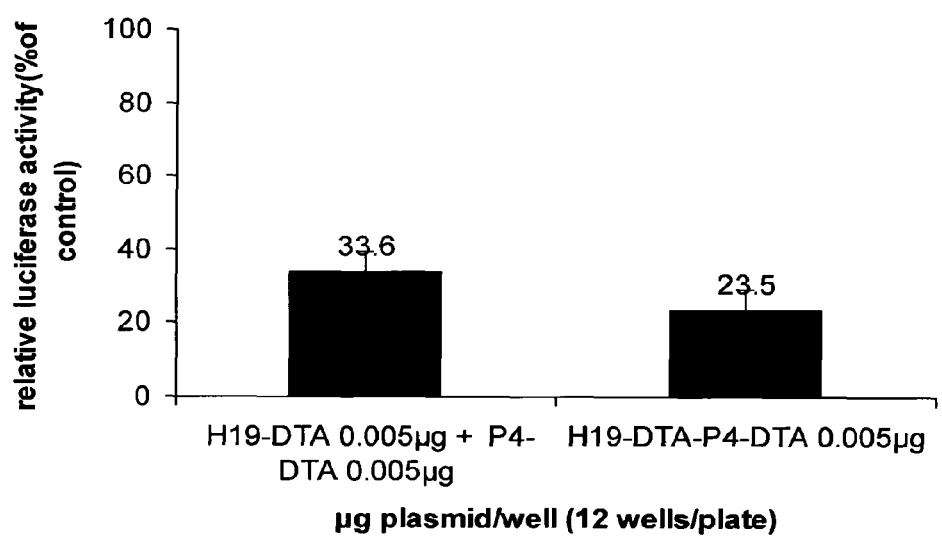

Example 7: DTA Genes Separately Expressed from H19 and P4 Promoters Exhibit Greater-than-Additive Anti-Cancer Activity when Present on a Single Construct Next, the presence of a greater-than-additive anti-cancer effect of the double promoter construct H19-DTA-P4-DTA was tested in the human bladder cancer cell lines T24P and HT-1376, the human ovarian cancer cell line ES-2, the human liver cancer cell line Hep3B, the hamster pancreatic cell line PC-1, and the human pancreatic cancer cell line CRL-1469. T24P, ES-2, Hep3B, PC-1 and CRL-1469 were co-transfected with 2 μg of LucSV40 and either (a) the concentrations indicated in the figures of single-promoter constructs H19-DTA+P4-DTA in combination, or (b) the same amount of H19-DTA-P4-DTA as for one of the single-promoter constructs. The total amount of DNA co-transfected in samples receiving both single promoter constructs was therefore twice than the cells transfected with H19-DTA-P4-DTA. Luciferase activity was determined and compared to that of cells transfected with LucSV40 alone. Double-promoter construct H19-DTA-P4-DTA exhibited superior efficiency in lysing the cancer cell lines, relative to the combined activity of both single promoter constructs (H19-DTA+P4-DTA), in T24P cells (FIGS. 15A-B). Very similar results were obtained in Hep3B human liver cancer cells (FIGS. 16A-B), ES-2 human ovarian cancer cells (FIGS. 17A-B), PC-1 hamster pancreatic cells (FIGS. 18A-B), CRL-1469 human pancreatic cancer cells (FIGS. 19A-B) and HT-1376 cells (FIG. 23A-B).

Thus, H19-driven and IGF-II P4-driven DTA-encoding genes present on a single expression vector exhibited greater-than-additive anti-cancer activity relative to expression vectors carrying either gene alone when tested against a broad spectrum of tumor cells. The consistency of these results across each of these cancer cell lines demonstrates the superior ability of H19/P4 constructs of the present invention against cancer in general.

Figure 20A:
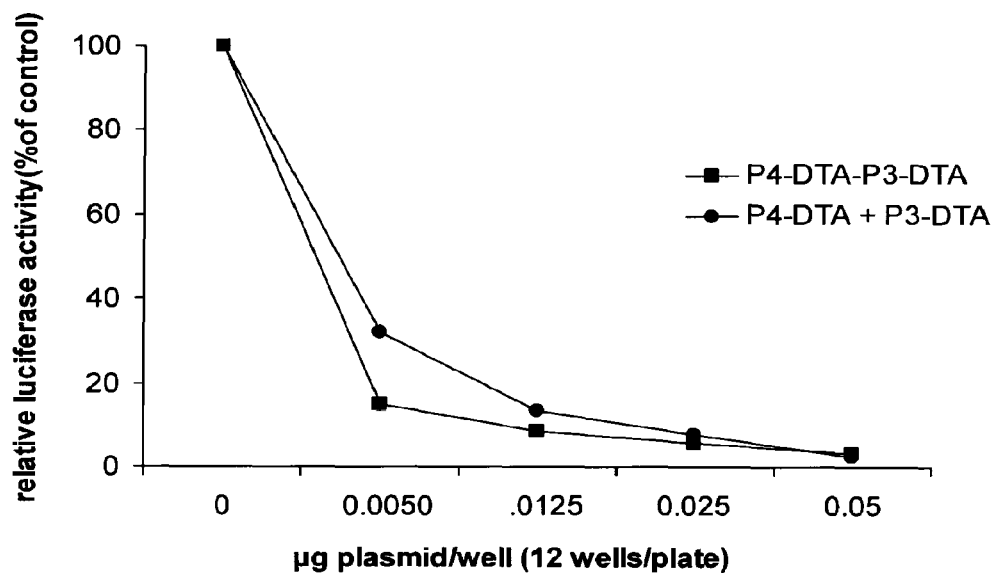
FIGS. 20A-20B. Relative in-vitro activity in HT-1376 cells of P4-DTA-P3-DTA vs. P3-driven and P4-driven constructs in combination. HT-1376 cells were co-transfected with 2 μg of LucSV40 and the indicated concentrations of P4-DTA-P3-DTA or an equal amount of each of P3-DTA+P4-DTA.
Figure 20B:
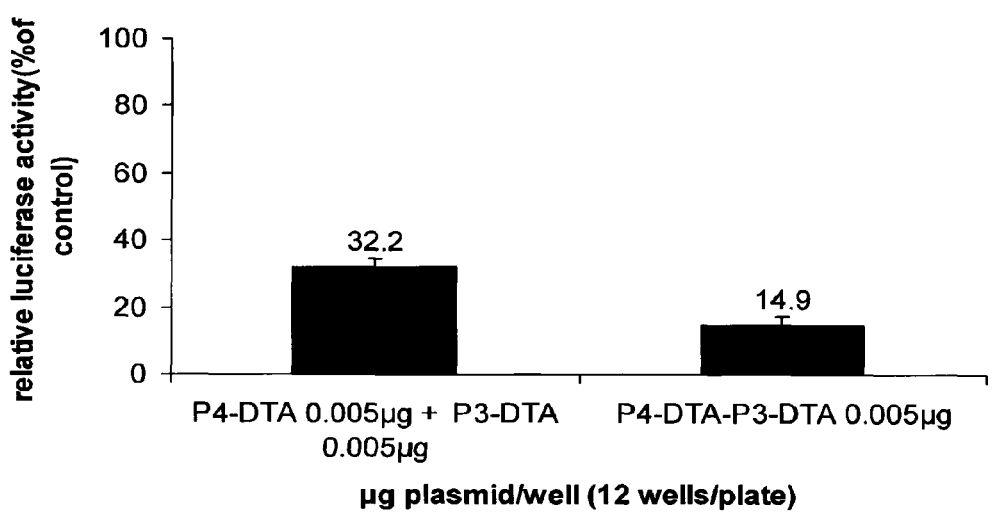
Figure 21A:
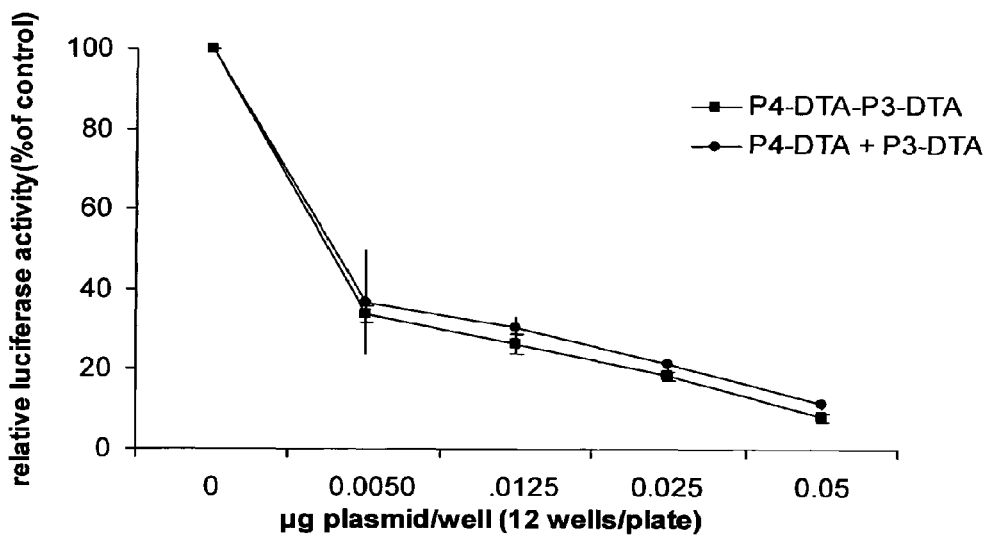
FIGS. 21A-21B. Relative in-vitro activity in ES-2 cells of P4-DTA-P3-DTA vs. P3-driven and P4-driven constructs in combination. ES-2 cells were co-transfected with 2 μg of LucSV40 and the indicated concentrations of P4-DTA-P3-DTA or an equal amount of each of P3-DTA+P4-DTA.
Figure 21B:
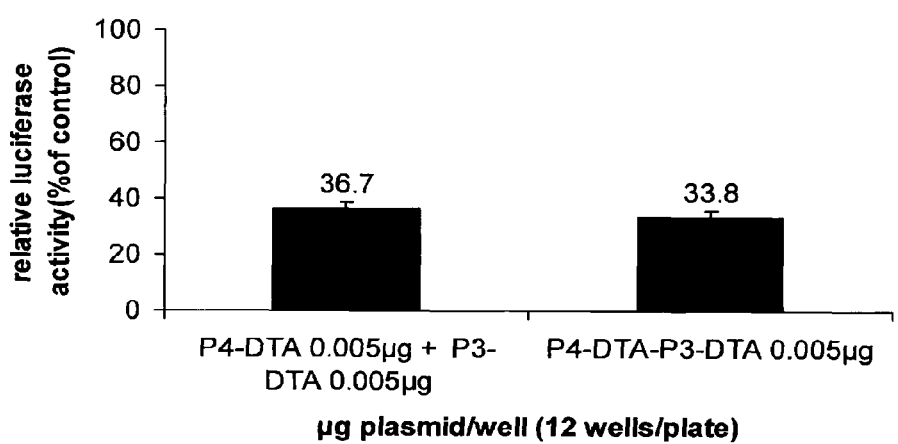
Figure 22:
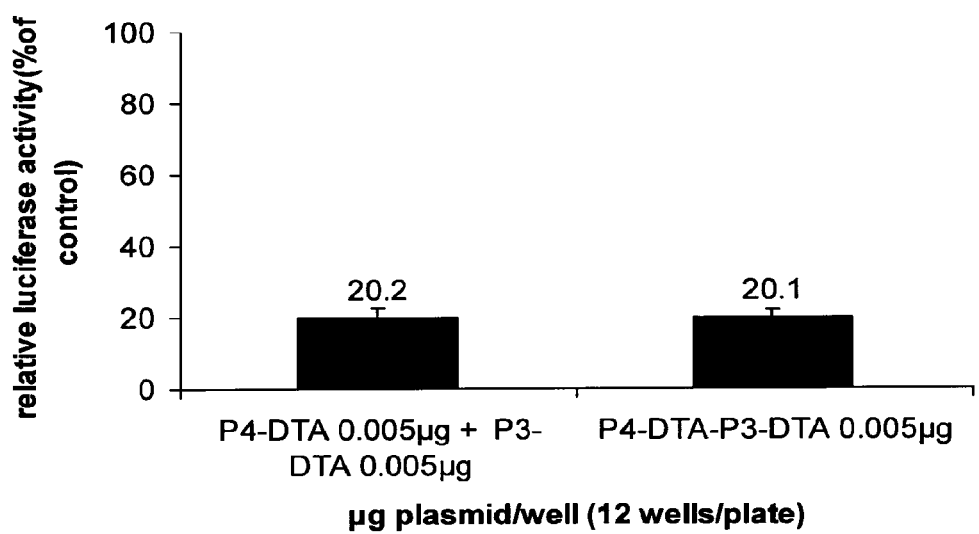
FIG. 22. Relative in-vitro activity in Hep-3B cells of 0.005 μg of P4-DTA-P3-DTA vs. 0.005 μg of each of P3-driven and P4-driven constructs in combination. Experiment was performed as described for FIG. 21. Axes are same as for FIG. 15B.
Figure 24A:
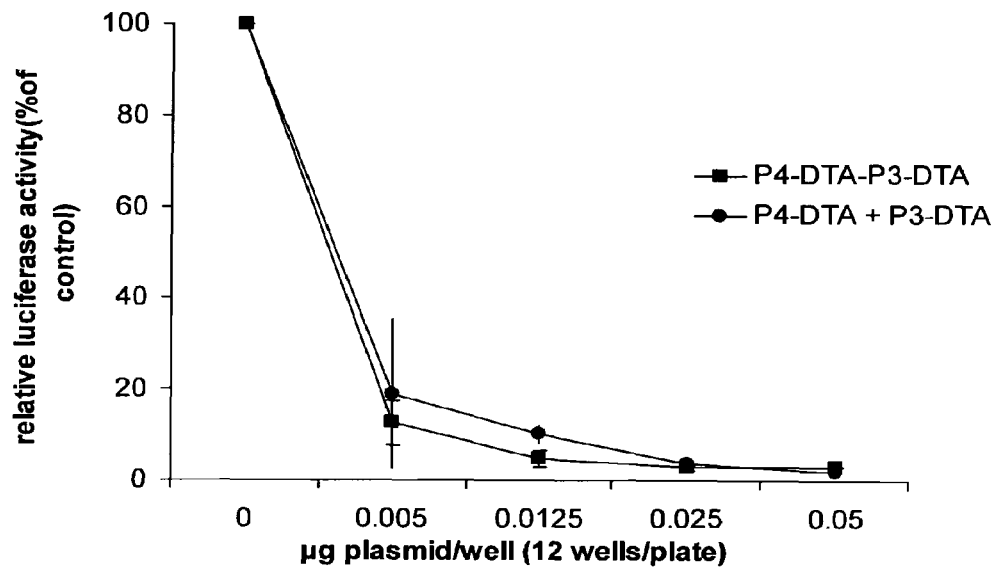
FIGS. 24A-24B. Relative in-vitro activity in CRL-1469 cells of 0.005 μg of P4-DTA-P3-DTA vs. 0.005 μg of each of P3-driven and P4-driven constructs in combination.
Figure 24B:
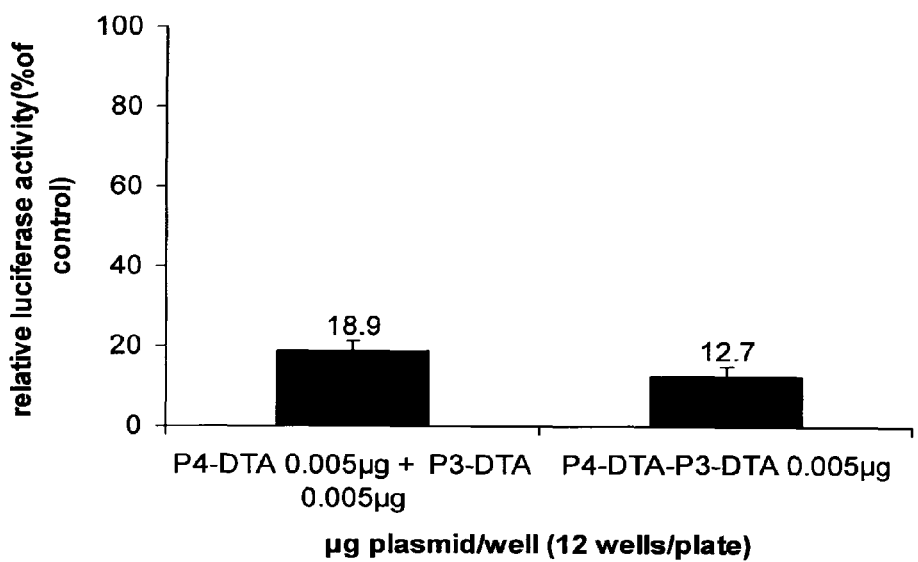

Example 8: DTA Genes Separately Expressed from P3 and P4 Promoters Exhibit Greater-than-Additive Anti-Cancer Activity when Present on a Single Construct Next, the presence of a greater-than-additive anti-cancer effect of the P4-DTA-P3-DTA double promoter plasmids was tested in HT-1376, ES-2, Hep3B, PC-1, and CRL-1469 cells, exactly as described in the previous Example. The double promoter construct P4-DTA-P3-DTA exhibited superior efficiency in lysing the cancer cell lines, relative to the combined activity of both single promoter constructs (P3-DTA+P4-DTA), in HT-1376 cells (FIGS. 20A-B). Very similar results were obtained in ES-2 cells (FIGS. 21A-B), Hep3B cells (FIG. 22) and CRL-1469 cells (FIGS. 24A-B).

Thus, IGF-II P3-driven and IGF-II P4-driven DTA-encoding genes present on a single expression vector exhibited greater-than-additive anti-cancer activity relative to expression vectors carrying either gene alone when tested against a broad spectrum of tumor cells. The consistency of these results across each of these cancer cell lines demonstrates the superior ability of P3-DTA-P4-DTA constructs of the present invention against cancer in general.

Example 9: Bladder Carcinoma Animal Model

The Heterotopic Model for Subcutaneous Bladder Tumors
$2 \times 10^6$ T24P or $3 \times 10^6$ HT-1376 human bladder carcinoma cells in phosphate-buffered saline were subcutaneously injected into the dorsa of 6-7 weeks old nude female mice in order to establish heterotopic bladder tumors. 10 days after inoculation, measurable tumors appeared that were treated with the H19-DTA-P4-DTA, P4-DTA-P3-DTA and H19-DTA-P3-DTA expression vectors.

Treatment of the Heterotopic Subcutaneous Tumors
Animals were separated into groups of the same size (n=6). 3 injections of 25 μg/tumor of the expression vectors (P4-DTA-P3-DTA, H19-DTA-P4-DTA, or H19-DTA-P3-DTA respectively) or the control vector (P4-Luc-P3-Luc, H19-Luc-P4-Luc, or H19-Luc-P3-Luc respectively) were administered into each tumor. At each time point, tumor dimensions were measured using a caliper, and tumor volume was calculated according to the formula width×length× 0.5. Animals were sacrificed 3 days after the last injection, tumors were excised, and their ex-vivo weight and volume were measured.

Example 10: The H19-DTA-P4-DTA Construct Exhibits Greater-than-Additive Anti-Cancer Activity in Several In Vivo Bladder Cancer Models T24P Results
The anti-cancer therapeutic activity of H19-DTA-P4-DTA was tested in an in vivo bladder cancer model. T24P human bladder carcinoma cells were subcutaneously injected into the dorsa of athymic female mice in order to model heterotopic bladder cancer. 10 days later, mice developed measurable heterotopic tumors. The therapeutic potency of the vectors was tested by directly administering 3 injections of 25 μg of the expression vectors or the control vector (H19-Luc, P4-Luc, and H19-Luc-P4-Luc, expressing luciferase under the H19 promoter, P4 promoter or both promoters, respectively) into each heterotopic bladder cancer tumor.

Tumor size was determined and in-vivo fold increase of the tumor size was calculated at the end of each treatment.

Figure 25:
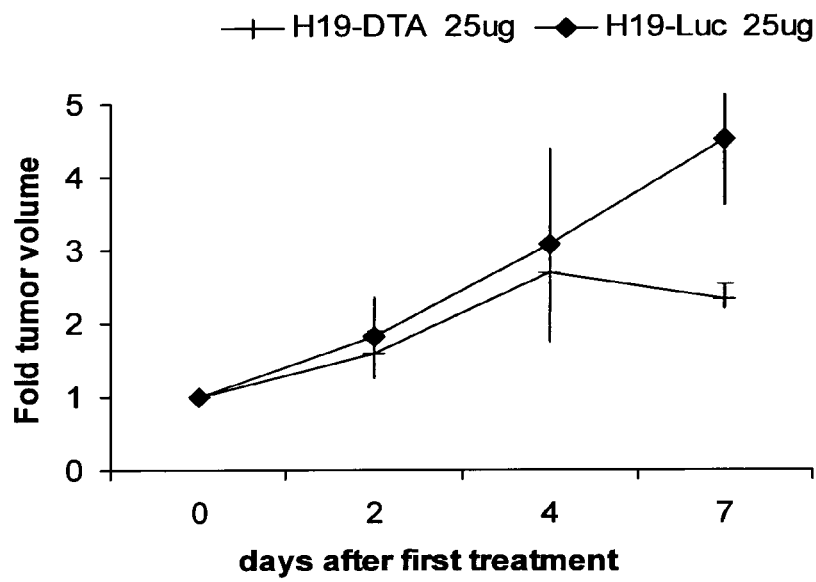
FIG. 25. In vivo anti-tumor effect of injection of 25 μg of H19-DTA. Y-axis: fold-tumor volume increase. X-axis: time (days).
Figure 26:
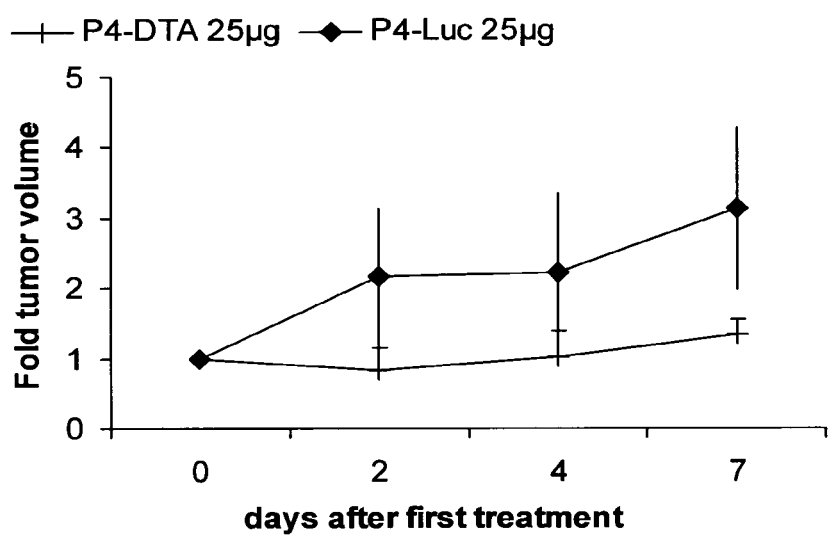
FIG. 26. In vivo anti-tumor effect of injection of 25 μg of P4-DTA. Y-axis: fold-tumor volume increase. X-axis: time (days).
Figure 27:
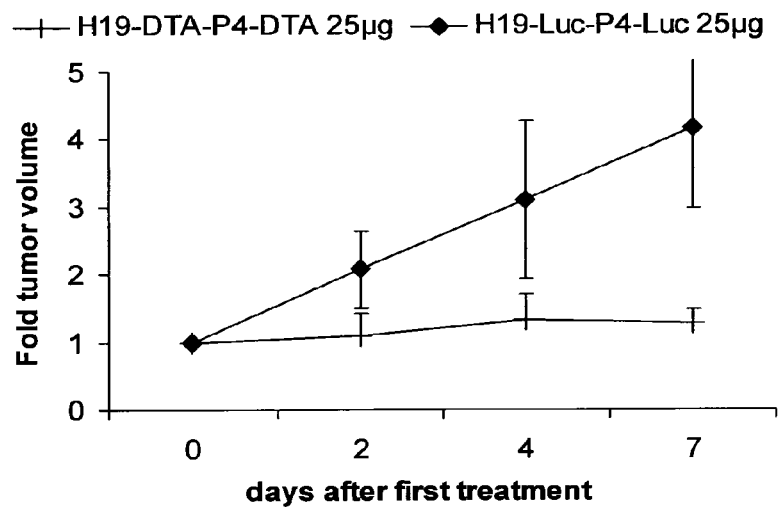
FIG. 27. In vivo anti-tumor effect of injection of 25 μg of H19-DTA-P4-DTA. Y-axis: fold-tumor volume increase. X-axis: time (days).

Three injections of H19-DTA (FIG. 25) and P4-DTA (FIG. 26) at two-day intervals were able to inhibit tumor development by at least 49% and 57%, respectively compared to H19-Luc and P4-Luc treatment, respectively. However, three injections of the double promoter plasmid H19-DTA-P4-DTA at two-day intervals inhibited tumor development by at least 70% compared to H19-Luc-P4-Luc treatment (FIG. 27). The double promoter construct thus exhibited enhanced ability to inhibit tumor development in vivo, compared to each of the single-promoter constructs (H19-DTA and P4-DTA).

Figure 28:
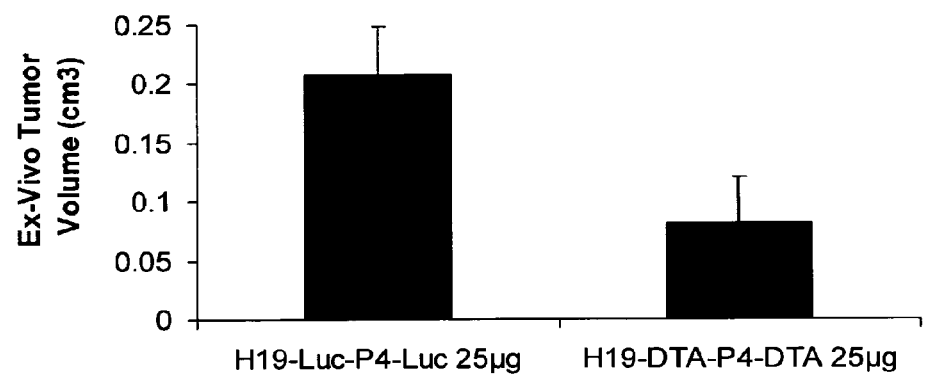
FIG. 28. Ex-vivo volume of tumors from H19-DTA-P4-DTA-treated mice.
Figure 29:
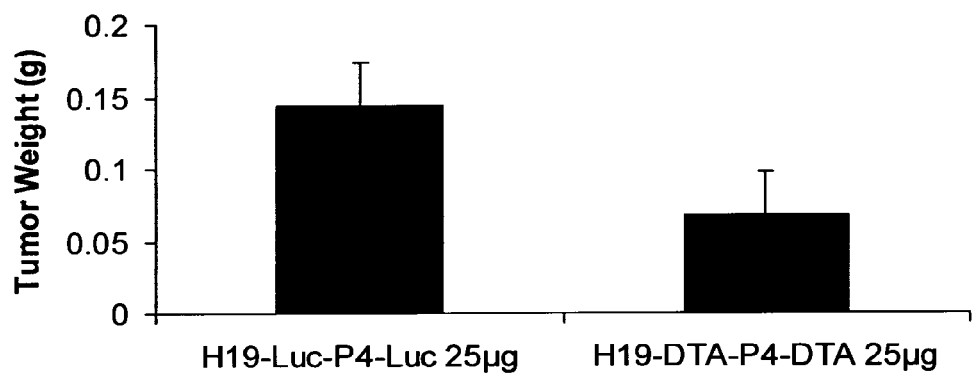
FIG. 29. Ex-vivo weight of tumors from H19-DTA-P4-DTA-treated mice.

To confirm the difference between the H19-DTA-P4-DTA and H19-Luc-P4-Luc groups, tumors were excised and their weight and volume determined ex vivo. Mice treated with H19-DTA-P4-DTA exhibited at least a 61% reduction of the ex-vivo tumor volume (FIG. 28) and at least a 54% reduction of ex-vivo tumor weight (FIG. 29) compared to H19-Luc-P4-Luc treatment.

Figure 30:
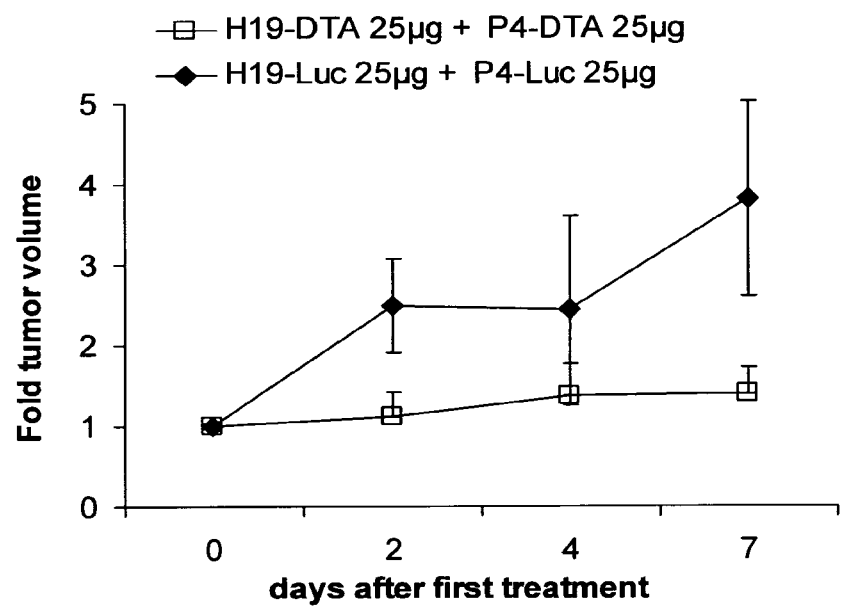
FIG. 30. In vivo anti-tumor effect of injection of 25 μg each of H19-DTA and P4-DTA. Y-axis: fold-tumor volume increase. X-axis: time (days).

To test whether the in vivo anti-cancer activity of H19-DTA-P4-DTA was greater-than-additive, an additional group of T24P tumor-containing mice were treated with three injections of 25 µg each of single-promoter constructs H19-DTA+P4-DTA in combination. The total amount of DNA co-transfected administered was therefore twice than the H19-DTA-P4-DTA group. As can be seen in FIG. 30, tumor development in mice receiving both H19-DTA and P4-DTA plasmids was inhibited by 63% compared to combined H19-Luc+P4-Luc treated mice. An enhanced effect was observed in mice treated with the double-promoter construct H19-DTA-P4-DTA, wherein tumor development was inhibited by 70% compared to the mice treated with the control plasmid H19-Luc-P4-Luc (FIG. 27). Thus, the H19-DTA-P4-DTA vector exhibits greater-than-additive in vivo anti-cancer activity.

Figure 31:
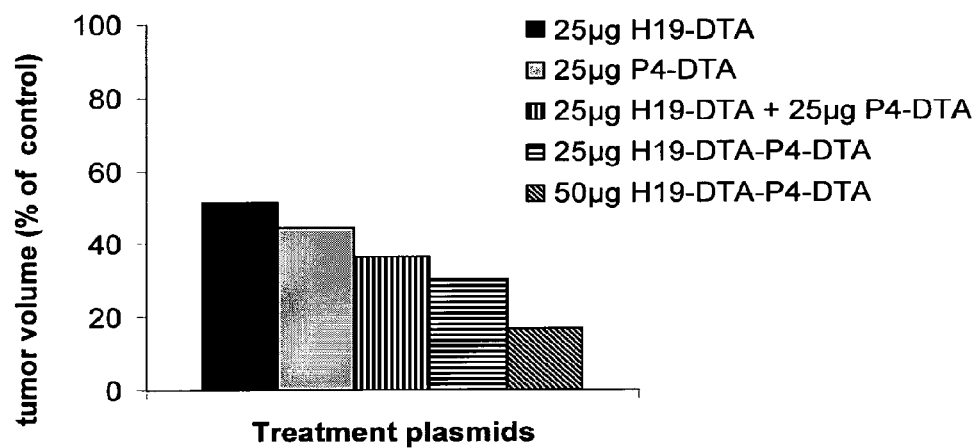
FIG. 31. Summary of T24P bladder cancer model data.

FIG. 31 summarizes all the T24P bladder cancer model data. H19-DTA-P4-DTA clearly exhibits activity superior to each of the single promoter plasmids alone and also superior to their combined activity.

HT-1376 Results

Figure 32:
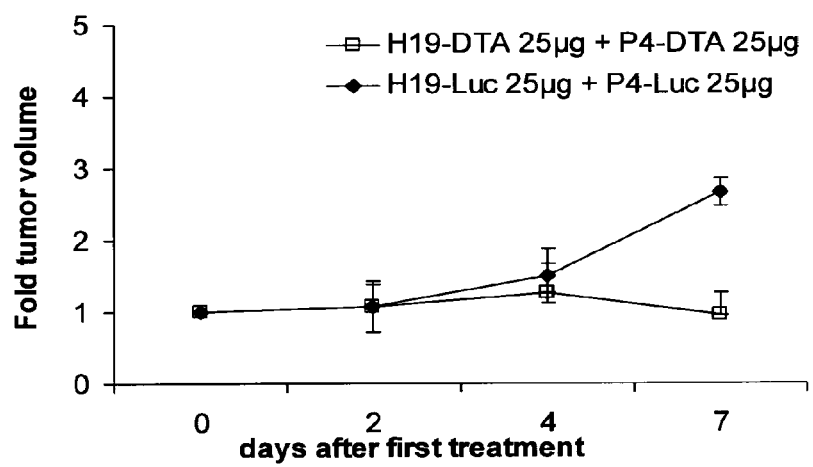
FIG. 32. In vivo anti-tumor effect of injection of 25 μg each of H19-DTA and P4-DTA in the HT-1376 model. Y-axis: fold-tumor volume increase. X-axis: time (days).
Figure 33:
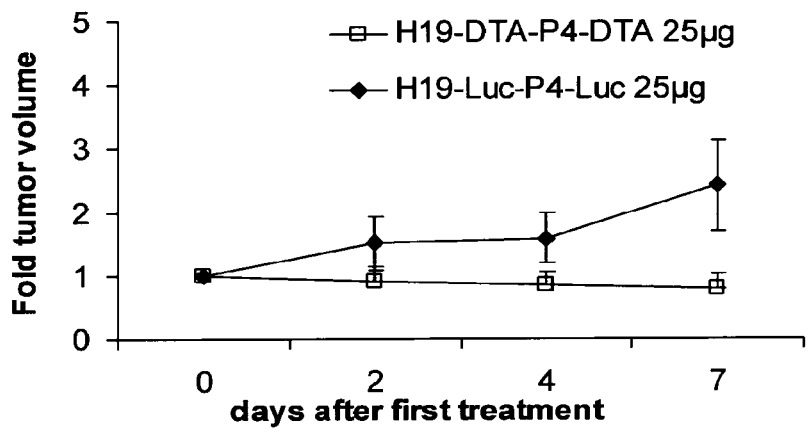
FIG. 33. In vivo anti-tumor effect of injection of 25 μg of H19-DTA-P4-DTA in the HT-1376 model. Y-axis: fold-tumor volume increase. X-axis: time (days).

The therapeutic ability of H19-DTA-P4-DTA was tested in another bladder cancer, model, HT-1376. Experiments were conducted as described for the T24P model. Mice containing HT-1376 tumors were administered 25 µg each of H19-DTA and P4-DTA in combination or 25 µg of H19-DTA-P4-DTA. Administration of H19-DTA and P4-DTA in combination inhibited tumor development by at least 64.5% compared to combined H19-Luc+P4-Luc treated tumors (FIG. 32), while H19-DTA-P4-DTA inhibited tumor development by at least 67% compared to H19-Luc-P4-Luc treatment (FIG. 33). Thus, H19-DTA-P4-DTA exhibited enhanced anti-tumor activity, compared to the combined activity of the single-promoter constructs.

Example 11: The P4-DTA-P3-DTA Construct Exhibits Greater-than-Additive Anti-Cancer Activity in an In Vivo Bladder Cancer Model Next, the anti-cancer therapeutic activity of P4-DTA-P3-DTA was tested in the T24P in vivo bladder cancer model described hereinabove in Examples 9-10. Experiments were performed as described above.

Figure 34:
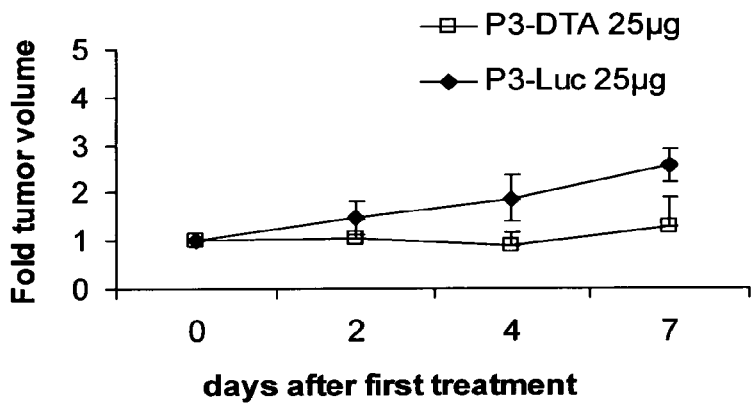
FIG. 34. In vivo anti-tumor effect of injection of 25 μg of P3-DTA. Y-axis: fold-tumor volume increase. X-axis: time (days).
Figure 35:
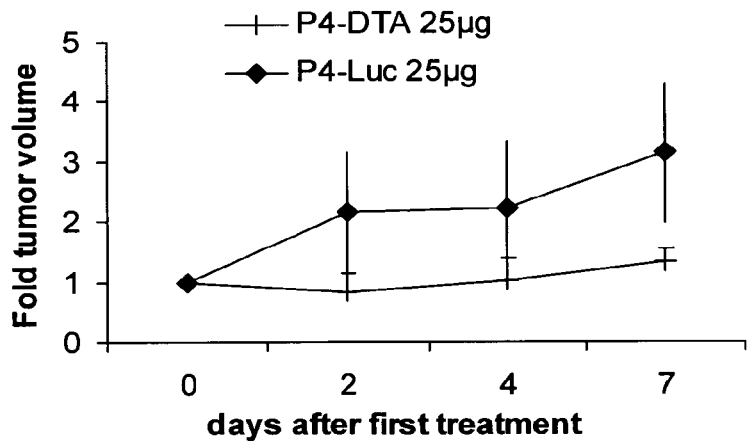
FIG. 35. In vivo anti-tumor effect of injection of 25 μg of P4-DTA. Y-axis: fold-tumor volume increase. X-axis: time (days).
Figure 36:
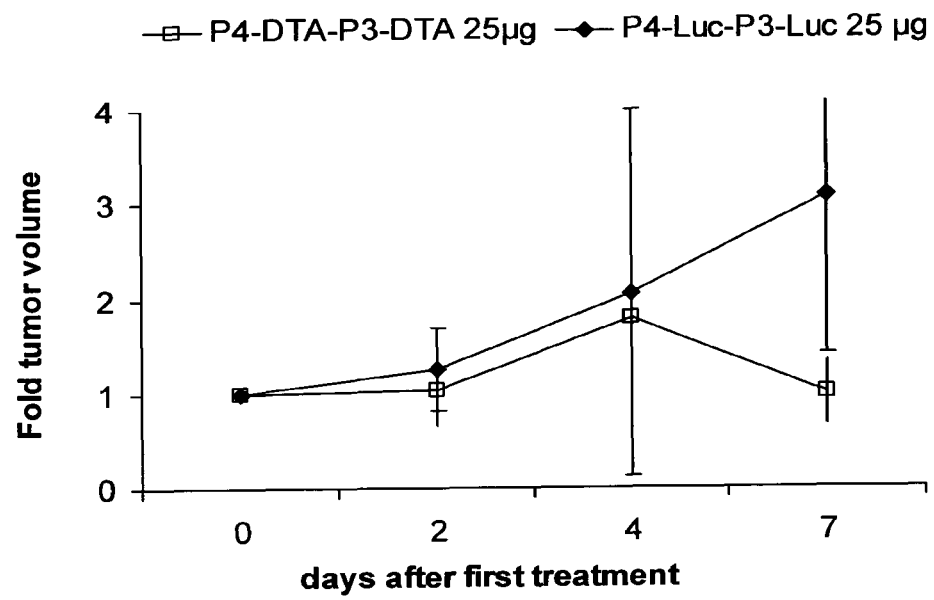
FIG. 36. In vivo anti-tumor effect of injection of 25 μg of P4-DTA-P3-DTA. Y-axis: fold-tumor volume increase. X-axis: time (days).

Three injections of P3-DTA at two-day intervals were able to inhibit the tumor growth by at least 50.5% compared to P3-Luc treatment (FIG. 34), while P4-DTA administered in the same manner inhibited tumor growth by at least 57% compared to P4-Luc treatment (FIG. 35). In contrast, 3 injections of the double promoter plasmid P4-DTA-P3-DTA at two-day intervals inhibited tumor development by at least 70% compared to P3-Luc/P4-Luc treatment (FIG. 36). Thus, P4-DTA-P3-DTA exhibited enhanced anti-tumor activity, compared to each of the single-promoter constructs (P3-DTA and P4-DTA).

Figure 37:
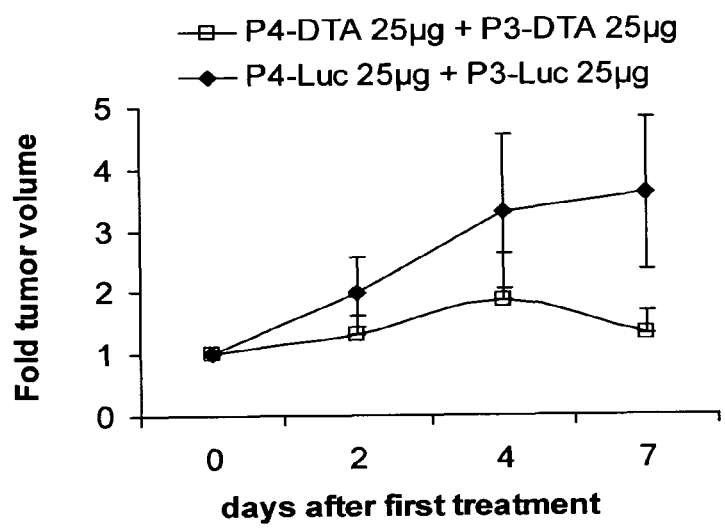
FIG. 37. In vivo anti-tumor effect of injection of 25 μg each of P3-DTA and P4-DTA. Y-axis: fold-tumor volume increase. X-axis: time (days).

To test whether the in vivo anti-cancer activity of P4-DTA-P3-DTA was greater-than-additive, an additional group of T24P tumor-containing mice was treated with 3 injections of 25 µg each of single-promoter constructs P3-DTA+P4-DTA in combination. The total amount of DNA co-transfected administered was therefore twice than the P4-DTA-P3-DTA group. Tumor development was inhibited by at least 63.3% compared to combined P3-Luc+P4-Luc treatment (FIG. 37), an amount less than the 70% observed with P4-DTA-P3-DTA treatment (FIG. 36). Thus, the P4-DTA-P3-DTA vector exhibits greater-than-additive in vivo anti-cancer activity.

Example 12: In Vivo Tumor Growth Inhibition by H19-DTA-P3-DTA Expression Vectors Next, the anti-cancer therapeutic activity of the double promoter plasmid H19-DTA-P3-DTA was tested in the T24P in vivo bladder cancer model described hereinabove in Examples 9-10. Experiments were performed as described above.

Figure 38:
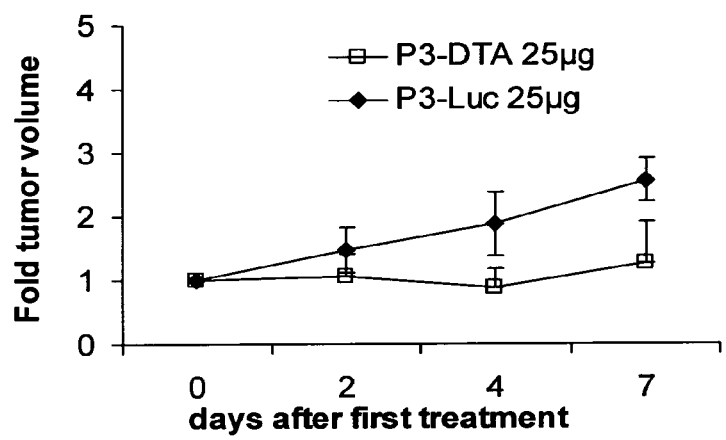
FIG. 38. In vivo anti-tumor effect of injection of 25 μg of P3-DTA. Y-axis: fold-tumor volume increase. X-axis: time (days).
Figure 39:
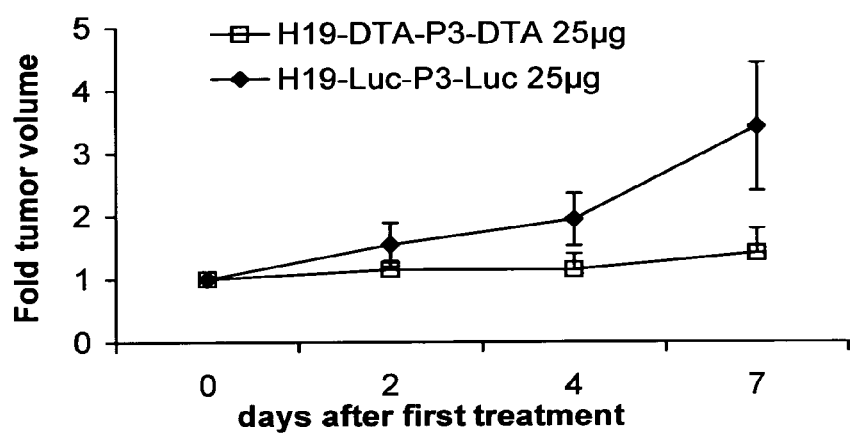
FIG. 39. In vivo anti-tumor effect of injection of 25 μg of H19-DTA-P3-DTA. Y-axis: fold-tumor volume increase. X-axis: time (days).

Three injections of H19-DTA at two-day intervals were able to inhibit the tumor growth by at least 49% compared to H19-Luc treatment (FIG. 25), and P3-DTA administered in the same manner inhibited tumor growth by at least 50.5% compared to P3-Luc treatment (FIG. 38). In contrast, 3 injections of H19-DTA-P3-DTA at two-day intervals inhibited tumor development by at least 59% compared to H19-Luc-P3-Luc treatment (FIG. 39). Thus, H19-DTA-P3-DTA exhibited enhanced anti-tumor activity, compared to each of the single-promoter constructs (H19-DTA and P3-DTA).

Overall, the results presented herein demonstrate that multiple promoter constructs of the present invention exhibit enhanced, greater-than-additive ability to inhibit tumor development, compared to the corresponding single-promoter constructs.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. A method for treating a tumor in a human subject in need thereof, wherein a cell of the tumor is capable of expressing a transcript directed by an H19 promoter, a transcript directed by an IGF-IIP3 promoter and/or a transcript directed by an IGF-IIP4 promoter, the method comprising injecting intratumorally a nucleic acid construct comprising:

a) a first open reading frame encoding a diphtheria toxin, the first open reading frame being operably linked to an H19 promoter; and b) a second open reading frame encoding a diphtheria toxin A, the second open reading frame being operably linked to an IGF-II promoter selected from IGF-II P3 and IGF-II P4 promoter sequences, wherein the diphtheria toxin is diphtheria toxin A (DTA) or comprises a sequence that is at least 90% homologous to the amino acid sequence as set forth in SEQ ID NO: 7; and wherein the nucleic acid sequence of the H19 promoter exhibits H19 promoter activity and is at least 90% homologous to the nucleic acid sequence as set forth in SEQ ID NO: 1 or 2, and the nucleic acid sequence of the IGF-II P4 promoter exhibits IGF-II P4 promoter activity and is at least 90% homologous to the nucleic acid sequence as set forth in SEQ ID NO: 9, or the nucleic acid sequence of the IGF-II P3 promoter that exhibits IGF-II P3 promoter activity and is at least 90% homologous to the nucleic acid sequence as set forth in SEQ ID NO: 8, SEQ ID NO: 12, or SEQ ID NO: 17;

wherein said nucleic acid is expressed in a cell of the tumor, thereby treating said tumor in said subject.

2. The method according to claim 1, wherein the tumor is a carcinoma.

3. The method according to claim 2, wherein the carcinoma is selected from the group consisting of a bladder carcinoma, a hepatocellular carcinoma, an ovarian carcinoma, a lung carcinoma and a pancreatic carcinoma.

4. The method of claim 1, wherein the diphtheria toxin is diphtheria toxin A (DTA) comprises the amino acid sequence as set forth in SEQ ID NO: 7.

5. The method of claim 1, wherein the H19 promoter comprises the nucleic acid sequence as set forth in SEQ ID NO: 1 or 2, and, wherein the IGF-II P4 promoter comprises the nucleic acid sequence as set forth in SEQ ID NO: 9, or wherein the IGF-II P3 promoter comprises the nucleic acid sequence as set forth in SEQ ID NO: 8, SEQ ID NO: 12, or SEQ ID NO: 17.

6. The method of claim 1, wherein the nucleic acid construct is a plasmid or a eukaryotic expression vector.

7. The method of claim 1 wherein the IGF-II promoter is an IGF-II P3 promoter and said construct further comprises a third open reading frame encoding a diphtheria toxin, with the third open reading frame being operably linked to an IGF-II P4 promoter.

8. The method of claim 1, for treating a tumor in said subject.

9. The method of claim 1, for inhibiting tumor progression in said subject.

10. The method of claim 1, for inhibiting tumor metastases in said subject.

11. The method of claim 1, wherein said construct is administered in the form of a pharmaceutical composition in the form of naked DNA.

12. A method for treating a tumor in a human subject in need thereof, wherein a cell of the tumor is capable of expressing a transcript directed by an IGF-IIP3 promoter and/or a transcript directed by an IGF-II P4 promoter, comprising injecting intratumorally a nucleic acid construct comprising:
   a) a first open reading frame encoding a diphtheria toxin A, said first open reading frame being operably linked to an IGF-II P3 promoter; and
   b) a second open reading frame encoding a diphtheria toxin, said second open reading frame being operably linked to an IGF-II P4 promoter,
   wherein the diphtheria toxin is diphtheria toxin A (DTA) or comprises a sequence that is at least 90% homologous to the amino acid sequence as set forth in SEQ ID NO: 7; and
   wherein the nucleic acid sequence of the IGF-II P4 promoter exhibits IGF-II P4 promoter activity and is at least 90% homologous to the nucleic acid sequence as set forth in SEQ ID NO: 9, or the nucleic acid sequence of the IGF-II P3 promoter that exhibits IGF-II P3 promoter activity and is at least 90% homologous to the nucleic acid sequence as set forth in SEQ ID NO: 8, SEQ ID NO: 12, or SEQ ID NO: 17;
   wherein said nucleic acid is expressed in a cell of the tumor, thereby treating said tumor in said subject.

13. The method of claim 12, wherein the tumor is a carcinoma.

14. The method according to claim 13, wherein the carcinoma is selected from the group consisting of a bladder carcinoma, a hepatocellular carcinoma, an ovarian carcinoma, a lung carcinoma and a pancreatic carcinoma.

15. The method of claim 12, wherein the diphtheria toxin is diphtheria toxin A (DTA) comprises the amino acid sequence as set forth in SEQ ID NO: 7.

16. The method of claim 12, wherein the IGF-II P4 promoter comprises the nucleic acid sequence as set forth in SEQ ID NO: 9, or wherein the IGF-II P3 promoter comprises the nucleic acid sequence as set forth in a sequence selected from SEQ ID NO: 8, SEQ ID NO: 12, and SEQ ID NO: 17.

17. The method of claim 12, wherein said construct is administered in the form of a pharmaceutical composition in the form of naked DNA.

18. A method for treating tumor in a human subject in need thereof, wherein a cell of the tumor is capable of expressing a transcript directed by an HI 9 promoter, a transcript directed by an IGF-II P3 promoter and/or a transcript directed by an IGF-II P4 promoter, the method comprising injecting intratumorally a nucleic acid construct comprising:
   a) a first open reading frame encoding a cytotoxic or cytostatic gene product, the first open reading frame being operably linked to a first promoter; and
   b) a second open reading frame encoding the cytotoxic or cytostatic gene product, the second open reading frame being operably linked to a second promoter,
   wherein the first promoter and the second promoter are selected from the group consisting of:
   i) a first promoter being an H19-promoter, and a second promoter being an IGF-II P4 promoter;
   ii) a first promoter being an H19 promoter, and a second promoter being an IGF-II P3 promoter; and
   iii) a first promoter being an IGF-II P4 promoter, and a second promoter being an IGF-II P3 promoter,
   wherein the first promoter and the second promoter are selected from the group consisting of:
   i) the first promoter being an H19 promoter comprising the nucleic acid sequence as set forth in SEQ ID NO: 1 or 2, and the second promoter being an IGF-IIP4 promoter comprising the nucleic acid sequence as set forth in SEQ ID NO: 9;
   ii) the first promoter being an H19 promoter comprising the nucleic acid sequence as set forth in SEQ ID NO: 1 or 2, and the second promoter being an IGF-II P3 promoter comprising the nucleic acid sequence as set forth in SEQ ID NO: 8, SEQ ID NO: 12, or SEQ ID NO: 17; and
   iii) the first promoter being an IGF-II P4 promoter comprising the nucleic acid sequence as set forth in SEQ ID NO: 9, and the second promoter being an IGF-II P3 promoter comprising the nucleic acid sequence as set forth in SEQ ID NO: 8, SEQ ID NO: 12, or SEQ ID NO: 17,
   wherein said nucleic acid is expressed in a cell of the tumor, thereby treating said tumor in said subject.

19. The method of claim 18, wherein the tumor is a carcinoma.

* * * * *